US012590133B2

(12) United States Patent
Garcia et al.

(10) Patent No.: US 12,590,133 B2
(45) Date of Patent: Mar. 31, 2026

(54) IL-13/IL-4 SUPERKINES: IMMUNE CELL TARGETING CONSTRUCTS AND METHODS OF USE THEREOF

(71) Applicants: The Board of Trustees of the Leland Stanford Junior University, Stanford, CA (US); Medicenna Therapeutics, Inc., Toronto (CA)

(72) Inventors: Kenan Christopher Garcia, Menlo Park, CA (US); Ignacio Moraga Gonzalez, Palo Alto, CA (US); Fahar Merchant, Vancouver (CA)

(73) Assignees: The Board of Trustees of the Leland Stanford Junior University, Stanford, CA (US); Medicenna Therapeutics Inc., Toronto (CA)

( * ) Notice: Subject to any disclaimer, the term of this patent is extended or adjusted under 35 U.S.C. 154(b) by 1223 days.

(21) Appl. No.: 17/059,937

(22) PCT Filed: Jun. 3, 2019

(86) PCT No.: PCT/US2019/035186
§ 371 (c)(1),
(2) Date: Nov. 30, 2020

(87) PCT Pub. No.: WO2019/232523
PCT Pub. Date: Dec. 5, 2019

(65) Prior Publication Data
US 2021/0214410 A1     Jul. 15, 2021

Related U.S. Application Data

(60) Provisional application No. 62/687,225, filed on Jun. 19, 2018, provisional application No. 62/679,692, filed on Jun. 1, 2018.

(51) Int. Cl.
| | |
|---|---|
| *C07K 14/54* | (2006.01) |
| *A61K 40/11* | (2025.01) |
| *A61K 40/31* | (2025.01) |
| *A61K 40/42* | (2025.01) |
| *C07K 14/55* | (2006.01) |
| *C07K 14/705* | (2006.01) |
| *C07K 14/725* | (2006.01) |
| *C07K 14/73* | (2006.01) |
| *C07K 14/735* | (2006.01) |
| *C07K 16/28* | (2006.01) |

(52) U.S. Cl.
CPC .......... *C07K 14/5437* (2013.01); *A61K 40/11* (2025.01); *A61K 40/31* (2025.01); *A61K 40/4217* (2025.01); *A61K 40/428* (2025.01); *C07K 14/5406* (2013.01); *C07K 14/55* (2013.01); *C07K 14/7051* (2013.01); *C07K*

*14/70514* (2013.01); *C07K 14/70521* (2013.01); *C07K 14/70535* (2013.01); *C07K 16/2809* (2013.01); *C07K 2319/02* (2013.01); *C07K 2319/03* (2013.01); *C07K 2319/30* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 4,816,249 | A | 3/1989 | Levy et al. |
| 5,068,177 | A | 11/1991 | Carson et al. |
| 5,227,159 | A | 7/1993 | Miller |
| 5,538,866 | A | 7/1996 | Israeli et al. |
| 5,641,640 | A | 6/1997 | Hanning |
| 6,011,002 | A | 1/2000 | Pastan et al. |
| 6,028,176 | A | 2/2000 | Greve et al. |
| 6,130,318 | A | 10/2000 | Wild et al. |
| 6,335,426 | B1 | 1/2002 | Shanafelt et al. |
| 6,410,008 | B1 | 6/2002 | Strom et al. |
| 6,451,308 | B1 | 9/2002 | Strom et al. |
| 6,617,135 | B1 | 9/2003 | Gillies et al. |
| 6,673,602 | B1 | 1/2004 | Spear et al. |
| 6,682,736 | B1 | 1/2004 | Hanson et al. |
| 6,737,511 | B1 | 5/2004 | Youle et al. |
| 6,984,720 | B1 | 1/2006 | Korman et al. |
| 7,741,465 | B1 | 6/2010 | Eshhar et al. |
| 7,943,743 | B2 | 5/2011 | Korman et al. |
| 8,008,449 | B2 | 8/2011 | Korman et al. |
| 9,512,194 | B2 | 12/2016 | Garcia et al. |

(Continued)

FOREIGN PATENT DOCUMENTS

| | | |
|---|---|---|
| CN | 102792358 | 3/2015 |
| JP | 6936934 B2 | 9/2021 |

(Continued)

OTHER PUBLICATIONS

U.S. Appl. No. 08/355,502, filed Dec. 12, 1994, Strom et al., Related to U.S. Pat. No. 6,410,008 B1.

(Continued)

*Primary Examiner* — Blaine Lankford
(74) *Attorney, Agent, or Firm* — Sara Sims; Christina A. MacDougall; Morgan, Lewis & Bockius, LLP

(57) ABSTRACT

Methods and compositions are provided for enhancing anti-tumor effector immune cells with a targeting construct comprising a human IL-13 superkine and/or a human IL-4 superkine. Cytokine or additional co-stimulatory sequences may also be included to enhance the tumoricidal effects of the cells.

4 Claims, 21 Drawing Sheets

Specification includes a Sequence Listing.

(56) References Cited

U.S. PATENT DOCUMENTS

| | | | |
|---|---|---|---|
| 9,629,899 B2 | 4/2017 | Puri | |
| 9,738,696 B2 | 8/2017 | Garcia et al. | |
| 10,093,708 B2 | 10/2018 | Merchant | |
| 10,106,592 B2 | 10/2018 | Merchant | |
| 2002/0039581 A1 | 4/2002 | Carreno et al. | |
| 2002/0086014 A1 | 7/2002 | Korman et al. | |
| 2003/0013851 A1 | 1/2003 | Powers et al. | |
| 2004/0248260 A1 | 12/2004 | Heavner et al. | |
| 2005/0106148 A1 | 5/2005 | Kay et al. | |
| 2005/0201994 A1 | 9/2005 | Korman et al. | |
| 2006/0035856 A1 | 2/2006 | Caput et al. | |
| 2007/0160658 A1 | 7/2007 | Connor et al. | |
| 2010/0183545 A1 | 7/2010 | Puri | |
| 2010/0317577 A1 | 12/2010 | Youle | |
| 2011/0023680 A1 | 2/2011 | Wang | |
| 2011/0150892 A1 | 6/2011 | Thudium et al. | |
| 2011/0319336 A1 | 12/2011 | Kawakami et al. | |
| 2012/0294931 A1 | 11/2012 | Kim et al. | |
| 2013/0022623 A1 | 1/2013 | Karsunky et al. | |
| 2013/0149236 A1 | 6/2013 | Johnson et al. | |
| 2014/0050709 A1* | 2/2014 | Leen | A61K 39/4611 |
| | | | 435/372 |
| 2016/0151490 A1 | 6/2016 | Sampath et al. | |
| 2016/0271231 A1 | 9/2016 | Merchant | |
| 2016/0340649 A1* | 11/2016 | Brown | A61K 35/17 |
| 2017/0224733 A1 | 8/2017 | Badie et al. | |
| 2019/0016797 A1 | 1/2019 | Arenas-Ramirez et al. | |

FOREIGN PATENT DOCUMENTS

| | | |
|---|---|---|
| WO | WO1994004680 A1 | 3/1994 |
| WO | WO2001018051 A2 | 9/2000 |
| WO | WO2001025282 A1 | 4/2001 |
| WO | WO2001034645 A2 | 5/2001 |
| WO | WO2001062933 A3 | 8/2001 |
| WO | WO2002018422 A1 | 3/2002 |
| WO | WO2006074451 A2 | 7/2006 |
| WO | WO2007146046 A2 | 12/2007 |
| WO | WO2008101671 A2 | 8/2008 |
| WO | WO2009029601 A2 | 3/2009 |
| WO | WO2009140598 A1 | 5/2009 |
| WO | WO2010031185 A1 | 3/2010 |
| WO | WO2011106779 A1 | 9/2011 |
| WO | WO2012054929 A2 | 4/2012 |
| WO | WO2012088446 A1 | 6/2012 |
| WO | WO 2012/120125 A1 | 9/2012 |
| WO | WO2012139112 A1 | 10/2012 |
| WO | WO2013112871 A1 | 8/2013 |
| WO | WO 2014/127261 A1 | 8/2014 |
| WO | WO2015042705 A1 | 9/2014 |
| WO | WO2015042707 A1 | 4/2015 |
| WO | WO 2015/070210 A1 | 5/2015 |
| WO | WO 2015/117229 A1 | 8/2015 |
| WO | WO 2016/044811 A1 | 3/2016 |
| WO | WO2016040441 A1 | 3/2016 |
| WO | WO 2017/136829 A1 | 8/2017 |
| WO | WO 2018/112266 A1 | 6/2018 |
| WO | WO2019051204 A1 | 3/2019 |
| WO | WO2019073299 A1 | 4/2019 |
| WO | WO2020160639 A1 | 8/2020 |
| WO | WO2021200896 A1 | 10/2021 |
| WO | WO2021258213 A1 | 12/2021 |

OTHER PUBLICATIONS

Batlevi, Connie Lee et al. "Novel immunotherapies in lymphoid malignancies." Nature reviews. Clinical oncology vol. 13,1 (2016): 25-40. doi:10.1038/nrclinonc.2015.187.

Blanar, M A, and W J Rutter. "Interaction cloning: identification of a helix-loop-helix zipper protein that interacts with c-Fos." Science (New York, N.Y.) vol. 256,5059 (1992): 1014-8. doi:10.1126/science. 1589769.

Boder, E T, and K D Wittrup. "Yeast surface display for screening combinatorial polypeptide libraries." Nature biotechnology vol. 15,6 (1997): 553-7. doi: 10.1038/nbt0697-553.

Brekke et al., Structure-Function Relationships of Human IgG, The. Immunologist 2:125-130 (1994).

Clinical Trial NCT00730613 history, dated Aug. 8, 2008 (8 total pages).

Clinical Trial NCT01082926 history, dated Mar. 9, 2010 (9 total pages).

Clinical Trial NCT02208362 history, dated Aug. 5, 2014 (16 total pages).

Eisenberg, D et al. "Analysis of membrane and surface protein sequences with the hydrophobic moment plot." Journal of molecular biology vol. 179,1 (1984): 125-42. doi:10.1016/0022-2836(84)90309-7.

Genbank Accession No. NM_000640, Homo sapiens interleukin 13 receptor subunit alpha 2 (IL13RA2) [Homo sapiens] Jun. 2, 2022.

Genbank Accession No. NM_001560, Homo sapiens interleukin 13 receptor subunit alpha 1 (IL13RA1) [Homo sapiens] May 4, 2022.

Hegde, Meenakshi et al. "Tandem CAR T cells targeting HER2 and IL13Ra2 mitigate tumor antigen escape." The Journal of clinical investigation vol. 126,8 (2016): 3036-52. doi:10.1172/JCI83416.

International Search Report and Written Opinion for International Patent Application No. PCT/US2019/035186 dated Sep. 10, 2019, 20 pages.

Kahlon, Kanwarpal S et al. "Specific recognition and killing of glioblastoma multiforme by interleukin 13-zetakine redirected cytolytic T cells." Cancer research vol. 64,24 (2004):9160-6. doi:10.1158/0008-5472.CAN-04-0454.

Kong, Seogkyoung et al. "Suppression of human glioma xenografts with second-generation IL13R-specific chimeric antigen receptor-modified T cells." Clinical cancer research : an official journal of the American Association for Cancer Research vol. 18,21 (2012): 5949-60. doi:10.1158/1078-0432.CCR-12-0319.

Leclair, K P et al. "The p50 subunit of NF-kappa B associates with the NF-IL6 transcription factor." Proceedings of the National Academy of Sciences of the United States of America vol. 89,17 (1992): 8145-9. doi:10.1073/pnas.89.17.8145.

Morrison et al., "Structural Determinants of Human IgG Function" The Immunologist 2:119-124 (1994).

Sjölander, S, and C Urbaniczky. "Integrated fluid handling system for biomolecular interaction analysis." Analytical chemistry vol. 63,20 (1991): 2338-45. doi:10.1021/ac00020a025.

Szabo, A et al. "Surface plasmon resonance and its use in biomolecular interaction analysis (BIA)." Current opinion in structural biology vol. 5,5 (1995): 699-705. doi:10.1016/0959-440x(95)80064-6.

Thaci, Bart et al. "Significance of interleukin-13 receptor alpha 2-targeted glioblastoma therapy." Neuro-oncology vol. 16,10 (2014): 1304-12. doi: 10.1093/neuonc/nou045.

Vogelstein, Bert et al. "Cancer genome landscapes." Science (New York, N.Y.) vol. 339,6127 (2013): 1546-58. doi:10.1126/science. 1235122.

Wu, Chia-Yung et al. "Synthetic biology approaches to engineer T cells." Current opinion in immunology vol. 35 (2015): 123-30. doi:10.1016/j.coi.2015.06.015.

"Alzheimer's Disease", ninds.nih.gov/disorders/alzheimersdisease/alzheimersdisease.htm; Jan. 4, 2012; 3 total pages.

Agholme et al. "An in vitro model for neuroscience: differentiation of SH-SY5Y cells into cells with morphological and biochemical characteristics of mature neurons." J Alzheimer's Disease 20: 1069-1082, 2010.

Allen et al. "Interleukin-13 Displaying Retargeted Oncolytic Measles Virus Strains Have Significant Activity Against Gliomas With Improved Specificity". Molecular Therapy, Sep. 2008 (Sep. 2008), vol. 16, No. 9, pp. 1556-1564, ISSN 1525-0016 See whole document.

Bachran et al. "Anthrax Toxin-Mediated Delivery of the Pseudomonas Exotoxin A Enzymatic Domain to the Cytosol of Tumor Cells via Cleavable Ubiquitin Fusions" mBio vol. 4, oo. 201-213 (2013).

Baeurle Patrick A. et al. "Bispecific T-cell engaging antibodies for cancer therapy", Cancer Research, AACR, US Philadephia, PA, vol.

(56)          References Cited

OTHER PUBLICATIONS

69, No. 12, Jun. 15, 2009 (Jun. 15, 2009), pp. 4941-4944, XP002665118, ISSN: 1538-7445, CAN-09-0547 [retrieved on Jun. 9, 2009] the whole document.

Bates, D.L., et al., "3QB7: Interleukin-4 mutant RGA bound to cytokine receptor common qamma," «RCSB PDB» Protein Data Bank, oaqes 1-2 (Aoril 25, 2012).

Bhatia et al., Innovative approaches for enhancing cancer gene therapy. Discovery Medicine 15(84): 309-317, 2013.

Bhattacharya et al. Impact of genetic variation on three dimensional structure and function of proteins. PLoS ONE 12(3): e0171355, 2017.

Boise et al. "bcl-x, a bcl-2-Related Gene That Functions as a Dominant Regulator of Apoptotic Cell Death" Cell, vol. 74, 00.597-608 (1993).

Bork, P. Powers and pitfalls in sequence analysis: the 70% hurdle. Genome Res 10: 398-400, 2000.

Brenner. S.E. Errors in genome annotation. Trends in Genetics 15:132-133, 1999.

Burt, B.M. et al. "Expression of Interleukin-4 Receptor Alpha in Human Pleural Mesothelioma Is Associated with Poor Survival and Promotion of Tumor Inflammation". Clinical Cancer Research, Mar. 15, 2012 (Mar. 15, 2012), vol. 18, No. 6, pp. 1568-1577 See entire document.

C.E. Brown et al.: "Bioactivity and Safety of IL13R?2-Redirected Chimeric Antigen Receptor CD8+ T Cells in Patients with Recurrent Glioblastoma", Clinical Cancer Research, vol. 21, No. 18, Jun. 9, 2015 (Jun. 9, 2015), pp. 4062-4072, XP055362974, US ISSN: 1078-0432, DOI: 10.1158/1072-0432.CCR-15-0428 The whole document.

Candolfini et al. "Gene therapy-mediated delivery of targeted cytotoxin for glioma therapeutics". Proceedings of the National Academy of Sciences of the United States of America, Nov. 16, 2010 (Nov. 16, 2010), vol. 107, No. 46, pp. 20021-20026, ISSN 1091-6490.

Cao et al., In vivo delivery of a Bel-xi fusion protein containing the TAT protein transduction domain protects against ischemic brain injury and neuronal apoptosis. J Neurosci 22(13): 5423-5431, 2002.

Castro et al. "Therapy and Targeted Toxins for Glioma". Current Gene Therapy, Jun. 1, 2011 (Jan. 6, 2011), vol. 11, No. 3, pp. 155-180, ISSN 1875-5631.

Chen et al. Fusion protein linkers: property, design, and functionality. Adv Drug Rev 65: 1357-1369, 2013 (online Sep. 29, 2012).

Cleary et al "Cloning and structural analysis of cDNAs for bcl-2 and a hybrid bcl-2/immunoglobulin transcript resulting from the t(14;18) translocation" Cell Press, vol. 47, No. 1, DD. 19-28 (1986).

CN 102792358 translation, 2012, pp. 1-40.

Corren et al. "Lebrikizumab treatment in adults with asthma.", N Eng I J Med., Sep. 22, 2011, pp. 1088-1098, 365(1), Massachusetts Medical Society, Waltham, MA.

Creusot, et al., "Engineering cell-type selective immune responses using mechanism-based designer IL-4 cvtokines," The Journal of Immunoloov, 186:57.8 (2011).

Cuny, G.D. Neurodegenerative diseases: challenges and opportunities. Future Med Chem 4(13): 1647-1649, 2012.

Diehn et al. "Cancer Stem Cells and Radiotherapy: New Insights Into Tumor Radioresistance" Journal of National Cancer Institute, vol. 98, pp. 1755-1757 (2006).

Doerks et al. Protein annotation: detective work for function prediction. Trends in Genetics 14:248-250, 1998.

Eisenmesser et al., "Solution structure of interleukin-13 and insights into receptor engagement." J Mol. Biol., Jun. 2001, pp. 231-241, 310(1), Elsevier, Amsterdam, Netherlands.

Elgert, K. Immunology, understanding the immune system. New York: Wiley-Liss, Inc., 1996; pp. 323-326.

Feigin et al. Recent advances in Huntington's disease: implications for experimental therapeutics. Curr Opin Neural 15: 483-489, 2002.

Fenton et al. Rheostat positions: a new classification of protein positions relevant to pharmacogenomics. Medicinal Chem Res 29:1133-1146, 2020.

Fernandez et al. "Genetically Engineered Vesicular Stomatitis Virus in Gene Therapy; Application for Treatment of Malignant Disease". Journal of Virology, Jan. 2002 (2002), vol. 76, No. 2, DD. 895-904, ISSN 0022-538X See whole document.

Fernando, R. et al. "Breast cancer cell proliferation is inhibited by bAD: regulation of cyclin D1." The Journal of biological chemistry vol. 282,39 (2007): 28864-73.

Forster et al. Characterization of differentiated SH-SY5Y as neuronal screening model reveals increased oxidative vulnerability. J Biomlecul Screen 21(5): 496-509, 2016.

Fueller, J et al. "C-RAF activation promotes BAD poly-ubiquitylation and turn-over by the proteasome." Biochemical and biophysical research communications vol. 370,4 (2008): 552-6.

Gardai et al. Phosphorylation of Bax Ser184 by Akt regulates its activity and apoptosis in neutrophils. J Biol Chem 279(20): 21085-21095, 2004.

Garland, L. et al. "Phase I trial of intravenous IL-4 Pseudomonas Exotoxin protein (NBI-3001) in patients with advanced solid tumors that express the IL-4 receptor". Journal of Immunotherapy, 2005, vol. 28; No. 4, pp_ 376-381.

GenBank Accession No. 3QB7_A, chain A, Interleukin 4 [homo sapiens] Apr. 25, 2012.

GenBank Accession No. Q07817, bcl gene apotosis [homo sapiens] Feb. 28, 2018.

GenBank Accession No. Z23115, bcl XL gene [homo sapiens] Oct. 7, 2008.

Guo et al. Protein tolerance to random amino acid change. Proc Natl Acad Sci USA 101 (25): 9205-9210, 2004.

Hallett, Miranda A et al. "Cytokine stimulation of epithelial cancer cells: the similar and divergent functions of IL-4 and IL-13." Cancer research vol. 72,24 (2012): 6338-43. doi:10.1158/0008-5472.CAN-12-3544.

Halliday et al. Alzheimer's disease and inflammation: a review of cellular and therapeutic mechanisms. Clin Exp Pharmacol Physiol 27: 1-8, 2000.

Han, J. et al. "Analysis of the cancer genome atlas (TCGA) database identifies an inverse relationship between interleukin-13 receptor a1 and a2 gene expression and poor prognosis and drug resistance in subjects with glioblastoma multiforme". Journal of Neuro-Oncology, Nov. 22, 2017 (Nov. 22, 2017), vol. 136, No. 3, pp. 463-474 See entire document.

Harvey, A. "Overview of Cell Signaling Pathways in Cancer." Predictive Biomarkers in Oncology, edited by Sunil Badve and George Louis Kumar. 2019, pp. 167-182.

Hotchkiss et al., TAT-BH4 and TAT-Bel-xi peptides protect against sepsis-induced lymphocyte apoptosis in vivo. J Immunol 176: 5471-5477, 2006.

Ichinose, M et al. "Extracellular Bad fused to toxin transport domains induces apoptosis." Cancer research vol. 62,5 (2002): 1433-8.

ISR and WO issued in PCT/US2013/054164 on May 7, 2014.

ISR issued in PCT/US2017/066529 on Apr. 9, 2018, and IPRP issued in PCT/US2017/066529 on Jun. 18, 2019.

ISR/WO issued in PCT/CA2020/000013 on May 15, 2020.

ISR/WO issued in PCT/IB2018/001284 on Mar. 11, 2019.

ISR/WO issued in PCT/IB2019/000759 on Jan. 20, 2020.

Ito, et al., "Distinct structural requirements for interleukin-4 (IL-4) and IL-13 binding to the shared IL-13 receptor facilitate cellular tuning of cytokine responsiveness." J. Biol. Chem., Sep. 4, 2009, pp. 24289-24296, 284(36), ASBMB, Rockville, MD.

Joshi et al. "In Situ Expression of Interleukin-4 (IL-4) Receptors in Human Brain Tumors and Cytotoxicity of a Recombinant IL-4 Cytotoxin in Primary Glioblastoma Cell Cultures", Cancer Research, Nov. 15, 2001, DD. 8058-8061, vol. 61.

Juengst, E.T. What next for human gene therapy? BMJ 326: 1410-1411, 2003.

Junttila et al."Redirecting cell-type specific cytokine responses with engineered interleukin-4 superkines" Nat Chem Biol., vol. 8, No. 12, pp. 990-998 (2012).

Kahlon, et al., "Specific Recognition and Killing of Glioblastoma Multiforme by Interleukin 13-Zetakine Redirected Cytolytic T Cells", Cancer Research, 64:9160-9166 (2004).

(56)                    References Cited

OTHER PUBLICATIONS

Kawakami, Mariko et al. "Interleukin-4-Pseudomonas exotoxin chimeric fusion protein for malignant glioma therapy." Journal of neuro-oncology vol. 65,1 (2003): 15-25. doi:10.1023/a:1026294416718.

Kazunari et al. Neurosurgery 38(4):p. 733-736, Apr. 1996.

Kreitman et al. "Recombinant Toxins Containing Human Granulocyte-Macrophage Colony-Stimulating Factor and Either Pseudomonas Exotoxin or Diphtheria Toxin Kill Gastrointestinal Cancer and Leukemia Cells" Blood vol. 90, pp. 252-259 (1997).

Laske et al. "Tumor regression with regional distribution of the targeted toxin TF- CRM107 in patients with malignant brain tumors" Nature, vol. 3, pp. 1362-1368 (1997).

Levin, et al., "Exploiting a natural conformational switch to engineer an interleukin-2 "superkine"," Nature 484:529-533 (A & B) (2012).

Lomonosova and Chinnadurai "BH3-only proteins in apoptosis and beyond: an overview" Oncogene, vol. 27, pp. S2-S19 (2009).

Madhankumar et al., "interleukin 13 mutants of enhanced avidity toward the glioma-associated receptor, IL 13Ralpha2." Neoplasia, Jan./Feb. 2004, pp. 15-22, 6(1), Neoplasia Press, Ann Arbor, MI.

Mardor, Y. et al. "Convection-Enhanced Drug Delivery of Interleukin-4 Pseudomonas Exotoxin (PRX321): Increased Distribution and Magnetic Resonance Marketing". J Pharmacol Exp Ther., Aug. 2009 (Aug. 2009). Vol. 330(2), pp. 520-525, ISSN 0022-3565 (Print), 1521-0103 (Electronic), 0022-3565 (Linking) [online] [retrieved on Feb. 12, 2019 (Dec. 2, 2019)].

McCormick et al. Commentary: IL-4 and IL-13 receptors and signaling. Cytokine 75: 38-50, 2015.

Munitz et al. 2008. PNAS 105:7240-7245 (Year: 2008).

Murray, E.J. "Cloning Genes in Mammalian Cell-lines" in Molecular Biology and Biotechnology. Great Britain: The Royal Society of Chemistry, 2000, pp. 177-201.

Natoli, A. et al. "Targeting the IL-4/IL-13 signaling pathway sensitizes Hodgkin lymphoma cells to chemotherapeutic drugs." International journal of cancer vol. 133,8(2013): 1945-54.

Ngo et al. "Computational complexity, protein structure prediction, and the Levinthal paradox" in The Protein Folding Problem and Tertiary Structure Prediction, pp. 492-495, 1994.

Oka K, Yamamoto M, Nonaka T, Tomonaga M. The significance of artificial cerebrospinal fluid as perfusate and endoneurosurgery. Neurosurgery.Apr. 1996;38(4):733-6. PMID: 8692392.

Oshima et al., "Characterization of a powerful high affinity antagonist that inhibits biological activities of human interleukin-13." J. Biol. Chem., May 4, 2001, pp. 15185-15191, 276(18), ASBMB, Rockville, MD.

Pahlman et al. Differentiation and survival influences of growth factors in human neuroblastoma. Eur J Cancer 31A(4): 453-458, 1995.

Partaledis et al., "In vitro selection and characterization of human immunodeficiency virus type 1 (HIV-1) isolates with reduced sensitivity to hydroxyethylamino sulfonamide inhibitors of HIV-1 aspartyl protease." J. Viral, Sep. 1995, pp. 5228-5235, 69(9), American Society for Microbiology, Washington DC.

Phillips, A.J. The challenge of gene therapy and DNA delivery. J Pharmacy and Pharmacol53: 1169-1174,2001.

Polzein, L. et al. "Identification of novel in vivo phosphorylation sites of the human proapoptotic protein BAD: pore-forming activity of BAD is regulated by phosphorylation." The Journal of biological chemistry vol. 284,41 (2009): 28004-20.

Post et al. "Targeted Cancer Gene Therapy Using a Hypoxia Inducible Factor- Dependent Oncolytic Andenovirus Armed with Interleukin-4". Cancer Research, Jul. 15, 2007 (Jul. 15, 2007), vol. 67, No. 14, pp. 6872-6881, ISSN 1538-7445 See whole document.

Post, Dawn E., et al. "Local delivery of the anti-tumorigenic interleukin-4 (IL-4) cytokine to tumors using an oncolytic adenovirus." Cancer Res May 1, 2005; 65 (9_Supplement): 317.

Puri et al. "Human Neurological Cancer Cells Express Interleukin-4 (IL-4) Receptors Which Are Targets for the Toxic Effects of IL4-Pseudomonas Exotoxin Chimeric Protein". The International Journal of Cancer, 1994, vol. 58, pp. 574-581, ISSN 1097-0215.

Reynolds et al., "Genetic Instability Induced by the Tumor Microenvironment", Cancer Research, vol. 56, pp. 5754-5757 (1996).

Rochman et al., 2009. 9(7) p. 1-23 (Year: 2009).

Rubanyi, G.M., The future of human gene therapy. Molecular Aspects Med 22: 113-142, 2001.

Rubin "Neuronal cell death: when, why and how" British Medical Bulletin, vol. 53, Issue 3, pp. 617-631 (1997).

Sakariassen et al. "Cancer Stem Cells as Mediators of Treatment Resistance in Brain Tumors: Status and Controversies" Neoplasia, vol. 9, No. 11, pp. 882-892 (2007).

Schnare et al., "Specific Antagonism of Type I IL-4 Receptor with a Mutated Form of Murine IL-4," The Journal of Immunology, 161:7, pp. 3484-3492 (1998).

Sharma et al. "Interleukin-4 Mediates Down Regulation of Antiviral Cytokine Expression and Cytotoxic T-Lymphocyte Responses and Exacerbates Vaccinia Virus Infection In Vivo". Journal of Virology, Oct. 1996, vol. 70, No. 10, pp. 7103-7107, ISSN 0022-538X See whole document.

Shimamura et al. "Interleukin-4 Cytotoxin Therapy Synergizes with Gemcitabine in a Mouse Model of Pancreatic Ductal Adenocarcinoma" Cancer Research, vol. 67, pp. 9903-9912 (2007).

Shimamura et al. "The IL-4 and IL-13 pseudomonas exotoxins: new hope for brain tumor therapy". Neurosurgical FOCUS, 2006, vol. 20, No. 3:E11, ISSN 1092-0684.

Skolnick et al. From genes to protein structure and function: novel applications of computational approaches in the genomic era. Trends Biotechnol 18(1) :34-39 2000.

Smith et al. The challenges of genome sequence annotation or "the devil is in the details". Nature Biotechnol 15: 1222-1223, 1997.

Sosman, J A et al. "A phase I trial of continuous infusion interleukin-4 (IL-4) alone and following interleukin-2 (IL-2) in cancer patients." Annals of oncology : official journal of the European Society for Medical Oncology vol. 5,5 (1994): 447-52. doi: 10.1093/oxfordjournals.annonc.a058878.

Steece-Collier et al. Etiology of Parkinson's disease: genetics and environment revisited. Proc Natl Acad Sci USA 99(22): 13972-13974, 2002.

Suga et al. "Transplant Immunosuppression Enhances Efficiency of Adenoviral-Mediated Gene Retransfection: Inhibition of Interferon-y and Immunoglobin G" The Society of Thoracic Surgeons, vol. 73, pp. 1092-1097 (2002).

Suzuki, Akiko et al. "Targeting of IL-4 and IL-13 receptors for cancer therapy." Cytokine vol. 75,1 (2015): 79-88. doi:10.1016/j.cyto.2015.05.026.

Thompson, et al., "Mutants of interleukin 13 with altered reactivity toward interleukin 13 receptors." J. Biol. Chem., Oct. 15, 1999, pp. 29944-29950, 274(42), ASBMB, Rockville, MD.

Thorpe et al. "Toxicity of diphtheria toxin for lymphoblastoid cells is increased by conjugation to antilymphocytic qlobulin" Nature, vol. 271, oo. 752-755 (1978).

Tokuriki et al. Stability effects of mutations and protein evolvability. Curr Opin Structural Biol 19: 596-604, 2009.

Tsujimoto and Croce "Analysis of the structure, transcripts, and protein products of bcl-2, the gene involved in human follicular lymphoma" Proc. Natl. Acad. Sci., vol. 83, pp. 5214-5218 (1986).

UniProtKB database P05112 (Aug. 13, 1987).

Vallera, D.A. et al. "Retroviral immunotoxin gene therapy of leukemia in mice using leukemia-specific T cells transduced with an interleukin-3/Bax fusion protein gene." Human qene theraov vol. 14, 18 (2003): 1787-98.

Van Den Broek, et al. "IL-4 and IL-10 Antagonize IL-12-Mediated Protection Against Acute Vaccinia Virus Infection with a Limited Role of IFN-y and Nitric Oxide Synthetase 2". Journal of Immunology, Jan. 1, 2000 (Jan. 1, 2000), vol. 164, No. 1, pp. 371-378, ISSN 1550-6606.

Wang et al. Mono- or double-site phosphorylation distinctly regulates the proapoptotic function of Bax. PLoS One 5(10): e13393, 2010 (8 total pages).

Wells, J.A. Additivity of mutational effects in proteins. Biochemistry 29(37): 8509-8517, 1990.

(56)        References Cited

OTHER PUBLICATIONS

White "Life, Death, and the Pursuit of Apoptosis" Genes and Development 10, pp. 1-15 (1996).
Yang et al. "Bad, a heterodimeric partner for Bcl-XL and Bcl-2, displaces Bax and promotes cell death" Cell, vol. 80, pp. 285-291 (1995).
Yang et al. Targeting cancer stem cell pathways for cancer therapy. Signal Transd Targeted Ther 5:8, 2020 (35 total pages).
Yeung et al. Signaling pathways in inflammation and anti-inflammatory therapies. Curr Pharm Design 24: 1449-1484, 2018.
Youle et al. "Receptor-mediated uptake of an extracellular Bcl-xL fusion protein inhibits apoptosis" Proceedings of Nat'l Academy of Sciences, vol. 96, oo. 9563-9567 (1999).
Ding et al., Convection-enhanced Delivery of Free Gadolinium with the Experimental Chemotherapeutic Agent PRX321., Neurol Res. Oct. 2010; 32(8): 810-815.
Weber et al., Safety, tolerability, and tumor response of IL4-Pseudomonas exotoxin (NBI- 3001) in patients with recurrent malignant glioma., J Neurooncol. Aug.-Sep. 2003;64(1-2):125-37. doi: 10.1007/BF02700027.
Chatel, Celine, International Search Report and Written Opinion for International Patent Application No. PCT/CA2021/051433, 7 pages, published Apr. 21, 2022.
Sampson et al., "MDNA55, a Locally Administered IL4 Guided Toxin for Targeted Treatment of Recurrent Glioblastoma Shows Long Term Survival Benefit," European Journal of Cancer (2020). 138. S6. 10.1016/S0959-8049(20)31084-4.
Medicenna, "Convection-Enhanced Delivery (CED) of MDNA55 in Adults With Recurrent or Progressive Glioblastoma," Clinical Trial NCT02858895, First posted Aug. 8, 2016. (https://clinicaltrials.gov/study/NCT02858895).
Bautz, "Medicenna Therapeutics Corp.," Zacks Small-Cap Research, May 14, 2019 (May 14, 2019), acquired from: http://s27.q4cdn.com/906368049/files/News/2019/Zacks_SCR_Research_05142019_T.MDNA_Bautz.pdf.
Yu et al., "Efficacy and safety of bevacizumab for the treatment of glioblastoma," Exp Ther Med. Feb. 2016;11(2):371-380.
Gramatzki et al., "Bevacizumab may improve quality of life, but not overall survival in glioblastoma: an epidemiological study," Ann Oncol. Jun. 1, 2018;29(6):1431-1436.
Bargou et al., New immunotherapeutic principles., Onkologe 2017 • 23:532-536.
Bluemel et al., Epitope distance to the target cell membrane and antigen size determine the potency of T cell-mediated lysis by BiTE antibodies specific for a large melanoma surface antigen., Cancer Immunol Immunother. Aug. 2010;59(8):1197-209. doi: 10.1007/s00262-010-0844-y. Epub Mar. 23, 2010.
Dickopf et al., Format and geometries matter: Structure-based design defines the functionality of bispecific antibodies., Computational and Structural Biotechnology Journal, vol. 18, 2020, pp. 1221-1227.
Engelberts et al., DuoBody-CD3xCD20 induces potent T-cell-mediated killing of malignant B cells in preclinical models and provides opportunities for subcutaneous dosing., EBioMedicine. Feb. 2020:52:102625. doi: 10.1016/j.ebiom.2019.102625. Epub Jan. 23, 2020.
Charo et al. Bcl-2 Overexpression Enhances Tumor-Specific T-Cell Survival. Cancer Res 65(5): 2001-2008, 2005.
Vella et al. Interleukin 4 (IL-4) or IL-7 Prevents the Death of Resting T Cells: Stat6 Is Probably Not Required for the Effect of IL-4. J Exp Med 186(2): 325-330, 1997.
Wilkie et al. Selective Expansion of Chimeric Antigen Receptor-targeted T-cells with Potent Effector Function using Interleukin-4. J Biol Chem 285(33): 25538-25544, 2010 (and supplementary materials) (17 total pages).

* cited by examiner

First batch:

| Construct | | Titer | Volume |
|---|---|---|---|
| PMC 393 | IL13-CAR | $2.9 \times 10^7$ particles/ml | 180 ul |
| PMC 394 | IL13-CAR-IL2 | $1.0 \times 10^8$ particles/ml | 180 ul |

Second batch (12/13/18):

| Construct | | Titer | Volume |
|---|---|---|---|
| PMC 393 | IL13-CAR | $4.9 \times 10^9$ particles/ml | 180 ul |
| PMC 394 | IL13-CAR-IL2 | $1.06 \times 10^9$ particles/ml | 180 ul |

IL-13/IL-4 SUPERKINES: IMMUNE CELL TARGETING CONSTRUCTS AND METHODS OF USE THEREOF

CROSS-REFERENCE TO RELATED APPLICATIONS

The present application claims priority to U.S. Provisional Application No. 62/679,692, filed Jun. 1, 2018; and U.S. Provisional Application No. 62/687,225 filed Jun. 19, 2018, the disclosures of which are hereby incorporated by reference in their entireties for all purposes.

BACKGROUND

Cytokines are small cell-signaling molecules that are secreted by numerous cells and are a category of signaling molecules used extensively in intercellular communication. Cytokines regulate key cellular functions, including differentiation, proliferation and apoptosis/anti-apoptosis.

Many cytokines mediate stimulation by first interacting with a relatively high affinity cytokine receptor chain, usually designated "a," followed by a relatively low affinity interaction with a receptor chain that is shared among different cytokines, a shared receptor chain. Binding of a cytokine to the first high affinity receptor creates a composite surface that the shared receptor chain can then bind.

Interleukin-4 (IL-4) typifies such cytokines. The primary binding chain of IL-4 is IL-4 Receptor α (IL-4Rα). The IL-4/IL-4Rα complex serves as a ligand for the second component of the IL-4 receptor, γc. Additionally, the IL-4/IL-4Rα complex serves as a ligand for the interleukin-13 (IL-13) Receptor α1 (IL-13Rα1). Unlike IL-4, IL-13 does not bind to IL-4Rα however, IL-13/IL-13Rα1 complex binds does bind to IL-4Rα.

Because IL-4 and IL-13 can signal through distinct receptors, it can be postulated that they are be able to activate different signal transduction pathways. Indeed, γc activates the tyrosine kinase Janus kinase 3 (JAK3), whereas IL-13Rα1 activates Tyk2 and JAK2. Activated JAKs mediate the phosphorylation of the cytoplasmic tail of IL-4R on conserved tyrosine residues that serve as docking sites for proteins containing Src homology 2 (SH2) domains. Three closely clustered tyrosine residues serve as docking sites for signal transducer and activator of transcription 6 (STAT6), a transcription factor selectively coupled to the IL-4Rα chain. The binding of IL-13 to IL-13Rα1 also activates STAT6 through the binding of IL-4Rα by IL-13/IL-13Rα1 complex.

In addition to STAT6, IL-4 recruits and activates IRS-2. Structure-function analyses have revealed that a tyrosine residue [Tyr.sup.497, part of the insulin/IL-4R motif (14R)] on the transmembrane domain of IL-4Rα is necessary for the docking of IRS-2 to IL-4Rα after IL-4Rα has been activated by IL-4. JAK1 and JAK3 then phosphorylate IL-4Rα-bound IRS-2. The activation of IRS-2 leads to the activation of phosphoinositide 3-kinase (PI3K) and the downstream protein serine/threonine kinase Akt, a pathway that is thought to mediate growth and survival signals in many cell types. Indeed, this pathway is important in IL-4-mediated growth in cells expressing the type I IL-4R (NK cells, T cells, and B cells).

Although IL-4Rα is ubiquitously present, γc, but not IL-13Rα1 is found on T cells, natural killer (NK) cells, basophils, mast cells, and most mouse B cells (most human B cells express both γc, and IL-13Rα1). Consequently, IL-4, but not IL-13, promotes the differentiation of naive T cells into T$_{H2}$ cells, and IL-4 appears much more important than IL-13 for the induction of mouse IgE responses.

Some bone marrow-derived cells, including macrophages and dendritic cells, express both γc and IL-13Rα1 and consequently respond to both IL-4 and IL-13. Differences in the relative abundance of these two receptor subunits on different subpopulations of these cells may account, in part, for their relative responsiveness to IL-4 versus IL-13. IL-13Rα1, but little or no γc subunit, is found on most non-bone marrow-derived cells, including smooth muscle and epithelial cells; consequently, IL-4 has no inherent advantage over IL-13 in stimulating these cells.

In the early 1990's, clinical trials were performed utilizing IL-4 to treat cancer. It had been observed that IL-4 induces growth arrest and apoptosis in leukemia lymphoblasts in vitro. These observations were confirmed in experiments with human leukemic cells engrafted in immunodeficient mice. Unfortunately, the clinical usefulness of IL-4 is limited by the pleiotropic activities of the cytokine including renal, hepatic, neurologic, and gastrointestinal toxicities as well as vascular leak syndrome, which is associated with binding of IL-4 to non-hematopoietic cells. Thus, the use of "wild-type" IL-4 as a therapeutic is limited by its capacity to bind cell types that cause undesirable responses.

Consequently, a need in the art exists for molecules with increased selectively for one receptor relative to another; using IL-4 as an example, increased selectivity for γc relative to IL-13Rα1 can be advantageous or vice a versa.

Furthermore, some toxicity associated with the use of wild-type cytokines can be the result of the administration of high doses. Thus, molecules which can achieve activation of the desired shared receptor with lower doses would also be advantageous. Interleukin-13 (IL-13) is a cytokine secreted by T lymphocytes and mast cells, which shares several biological activities with IL-4, as a mediator of allergic inflammation and disease. IL-13 is involved in the allergic response via its actions on epithelial and smooth muscle cells. IL-13 induces many features of allergic lung disease, including airway hyperresponsiveness, goblet cell metaplasia and mucus hypersecretion, which all contribute to airway obstruction. IL-13 also induces secretion of chemokines that are required for recruitment of allergic effector cells to the lung.

An important factor in IL-13 biology is the nature of its receptor interactions. Its diverse functions are mediated by a complex receptor system including IL-4 receptor α (IL-4Rα; CD124) and two other cognate cell surface proteins, IL-13Rα1 (CD213a1) and IL-13Rα2 (CD213a2). IL-13Rα1 forms a heterodimer with IL-4Rα that is a signaling IL-13 receptor. In contrast, IL-13Rα2 has been thought to be a decoy receptor due to its short cytoplasmic tail. IL-13Rα2 exists on the cell membrane, intracellularly, and in soluble form. IL-13Rα2 has an extremely high affinity for IL-13, and can out-compete antibodies for IL-13 binding. The other receptor, IL-13Rα1, has a much lower affinity, but is associated with signaling events mediated by IL-4Rα. It induces its effects through a multi-subunit receptor that includes the alpha chain of the IL-4 receptor (IL-4Rα) and IL-13Rα1. Most of the biological effects of IL-13, like those of IL-4, are linked to a single transcription factor, signal transducer and activator of transcription 6 (STAT6).

IL13Rα2 is highly expressed in many tumor types, such as colorectal, glioblastoma, ovarian, head and neck, breast, pancreatic, kidney, and mesothelioma, but not by most normal cells such as immune cells or endothelial cells. IL13Rα2 is also associated with poor prognosis in human cancers and a target for cancer therapy. High IL13Rα2 expression levels have been shown to promote invasion and metastasis of brain, pancreatic, ovarian, breast and colorectal cancers. Increased IL13Rα2 levels were also associated with poor metastasis-free survival of patients with breast cancer. IL13Rα2 expression is also a prognostic marker for glioma malignancy grade and for poor patient survival.

Targeted immunotherapy has emerged as promising field of research in the treatment of malignancies and has received a great deal of interest in recent years. Indeed, cures have been reported of lymphoma patients with engineered or genetically modified T cells targeting CD19 malignant cells. This has increased the focus towards antigens present on cancer cells as targets for gene- and immunotherapy.

Genetic manipulation of autologous or allogeneic T cells or NK cells to specifically target a particular tumor antigen provides a strategy to bypass the failure of cytotoxic immune response induction by most tumor cells. These technologies are based on the genetic modification of human immune cells, where the cells may be extracted from a patient or donor by leukapheresis. Specific cells, usually T-cells, are purified and engineered to express a receptor targeting a cancer antigen of interest. Engineering may utilize transduction by retroviral, lentiviral, transposon, mRNA electroporation, and the like. The immune cells may be expanded to the desired dose, and introduced into a patient. The engineered cells can specifically kill cancer cells through cell-mediated toxicity (cytotoxic T-cells) and/or eliciting an immune response to the cancer cell by immune recognition of tumor, cytokine release and immune cell recruitment.

For example, the application of chimeric antigen receptors (CAR) for immunogene therapy of malignant tumors is a promising strategy in which an antibody or ligand binding domain is fused with the zeta signaling chain of the T cell receptor. The resulting CAR immune cells are redirected by the neospecificity to attack tumors expressing the surface antigen or receptors recognized by the gene-modified T cell receptors and provide cellular therapy that attacks the tumor through normal host immune response in a highly regulated fashion. These cells are free to circulate throughout the brain and systemic circulation, making the need for colocalization and bioavailability less of a problem.

A number of generations of CAR immune cells have been developed. CARs are created by the fusion of a tumour-specific scFv antibody or other extracellular ligand binding domain to either the TCR-associated CD3ζ signalling domain or another intracellular signalling domains from co-stimulatory protein receptors. This structure allows CARs to have the tumor specificity of the B cell antigen receptor, and to activate T cells through the T cell antigen receptor independently of MHC binding. The first-generation CAR contained one intracellular signalling domain, typically with the CD3ζ signalling domain to allow for TCR signalling. Second-generation CARs have two intracellular signalling domains: a co-stimulatory domain comprising either a CD28 or a 4-1BB signalling domain, coupled with a CD3ζ signalling domain. This arrangement enables T-cell activation and proliferation upon antigen recognition by the scFv region of the CAR. The third-generation CARs have two co-stimulatory domains and a CD3ζ signalling domain. The first co-stimulatory domain is either a CD28 or a 4-1BB domain, with the second co-stimulatory domain consisting of either a CD28, a 4-1BB or a OX40 domain. Fourth-generation "armoured CAR T cells" combine a second-generation CAR with the addition of various genes, including cytokine and co-stimulatory ligands, to enhance the tumoricidal effect of the CAR T cells. See, for example, Batlevi et al. (2016) Nature Reviews Clinical Oncology 13:25-40. See also, U.S. Pat. No. 7,741,465 and International Patent Publication No. WO2014127261; all of which are incorporated by reference herein in their entireties.

Alternative approaches to T cell targeting include T cell antigen couplers, as described in International application WO2015/117229, entitled "Trifunctional T cell antigen Coupler and Methods and Uses thereof", herein specifically incorporated by reference. The T cell antigen coupler system comprises three linked domains: a target-specific polypeptide ligand; a ligand that binds a protein associated with the TCR complex, for example an scFv binding to CD3 (TCR, T-cell receptor) to stimulate T cell activation; and a T cell receptor signaling domain, for example a CD4 transmembrane and intracellular domain to amplify T cell activation. By stimulating T cell activation through the TCR, TACs were engineered to work with the T cell's essential molecular machinery.

Antibody coupled T cell receptors are another approach to T cell targeting. ACTRs are a hybrid approach to CARs and the established monoclonal antibody oncology therapeutics. ACTRs are composed of a typical CAR construct that can bind the heavy chain of an antibody through a high-affinity variant of the Fc receptor CD16. ACTR-T cells can target tumours by binding a ligand targeted to a specific cancer antigen. T cell activation is performed by the CAR module.

Bispecific T cell exchangers (BiTEs) are bispecific antibodies that can bind the TCR of T cells and target tumour cells through two modules: a cancer targeting ligand; and a CD3-binding scFv domain that bridges T cells to the tumor.

Targeted therapies have been developed against IL13Rα2, including bacterial toxins conjugated to IL13, nanoparticles, oncolytic virus, as well as immunotherapies using monoclonal antibodies, IL13Rα2-pulsed dendritic cells, and IL13Rα2-targeted chimeric antigen receptors (see Kahlon et al. (2004) Cancer Research. 64(24):9160-9166; Kong et al. (2012) Clinical Cancer Research. 18(21):5949-5960; Thaci et al. (2014) Neuro-Oncology; and clinical trials NCT02208362, NCT00730613 and NCT01082926).

Biologicals that provide for selective alteration of IL-13 activity are of interest for a number of therapeutic purposes, including the treatment of certain cancers with by engineering of T cell specificities. The present invention addresses this issue.

BRIEF SUMMARY OF THE INVENTION

Methods and compositions are provided for enhancing anti-tumor immune effector cells, e.g. T cells, NK cells, etc. with targeted compositions, including without limitation chimeric antigen receptors (CARs); T cell antigen couplers (TACs); antibody coupled T cell receptors (ACTRs); and bispecific T cell exchangers (BiTEs), where an IL-13 superkine provides the target-specific ligand. In some embodiments, the enhanced effector cell expresses and IL-4 superkine, and IL-13 superkine or an IL-4/IL-13 dual cytokine. In some embodiments, the enhanced immune cell expresses an IL-4 mutein for targeting, and expresses an IL-2 mutein as the therapy target. In some embodiments, the enhanced immune cell expresses an IL-13 cytokine for targeting, and expresses an IL-2 mutein as the therapy target. In some embodiments, the enhanced immune cell expresses an IL-4/IL-13 dual cytokine for targeting, and expresses an IL-2 mutein as the therapeutic payload. In some embodiments, the enhanced immune cell expresses an IL-2 mutein for targeting, and expresses an IL-4 mutein as the therapy target. In some embodiments, the enhanced immune cell expresses an IL-2 cytokine for targeting, and expresses and IL-13 mutein as the therapy target. In some embodiments, the enhanced immune cell expresses an IL-2 for targeting, and expresses an IL-4/IL-13 dual cytokine as the therapeutic payload.

The IL-13 superkine sequence is engineered to have: (a) increased affinity for IL-13Rα2, relative to the native human IL-13 protein; and (b) decreased affinity for IL-13Rα1 relative to the native human IL-13 protein. The increase in affinity for human IL-13Rα2 may be at least two-fold, at least 5-fold, at least 10-fold or more relative to the native protein. The decrease in affinity for human IL-13Rα1 may be at least 10-fold, at least 20-fold, at least 50-fold, at least 100-fold, or more.

Amino acid modifications may be made at one or more of the amino acids within the set of contact residues that interact with IL-13Rα1 and IL-13Rα2, which residues include, without limitation, L10, R11, I14, V18, R86, D87, T88, K89, L101, K104, K105 and R108 (for reference purposes the sequence of wild-type human IL-13 is provided herein as SEQ ID NO:1, to which the numbering of amino acids will refer). In other embodiments, modified residues are at two or more, three or more, four or more, five or more, and not more than 14 amino acids within the combined set of contact residues defined above.

The IL-13 interface that contacts IL-13Rα1 and IL-13Rα2 is the same, and thus there can be overlap in the altered residues that control affinity for these two receptors. In some embodiments one or more of the native amino acid residues L10, R11, I14, V18, R86, D87, T88, K89, L101, K104, K105, F107, and R108 is substituted, and provides for an altered affinity for one or both of IL-13Rα1 and IL-13Rα2.

In some embodiments an IL-13 superkine sequence comprises one or more of the amino acids substitutions relative to SEQ ID NO:1: (1) L10F; L10I; L10V; L10A; L10D; L10T; L10H; (2) R11S; R11N; R11H; R11L; R11I; (3) I14L; I14F; I14V; I14M; (4) V18L; V18F; V18I; (5) E12A; (6) R65D; (7) R86K; R86T; R86M; (8) D87E; D87K; D87R; D87G; D87S; (9) T88S; T88I; T88K; T88R; (10) K89R; K89T; K89M; (11) L101F; L101I; L101Y; L101H; L101N; (12) K104R; K104T; K104M; (13) K105T; K105A; K105R; K105E; (14) F107L; F107I; F107V; F107M; and (15) R108K; R108T; R108M, which substitutions cause an altered affinity for one or both of IL-13Rα1 and IL-13Rα2. In other embodiments, modified residues are at two or more, three or more, four or more, five or more, and not more than 14 amino acids within the combined set of contact residues defined above.

In some embodiments an IL-13 superkine sequence comprises a set of amino acid substitutions relative to SEQ ID NO:1 selected from [L10D, R11I, V18I, R86K, D87K, K89R, R108K]; [L10A, R86T, D87G, T88K, K89R, L101N, K104R, K105A, R108K]; [L10V, K89R, L101N, K105E, R108T]; [R11S, I14M, T88S, L101N, K105A, R108K]; [L10H, R11L, V18I, R86K, D87E, K89R, L101N, K105T, R108K]; [L10H, R11L, V18I, R86M, K89R, R108K]; [L10H, R86T, D87G, T88R, R108K]; [L10H, R86M, T88S, K89R, L101N, K104R, K105A, R108K]; [L10A, V18F, R86K, K89R, L101I, K104R, R108K]. In some such embodiments the IL-13 superkine sequence comprises the set of amino acid substitutions [L10H, R86T, D87G, T88R, R108K], which may be referred to in the Examples as C11. In some such embodiments the IL-13 superkine sequence comprises the set of amino acid substitutions L10A, V18F, R86K, D87K, K89R, L101I, K104R, and R108K, which may be referred to in the figures as D7.

In a CAR sequence the IL-13 superkine may be fused or otherwise joined to a linker sequence that tethers the superkine to the cell. The linker may provide a hinge sequence. The linker may comprise a transmembrane domain connecting the IL-13 superkine to one or more intracellular signaling region of the CAR. Various transmembrane sequences are useful for this purpose, including without limitation those derived from immunoglobulin sequences such as IgG1, IgG4, IgG2, IgG3, etc.; from T cell receptor sequences, from CD3, CD4, CD8, CD28 sequences, etc. The intracellular signaling region comprises one or more signaling domain(s). The signaling region generally includes at least a functional signaling domain from the zeta chain of the human CD3 complex (CD3ζ). Additional signaling domains are optionally included and may comprise, without limitation, one or more of a CD28 signaling domain, a CD137 signaling domain, an OX-40 signaling domain, an ICOS signaling domain, a DAP10 signaling domain, etc. or a combination thereof. The signaling domains may be human.

In some embodiments, a CAR polypeptide comprising an IL-13 superkine is provided. In some embodiments, a nucleic acid encoding a CAR polypeptide comprising an IL-13 superkine is provided.

In some embodiments, a TAC polypeptide comprising an IL-13 superkine is provided. In some embodiments a nucleic acid encoding a TAC polypeptide comprising an IL-13 superkine is provided.

In some embodiments, an ACTR polypeptide system comprising an IL-13 superkine is provided. The IL-13 superkine may be fused to an antibody Fc region with high affinity for CD16 to enhance the interaction with the CAR component of the system. In some embodiments, a nucleic acid encoding an ACTR polypeptide system comprising an IL-13 superkine is provided.

In some embodiments, a BiTE polypeptide comprising an IL-13 superkine is provided. The IL-13 superkine may be joined to a CD3-binding scFv domain that bridges T cells to a tumour. In some embodiments, a nucleic acid encoding a BiTE polypeptide comprising an IL-13 superkine is provided.

Nucleic acid coding sequences may be operably joined to control regions for expression in a T cells. The nucleic acid may be provided in a vector for transfer to a T cell of interest. Vectors of interest include, without limitation, lentivirus vectors, sleeping beauty vectors, plasmid vectors, retrovirus vectors, and the like.

In some embodiments of the invention a population of genetically modified immune cells is provided, which cells are engineered to express a targeting construct comprising an IL-13 superkine. Such cells may be referred to as superkine targeting immune-cells, including targeting T cells, targeting NK cells, etc. In some embodiments, the T cells are CD8+ T cells. In some embodiments, the T cells are CD4+ T cells. In other embodiments the targeting immune cells are NK cells, e.g. modified NK cell lines, peripheral blood NK cells, iPSC derived NK cells, and the like. The immune cells may be human, and may be autologous or allogeneic relative to an individual selected for treatment. The immune cells may be further modified to enhance therapeutic potential, e.g. by the introduction of one or more transgenes encoding cytokines, co-stimulatory ligands, etc. The immune cells may be modified by deletion of glucocorticoid receptor sites to provide resistance to glucocorticoid treatment. The immune cells may be isolated, and manipulated, expanded, etc. in culture. The population of immune cells may be provided as a pharmaceutical formulation, optionally in a unit dose formulation.

Embodiments of the invention include methods of cancer immunotherapy, which methods comprise administering to a patient in need thereof nucleic acids, vectors, or genetically modified T cells that encode or comprise a T cell targeting construct comprising an IL-13 superkine. Cancers of interest for treatment include hematologic cancers, e.g. leukemias and lymphomas, and solid tumors, e.g. glioblastoma, medulloblastoma, breast cancer, head and neck cancer, kidney cancer, ovarian cancer, Kaposi's sarcoma, acute myelogenous leukemia, B-lineage malignancies, colorectal, pancreatic, kidney, mesothelioma, etc.

In some embodiments, the present invention provides an immune cell targeting construct comprising: an IL-4 superkine engineered to have a higher affinity binding to a shared cytokine receptor relative to a wild-type cytokine, wherein the IL-4 mutein comprises one or two amino acid substitutions at positions S128 and/or S129, and wherein the amino acid numbering is in accordance with wild-type human IL-4 of SEQ ID NO:49 or SEQ ID NO:50, linked to an immune cell targeting construct.

In some embodiments, the immune cell targeting construct exhibits a cytotoxic effect on a T-cell, for example a CD8+ T-cell or a CD4+ T-cell.

In some embodiments, the construct is a chimeric antigen receptor (CAR) and wherein the IL-4 superkine is fused to a transmembrane domain; linked to an intracellular signaling region.

In some embodiments, the intracellular signaling region comprises a CD3ζ signaling domain.

In some embodiments, the intracellular signaling region comprises one or more of a CD28 signaling domain, a CD137 signaling domain, an OX-40 signaling domain, an ICOS signaling domain, a DAP10 signaling domain.

In some embodiments, the construct is a T cell antigen coupler (TAC), wherein the IL-4 superkine is fused to a ligand that binds a protein associated with the TCR complex; fused to a T cell receptor signaling domain polypeptide.

In some embodiments, the protein associated with the TCR complex is CD3.

In some embodiments, the T cell receptor signaling domain polypeptide comprises CD4 cytosolic domain and CD4 transmembrane domain.

In some embodiments, the construct is an antibody coupled T cell receptors (ACTR), comprising a chimeric antigen receptor component that binds to the IL-4 superkine at a high affinity.

In some embodiments, the CAR component comprises CD16, and the IL-4 superkine is fused to an Fc sequence.

In some embodiments, the construct is a bispecific T cell exchanger (BiTE) comprising an IL-4 superkine fused to a variable region of an antibody that binds to a component of a T cell receptor.

In some embodiments, the component of a T cell receptor is CD3.

In some embodiments, the IL-4 superkine further comprises one or more amino acid substitutions selected from the group consisting of K117, T118, R121, E122, Y124, and S125.

In some embodiments, the IL-4 superkine comprises one or more amino acid substitutions selected from the group consisting of K117R, T118V, R121Q, E122S, Y124W, S125F, S128G, and S129A.

In some embodiments, the IL-4 mutein comprises the following amino acid substitutions: K117R, T118V, R121Q, E122S, Y124W, S125F, S128G, and S129A.

In some embodiments, the IL-4 mutein comprises an amino acid sequence set forth in SEQ ID NO:51-SEQ ID NO:55, SEQ ID NO:58-SEQ ID NO:62, and/or SEQ ID NO:64-SEQ ID NO:69.

In some embodiments, the invention provides a nucleic acid encoding a construct as described herein.

In some embodiments, the invention provides a vector comprising the nucleic acid of encoding a construct as described herein.

In some embodiments, the invention provides a T cell comprising a construct as described herein. In some embodiments, the T cell is a CD4+ T cell. In some embodiments, the T cell is a CD8+ T cell.

In some embodiments, the invention provides an NK cell comprising a construct as described herein.

In some embodiments, the invention provides an isolated population of immune cells.

In some embodiments, the invention provides a pharmaceutical formulation comprising the immune cell population as described herein.

In some embodiments, the invention provides a method of treating cancer, the method comprising contacting an individual having cancer with an effective dose of a formulation as described herein.

In some embodiments, the cancer is a leukemia, lymphoma, glioblastoma, medulloblastoma, breast cancer, head and neck cancer, kidney cancer, ovarian cancer, Kaposi's sarcoma, acute myelogenous leukemia, B-lineage malignancies, colorectal, pancreatic, kidney, or mesothelioma.

In some embodiments, the invention provides an immune cell targeting construct comprising: an IL-13 superkine engineered to have increased affinity for interleukin 13 receptor α1 (IL-13Rα1), relative to native human IL-13 protein and optionally decreased affinity for interleukin 13 receptor α1 (IL-13Rα2) relative to native human IL-13 protein, linked to an immune cell targeting construct.

In some embodiments, the invention provides an immune cell targeting construct comprising: an IL-13 superkine engineered to have increased affinity for interleukin 13 receptor α1 (IL-13Rα1), relative to native human IL-13 protein relative to native human IL-13 protein, linked to an immune cell targeting construct, wherein the IL-13 superkine target immunosuppressive cells of the TME such as tumor associated macrophages and MDSCs and/or targets to tumor antigens.

In some embodiments, the invention provides an immune cell targeting construct comprising: an IL-13 superkine engineered to have increased affinity for interleukin 13 receptor α1 (IL-13Rα), relative to native human IL-13 protein and comprising at least one amino acid change relative to the wild-type IL-13 at one or more of positions selected from L10, E12, V18, R65, D87, T88, L101, K104, K105; linked to an immune cell targeting construct.

In some embodiments, the invention provides an immune cell targeting construct comprising: an IL-13 superkine engineered to have increased affinity for interleukin 13 receptor α2 (IL-13Rα2), relative to native human IL-13 protein and decreased affinity for interleukin 13 receptor α1 (IL-13Rα1) relative to native human IL-13 protein and comprising at least one amino acid change relative to the wild-type IL-13 at one or more of positions selected from L10, R11, E12, I14, V18, R65, R86, D87, T88, K89, L101, K104, K105, F107, and R108; linked to an immune cell targeting construct, wherein the immune cell targeting targets a tumor and/or tumor microenvironment and/or targeting tumor antigens.

In some embodiments, the construct is a chimeric antigen receptor (CAR) and wherein the IL-13 superkine is fused to a transmembrane domain; linked to an intracellular signaling region.

In some embodiments, the intracellular signaling region comprises a CD3Q signaling domain.

In some embodiments, the intracellular signaling region comprises one or more of a CD28 signaling domain, a CD137 signaling domain, an OX-40 signaling domain, an ICOS signaling domain, a DAP10 signaling domain.

In some embodiments, the construct is a T cell antigen coupler (TAC), wherein the IL-13 superkine is fused to a ligand that binds a protein associated with the TCR complex; fused to a T cell receptor signaling domain polypeptide.

In some embodiments, the protein associated with the TCR complex is CD3.

In some embodiments, the T cell receptor signaling domain polypeptide comprises CD4 cytosolic domain and CD4 transmembrane domain.

In some embodiments, the construct is an antibody coupled T cell receptors (ACTR), comprising a chimeric antigen receptor component that binds to the IL-13 superkine at a high affinity.

In some embodiments, the CAR component comprises CD16, and the IL-13 superkine is fused to an Fc sequence.

In some embodiments, the construct is a bispecific T cell exchanger (BiTE) comprising an IL-13 superkine fused to a variable region of an antibody that binds to a component of a T cell receptor.

In some embodiments, the component of a T cell receptor is CD3.

In some embodiments, the IL-13 superkine comprises a set of amino acid substitutions selected from: [L10D, R11I, V18I, R86K, D87K, K89R, R108K]; [L10A, R86T, D87G, T88K, K89R, L101N, K104R, K105A, R108K]; [L10V, K89R, L101N, K105E, R108T]; [R11S, I14M, T88S, L101N, K105A, R108K]; [L10H, R11L, V18I, R86K, D87E, K89R, L101N, K105T, R108K]; [L10H, R11L, V18I, R86M, K89R, R108K]; [L10H, R86T, D87G, T88R, R108K]; [L10H, R86M, T88S, K89R, L101N, K104R, K105A, R108K]; and [L10A, V18F, R86K, K89R, L101I, K104R, R108K].

In some embodiments, the IL-13 superkine comprises the set of amino acid substitutions: [L10H, R86T, D87G, T88R, R108K].

In some embodiments, the construct comprises an amino acid sequence set forth in SEQ ID NO:2-SEQ ID NO:48, SEQ ID NO:56, SEQ ID NO:57, and/or SEQ ID NO:63.

In some embodiments, the present invention provides a nucleic acid encoding a construct as described herein.

In some embodiments, the present invention provides a vector comprising the nucleic acids as described herein.

In some embodiments, the present invention provides a T cell comprising a construct as described herein.

In some embodiments, the present invention provides an NK cell comprising a construct as described herein.

In some embodiments, the T cell is a CD4$^+$ T cell.

In some embodiments, the T cell is a CD8$^+$ T cell.

In some embodiments, the present invention provides an isolated population of immune cells comprising T cells and NK cells as described herein.

In some embodiments, the present invention provides a pharmaceutical formulation comprising the immune cell population as described herein.

In some embodiments, the present invention provides a method of targeting a cell expressing an IL-13Rα2 receptor, the method comprising contacting a cell with a pharmaceutical formulation as described herein.

In some embodiments, the contacting is in vitro.

In some embodiments, the contacting is in vivo.

In some embodiments, the present invention provides a method of treating cancer, the method comprising contacting an individual having cancer with an effective dose of a pharmaceutical formulation as described herein.

In some embodiments, the cancer is a leukemia, lymphoma, glioblastoma, medulloblastoma, breast cancer, head and neck cancer, kidney cancer, ovarian cancer, Kaposi's sarcoma, acute myelogenous leukemia, B-lineage malignancies, colorectal, pancreatic, kidney, or mesothelioma.

In some embodiments, the present invention provides an immune cell targeting construct comprising: an IL-4 superkine engineered to have a higher affinity binding to a shared cytokine receptor relative to a wild-type cytokine, wherein the IL-4 mutein comprises one or two amino acid substitutions at positions S128 and/or S129, and wherein the amino acid numbering is in accordance with wild-type human IL-4 of SEQ ID NO:49 or SEQ ID NO:50, linked to an immune cell targeting construct.

In some embodiments, the immune cell targeting construct exhibits a cytotoxic effect on a T-cell, for example a CD8+ T-cell or a CD4+ T-cell.

In some embodiments, the construct is a chimeric antigen receptor (CAR) and wherein the IL-4 superkine is fused to a transmembrane domain; linked to an intracellular signaling region.

In some embodiments, the intracellular signaling region comprises a CD3Q signaling domain.

In some embodiments, the intracellular signaling region comprises one or more of a CD28 signaling domain, a CD137 signaling domain, an OX-40 signaling domain, an ICOS signaling domain, a DAP10 signaling domain.

In some embodiments, the construct is a T cell antigen coupler (TAC), wherein the IL-4 superkine is fused to a ligand that binds a protein associated with the TCR complex; fused to a T cell receptor signaling domain polypeptide.

In some embodiments, the protein associated with the TCR complex is CD3.

In some embodiments, the T cell receptor signaling domain polypeptide comprises CD4 cytosolic domain and CD4 transmembrane domain.

In some embodiments, the construct is an antibody coupled T cell receptors (ACTR), comprising a chimeric antigen receptor component that binds to the IL-4 superkine at a high affinity.

In some embodiments, the CAR component comprises CD16, and the IL-4 superkine is fused to an Fc sequence.

In some embodiments, the the construct is a bispecific T cell exchanger (BiTE) comprising an IL-4 superkine fused to a variable region of an antibody that binds to a component of a T cell receptor.

In some embodiments, the the component of a T cell receptor is CD3.

In some embodiments, the IL-4 superkine further comprises one or more amino acid substitutions selected from the group consisting of K117, T118, R121, E122, Y124, and S125.

In some embodiments, the IL-4 superkine comprises one or more amino acid substitutions selected from the group consisting of K117R, T118V, R121Q, E122S, Y124W, S125F, S128G, and S129A.

In some embodiments, the IL-4 mutein comprises the following amino acid substitutions: K117R, T118V, R121Q, E122S, Y124W, S125F, S128G, and S129A.

In some embodiments, the construct comprises an amino acid sequence set forth in SEQ ID NO:51-SEQ ID NO:55, SEQ ID NO:58-SEQ ID NO:62, and/or SEQ ID NO:64-SEQ ID NO:69.

In some embodiments, the present invention provides nucleic acid encoding a construct as described herein.

In some embodiments, the present invention provides a vector comprising the nucleic acid as described herein.

In some embodiments, the present invention provides a T cell comprising a construct as described herein.

In some embodiments, the present invention provides an NK cell comprising a construct as described herein.

In some embodiments, the T cell is a CD4+ T cell.

In some embodiments, the T cell is a CD8+ T cell.

In some embodiments, the present invention provides an isolated population of immune cells comprising T cells and NK cells as described herein.

In some embodiments, the present invention provides pharmaceutical formulation comprising the immune cell population as described herein.

In some embodiments, the present invention provides a method of treating cancer, the method comprising contacting an individual having cancer with an effective dose of a pharmaceutical formulation as described herein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 2. Comparative analysis of the IL-13Rα1- and the IL-13Rα2-selective IL-13 variants (a) Human IL-13 and IL-13Rα1 and IL-13Rα2 selective variants sequences are given for the indicated residue numbers. Kinetic and affinity parameters were determined by surface plasmon resonance. (b) Histogram representation of the normalized $K_D$ binding affinity values for IL-13Rα1 (purple) and IL-13Rα2 (orange) selective variants. IL-13 wt $K_D$ value was normalized to one and the rest of the values were changed accordingly.

12 were analyzed on day 6 with mAbs against HLA-DR, CD86, CD209. Data (mean and SEM) are from 3 donors. (b) TF-1 cells were seeded in a p96 well plate (100.000 cells/well) and stimulated for five days with the indicated doses of the IL-13 variants. Cells were then washed twice with cold PBS and fixed with 4% PFA. The number of cells in each well was determined by flow cytometry. The experiment was repeated three times and the means and SEMs were plotted versus the concentration of cytokine used.

Figure 1:
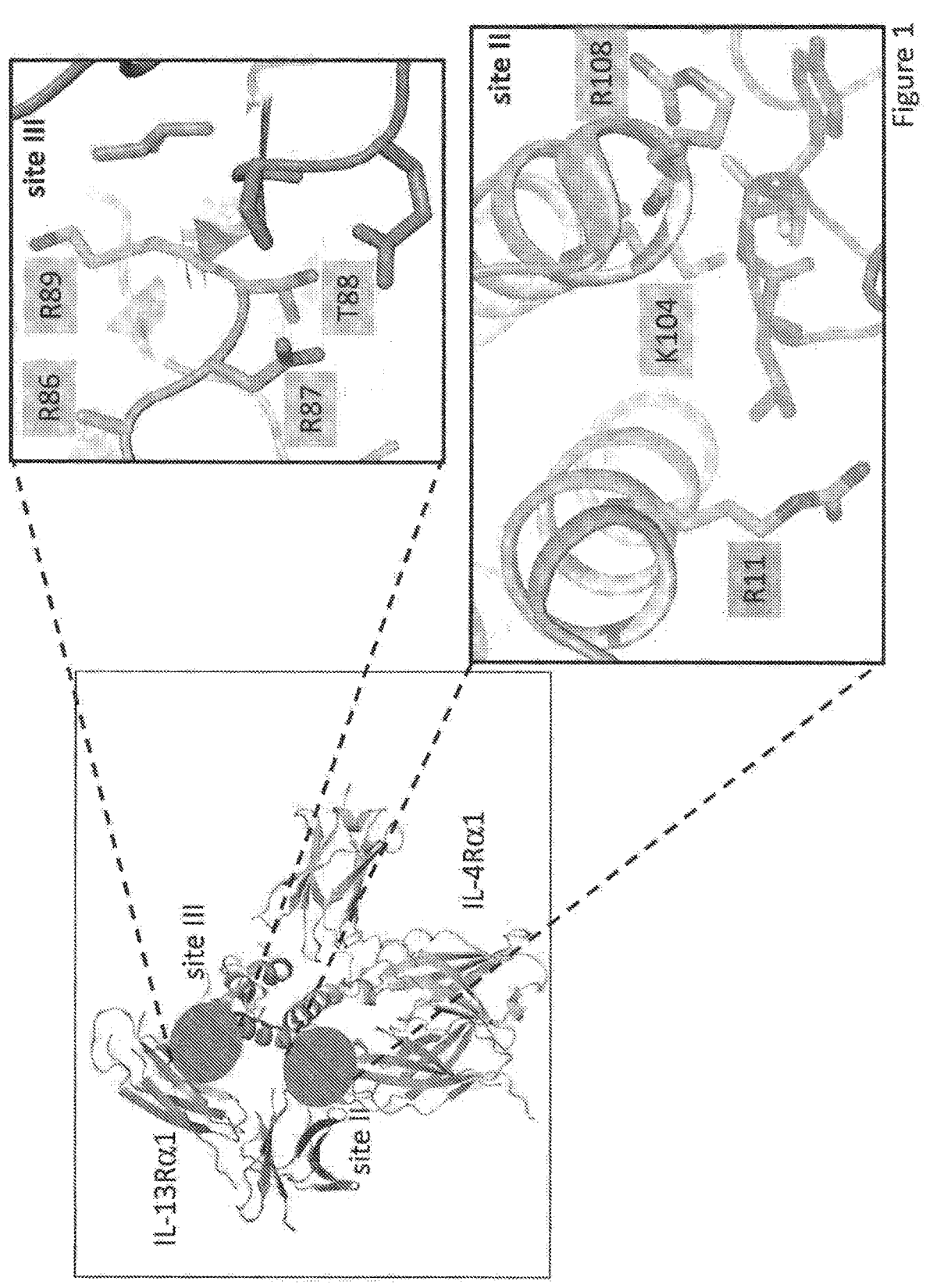
FIG. 1. Crystal structure of the IL-13 ternary ectodomain complex. Site II and site III interfaces are indicated with a red circle. Left panels show a zoom in on the interfaces where representative positions mutated in the site II (helix A and D) and site III (C-D loop) are highlighted in orange. IL-13 is in orange, IL-13Rα1 is in purple and IL-4Rα1 is in cyan.
Figure 3:
FIG. 3. Signaling activation induced by the IL-13Rα1- and the IL-13Rα2-selective IL-13 variants. (a) The IL-13 responsive cell line A549 was stimulated with doses ranging from 500 nM to 5E-06 nM of the different IL-13 variants for fifteen minutes. Cells were then fixed and permeabilized with 100% cold methanol and stained with antibody against phosphorylated Stat6. The percentage of the MFI value was used to plot the data. (b) A549 cells were stimulated with 500 nM of the IL-13 variants for the indicated times, fixed, permeabilized and stained with phospho-specific Stat antibodies as indicated above and the ratio P-Stat6/P-Stat3 was plotted against time.
Figure 4:
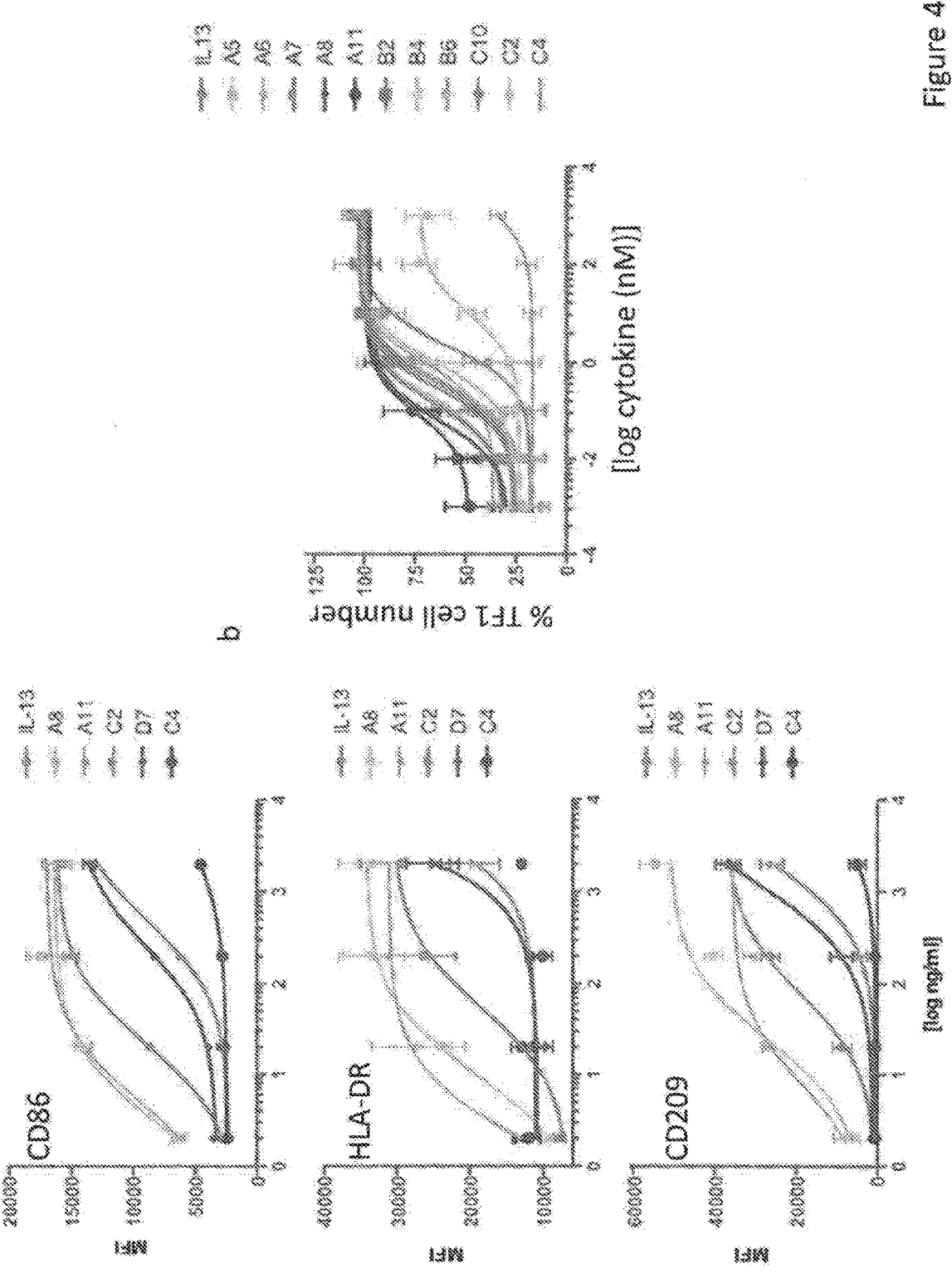
FIG. 4. Functional outcomes induced by the IL-13Rα1- and the IL-13Rα2-selective IL-13 variants. (a) Human monocytes were purified from peripheral blood mononuclear cells and cultured with 50 ng/ml GM-CSF alone or with the indicated doses of the different IL-13 variants Cells
Figure 5:
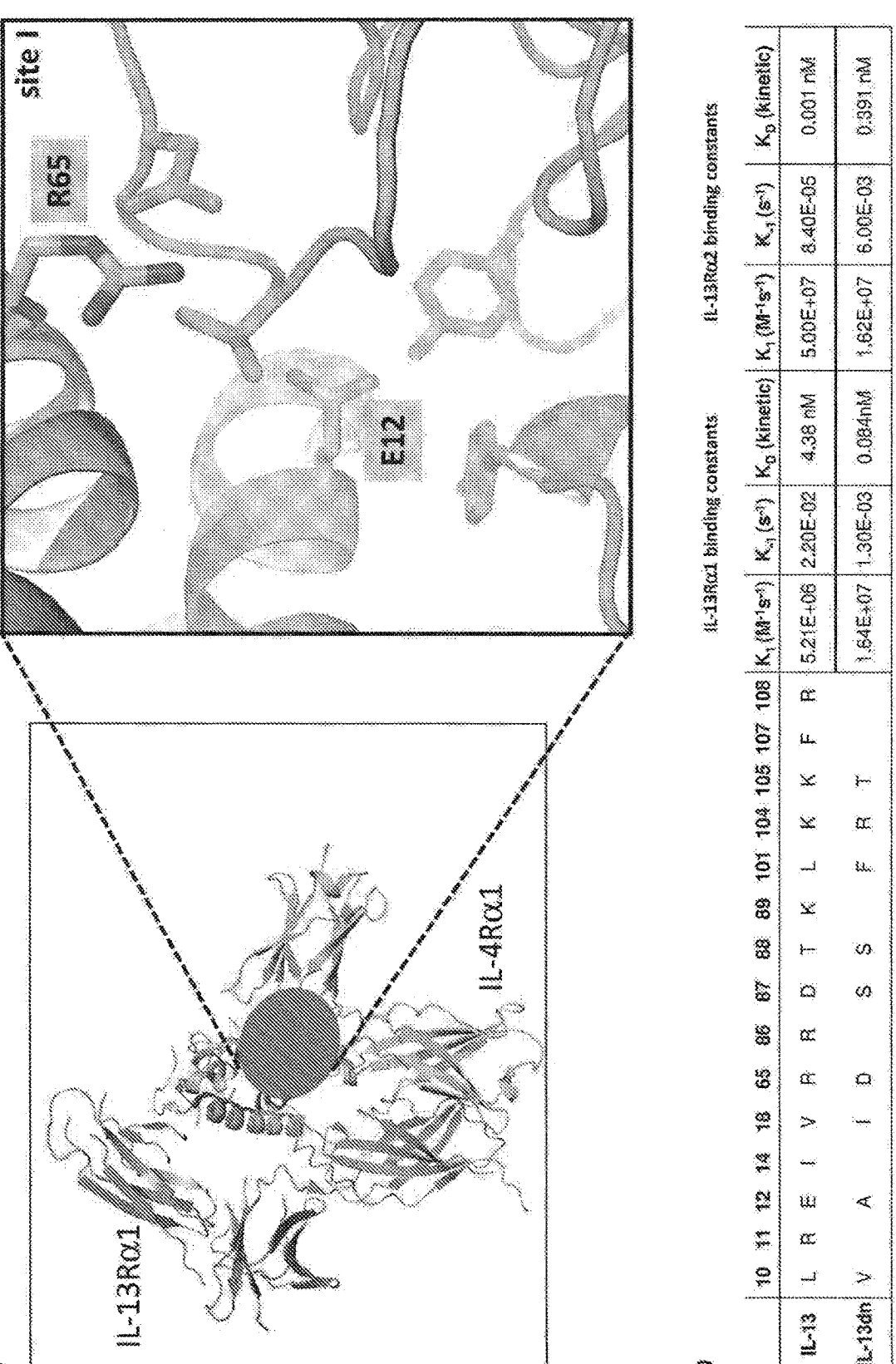
Figure 6:
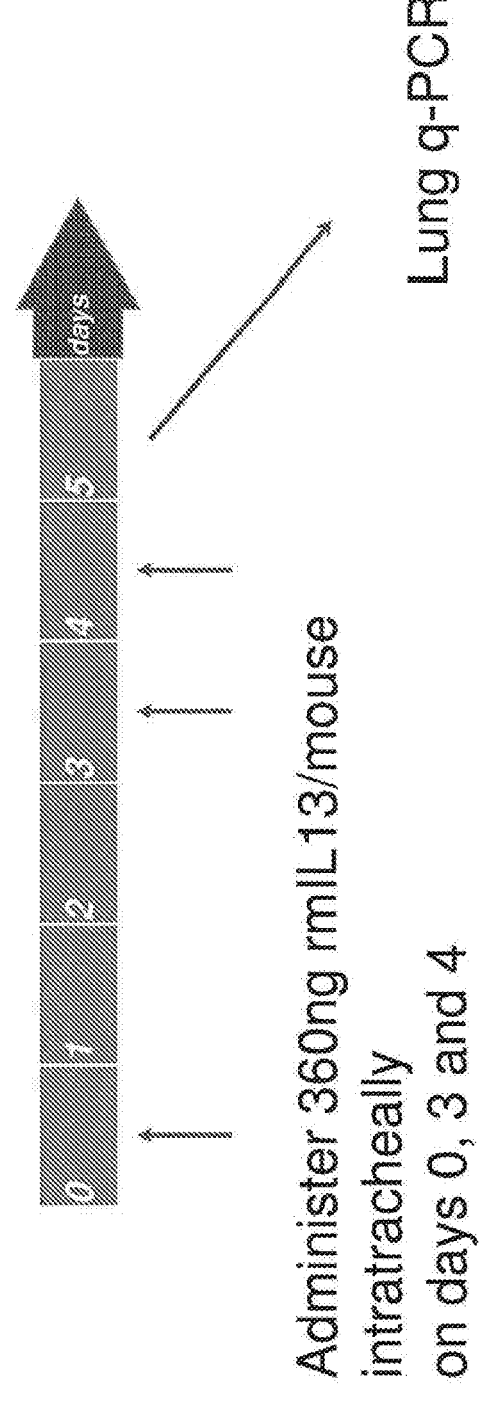
Figure 6I:
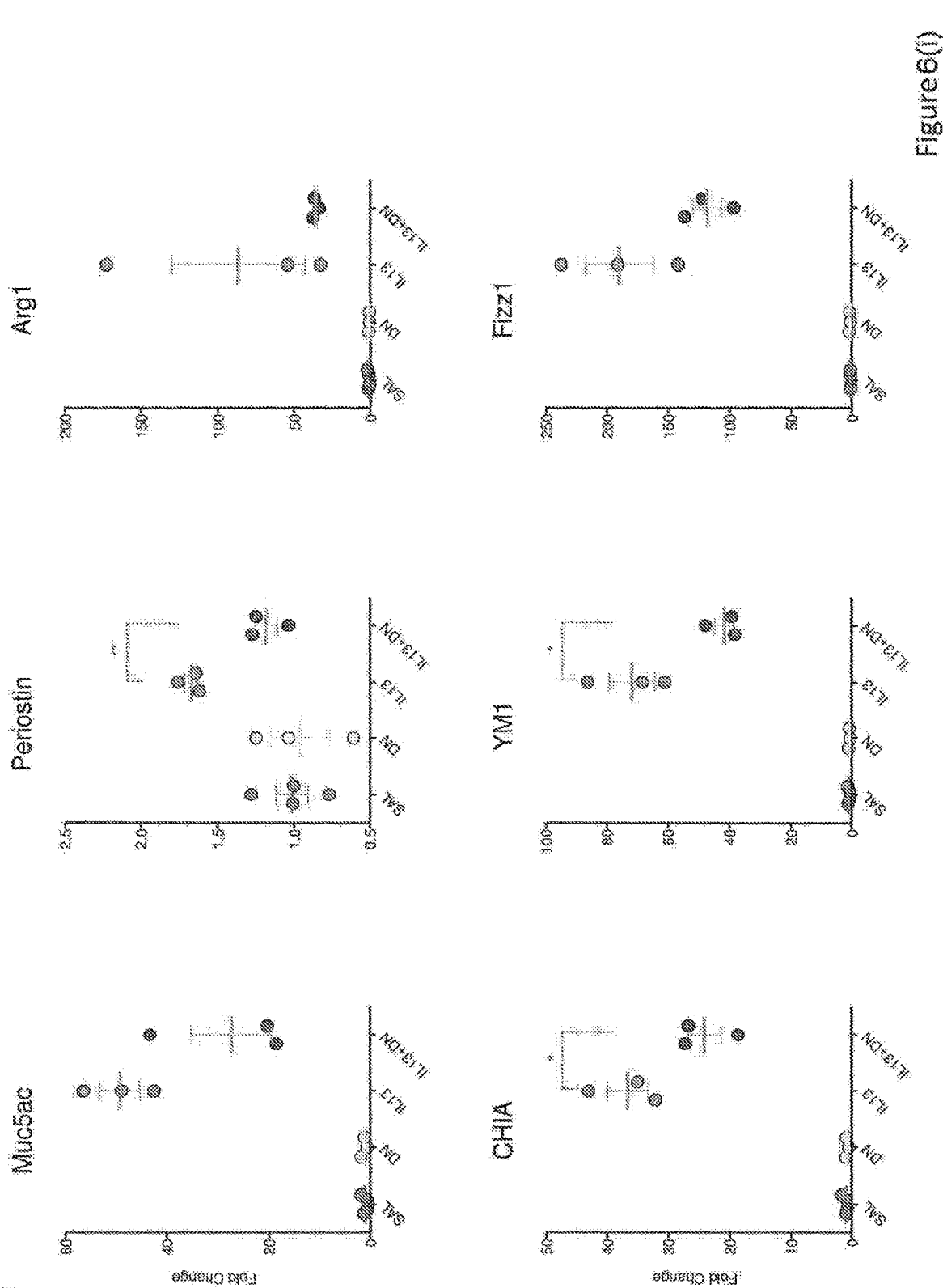

FIG. 5. Crystal structure of the IL-13 ternary ectodomain complex. (a) Site I is highlighted with a red circle. Left panel show a closer look of the site I interface where amino acids mutated in the C helix are colored in orange. IL-13 is in orange, IL-13Rα1 is in purple and IL-4Rα1 is in cyan. (b) Sequences for human IL-13 and IL-13dn are given for the indicated residue numbers. Kinetic and affinity parameters were determined by surface plasmon resonance FIG. 6. Analysis of the IL-13dn efficacy in vivo. (a) Schematic flowchart where the doses and times used to test the efficacy of IL-13dn in vivo are indicated. (b) qPCR analysis of the expression levels of the Th2 inflammation markers (Muc5ac, Periostin, Arg1, CHIA, YM1, Fizz1) induced by mouse IL-13 in the presence of the indicated dose of IL-13dn.

Figure 7:
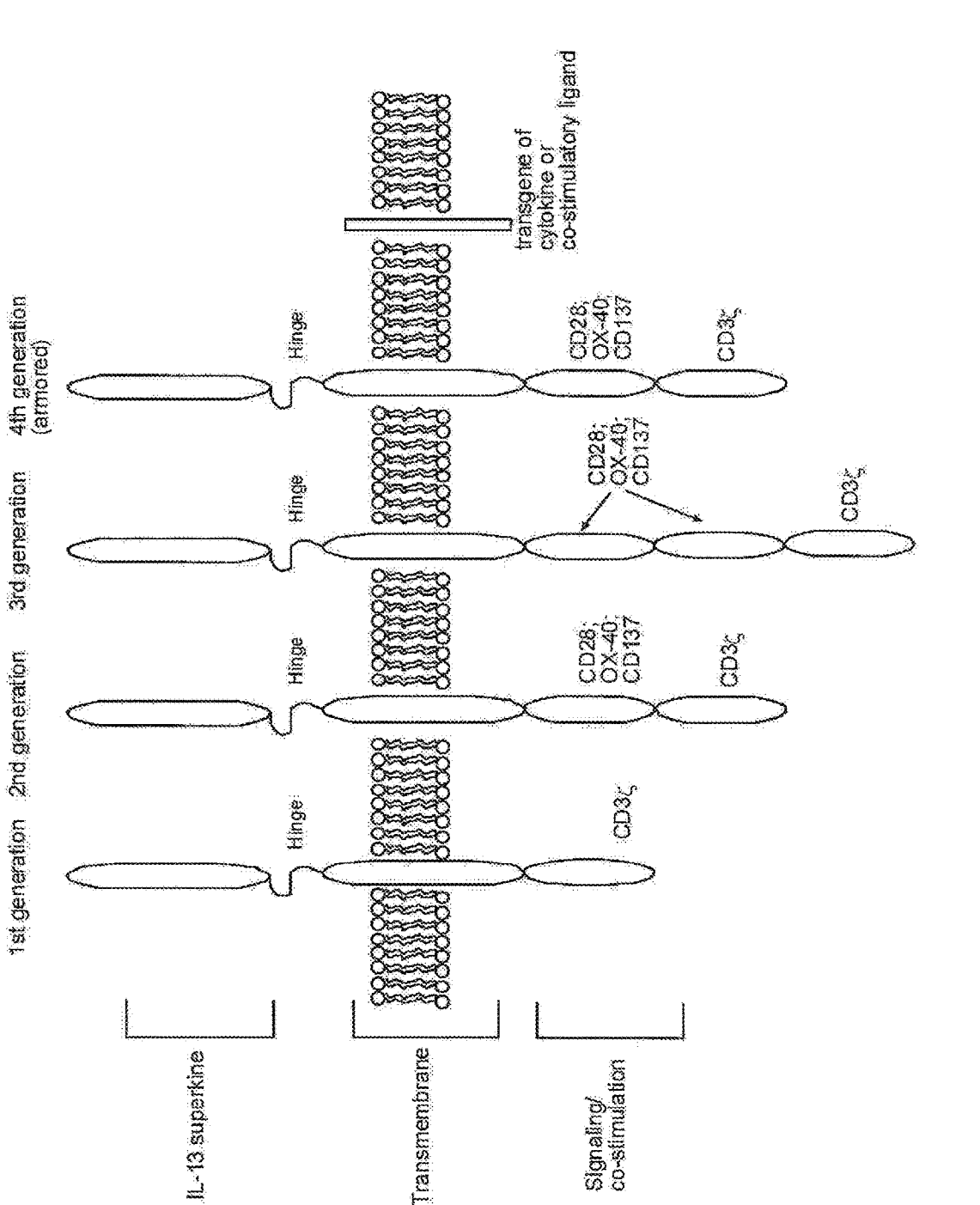

FIG. 7. Diagram of $1^{st}$, $2^{nd}$, $3^{rd}$ and $4^{th}$ generation chimeric antigen receptors with an IL-13 superkine.

Figure 8:
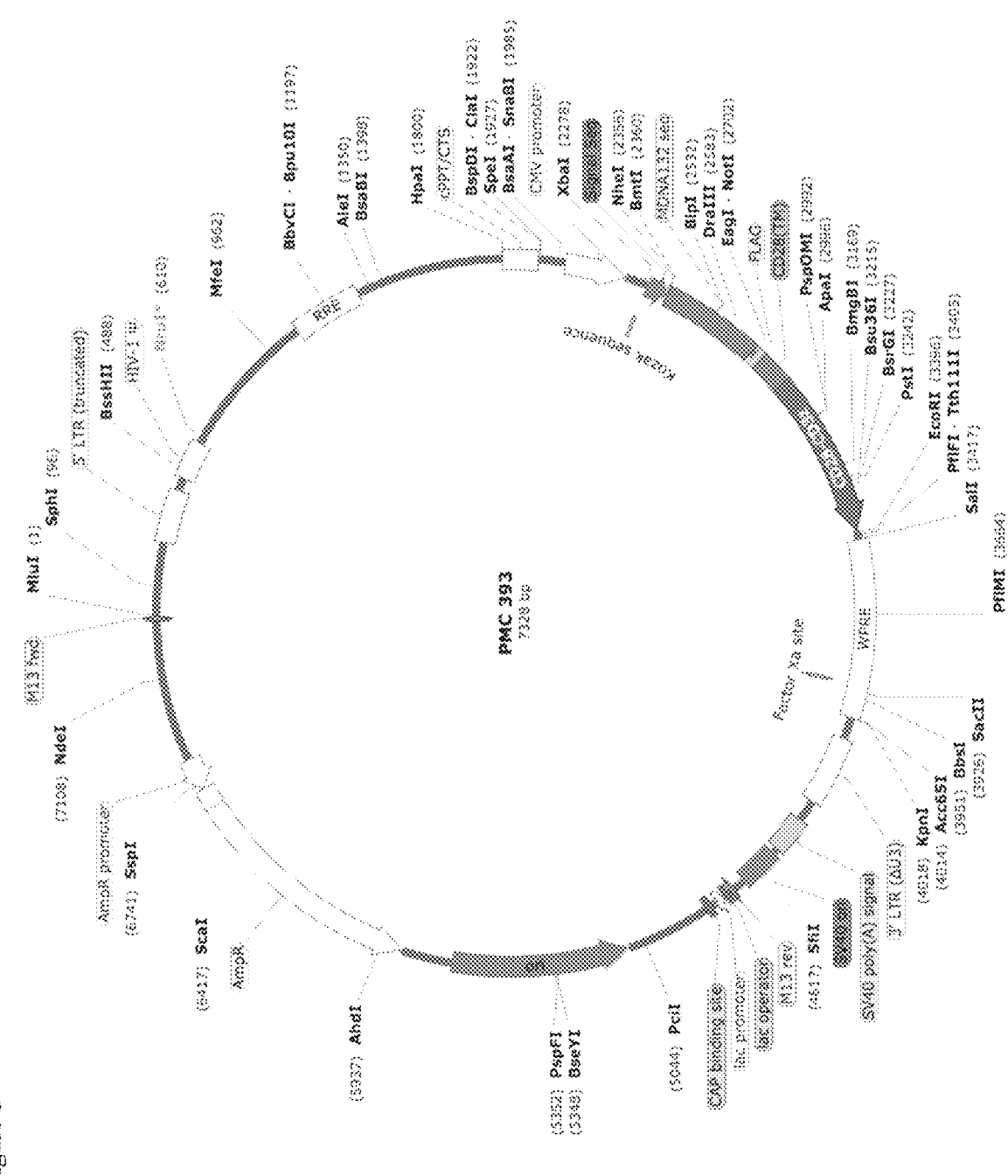

FIG. 8. PMC 393 vector map diagram.

Figure 9:
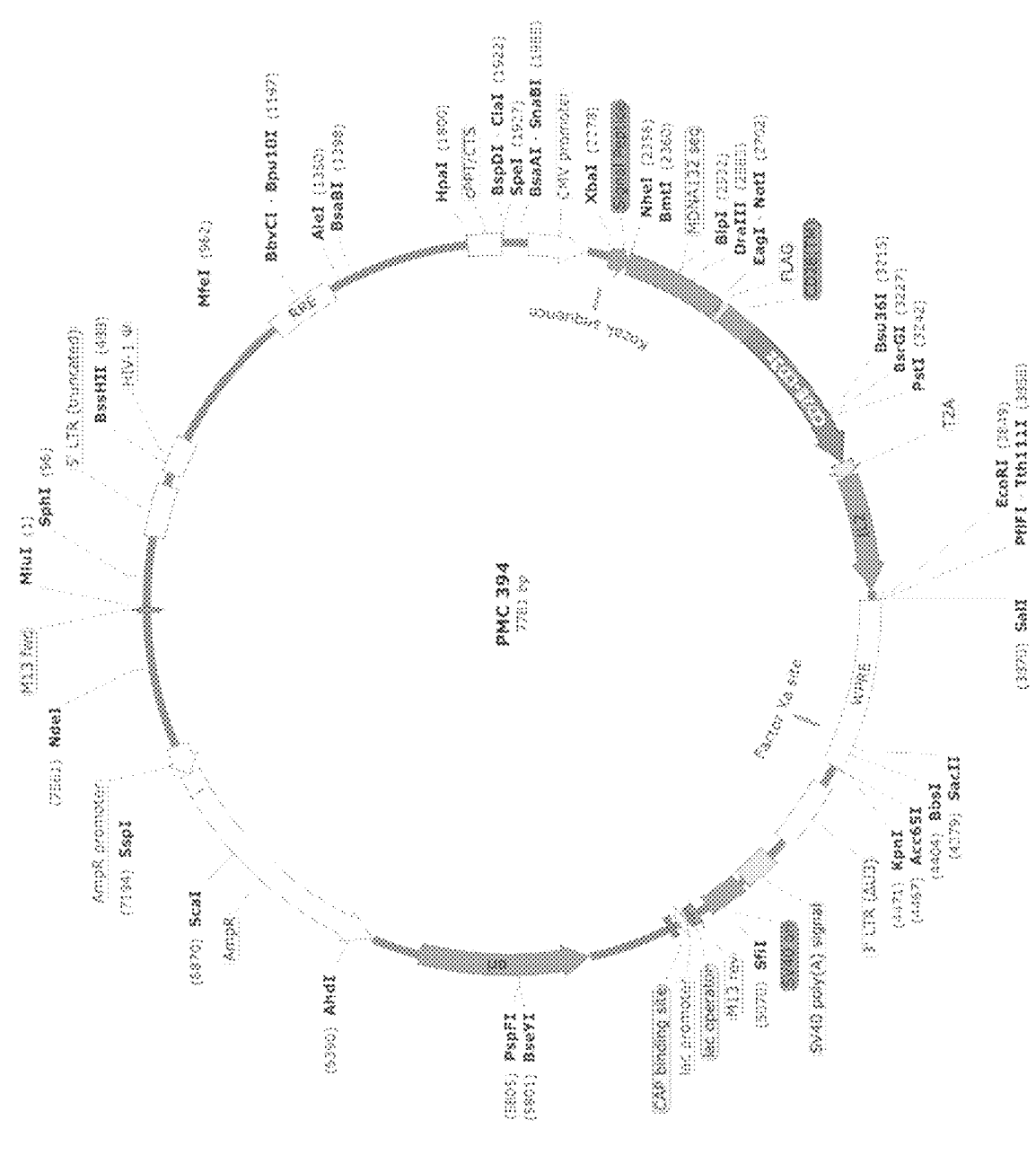

FIG. 9. PMC 394 vector map diagram.

Figure 10:
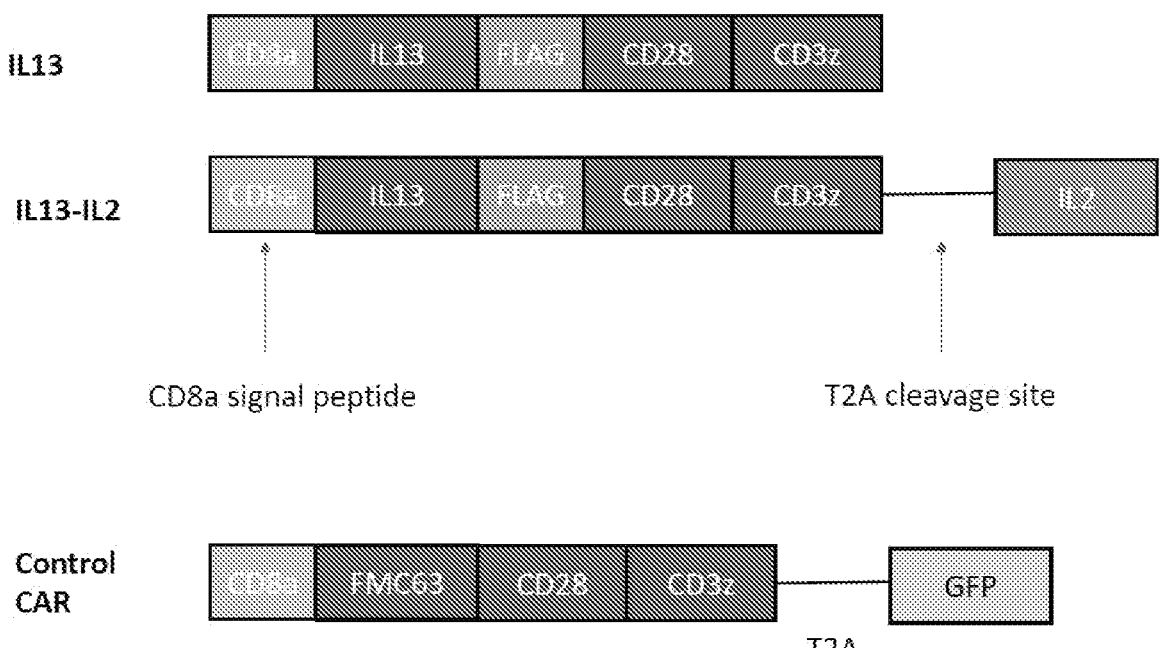

FIG. 10. Diagrams showing the structure of the CAR constructs described in Example 2.

Figure 11:
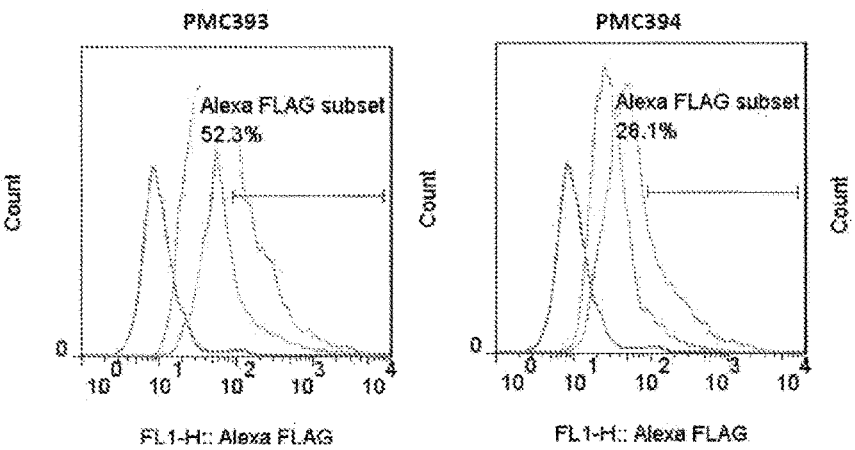

FIG. 11. FACs data showing transient transfection in HEK293 wugt tge PMC 393 and PMC 394 vectors.

FIG. 12. Data showing the virus titer from the transient transfection in HEK293 wugt tge PMC 393 and PMC 394 vectors. These are VSV-G pseudotyped lentiviral particles. They will be used to transduce human T cells at 5 MOI in the next phase.

Figure 13:
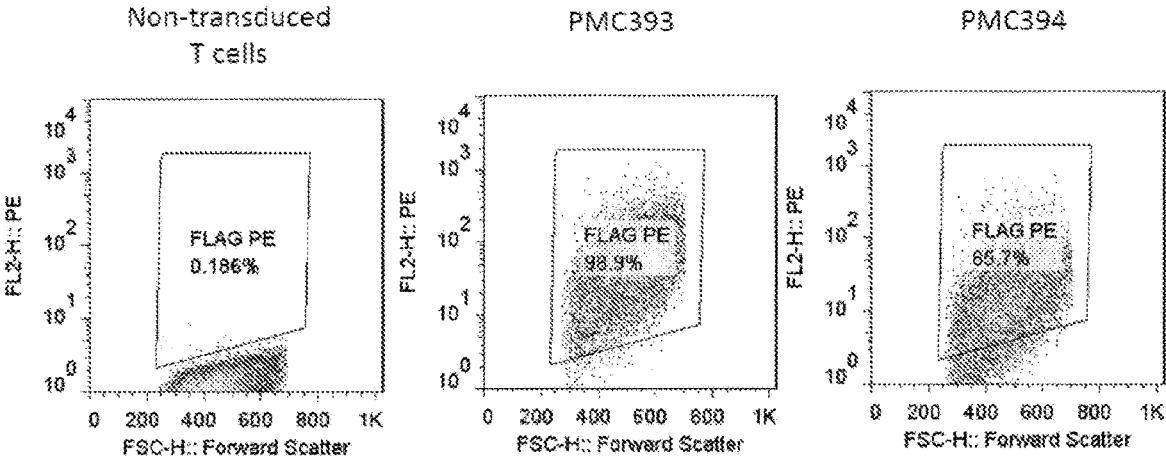

FIG. 13. FACs data showing CAR T cells with the PMC 393 and PMC 394 vectors.

Figure 14:
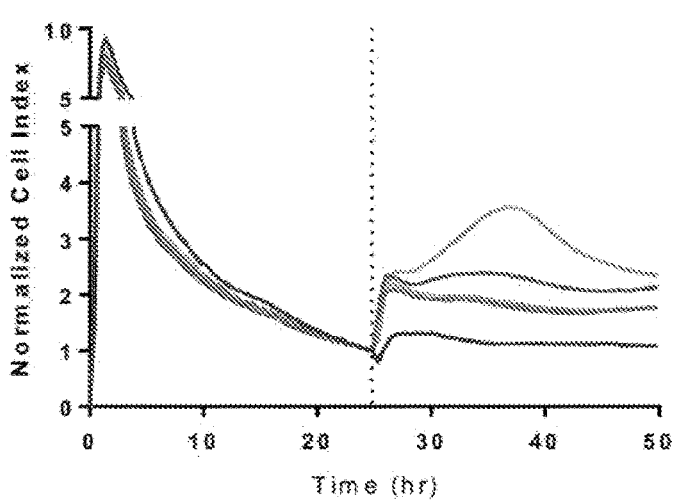

FIG. 14. FACs data showing CAR T cells against U87. RTCA data indicated that IL13RA2-CARs, PMC 393 and 394, did not kill U87 target cells. CAR T cells or nontransduced T cells were added after 24 hours of target cell culture (dotted line). Anti-CD19 CAR T cells, shown in orange, was a negative control. 10:1 E:T ratio. Each condition ran in triplicates.

Figure 15:
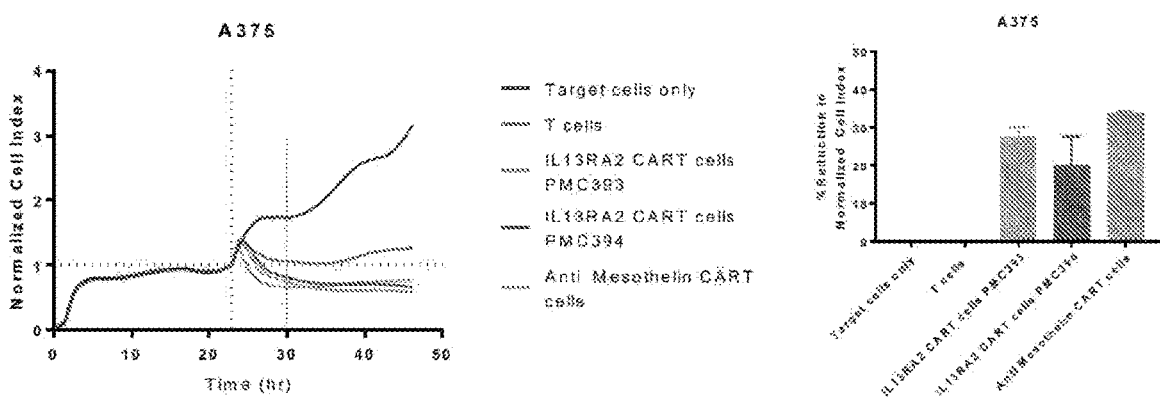

FIG. 15. FACs data showing CAR T cells against A375. RTCA data indicated that IL13RA2-CARs, PMC 393 and 394, were able to kill A375 target cells. There was a significant reduction in Cell Index by about 30% as compared to T cell only (red dotted line). Anti-Mesothelin CAR T cells, shown in orange, was a positive control. 10:1 E:T ratio. Each condition ran in triplicates.

Figure 16:
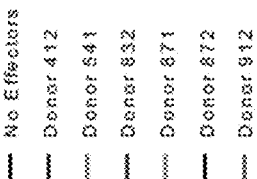
Figure 16:
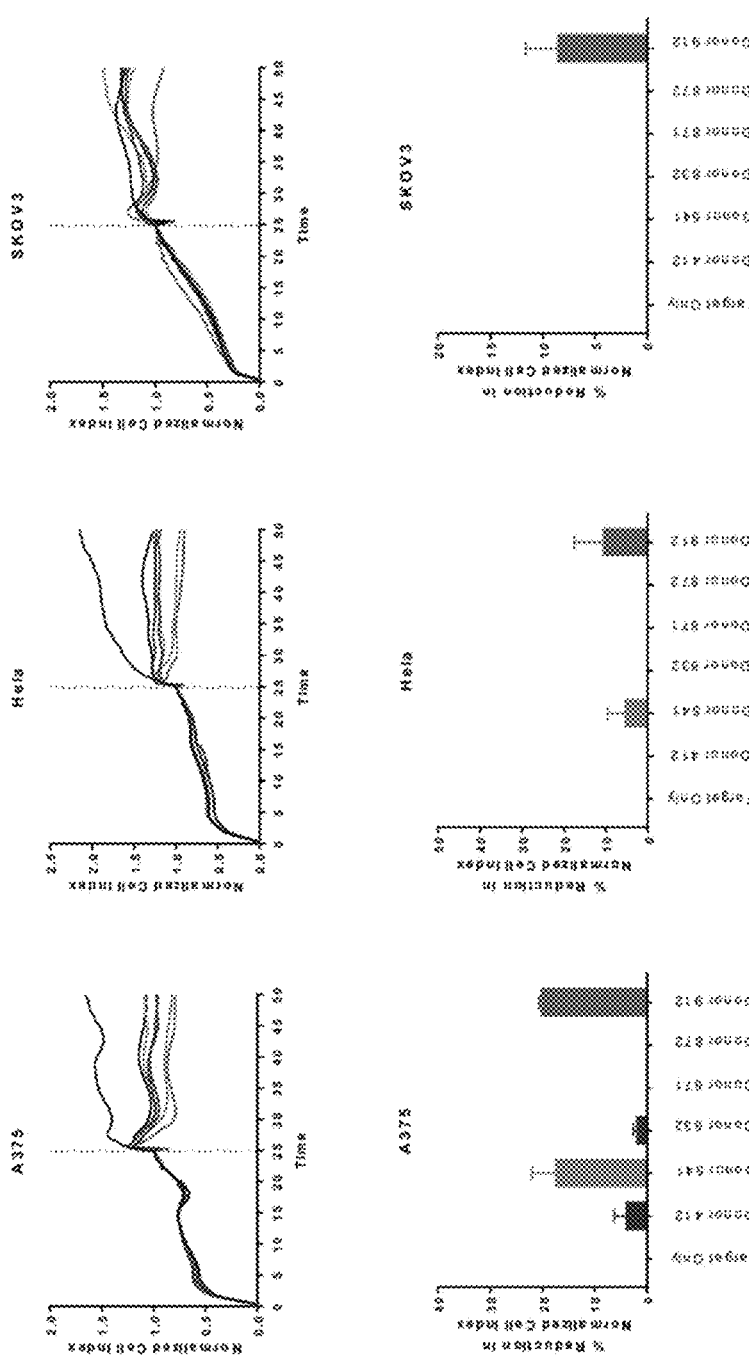

FIG. 16. RTCA data showing results from multiple donors. Non-transduced T cells from multiple donors were run against target cells, A375, HeLa, and SKOV3.

Figure 17:
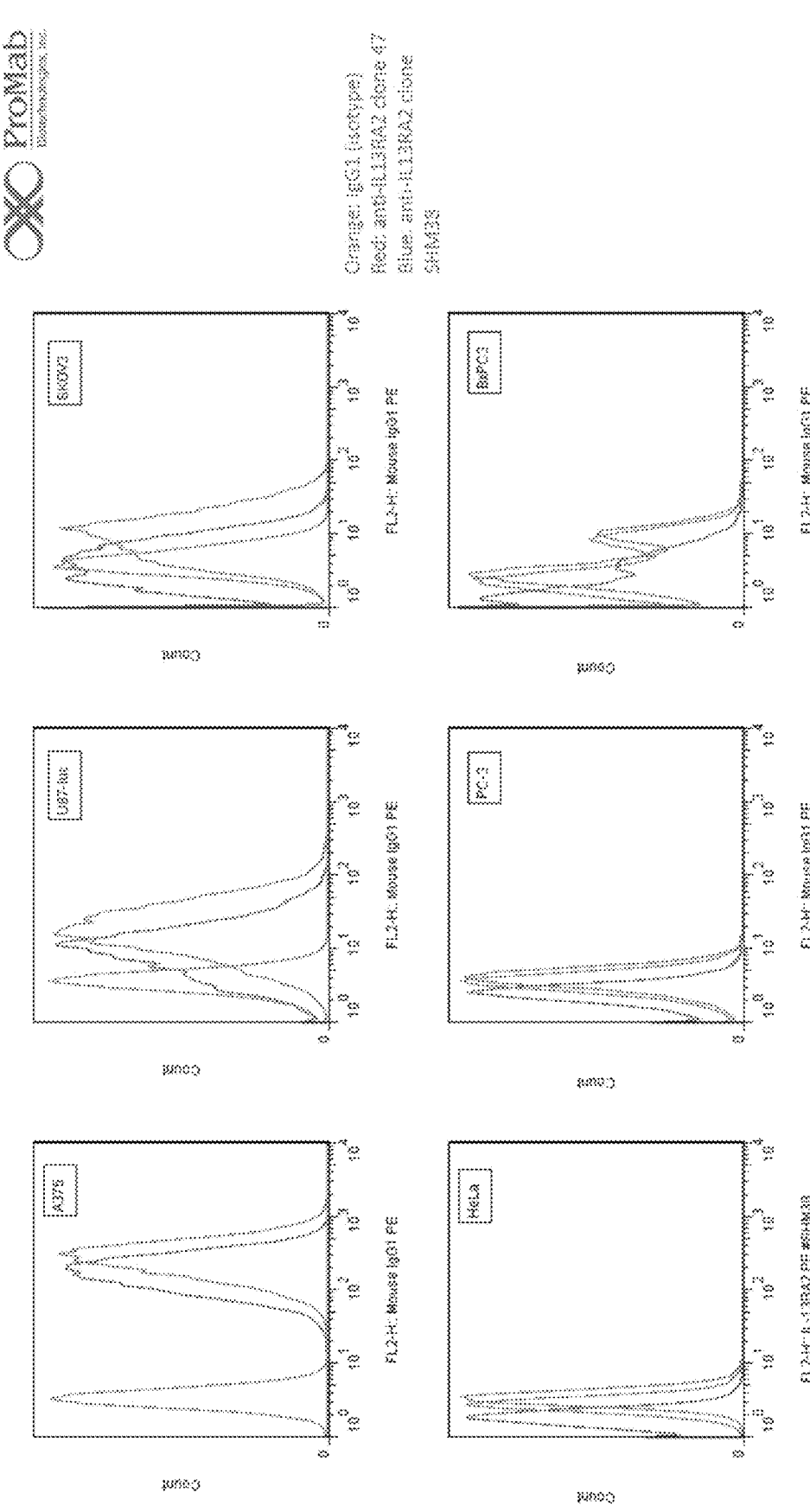

FIG. 17. FACs analysis showing various clones staining with anit-ILRA2.

Figure 18:
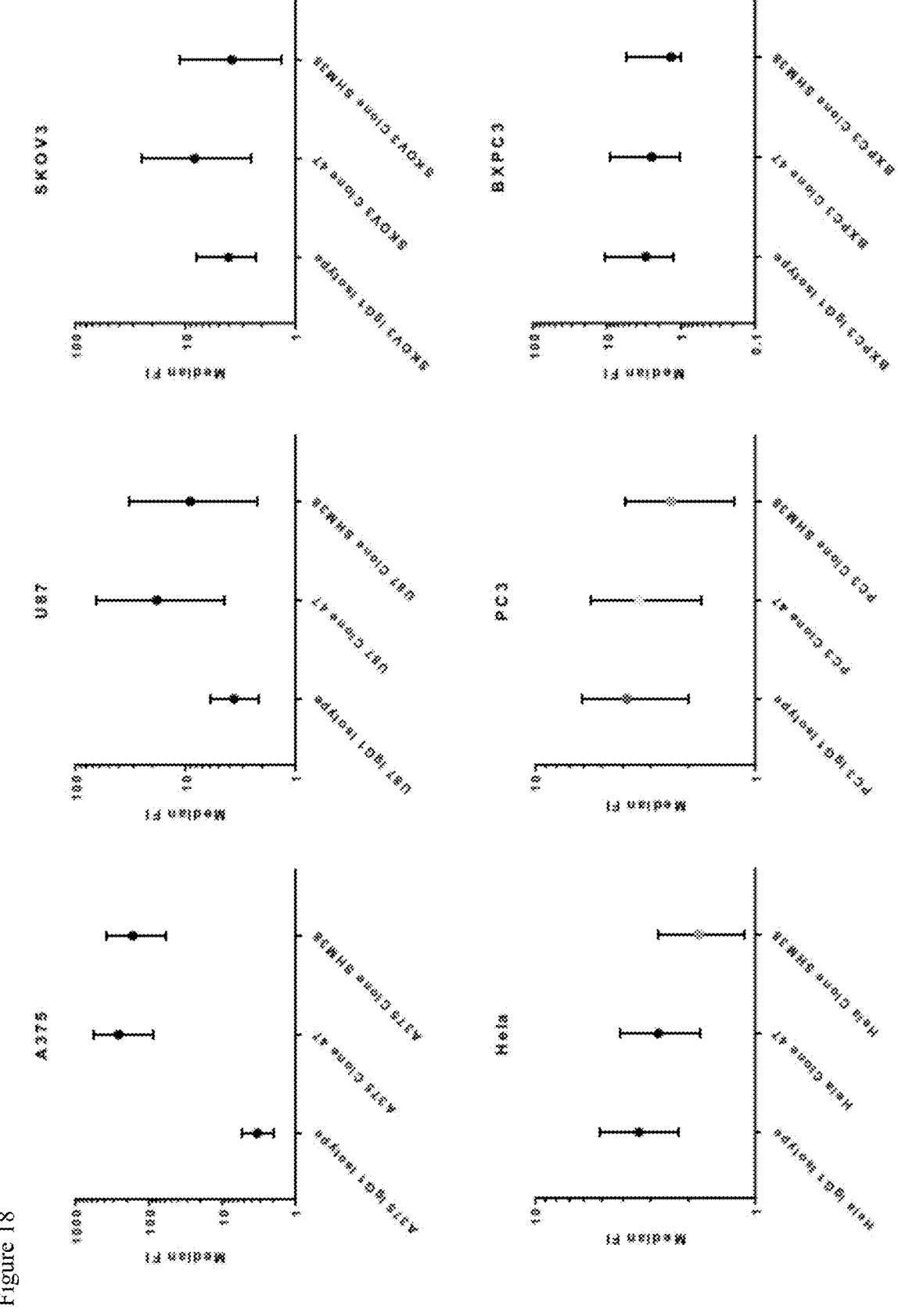

FIG. 18. Data showing plots with median fluorescence (MFIs) with 5th and 95th percentile.

Figure 19:
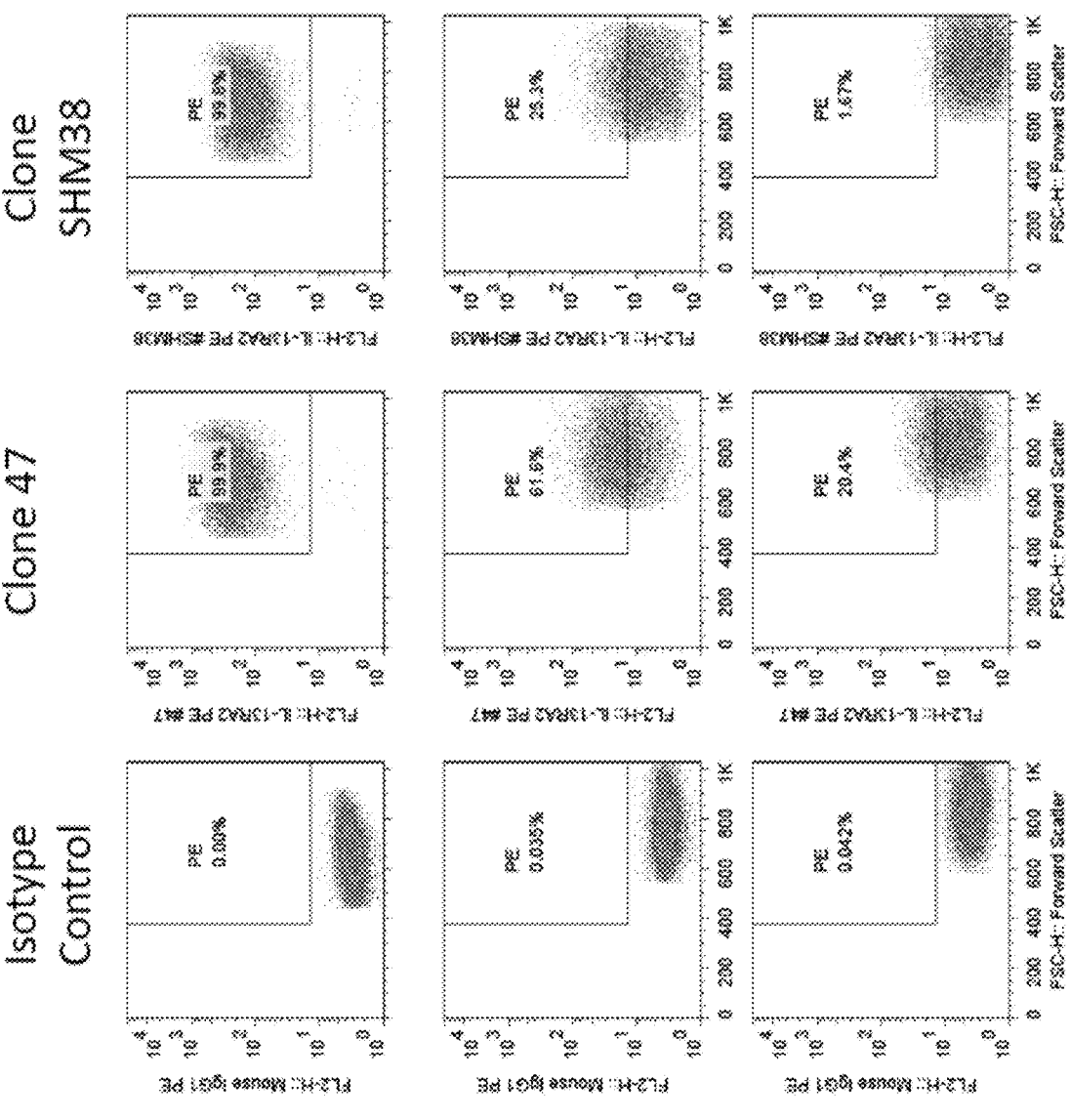

FIG. 19. Data showing cell lines with positive staining for the clones.

Figure 20:
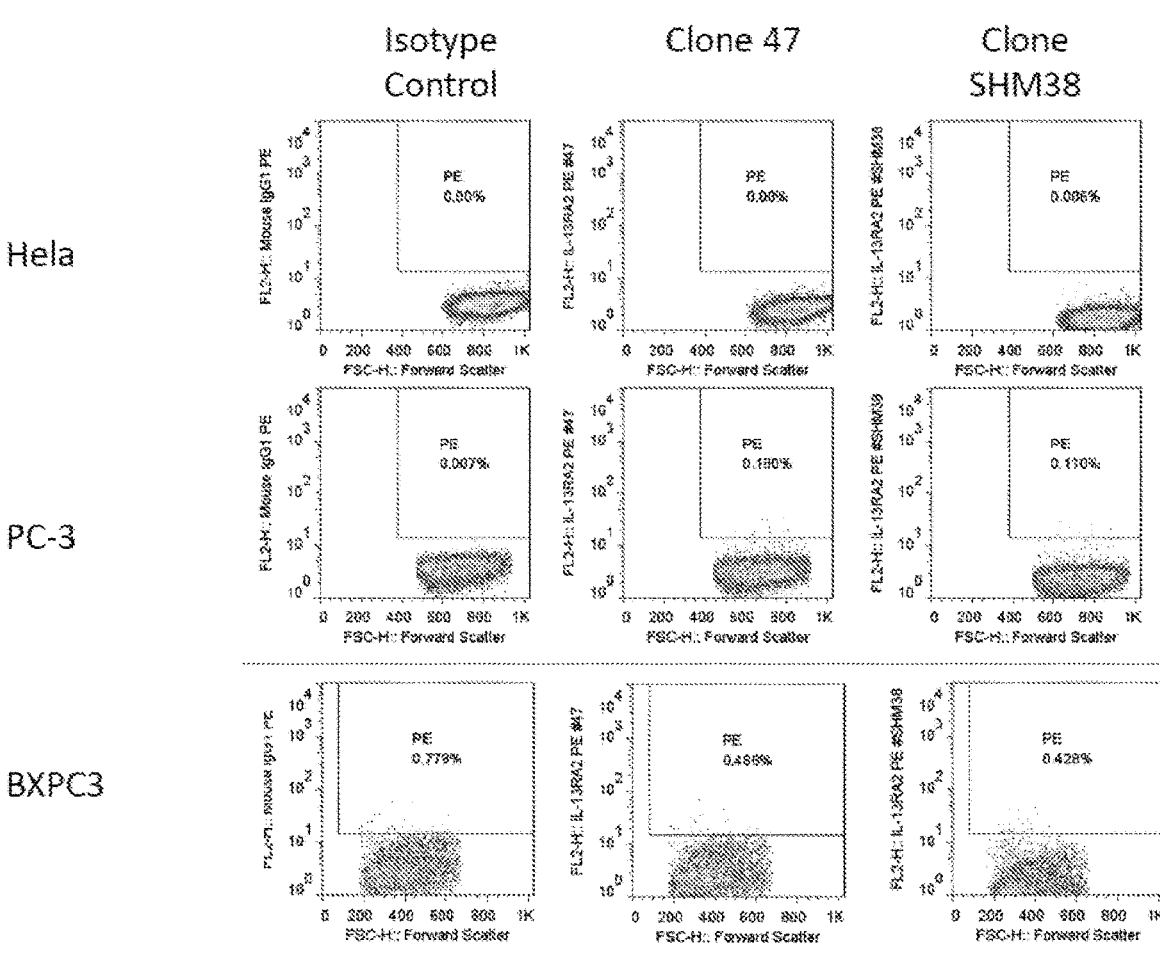

FIG. 20. Data showing cell lines with negative staining for the clones.

DEFINITIONS

In the description that follows, a number of terms conventionally used in the field of cell culture are utilized. In order to provide a clear and consistent understanding of the specification and claims, and the scope to be given to such terms, the following definitions are provided.

An "IL-13 superkine", as used herein, refers to IL-13 polypeptides comprising amino acid substitutions that alter the affinity of the polypeptide to it's receptors, which are one or more of L-13Rα2, IL-13Rα1 and IL-4R. Amino acid modifications may be made at one or more of the amino acids within the set of contact residues that interact with IL-13Rα1 and IL-13Rα2, which residues include, without limitation, L10, R11, I14, V18, R86, D87, T88, K89, L101, K104, K105 and R108 (for reference purposes the sequence of wild-type human IL-13 is provided herein as SEQ ID NO:1, to which the numbering of amino acids will refer). In other embodiments, modified residues are at two or more, three or more, four or more, five or more, and not more than 14 amino acids within the combined set of contact residues defined above. The IL-13 interface that contacts IL-13Rα1 and IL-13Rα2 is the same, and thus there can be overlap in the altered residues that control affinity for these two receptors. In some embodiments one or more of the native amino acid residues L10, R11, I14, V18, R86, D87, T88, K89, L101, K104, K105, F107, and R108 is substituted, and provides for an altered affinity for one or both of IL-13Rα1 and IL-13Rα2.

According to the present invention, amino acid modifications include any naturally occurring or man-made amino acid modifications known or later discovered in the field. In some embodiments, amino acid modifications include any naturally occurring mutation, e.g., substitution, deletion, addition, insertion, etc. In some other embodiments, amino acid modifications include replacing existing amino acid with another amino acid, e.g., a conservative equivalent thereof. In yet some other embodiments, amino acid modifications include replacing one or more existing amino acids with non-natural amino acids or inserting one or more non-natural amino acids. In still some other embodiments, amino acid modifications include at least 1, 2, 3, 4, 5, 6, 8, 10, 12 or 14 amino acid mutations or changes. In some exemplary embodiments, one or more amino acid modifications can be used to alter properties of the IL-13 polypeptide, e.g., affecting the binding activity and/or specificity, etc. Techniques for in vitro mutagenesis of cloned genes are known in the art and described in the Examples herein.

The terms "inhibitors," "antagonists" refer to an agent that reduces the effective biological activity of IL-13 present in the system, e.g. an animal, a tissue, an in vitro culture system, etc., for example endogenous IL-13 in an individual, usually by interfering with the interaction between IL-13 and one or more of its receptors. For example, an antagonist of the invention may bind tightly to the IL-13Rα1 receptor, but have low affinity to IL-13Rα2, so that it is not "trapped" by that receptor. Antagonists may also have ablated binding to IL-4Rα, to prevent signaling through that receptor. For development purposes the binding may be performed under experimental conditions, e.g. using isolated proteins as binding partners, using portions of proteins as binding partners, using yeast display of proteins or portions of proteins as binding partners, and the like.

Altered affinity for IL-13Rα2, relative to the native human IL-13 protein. The human interleukin 13 receptor, alpha 2 (IL13RA2) may be referenced with the genetic sequence of Genbank accession number NM_000640. The predicted 380-amino acid protein contains a putative signal sequence, an extracellular region with a fibronectin-like domain and typical cytokine receptor motifs, a transmembrane domain, and a short intracellular tail. Amino acid substitutions that provide for altered Rα2 affinity include without limitation (1) L10H; L10A; (2) R11L; (4) V18I; (7) R86M; R86K; R86T; (8) D87K; D87G; (9) T88S; T88R, T88K; (10) K89R; (11) L101N; (12) K104R; (13) K105A; K105E; (14) R108K.

IL13 binds with high affinity to IL13RA1, which induces heterodimerization with IL4R to form a complex, or alternatively, IL13 may bind with even greater affinity to IL13RA2, which fails to induce a signal, indicating that it acts as a decoy receptor. The C-terminal tails of the IL4 and IL13 receptor subunits interact with tyrosine kinases of the Janus kinase family (e.g., JAK1), leading to interaction with STAT6, which binds to consensus sequences in the promoters of IL4- and IL13-regulated genes.

Affinity for IL-13Rα2 to wild-type IL-13 is high, and therefore only modest increases in affinity will be found in polypeptides of the invention, for example equivalent, 2-fold increase, 3-fold increase, 5-fold, 10-fold increase of kinetic $K_D$. In some embodiments, the increase in affinity for IL-13Rα2 as compared to wild-type IL-13 is 2-fold increase increase of kinetic $K_D$. In some embodiments, the increase in affinity for IL-13Rα2 as compared to wild-type IL-13 is 3-fold increase increase of kinetic $K_D$. In some embodiments, the increase in affinity for IL-13Rα2 as compared to wild-type IL-13 is, 5-fold increase of kinetic $K_D$. In some embodiments, the increase in affinity for IL-13Rα2 as compared to wild-type IL-13 is 10-fold increase of kinetic $K_D$. For example, polypeptide C11 (SEQ ID NO:18 or SEQ ID NO:35) and D7 (SEQ ID NO:20 or SEQ ID NO:37) show increased binding to IL-13Rα2 and decreased binding to L-13Rα1, and have the set of amino acid substitutions [L10H, R86T, D87G, T88R, R108K] and [L10A, V18F, R86K, D87K, K89R, L101I, K104R, R108K], respectively. In some embodiments, polypeptide with an increase in affinity for IL-13Rα2 as compared to wild-type IL-13 comprises substitutions L10A, V18F, R86K, D87K, K89R, L101I, K104R, and R108K. In some embodiments, polypeptide with an increase in affinity for IL-13Rα2 as compared to wild-type IL-13 comprises substitutions L10H, R86T, D87G, T88R, R108K. In some embodiments, polypeptide with an increase in affinity for IL-13Rα2 as compared to wild-type IL-13 comprises C11 (SEQ ID NO:18 or SEQ ID NO:35). In some embodiments, polypeptide with an increase in affinity for IL-13Rα2 as compared to wild-type IL-13 comprises D7 (SEQ ID NO:20 or SEQ ID NO:37).

Figure 2:
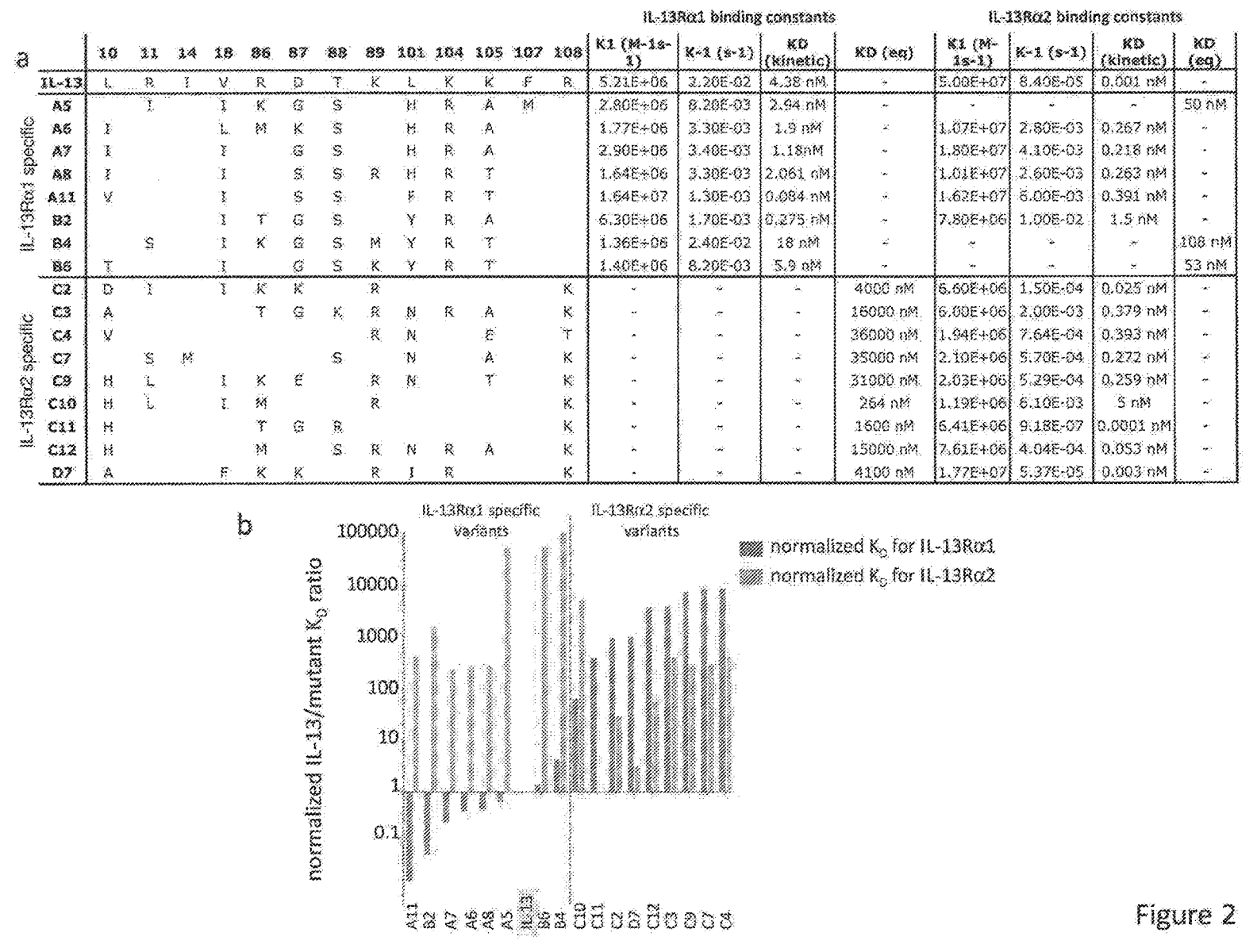

Altered affinity for IL-13Rα1 relative to the native human IL-13 protein. The human interleukin 13 receptor, alpha 1 (IL13RA1) may be referenced with the genetic sequence of Genbank accession number NM_001560. It is a protein of 424 amino acid residues, containing a putative signal sequence and transmembrane domain, which is a low-affinity receptor. Amino acid substitutions that provide for altered Rα1 affinity include without limitation (1) L10I, L10V; (4) V18I; (7) R86K, R86M; (8) D87G, D87S; (9) T88S; (10) K89R, K89M; (11) L101H, L101Y; (12) K104R; and (13) K105A; K105T. In some embodiments, amino acid substitutions that provide for altered IL-13Rα1 affinity include without limitation those provided in FIG. 2.

Decreases in affinity may be modest, for example equivalent, 2-fold decrease, 3-fold decrease, 5-fold decrease of kinetic $K_D$. Decrease in affinity can also be greater than about 10-fold, greater than about $10^2$-fold, greater than about $10^3$-fold or more. In some embodiments, the decrease in affinity for IL-13Rα1 is about a 2-fold decrease of kinetic $K_D$. In some embodiments, the decrease in affinity for IL-13Rα1 is about a 3-fold decrease of kinetic $K_D$. In some embodiments, the decrease in affinity for IL-13Rα1 is about a 4-fold decrease of kinetic $K_D$. In some embodiments, the decrease in affinity for IL-13Rα1 is a 5-fold decrease of kinetic $K_D$. In some embodiments, the decrease in affinity for IL-13Rα1 is a greater than about 10-fold decrease of kinetic $K_D$. In some embodiments, the decrease in affinity for IL-13Rα1 is a greater than about $10^2$-fold decrease of kinetic $K_D$. In some embodiments, the decrease in affinity for IL-13Rα1 is a greater than about $10^3$-fold decrease of kinetic $K_D$. In some embodiments, the decrease in affinity for IL-13Rα1 is a greater than about $10^4$-fold decrease of kinetic $K_D$. For example, polypeptide B4 (SEQ ID NO:9) provides a decreased affinity to IL-13Rα1, and has the set of amino acid substitutions [R11S, V18I, R86K, D87G, T88S, K89M, L101Y, K104R, K105T]. Polypeptide C4 provides a decreased affinity to IL-13Rα1, and has the set of amino acid substitutions [L10V, K89R, L101N, K105E, R108T]. In some embodiments, variants that provide for decreased Rα1 affinity include without limitation those provided in FIG. 2.

The binding properties of a binding agent may be measured by any method, e.g., one of the following methods: BIACORE™ analysis, Enzyme Linked Immunosorbent Assay (ELISA), x-ray crystallography, sequence analysis and scanning mutagenesis. The ability of a protein to neutralize and/or inhibit one or more IL-13-associated activities may be measured by the following methods: assays for measuring the proliferation of an IL-13 dependent cell line, e.g. TF1; assays for measuring the expression of IL-13-mediated polypeptides, e.g., flow cytometric analysis of the expression of CD23; assays evaluating the activity of downstream signaling molecules, e.g., STAT6; assays evaluating production of tenascin; assays testing the efficiency of an described herein to prevent asthma in a relevant animal model, e.g., the cynomolgus monkey, and other assays. An IL-13 polypeptide can have a statistically significant effect in one or more of these assays. Exemplary assays for binding properties include the following.

The binding interaction of an IL-13 polypeptide and a target (e.g., receptor) can be analyzed using surface plasmon resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden).

Information from SPR can be used to provide an accurate and quantitative measure of the equilibrium dissociation constant (Kd), and kinetic parameters, including Kon and Koff, for the binding of a molecule to a target. Such data can be used to compare different molecules. Information from SPR can also be used to develop structure-activity relationships (SAR). For example, the kinetic and equilibrium binding parameters of different molecule can be evaluated. Variant amino acids at given positions can be identified that correlate with particular binding parameters, e.g., high affinity and slow Koff. This information can be combined with structural modeling (e.g., using homology modeling, energy minimization, or structure determination by x-ray crystallography or NMR). As a result, an understanding of the physical interaction between the protein and its target can be formulated and used to guide other design processes.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the abbreviations for the genetically encoded L-enantiomeric amino acids used in the disclosure methods are conventional and are as follows in Table 1. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

TABLE 1

| Amino acid abbreviations | | |
| --- | --- | --- |
| Amino Acid | One-Letter Symbol | Common Abbreviation |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydrogen ion. Genetically encoded basic amino acids include His (H), Arg (R) and Lys (K).

"Polar Amino Acid" refers to a hydrophilic amino acid having a side chain uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (1), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C1-C21)) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (1).

The term "non-naturally" with regard to amino acids can include any amino acid molecule not included as one of the 20 amino acids listed in Table 1 above as well as any modified or derivatized amino acid known to one of skill in the art. Non-naturally amino acids can include but are not limited to β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitro-phenylalanine, hydroxy proline, 1,2,3, 4,-tetrahydroisoquinoline-3-carboxylic acid, and thioproline.

The term "variant" or "variants", with regard to polypeptides, such as capsid polypeptides refers to a polypeptide sequence differing by at least one amino acid from a parent polypeptide sequence, for example wildtype IL-13 (SEQ ID NO:1). Amino acids also include naturally occurring and non-naturally occurring amino acids as well as derivatives thereof. Amino acids also include both D and L forms.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure. A "separated" compound refers to a compound that is removed from at least 90% of at least one component of a sample from which the compound was obtained. Any compound described herein can be provided as an isolated or separated compound.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having disease. Subjects may be human, but also include other mammals, particularly those mammals useful as laboratory models for human disease, e.g. mouse, rat, etc.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as disease cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's disease cell, e.g., a sample comprising polynucleotides and/or polypeptides that is obtained from a patient's disease cell (e.g., a cell lysate or other cell extract comprising polynucleotides and/or polypeptides); and a sample comprising disease cells from a patient. A biological sample comprising a disease cell from a patient can also include non-diseased cells.

The term "diagnosis" is used herein to refer to the identification of a molecular or pathological state, disease or condition.

The term "prognosis" is used herein to refer to the prediction of the likelihood of death or progression, including recurrence, spread, and drug resistance. The term "prediction" is used herein to refer to the act of foretelling or estimating, based on observation, experience, or scientific reasoning. In one example, a physician may predict the likelihood that a patient will survive.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of an atopic disorder or tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Concomitant administration" of a known disease therapeutic drug with a pharmaceutical composition of the present invention means administration of the drug and IL-13 polypeptide at such time that both the known drug and the composition of the present invention will have a therapeutic effect. Such concomitant administration may involve concurrent (i.e. at the same time), prior, or subsequent administration of the drug with respect to the administration of a compound of the invention. A person of ordinary skill in the art would have no difficulty determining the appropriate timing, sequence and dosages of administration for particular drugs and compositions of the present invention.

Cancers of interest include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, gliobastoma multiforme, etc.; hematological malignancies, e.g. childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; sarcomas, melanomas, adenomas; benign lesions such as papillomas, and the like.

The present compositions and methods are applicable to brain tumors, particularly glioblastoma. In general, the goals of brain tumor treatments are to remove as many tumor cells as possible, e.g. with surgery, kill as many of the cells left behind after surgery as possible with radiation and/or chemotherapy, and put remaining tumor cells into a nondividing, quiescent state for as long as possible with radiation and chemotherapy. Careful imaging surveillance is a crucial part of medical care, because tumor regrowth requires alteration of current treatment, or, for patients in the observation phase, restarting treatment.

Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). WHO grade II astrocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

DETAILED DESCRIPTION OF THE EMBODIMENTS

Immune cell targeting constructs comprising IL-13 super-kine sequences are provided. The superkines have altered affinity for one or more receptors selected from IL-13Rα1, IL-13Rα2 and IL-4R, as described above in detail. Superkines are useful for targeting immune cells to cells, e.g. tumor cells, expressing the at least one receptor, e.g. IL-13α2.

The IL-13 superkine component of the construct may be at least about 50 amino acids in length, at least about 75, at least about 100, at least about 110, at least about 115 amino acids in length, up to the full-length of the wild-type protein at the transmembrane domain, i.e. about 116 amino acids in length. For example, the superkine may be fused to the hinge, transmembrane or signaling domains of a CAR. Exemplary polypeptide sequences are provided in SEQ ID NO:2-SEQ ID NO:48, SEQ ID NO:56, SEQ ID NO:57, and SEQ ID NO:63. In some embodiments, the polypeptide sequence is as provided in any one of SEQ ID NO:2 through SEQ ID NO:38. In some embodiments, the polypeptide sequence is SEQ ID NO:2. In some embodiments, the polypeptide sequence is SEQ ID NO:2. In some embodiments, the polypeptide sequence is SEQ ID NO:3. In some embodiments, the polypeptide sequence is SEQ ID NO:4. In some embodiments, the polypeptide sequence is SEQ ID NO:5. In some embodiments, the polypeptide sequence is SEQ ID NO:6. In some embodiments, the polypeptide sequence is SEQ ID NO:7. In some embodiments, the polypeptide sequence is SEQ ID NO:8. In some embodiments, the polypeptide sequence is SEQ ID NO:9. In some embodiments, the polypeptide sequence is SEQ ID NO:10. In some embodiments, the polypeptide sequence is SEQ ID NO:11. In some embodiments, the polypeptide sequence is SEQ ID NO:12. In some embodiments, the polypeptide sequence is SEQ ID NO:13. In some embodiments, the polypeptide sequence is SEQ ID NO:14. In some embodiments, the polypeptide sequence is SEQ ID NO:15. In some embodiments, the polypeptide sequence is SEQ ID NO:16. In some embodiments, the polypeptide sequence is SEQ ID NO:17. In some embodiments, the polypeptide sequence is SEQ ID NO:18. In some embodiments, the polypeptide sequence is SEQ ID NO:19. In some embodiments, the polypeptide sequence is SEQ ID NO:20. In some embodiments, the polypeptide sequence is SEQ ID NO:21. In some embodiments, the polypeptide sequence is SEQ ID NO:22. In some embodiments, the polypeptide sequence is SEQ ID NO:23. In some embodiments, the polypeptide sequence is SEQ ID NO:24. In some embodiments, the polypeptide sequence is SEQ ID NO:25. In some embodiments, the polypeptide sequence is SEQ ID NO:26. In some embodiments, the polypeptide sequence is SEQ ID NO:27. In some embodiments, the polypeptide sequence is SEQ ID NO:28. In some embodiments, the polypeptide sequence is SEQ ID NO:29. In some embodiments, the polypeptide sequence is SEQ ID NO:30. In some embodiments, the polypeptide sequence is SEQ ID NO:31. In some embodiments, the polypeptide sequence is SEQ ID NO:32. In some embodiments, the polypeptide sequence is SEQ ID NO:33. In some embodiments, the polypeptide sequence is SEQ ID NO:34. In some embodiments, the polypeptide sequence is SEQ ID NO:35. In some embodiments, the polypeptide sequence is SEQ ID NO:36. In some embodiments, the polypeptide sequence is SEQ ID NO:37. In some embodiments, the polypeptide sequence is SEQ ID NO:38. In some embodiments, the polypeptide sequence is 90% identical to any one of SEQ ID NO:2 through SEQ ID NO:38. In some embodiments, the polypeptide sequence is 95% identical to any one of SEQ ID NO:2 through SEQ ID NO:38. In some embodiments, the polypeptide sequence is 98% identical to any one of SEQ ID NO:2 through SEQ ID NO:38. In some embodiments, the polypeptide sequence is 99% identical to any one of SEQ ID NO:2 through SEQ ID NO:38. In some embodiments, any one of SEQ ID NO:2 through SEQ ID NO:38 are linked to an IL-13 and/or IL-4 superkine immune cell targeting construct. In some embodiments, SEQ ID NO:2 is linked to an IL-13 and/or IL-4 superkine immune cell targeting construct. In some embodiments, SEQ ID NO:3 is linked to an IL-13 and/or IL-4 superkine immune cell targeting construct. In some embodiments, SEQ ID NO:4 is linked to an IL-13 and/or IL-4 superkine immune cell targeting construct. In some embodiments, SEQ ID NO:5 is linked to an IL-13 and/or IL-4 superkine immune cell targeting construct. In some embodiments, SEQ ID NO:6 is linked to an IL-13 and/or IL-4 superkine immune cell targeting construct. In some embodiments, SEQ ID NO:7 is linked to an IL-13 and/or IL-4 superkine immune cell targeting construct. In some embodiments, SEQ ID NO:8 is linked to an IL-13 and/or IL-4 superkine immune cell targeting construct. In some embodiments, SEQ ID NO:9 is linked to an IL-13 and/or IL-4 superkine immune cell targeting construct. In some embodiments, SEQ ID NO:10 is linked to an IL-13 and/or IL-4 superkine immune cell targeting construct. In some embodiments, SEQ ID NO:11 is linked to an IL-13 and/or IL-4 superkine immune cell targeting construct. In some embodiments, SEQ ID NO:12 is linked to an IL-13 and/or IL-4 superkine immune cell targeting construct. In some embodiments, SEQ ID NO:13 is linked to an IL-13 and/or IL-4 superkine immune cell targeting construct. In some embodiments, SEQ ID NO:14 is linked to an IL-13 and/or IL-4 superkine immune cell targeting construct. In some embodiments, SEQ ID NO:15 is linked to an IL-13 and/or IL-4 superkine immune cell targeting construct. In some embodiments, SEQ ID NO:16 is linked to an IL-13 and/or IL-4 superkine immune cell targeting construct. In some embodiments, SEQ ID NO:17 is linked to an IL-13 and/or IL-4 superkine immune cell targeting construct. In some embodiments, SEQ ID NO:18 is linked to an IL-13 and/or IL-4 superkine immune cell targeting construct. In some embodiments, SEQ ID NO:19 is linked to an IL-13 and/or IL-4 superkine immune cell targeting construct. In some embodiments, SEQ ID NO:20 is linked to an IL-13 and/or IL-4 superkine immune cell targeting construct. In some embodiments, SEQ ID NO:21 is linked to an IL-13 and/or IL-4 superkine immune cell targeting construct. In some embodiments, SEQ ID NO:22 is linked to an IL-13 and/or IL-4 superkine immune cell targeting construct. In some embodiments, SEQ ID NO:23 is linked to an IL-13 and/or IL-4 superkine immune cell targeting construct. In some embodiments, SEQ ID NO:24 is linked to an IL-13 and/or IL-4 superkine immune cell targeting construct. In some embodiments, SEQ ID NO:25 is linked to an IL-13 and/or IL-4 superkine immune cell targeting construct. In some embodiments, SEQ ID NO:26 is linked to an IL-13 and/or IL-4 superkine immune cell targeting construct. In some embodiments, SEQ ID NO:27 is linked to an IL-13 and/or IL-4 superkine immune cell targeting construct. In some embodiments, SEQ ID NO:28 is linked to an IL-13 and/or IL-4 superkine immune cell targeting construct. In some embodiments, SEQ ID NO:29 is linked to an IL-13 and/or IL-4 superkine immune cell targeting construct. In some embodiments, SEQ ID NO:30 is linked to an IL-13 and/or IL-4 superkine immune cell targeting construct. In some embodiments, SEQ ID NO:31 is linked to an IL-13 and/or IL-4 superkine immune cell targeting construct. In some embodiments, SEQ ID NO:32 is linked to an IL-13 and/or IL-4 superkine immune cell targeting construct. In some embodiments, SEQ ID NO:33 is linked to an IL-13 and/or IL-4 superkine immune cell targeting construct. In some embodiments, SEQ ID NO:34 is linked to an IL-13 and/or IL-4 superkine immune cell targeting construct. In some embodiments, SEQ ID NO:35 is linked to an IL-13 and/or IL-4 superkine immune cell targeting construct. In some embodiments, SEQ ID NO:36 is linked to an IL-13 and/or IL-4 superkine immune cell targeting construct. In some embodiments, SEQ ID NO:37 is linked to an IL-13 and/or IL-4 superkine immune cell targeting construct. In some embodiments, SEQ ID NO:38 is linked to an IL-13 and/or IL-4 superkine immune cell targeting construct. In some embodiments, SEQ ID NO:40 is linked to an IL-13 and/or IL-4 superkine immune cell targeting construct. In some embodiments, SEQ ID NO:41 is linked to an IL-13 and/or IL-4 superkine immune cell targeting construct. In some embodiments, SEQ ID NO:43 is linked to an IL-13 and/or IL-4 superkine immune cell targeting construct. In some embodiments, SEQ ID NO:44 is linked to an IL-13 and/or IL-4 superkine immune cell targeting construct. In some embodiments, SEQ ID NO:45 is linked to an IL-13 and/or IL-4 superkine immune cell targeting construct. In some embodiments, SEQ ID NO:46 is linked to an IL-13 and/or IL-4 superkine immune cell targeting construct. In some embodiments, SEQ ID NO:47 is linked to an IL-13 and/or IL-4 superkine immune cell targeting construct. In some embodiments, SEQ ID NO:48 is linked to an IL-13 and/or IL-4 superkine immune cell targeting construct.

In some embodiments, an IL-13 and/or IL-4 superkine immune cell targeting construct comprises one or more signaling domains derived from CD3-ζ, CD28, DAP10, OX-40, ICOS and CD137. In some embodiments, an IL-13 and/or IL-4 superkine immune cell targeting construct comprises one or more signaling domains derived from CD3-ζ. In some embodiments, an IL-13 and/or IL-4 superkine immune cell targeting construct comprises one or more signaling domains derived from CD28. In some embodiments, an IL-13 and/or IL-4 superkine immune cell targeting construct comprises one or more signaling domains derived from DAP10. In some embodiments, an IL-13 and/or IL-4 superkine immune cell targeting construct comprises one or more signaling domains derived from OX-40. In some embodiments, an IL-13 and/or IL-4 superkine immune cell targeting construct comprises one or more signaling domains derived from CD137. In some embodiments an IL-13 peptide of the invention comprises one or more of the amino acids substitutions: (1) L10F, L10I, L10V, L10A, L10D, L10T, L10H; (2) R11S, R11N, R11H, R11L, R11I; (3) I14L, I14F, I14V, I14M; (4) V18L, V18F, V18I; (5) E12A, (6) R65D, (7) R86K, R86T, R86M; (8) D87E, D87K, D87R, D87G, D87S; (9) T88I, T88K, T88R; (10) K89R, K89T, K89M; (11) L101F, L101I, L101Y, L101H, L101N; (12) K104R, K104T, K104M; (13) K105T, K105A, K105R, K105E; (14) F107L, F107I, F107V, F107M; and (15) R108K, R108T, R108M, which substitutions cause an altered affinity for one or both of IL-13Rα1 and IL-13Rα2. In other embodiments, modified residues are at two or more, three or more, four or more, five or more, and not more than 14 amino acids within the combined set of contact residues defined above. As described in International Patent Publication WO 2013/112871, the disclosure of which is incorporated by reference herein in its entirety. In some embodiments, amino acid substitutions include without limitation those provided in FIG. 2.

Sets of modifications may include the following specific changes: (1) L10H; L10A; (2) R11L; (4) V18I; (7) R86M; R86K; R86T; (8) D87K; D87G; (9) T88R, T88S; T88K; (10) K89R; (11) L101N; (12) K104R; (13) K105A; K105E; (14) R108K. In some embodiments, the modification includes any one of the recited specific changes. In some embodiments, the modification includes L10H. In some embodiments, the modification includes 10A. In some embodiments, the modification includes R11L. In some embodiments, the modification includes V18I. In some embodiments, the modification includes R86M. In some embodiments, the modification includes R86K. In some embodiments, the modification includes R86T. In some embodiments, the modification includes D87K. In some embodiments, the modification includes D87G. In some embodiments, the modification includes T88R. In some embodiments, the modification includes T88S. In some embodiments, the modification includes T88K. In some embodiments, the modification includes K89R. In some embodiments, the modification includes L101N. In some embodiments, the modification includes K104R. In some embodiments, the modification includes K105A. In some embodiments, the modification includes K105E. In some embodiments, the modification includes R108K. In some embodiments, the polypeptide comprising the one or more modifications is linked to an IL-13 and/or IL-4 superkine immune cell targeting construct. In some embodiments, an IL-13 and/or IL-4 superkine immune cell targeting construct comprises one or more signaling domains derived from CD3-ζ, CD28, DAP10, OX-40, ICOS and CD137. In some embodiments, an IL-13 and/or IL-4 superkine immune cell targeting construct comprises one or more signaling domains derived from CD3-ζ. In some embodiments, an IL-13 and/or IL-4 superkine immune cell targeting construct comprises one or more signaling domains derived from CD28. In some embodiments, an IL-13 and/or IL-4 superkine immune cell targeting construct comprises one or more signaling domains derived from DAP10. In some embodiments, an IL-13 and/or IL-4 superkine immune cell targeting construct comprises one or more signaling domains derived from OX-40. In some embodiments, an IL-13 and/or IL-4 superkine immune cell targeting construct comprises one or more signaling domains derived from CD137. In some embodiments, amino acid substitutions include without limitation those provided in FIG. 2.

Specific sets of modifications that provide for greater selectivity in binding to IL-13Rα2 v IL-13Rα1 relative to a native IL-13 sequence may include, without limitation:

[L10D, R11I, V18I, R86K, D87K, k89R, R108K] (for example, C2, e.g. SEQ ID NO:11 or SEQ ID NO:29)

[L10A, R86T, D87G, T88K, K89R, L101N, K104R, K105A, R108K] (for example, C3, e.g. SEQ ID NO:12 or SEQ ID NO:30)

[L10V, K89R, L101N, K105E, R108T] (for example, C4, e.g. SEQ ID NO:13 or SEQ ID NO:31)

[R11S, I14M, T88S, L101N, K105A, R108K] (for example, C7, e.g. SEQ ID NO:14 or SEQ ID NO:32)

[L10H, R11L, V18I, R86K, D87E, K89R, L101N, K105T, R108K] (C9, e.g. SEQ ID NO:33)

[L10H, R86T, D87G, T88R, R108K] (C11 e.g. SEQ ID NO:18 or SEQ ID NO:35)

[L10A, V18F, R86K, D87K, K89R, L101I, K104R, R108K] (D7, e.g. SEQ ID NO:20 or SEQ ID NO:37)

[L10T/D; R11I; V18I; R86K; D87K/G; T88S; K89R; L101Y; K104R; K105T; R108K]

[L10A/V; R86T; D87G; T88K; K89R; L101N; K104R; K105A/E; R108K/T]

In some embodiments, the set of modifications comprises L10V, K89R, L101N, K105E, R108T. In some embodiments, the set of modifications comprises R11S, I14M, T88S, L101N, K105A, and R108K (C7, e.g. SEQ ID NO:15 or SEQ ID NO:32). In some embodiments, the set of modifications comprises L10H, R11L, V18I, R86K, D87E, K89R, L101N, K105T, and R108K (C9, e.g. SEQ ID NO:16 or SEQ ID NO:33). In some embodiments, the set of modifications comprises L10H, R86T, D87G, T88R, and R108K (C11 e.g. SEQ ID NO:18 or SEQ ID NO:35). In some embodiments, the set of modifications comprises L10A, V18F, R86K, D87K, K89R, L101I, K104R, and R108K (D7, e.g. SEQ ID NO:20 or SEQ ID NO:37). In some embodiments, the set of modifications comprises L10T/D, R11I, V18I, R86K, D87K/G, T88S, K89R, L101Y, K104R, K105T, and R108K. In some embodiments, the set of modifications comprises L10T, R11I, V18I, R86K, D87K, T88S, K89R, L101Y, K104R, K105T, and R108K. In some embodiments, the set of modifications comprises L10T, R11I, V18I, R86K, D87G, T88S, K89R, L101Y, K104R, K105T, and R108K. In some embodiments, the set of modifications comprises L10D, R11I, V18I, R86K, D87K, T88S, K89R, L101Y, K104R, K105T, and R108K. In some embodiments, the set of modifications comprises L10D, R11I, V18I, R86K, D87G, T88S, K89R, L101Y, K104R, K105T, R108K. In some embodiments, the set of modifications comprises L10A/V, R86T, D87G, T88K, K89R, L101N, K104R, K105A/E, and R108K/T. In some embodiments, the set of modifications comprises L10A, R86T, D87G, T88K, K89R, L101N, K104R, K105A, and R108K. In some embodiments, the set of modifications comprises L10A, R86T, D87G, T88K, K89R, L101N, K104R, K105E, and R108K. In some embodiments, the set of modifications comprises L10A, R86T, D87G, T88K, K89R, L101N, K104R, K105A, and R108T. In some embodiments, the set of modifications comprises L10A, R86T, D87G, T88K, K89R, L101N, K104R, K105E, and R108T. In some embodiments, the set of modifications comprises L10V, R86T, D87G, T88K, K89R, L101N, K104R, K105A, and R108K. In some embodiments, the set of modifications comprises L10V, R86T, D87G, T88K, K89R, L101N, K104R, K105E, and R108K. In some embodiments, the set of modifications comprises L10V, R86T, D87G, T88K, K89R, L101N, K104R, K105A, an dR108T. In some embodiments, the set of modifications comprises L10V, R86T, D87G, T88K, K89R, L101N, K104R, K105E, and R108T. In some embodiments, the amino acid sequence is 90% identical. In some embodiments, the amino acid sequence is 95% identical. In some embodiments, the amino acid sequence is 98% identical. In some embodiments, the amino acid sequence is 99% identical. In some embodiments, the polypeptide comprising the one or more modifications is linked to an IL-13 and/or IL-4 superkine immune cell targeting construct. In some embodiments, an IL-13 and/or IL-4 superkine immune cell targeting construct comprises one or more signaling domains derived from CD3-ζ, CD28, DAP10, OX-40, ICOS and CD137. In some embodiments, an IL-13 and/or IL-4 superkine immune cell targeting construct comprises one or more signaling domains derived from CD3-ζ. In some embodiments, an IL-13 and/or IL-4 superkine immune cell targeting construct comprises one or more signaling domains derived from CD28. In some embodiments, an IL-13 and/or IL-4 superkine immune cell targeting construct comprises one or more signaling domains derived from DAP10. In some embodiments, an IL-13 and/or IL-4 superkine immune cell targeting construct comprises one or more signaling domains derived from OX-40. In some embodiments, an IL-13 and/or IL-4 superkine immune cell targeting construct comprises one or more signaling domains derived from CD137. In some embodiments, amino acid substitutions include without limitation those provided in FIG. 2.

Specific sets of modifications that provide for greater selectivity in binding to IL-13Rα1 v IL-13Rα2 relative to a native IL-13 sequence may include, without limitation:

[L10V, V18I, D87S, D88S, L101F, K104R, K105T]

[R11S, V18I, R86K, D87G, T88S, K89M, L101Y, K104R, K105T]

[L10V, V18I, D87S, T88S, L101F, K104R, K105T]

[L10V/I; D87S; T88S; K89R; L101H/F; K104R; K105T]

[L10I; V18I; R86T; D87G; T88S; K89R; L101Y/H; K104R; K105A]

[L10V; V18I; D87S; T88S; L101F; K104R; K105T]

[V18I, R86T, D87G, T88S, L101Y, K104R, K105A]

[R11I, V18I, R86K, D87G, T88S, L101H, K104R, K105A, F107M]

which substitutions are optionally combined with the substitutions [E12A/G/S, R65D/E].

In some embodiments, the set of modifications comprises L10V, V18I, D87S, D88S, L101F, K104R, and K105T. In some embodiments, the set of modifications comprises R11S, V18I, R86K, D87G, T88S, K89M, L101Y, K104R, and K105T. In some embodiments, the set of modifications comprises L10V, V18I, D87S, T88S, L101F, K104R, and K105T. In some embodiments, the set of modifications comprises L10V/1, D87S, T88S, K89R, L101H/F, K104R, and K105T. In some embodiments, the set of modifications comprises L10I, V18I, R86T, D87G, T88S, K89R, L101Y/ H, K104R, and K105A. In some embodiments, the set of modifications comprises L10V, V18I, D87S, T88S, L101F, K104R, and K105T. In some embodiments, the set of modifications comprises V18I, R86T, D87G, T88S, L101Y, K104R, and K105A. In some embodiments, the set of modifications comprises R11I, V18I, R86K, D87G, T88S, L101H, K104R, K105A, and F107M. In some embodiments, the set of modifications comprises L10V, V18I, D87S, D88S, L101F, K104R, K105T, E12A/G/S, and R65D/

E. In some embodiments, the set of modifications comprises R11S, V18I, R86K, D87G, T88S, K89M, L101Y, K104R, K105T, E12A/G/S, and R65D/E. In some embodiments, the set of modifications comprises L10V, V18I, D87S, T88S, L101F, K104R, K105T, E12A/G/S, and R65D/E. In some embodiments, the set of modifications comprises L10V/1, D87S, T88S, K89R, L101H/F, K104R, K105T, E12A/G/S, and R65D/E. In some embodiments, the set of modifications comprises L10I, V18I, R86T, D87G, T88S, K89R, L101Y/H, K104R, K105A, E12A/G/S, and R65D/E. In some embodiments, the set of modifications comprises L10V, V18I, D87S, T88S, L101F, K104R, K105T, E12A/G/S, and R65D/E. In some embodiments, the set of modifications comprises V18I, R86T, D87G, T88S, L101Y, K104R, K105A, E12A/G/S, and R65D/E. In some embodiments, the set of modifications comprises R11I, V18I, R86K, D87G, T88S, L101H, K104R, K105A, F107M, E12A/G/S, and R65D/E. In some embodiments, the set of modifications comprises L10V, V18I, D87S, D88S, L101F, K104R, K105T, E12A, and R65D/E. In some embodiments, the set of modifications comprises R11S, V18I, R86K, D87G, T88S, K89M, L101Y, K104R, K105T, E12A, and R65D/E. In some embodiments, the set of modifications comprises L10V, V18I, D87S, T88S, L101F, K104R, K105T, E12A, and R65D/E. In some embodiments, the set of modifications comprises L10V/1, D87S, T88S, K89R, L101H/F, K104R, K105T, E12A, and R65D/E. In some embodiments, the set of modifications comprises L10I, V18I, R86T, D87G, T88S, K89R, L101Y/H, K104R, K105A, E12A, and R65D/E. In some embodiments, the set of modifications comprises L10V, V18I, D87S, T88S, L101F, K104R, K105T, E12A, and R65D/E. In some embodiments, the set of modifications comprises V18I, R86T, D87G, T88S, L101Y, K104R, K105A, E12A, and R65D/E. In some embodiments, the set of modifications comprises R11I, V18I, R86K, D87G, T88S, L101H, K104R, K105A, F107M, E12A, and R65D/E. In some embodiments, the set of modifications comprises L10V, V18I, D87S, D88S, L101F, K104R, K105T, E12G, and R65D/E. In some embodiments, the set of modifications comprises R11S, V18I, R86K, D87G, T88S, K89M, L101Y, K104R, K105T, E12G, and R65D/E. In some embodiments, the set of modifications comprises L10V, V18I, D87S, T88S, L101F, K104R, K105T, E12A/G/S, and R65D/E. In some embodiments, the set of modifications comprises L10V/I, D87S, T88S, K89R, L101H/F, K104R, K105T, E12G, and R65D/E. In some embodiments, the set of modifications comprises L10I, V18I, R86T, D87G, T88S, K89R, L101Y/H, K104R, K105A, E12G, and R65D/E. In some embodiments, the set of modifications comprises L10V, V18I, D87S, T88S, L101F, K104R, K105T, E12G, and R65D/E. In some embodiments, the set of modifications comprises V18I, R86T, D87G, T88S, L101Y, K104R, K105A, E12G, and R65D/E. In some embodiments, the set of modifications comprises R11I, V18I, R86K, D87G, T88S, L101H, K104R, K105A, F107M, E12G, and R65D/E. In some embodiments, the set of modifications comprises L10V, V18I, D87S, D88S, L101F, K104R, K105T, E12S, and R65D/E. In some embodiments, the set of modifications comprises R11S, V18I, R86K, D87G, T88S, K89M, L101Y, K104R, K105T, E12A/G/S, and R65D/E. In some embodiments, the set of modifications comprises L10V, V18I, D87S, T88S, L101F, K104R, K105T, E12S, and R65D/E. In some embodiments, the set of modifications comprises L10V/I, D87S, T88S, K89R, L101H/F, K104R, K105T, E12S, and R65D/E. In some embodiments, the set of modifications comprises L10I, V18I, R86T, D87G, T88S, K89R, L101Y/H, K104R, K105A, E12S, and R65D/E. In some embodiments, the set of modifications comprises L10V, V18I, D87S, T88S, L101F, K104R, K105T, E12S, and R65D/E. In some embodiments, the set of modifications comprises V18I, R86T, D87G, T88S, L101Y, K104R, K105A, E12S, and R65D/E. In some embodiments, the set of modifications comprises R11I, V18I, R86K, D87G, T88S, L101H, K104R, K105A, F107M, E12S, and R65D/E. In some embodiments, the set of modifications comprises L10V, V18I, D87S, D88S, L101F, K104R, K105T, E12A, and R65D. In some embodiments, the set of modifications comprises R11S, V18I, R86K, D87G, T88S, K89M, L101Y, K104R, K105T, E12A, and R65E. In some embodiments, the set of modifications comprises L10V, V18I, D87S, T88S, L101F, K104R, K105T, E12A, and R65D. In some embodiments, the set of modifications comprises L10V/I, D87S, T88S, K89R, L101H/F, K104R, K105T, E12A, and R65D. In some embodiments, the set of modifications comprises L10I, V18I, R86T, D87G, T88S, K89R, L101Y/H, K104R, K105A, E12A, and R65D. In some embodiments, the set of modifications comprises L10V, V18I, D87S, T88S, L101F, K104R, K105T, E12A, and R65D. In some embodiments, the set of modifications comprises V18I, R86T, D87G, T88S, L101Y, K104R, K105A, E12A, and R65D. In some embodiments, the set of modifications comprises R11I, V18I, R86K, D87G, T88S, L101H, K104R, K105A, F107M, E12A, and R65D. In some embodiments, the set of modifications comprises L10V, V18I, D87S, D88S, L101F, K104R, K105T, E12G, and R65D. In some embodiments, the set of modifications comprises R11S, V18I, R86K, D87G, T88S, K89M, L101Y, K104R, K105T, E12G, and R65D. In some embodiments, the set of modifications comprises L10V, V18I, D87S, T88S, L101F, K104R, K105T, E12A/G/S, and R65D. In some embodiments, the set of modifications comprises L10V/I, D87S, T88S, K89R, L101H/F, K104R, K105T, E12G, and R65D. In some embodiments, the set of modifications comprises L10I, V18I, R86T, D87G, T88S, K89R, L101Y/H, K104R, K105A, E12G, and R65D. In some embodiments, the set of modifications comprises L10V, V18I, D87S, T88S, L101F, K104R, K105T, E12G, and R65D. In some embodiments, the set of modifications comprises V18I, R86T, D87G, T88S, L101Y, K104R, K105A, E12G, and R65D. In some embodiments, the set of modifications comprises R11I, V18I, R86K, D87G, T88S, L101H, K104R, K105A, F107M, E12G, and R65D. In some embodiments, the set of modifications comprises L10V, V18I, D87S, D88S, E101F, K104R, K105T, E12S, and R65D. In some embodiments, the set of modifications comprises R11S, V18I, R86K, D87G, T88S, K89M, L101Y, K104R, K105T, E12S, and R65D. In some embodiments, the set of modifications comprises L10V, V18I, D87S, T88S, L101F, K104R, K105T, E12S, and R65D. In some embodiments, the set of modifications comprises L10V/1, D87S, T88S, K89R, L101H/F, K104R, K105T, E12S, and R65D. In some embodiments, the set of modifications comprises L10I, V18I, R86T, D87G, T88S, K89R, L101Y/H, K104R, K105A, E12S, and R65D. In some embodiments, the set of modifications comprises L10V, V18I, D87S, T88S, L101F, K104R, K105T, E12S, and R65D. In some embodiments, the set of modifications comprises V18I, R86T, D87G, T88S, L101Y, K104R, K105A, E12S, and R65D. In some embodiments, the set of modifications comprises R11I, V18I, R86K, D87G, T88S, L101H, K104R, K105A, F107M, E12S, and R65D. In some embodiments, the set of modifications comprises L10V, V18I, D87S, D88S, L101F, K104R, K105T, E12A, and R65E. In some embodiments, the set of modifications comprises R11S, V18I, R86K, D87G, T88S, K89M, L101Y, K104R, K105T, E12A, and R65E. In some embodiments, the set of modifications comprises L10V, V18I, D87S, T88S, L101F, K104R, K105T, E12A, and R65E. In some embodiments, the set of modifications comprises L10V/1, D87S, T88S, K89R, L101H/F, K104R, K105T, E12A, and R65E. In some embodiments, the set of modifications comprises L10I, V18I, R86T, D87G, T88S, K89R, L101Y/H, K104R, K105A, E12A, and R65E. In some embodiments, the set of modifications comprises L10V, V18I, D87S, T88S, L101F, K104R, K105T, E12A, and R65E. In some embodiments, the set of modifications comprises V18I, R86T, D87G, T88S, L101Y, K104R, K105A, E12A, and R65E. In some embodiments, the set of modifications comprises R11I, V18I, R86K, D87G, T88S, L101H, K104R, K105A, F107M, E12A, and R65E. In some embodiments, the set of modifications comprises L10V, V18I, D87S, D88S, L101F, K104R, K105T, E12G, and R65E. In some embodiments, the set of modifications comprises R11S, V18I, R86K, D87G, T88S, K89M, L101Y, K104R, K105T, E12G, and R65E. In some embodiments, the set of modifications comprises L10V, V18I, D87S, T88S, L101F, K104R, K105T, E12A/G/S, and R65E. In some embodiments, the set of modifications comprises L10V/1, D87S, T88S, K89R, L101H/F, K104R, K105T, E12G, and R65E. In some embodiments, the set of modifications comprises L10I, V18I, R86T, D87G, T88S, K89R, L101Y/H, K104R, K105A, E12G, and R65E. In some embodiments, the set of modifications comprises L10V, V18I, D87S, T88S, L101F, K104R, K105T, E12G, and R65E. In some embodiments, the set of modifications comprises V18I, R86T, D87G, T88S, L101Y, K104R, K105A, E12G, and R65E. In some embodiments, the set of modifications comprises R11I, V18I, R86K, D87G, T88S, L101H, K104R, K105A, F107M, E12G, and R65E. In some embodiments, the set of modifications comprises L10V, V18I, D87S, D88S, L101F, K104R, K105T, E12S, and R65E. In some embodiments, the set of modifications comprises R11S, V18I, R86K, D87G, T88S, K89M, L101Y, K104R, K105T, E12A/G/S, and R65E. In some embodiments, the set of modifications comprises L10V, V18I, D87S, T88S, L101F, K104R, K105T, E12S, and R65E. In some embodiments, the set of modifications comprises L10V/1, D87S, T88S, K89R, L101H/F, K104R, K105T, E12S, and R65E. In some embodiments, the set of modifications comprises L10I, V18I, R86T, D87G, T88S, K89R, L101Y/H, K104R, K105A, E12S, and R65E. In some embodiments, the set of modifications comprises L10V, V18I, D87S, T88S, L101F, K104R, K105T, E12S, and R65E. In some embodiments, the set of modifications comprises V18I, R86T, D87G, T88S, L101Y, K104R, K105A, E12S, and R65E. In some embodiments, the set of modifications comprises R11I, V18I, R86K, D87G, T88S, L101H, K104R, K105A, F107M, E12S, and R65E. In some embodiments, the set of modifications comprises L10V, E12A, V18I, R65D, D87S, T88S, L101F, K104R, and K105T (see, for example, IL-13dn; SEQ ID NO:38, SEQ ID NO:40, and/or SEQ ID NO:41). In some embodiments, the amino acid sequence is 90% identical. In some embodiments, the amino acid sequence is 95% identical. In some embodiments, the amino acid sequence is 98% identical. In some embodiments, the amino acid sequence is 99% identical. In some embodiments, the polypeptide comprising the one or more modifications is linked to an IL-13 and/or IL-4 superkine immune cell targeting construct. In some embodiments, an IL-13 and/or IL-4 superkine immune cell targeting construct comprises one or more signaling domains derived from CD3-ζ, CD28, DAP10, OX-40, ICOS and CD137. In some embodiments, an IL-13 and/or IL-4 superkine immune cell targeting construct comprises one or more signaling domains derived from CD3-ζ. In some embodiments, an IL-13 and/or IL-4 superkine immune cell targeting construct comprises one or more signaling domains derived from CD28. In some embodiments, an IL-13 and/or IL-4 superkine immune cell targeting construct comprises one or more signaling domains derived from DAP10. In some embodiments, an IL-13 and/or IL-4 superkine immune cell targeting construct comprises one or more signaling domains derived from OX-40. In some embodiments, an IL-13 and/or IL-4 superkine immune cell targeting construct comprises one or more signaling domains derived from CD137. In some embodiments, amino acid substitutions include without limitation those provided in FIG. 2.

In some embodiments the IL-4 muteins have altered relative binding activities as compared to wild-type IL-4 for the second chains of Type-I and Type-II receptors. In some embodiments the IL-4 muteins modulate or enhance signaling, rather than block it. In some embodiments, IL-4 muteins, which are referred to as "superkines," have a very high affinity for γc and diminished affinity for IL13Rα1, and conversely, those that bind with much higher affinity than IL-4 to IL-13Rα1, with little or no change in their affinity for γc. In some embodiments, the IL-4 muteins have relatively high affinity for γc and diminished affinity for IL13Rα1. In other embodiments, the IL-4 muteins have relatively much higher affinity than IL-4 to IL-13Rα1, with little or no change in their affinity for γc.

In some embodiments, the IL-4 muteins are superkines. In various embodiments, the present disclosure provides IL-4 mutant polypeptides, which may be, but are not necessarily, substantially purified and that can function as an agonist of wild-type IL-4; carrying out one or more of the biological activities of IL-4 (e.g., stimulation of cellular proliferation). In some embodiments, the mutant IL-4 polypeptide includes an amino acid sequence that is at least about 80% identical to SEQ ID NO:49 or SEQ ID NO:50 which binds γc with an affinity that is greater than the affinity with which the polypeptide represented by SEQ ID NO:49 or SEQ ID NO:50 binds the γc and diminished affinity for IL13Rα1. For example, a mutant IL-4 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-4, and that binds the γc with greater affinity than the IL-4 of SEQ ID NO:49 or SEQ ID NO:50 and diminished affinity for IL13Rα1 as compared to that of SEQ ID NO.:49. In some embodiments, the mutant IL-4 polypeptide includes an amino acid sequence that is at least about 80% identical to SEQ ID NO:49 or SEQ ID NO:50 which binds with higher affinity than IL-4 (SEQ ID NO:49 or SEQ ID NO:50) to IL-13Rα1, with little or no change in the relative affinity for γc relative to the polypeptide of SEQ ID NO:49 or SEQ ID NO:50. For example, a mutant IL-4 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-4, and that binds with higher affinity than IL-4 (SEQ ID NO:49 or SEQ ID NO:50) to IL-13Rα1, with little or no change in the relative affinity for γc relative to the polypeptide of SEQ ID NO:49 or SEQ ID NO:50.

Exemplary mutant IL-4 polypeptides can be at least about 50%, 55%, 60%, 65%, 70%, 75%, 80%, 85%, 90%, 95%, 96%, 97%, 98%, 99% identical to wild-type IL-4. The mutation can consist of a change in the number or content of amino acid residues. For example, the mutant IL-4 can have a greater or a lesser number of amino acid residues than wild-type IL-4. Alternatively, or in addition, an exemplary mutant polypeptide can contain a substitution of one or more amino acid residues that are present in the wild-type IL-4. In various embodiments, the mutant IL-4 polypeptide can differ from wild-type IL-4 by the addition, deletion, or substitution of a single amino acid residue, for example, a substitution of the residue at position 121. Similarly, exemplary mutant IL-4 polypeptides can differ from wild-type by a substitution of two, three, four, five, six, seven, eight or more amino acid residues, for example, the residues at positions 117, 118, 21, 122, 124, 125, 128 and 129 of SEQ ID NO:49 or SEQ ID NO:50.

In some embodiments, a polypeptide that includes an amino acid sequence that is at least 90% identical to a reference amino acid sequence of any of the SEQ ID NOs: disclosed herein is a polypeptide that includes a sequence that is identical to the reference sequence except for the inclusion of up to 13 alterations of the reference amino acid of any of the SEQ ID NOs: disclosed herein. For example, up to 10% of the amino acid residues in the reference sequence may be deleted or substituted with another amino acid, or a number of amino acids up to 10% of the total amino acid residues in the reference sequence may be inserted into the reference sequence. These alterations of the reference sequence can occur at the amino (N-) or carboxy (C-) terminal positions of the reference amino acid sequence or anywhere between those terminal positions, interspersed either individually among residues in the reference sequence or in one or more contiguous groups within the reference sequence.

In some embodiments, the mutant IL-4 polypeptides can have the ability to exhibit an increased association rate with the γc receptor subunit. Also provided in the instant disclosure are mutant IL-4 polypeptides that bind the γc with an affinity that is lower than the wild-type IL-4 polypeptide by at least about 2%, at least about 5%, at least about 10%, at least about 20%, at least about 30%, or at least about 40% lower affinity or more. The binding affinity of exemplary disclosed mutant IL-4 polypeptides can also be expressed as 1.2, 1.4, 1.5, 2, 3, 4, 5, 10, 15, 20, or more fold lower affinity for the γc than wild-type IL-4.

With respect to affinity, in some embodiments, the mutant IL-4 polypeptides bind the IL-13Rα1 with an affinity that is higher than the wild-type IL-4 polypeptide by at least about 2%, at least about 5%, at least about 10%, at least about 20%, at least about 30%, or at least about 40% higher affinity or more. The wild-type IL-4 polypeptide binds the IL-13Rα1 with a Kd of about 4200 nM. The binding affinity of exemplary disclosed mutant IL-4 polypeptides can also be expressed as 1.2, 1.4, 1.5, 2, 5, 10, 15, 20, 25, 50, 100, 200, 250, 400, 450, 500, 1000, 1500, 2000 or more fold higher affinity for the IL-13Rα1 than wild-type IL-4.

In some embodiments, the mutant IL-4 polypeptides can have the ability to exhibit an increased association rate with the IL-13Rα1 receptor subunit.

In some embodiments, the mutant IL-4 polypeptides that bind the IL-13Rα1 with an affinity that is lower than the wild-type IL-4 polypeptide by at least about 2%, at least about 5%, at least about 10%, at least about 20%, at least about 30%, or at least about 40% lower affinity or more. The binding affinity of exemplary disclosed mutant IL-4 polypeptides can also be expressed as 1.2, 1.4, 1.5, 2, 3, 4, 5, 10, 15, 20, or more fold lower affinity for the IL-13Rα1 than wild-type IL-4.

In some embodiments, the mutant IL-4 polypeptides possess both properties of increased affinity for the γc and decreased affinity for IL-13Rα1 as compared to wild-type IL-4. In some embodiments, the mutant IL-4 polypeptides possess both properties of increased affinity for the γc and IL-13Rα1 ass compared to wild-type IL-4. In some embodiments, the mutant IL-4 polypeptides possessing both properties of decreased affinity for the γc and increased affinity for IL-13Rα1 as compared to wild-type IL4 are also disclosed.

In some embodiments an IL-4 mutein comprises one or more of the amino acids substitutions at positions 117, 118, 121, 122, 124, 125, 128, and/or 129. In some embodiments, an IL-4 mutein encompassing two, three, four, five, six, seven, or eight amino acid substitutions at positions 117, 118, 121, 122, 124, 125, 128, and/or 129 are provided, wherein the amino acid numbering is accordance with wild-type human IL-4 (SEQ ID NO:49 or SEQ ID NO:50.). In some embodiments an IL-4 mutein comprises one or more of the amino acids substitutions: In some embodiments, an IL-4 mutein encompassing two, three, four, five, six, seven, or eight amino acid substitutions at positions K117, T118, R121, E122, Y124, S125, S128, and/or S129 are provided, wherein the amino acid numbering is accordance with wild-type human IL-4 (SEQ ID NO:49 or SEQ ID NO:50.). In some embodiments, a substitution is made at position 121 of IL-4 (e.g., R121). In some embodiments, substitutions are made at positions 121 and 124 of IL-4 (e.g., R121 and Y124). In some embodiments, substitutions are made at positions 128 and 129 of IL-4 (e.g., S128G and S129A). In other embodiments, substitutions are made at positions 121, 124, and 125. In some embodiments, substitutions are made at positions 117, 118, 121, 122, 124, 125, 128, and 129 of IL-4. In other embodiments, the IL-4 mutein has the sequence 117R, 118V, 121Q, 122S, 124W, 125F, 128G, and 129A. In other embodiments, the IL-4 mutein has the sequence K117R, T118V, R121Q, E122S, Y124W, S125F, S128G, and S129A. In some embodiments, the IL-4 mutein substitutions cause an altered affinity for one or both of IL-13Rα1 and IL-13Rα2. In some embodiments, one or more substitutions in the IL-4 mutein at positions 117, 118, 121, 122, 124, 125, 128, and/or 129 cause an altered affinity for one or both of IL-13Rα1 and IL-13Rα2. In some embodiments, one or more substitutions in the IL-4 mutein at positions K117, T118, R121, E122, Y124, S125, S128, and/or S129 cause an altered affinity for one or both of IL-13Rα1 and IL-13Rα2. In some embodiments, one or more substitutions in the IL-4 mutein at positions K117R, T118V, R121Q, E122S, Y124W, S125F, S128G, and S129A cause an altered affinity for one or both of IL-13Rα1 and IL-13Rα2. In other embodiments, modified residues are at two or more, three or more, four or more, five, six, seven or 18 amino acids within the combined set of contact residues defined above.

In some embodiments, the IL-4 mutein results in higher affinity binding to a shared cytokine receptor relative to a wild-type cytokine, and the IL-4 mutein comprises one or two amino acid substitutions at positions S128 and/or S129, wherein the amino acid numbering is in accordance with wild-type human IL-4 of SEQ ID NO:49 or SEQ ID NO:50. In some embodiments, the IL-4 mutein results in higher affinity binding to a first shared cytokine receptor relative to a wild-type cytokine and reduced affinity to a second shared cytokine receptor relative to a wild-type cytokine. In some embodiments, the IL-4 mutein the first shared cytokine receptor is expressed at lower levels than the second shared cytokine receptor. In some embodiments, the IL-4 mutein the first shared cytokine receptor is expressed at higher levels than the second shared cytokine receptor. In some embodiments, the IL-4 mutein the reduction in affinity is at least 5-fold. In some embodiments, the IL-4 mutein the first shared cytokine receptor is γc and the second shared cytokine receptor is IL-13Rα1. In some embodiments, the IL-4 mutein the first shared cytokine receptor is IL-13Rα1 and the second shared cytokine receptor is γc. In some embodiments, the IL-4 mutein the first and second shared cytokine receptors are γc and IL-13Rα1. In some embodiments, the IL-4 mutein the IL-4 mutein results in higher affinity binding to a first and a second shared cytokine receptor relative to a wild-type cytokine. In some embodiments, the IL-4 mutein the increase in affinity is at least 10-fold. In some embodiments, the IL-4 mutein the shared cytokine receptor is common γchain (γc) or interleukin-13 receptor alpha 1 (IL-13Rα1). In some embodiments, the IL-4 mutein the IL-4 mutein further comprises one or more amino acid substitutions at positions selected from the group consisting of: K117, T118, R121, E122, Y124, and S125 wherein the amino acid numbering is in accordance with wild-type human IL-4 of SEQ ID NO:49 or SEQ ID NO:50. In some embodiments, the IL-4 mutein the IL-4 mutein comprises one or more amino acid substitutions selected from the group consisting of: K117R, T118V, R121Q, E122S, Y124W, S125F, S128G, and S129A, wherein the amino acid numbering is in accordance with wild-type human IL-4 of SEQ ID NO:49 or SEQ ID NO:50. In some embodiments, the IL-4 mutein the IL-4 mutein comprises the following amino acid substitutions: K117R, T118V, R121Q, E122S, Y124W, S125F, S128G, and S129A, wherein the amino acid numbering is in accordance with wild-type human IL-4 of SEQ ID NO:49 or SEQ ID NO:50. In some embodiments, the IL-4 mutein is one as described in U.S. Pat. No. 9,738,696, the disclosure of which is incorporated by reference herein in its entirety. In some embodiments, amino acid substitutions include without limitation those provided in any of the sequence disclosed in U.S. Pat. No. 9,738,696. In some embodiments, the amino acid sequence is 90% identical to an IL-4 sequence disclosed herein. In some embodiments, the amino acid sequence is 95% identical to an IL-4 sequence disclosed herein. In some embodiments, the amino acid sequence is 98% identical to an IL-4 sequence disclosed herein. In some embodiments, the amino acid sequence is 99% identical to an IL-4 sequence disclosed herein. In some embodiments, the polypeptide comprising the one or more modifications is linked to an IL-13 and/or IL-4 superkine immune cell targeting construct. In some embodiments, an IL-13 and/or IL-4 superkine immune cell targeting construct comprises one or more signaling domains derived from CD3-ζ, CD28, DAP10, OX-40, ICOS and CD137. In some embodiments, an IL-13 and/or IL-4 superkine immune cell targeting construct comprises one or more signaling domains derived from CD3-ζ. In some embodiments, an IL-13 and/or IL-4 superkine immune cell targeting construct comprises one or more signaling domains derived from CD28. In some embodiments, an IL-13 and/or IL-4 superkine immune cell targeting construct comprises one or more signaling domains derived from DAP10. In some embodiments, an IL-13 and/or IL-4 superkine immune cell targeting construct comprises one or more signaling domains derived from OX-40. In some embodiments, an IL-13 and/or IL-4 superkine immune cell targeting construct comprises one or more signaling domains derived from CD137.

The IL-4 superkine component of the construct may be at least about 50 amino acids in length, at least about 75, at least about 100, at least about 110, at least about 115 amino acids in length, up to the full-length of the wild-type protein at the transmembrane domain, i.e. about 116 amino acids in length. For example, the superkine may be fused to the hinge, transmembrane or signaling domains of a CAR. Exemplary polypeptide sequences are provided in SEQ ID NO:51-SEQ ID NO:55, SEQ ID NO:58-SEQ ID NO:62, and SEQ ID NO:64-SEQ ID NO:69. In some embodiments, the polypeptide sequence is as provided in any one of SEQ ID NO through 51-SEQ ID NO:55, SEQ ID NO:58 through SEQ ID NO:62, and/or SEQ ID NO:64 through SEQ ID NO:66. In some embodiments, the polypeptide sequence is SEQ ID NO:51. In some embodiments, the polypeptide sequence is SEQ ID NO:52. In some embodiments, the polypeptide sequence is SEQ ID NO:53. In some embodiments, the polypeptide sequence is SEQ ID NO:54. In some embodiments, the polypeptide sequence is SEQ ID NO:55. In some embodiments, the polypeptide sequence is SEQ ID NO:58. In some embodiments, the polypeptide sequence is SEQ ID NO:59. In some embodiments, the polypeptide sequence is SEQ ID NO:60. In some embodiments, the polypeptide sequence is SEQ ID NO:61. In some embodiments, the polypeptide sequence is SEQ ID NO:62. In some embodiments, the polypeptide sequence is SEQ ID NO:64. In some embodiments, the polypeptide sequence is SEQ ID NO:65. In some embodiments, the polypeptide sequence is SEQ ID NO:66. In some embodiments, the polypeptide sequence is SEQ ID NO:67. In some embodiments, the polypeptide sequence is SEQ ID NO:68. In some embodiments, the polypeptide sequence is SEQ ID NO:69. In some embodiments, the polypeptide sequence is 98% identical to any one of SEQ ID NO through 51-SEQ ID NO:55, SEQ ID NO:58 through SEQ ID NO:62, and/or SEQ ID NO:64 through SEQ ID NO:66. In some embodiments, the polypeptide sequence is 99% identical to any one of SEQ ID NO through 51-SEQ ID NO:55, SEQ ID NO:58 through SEQ ID NO:62, and/or SEQ ID NO:64 through SEQ ID NO:66. In some embodiments, any one of SEQ ID NO through 51-SEQ ID NO:55, SEQ ID NO:58 through SEQ ID NO:62, and/or SEQ ID NO:64 through SEQ ID NO:66 are linked to an IL-13 and/or IL-4 superkine immune cell targeting construct. In some embodiments, SEQ ID NO:51 is linked to an IL-13 and/or IL-4 superkine immune cell targeting construct. In some embodiments, SEQ ID NO:52 is linked to an IL-13 and/or IL-4 superkine immune cell targeting construct. In some embodiments, SEQ ID NO:53 is linked to an IL-13 and/or IL-4 superkine immune cell targeting construct. In some embodiments, SEQ ID NO:54 is linked to an IL-13 and/or IL-4 superkine immune cell targeting construct. In some embodiments, SEQ ID NO:55 is linked to an IL-13 and/or IL-4 superkine immune cell targeting construct. In some embodiments, SEQ ID NO:58 is linked to an IL-13 and/or IL-4 superkine immune cell targeting construct. In some embodiments, SEQ ID NO:59 is linked to an IL-13 and/or IL-4 superkine immune cell targeting construct. In some embodiments, SEQ ID NO:60 is linked to an IL-13 and/or IL-4 superkine immune cell targeting construct. In some embodiments, SEQ ID NO:61 is linked to an IL-13 and/or IL-4 superkine immune cell targeting construct. In some embodiments, SEQ ID NO:62 is linked to an IL-13 and/or IL-4 superkine immune cell targeting construct. In some embodiments, SEQ ID NO:64 is linked to an IL-13 and/or IL-4 superkine immune cell targeting construct. In some embodiments, SEQ ID NO:65 is linked to an IL-13 and/or IL-4 superkine immune cell targeting construct. In some embodiments, SEQ ID NO:66 is linked to an IL-13 and/or IL-4 superkine immune cell targeting construct. In some embodiments, SEQ ID NO:67 is linked to an IL-13 and/or IL-4 superkine immune cell targeting construct. In some embodiments, SEQ ID NO:68 is linked to an IL-13 and/or IL-4 superkine immune cell targeting construct. In some embodiments, SEQ ID NO:69 is linked to an IL-13 and/or IL-4 superkine immune cell targeting construct.

Table of IL-13 sequences is provided below.

TABLE 2

| SEQ ID NO: (Information) | Amino acid sequence |
|---|---|
| SEQ ID NO: 1 (IL-13 wildtype) | PGPVPPSTALRELIEELVNITQNQKAPLCNGSMVW SINLTAGMYCAALESLINVSGCSAIEKTQRMLSGF CPHKVSAGQFSSLHVRDTKIEVAQFVKDLLLHLKK LFREGQFN |
| SEQ ID NO: 2 | PGPVPPSTAVRALIEELINITQNQKAPLCNGSMVW SINRTAGMYCAALESLINVSGCSAIEKTQDMLSGF CPHKVSAGQFSSLHVRSSKIEVAQFVKDLLFHLRT LFREGQFN |
| SEQ ID NO: 3 | PGPVPPSTAIRELIEELINITQNQKAPLCNGSMVW SINLTAGMYCAALESLINVSGCSAIEKTQRMLSGF CPHKVSAGQFSSLHVRGSKIEVAQFVKDLLHHLRA LFREGQFN |
| SEQ ID NO: 4 | PGPVPPSTAVRELIEELINITQNQKAPLCNGSMVW SINRTAGMYCAALESLINVSGCSAIEKTQRMLSGF CPHKVSAGQFSSLHVRSSKIEVAQFVKDLLFHLRT LFREGQFN |
| SEQ ID NO: 5 | PGPVPPSTALIELIEELINITQNQKAPLCNGSMVW SINLTAGIYCAALESLINVSGCSAIEKTQRMLSGF CPHKVSAGQFSSLHVKGSKIEVAQFVKDLLHHLRA LMREGQFN |
| SEQ ID NO: 6 | PGPVPPSTAIRELIEELLNITQNQKAPLCNGSMVW SINLTAGMYCAALESLINVSGCSAIEKTQRMLSGF CPHKVSAGQFSSLHVMKSKIEVAQFVKDLLHHLRA LFREGQFN |
| SEQ ID NO: 7 | PGPVPPSTAIRELIEELINITQNQKAPLCNGSMVW SINLTAGMYCAALESLINVSGCSAIEKTQRMLSGF CPHKVSAGQFSSLHVRSSRIEVAQFVKDLLHHLRT LFREGQFN |
| SEQ ID NO: 8 | PGPVPPSTALRELIEELINITQNEKAPLCNGSMVW SINLTAGIYCAALESLINVSGCSAIEKTQRMLSGF CPHKVSAGQFSSLHVTGSKIEVAQFVKDLLYHLRA LFREGQFN |
| SEQ ID NO: 9 | PGPVPPSTALSELIEELINITQNQKAPLCNGSMVW SINPTAGMYCAALESLINVSGCSAIEKTQRMLSGF CPHKVAAGQFSSLHDKGSMIEVAQFVKDLLYHLRT LFREGQFN |
| SEQ ID NO: 10 | PGPVPPSTATRELIEELINITQNQKAPLCNGSMVW SINLTADMYCAALESLINVSGCSAIEKTQRMLSGF CPHKVSVGQFSSLHVRGSKIEVAQFVKDLLYHLRT LFREGQFN |
| SEQ ID NO: 11 | PGPVPPSTADIELIAELINITQNQKAPLCNGSMVW SINLTADMYCAALESLINVSGCSAIEKTQRMLSGF CPHKVSAGQFSSLHVKKTRIEVAQFVKDLLLHLKK LFKEGQFN |
| SEQ ID NO: 12 | PGPVPPSTAARELIEELVNITQNQKAPLCNGSMVW SINLTAGMYCAALESLINVSGCSAIEKTQRMLSGF CPHKVSAGQLSSLHVTGKRIEVAQFVKDLLNHLRA LFKEGQFN |
| SEQ ID NO: 13 | PGPVPPSTAVRELIEELVNITQNQKAPLCNGSMVW SINLTAGMYCAALESLINVSGCSAIEKTQRMLSGF CPHKVSAGQFSSLHVRDTRIEVAQFVKDLLNHLKE LFTEGQFN |
| SEQ ID NO: 14 | PGPVPPSTALSELMEELVNITQNQKAPLCNGSMVW SINLTAGMYCAALESLINVSGCSAIEKTQRMLSGF CPHKVSAGQFSSLHVRDSKIEVAQFVKDLLNHLKA LFKEGQFN |
| SEQ ID NO: 15 | GPVPPSTAFRELIEELVNITQNQKAPLCNGSMVWS INLTAGMYCAALESLINVSGCSAIEKTQRMLSGFC PHKVSPGQFSSLHVTNSRIEVAQFVKDLLNHLKAL FKEGQYN |

TABLE 2-continued

<div align="center">List of IL-13 Amino Acid Sequences</div>

| SEQ ID NO:<br>(Information) | Amino acid sequence |
|---|---|
| SEQ ID NO: 16 | GPVPPSTAHLELIEELINITQNQKAPLCNGSMVWS<br>INLTAGMYCAALESLINVSGCSAIEKTQRMLSGFC<br>PHKVSAGQFSSLHVKETRIEVAQFVKDLLNHLKTL<br>FKEGQFN |
| SEQ ID NO: 17 | PGPVPPSTAHLELIEELINITQNQKAPLCNGSMVW<br>SINPTAGMYCAALESLINVSGCSAIEKTQRMLSGF<br>CPHKVSAGQFSSLHVMDTRIEVAQFVKDLLLHLKK<br>LFKEGQFN |
| SEQ ID NO: 18 | PGPVPPSTAHRELIEELVNITQNQKAPLCNGSMVW<br>SINLTAGMYCAALESLINVSGCSAIEKTQRMLSGF<br>CPHKVSAGQFSSLHVTGRKIEVAQFVKDLLLHLKK<br>LFKEGQFN |
| SEQ ID NO: 19 | PGPVPPSTAHRELIEELVNITQNQKAPLCNGSMVW<br>RINRTAGMYCAALESLINVSGCSAIEKTQRMLSGF<br>CPHKVSAGQFSSLHVMDSRIEVAQFVKDLLNHLRA<br>LFKEGQFN |
| SEQ ID NO: 20 | PGPVPPSTAARELIEELFNITQNQKAPLCNGSMVW<br>SINLTAGMYCAALESLINVSGCSAIEKTKRMLSGF<br>CPHKVSAGQFPSLHVKKTRIEVAQFVKDLLIHLRK<br>LFKEGQFN |
| SEQ ID NO: 21<br>(Exemplary sequence<br>comprising R11I, V18I, R86K,<br>D87G, T88S, L101H, K104R,<br>K105A, F107M, referred to<br>herein as A5) | PGPVPPSTALIELIEELINITQNQKAPLCNGSMVWS<br>INLTAGMYCAALESLINVSGCSAIEKTQRMLSGFCP<br>HKVSAGQFSSLHVKGSKIEVAQFVKDLLHHLRALMR<br>EGQFN |
| SEQ ID NO: 22<br>(Exemplary sequence<br>comprising L10I, V18L, R86M,<br>D87K, T88S, L101H, K104R,<br>K105A, referred to herein as A6) | PGPVPPSTAIRELIEELLNITQNQKAPLCNGSMVWS<br>INLTAGMYCAALESLINVSGCSAIEKTQRMLSGFCP<br>HKVSAGQFSSLHVMKSKIEVAQFVKDLLHHLRALFR<br>EGQFN |
| SEQ ID NO: 23<br>(Exemplary sequence<br>comprising L10I, V18I, D87G,<br>T88S, L101H, K104R, K105A,<br>referred to herein as A7) | PGPVPPSTAIRELIEELINITQNQKAPLCNGSMVWS<br>INLTAGMYCAALESLINVSGCSAIEKTQRMLSGFCP<br>HKVSAGQFSSLHVRGSKIEVAQFVKDLLHHLRALFR<br>EGQFN |
| SEQ ID NO: 24<br>(Exemplary sequence<br>comprising L10I, V18I, D87S,<br>T88S, K89R, L101H, K104R,<br>K105T; referred to herein as A8) | PGPVPPSTAIRELIEELINITQNQKAPLCNGSMVWS<br>INLTAGMYCAALESLINVSGCSAIEKTQRMLSGFCP<br>HKVSAGQFSSLHVRSSRIEVAQFVKDLLHHLRTLFR<br>EGQFN |
| SEQ ID NO: 25<br>(Exemplary sequence<br>comprising L10V, V18I, D87S,<br>T88S, L101F, K104R, K105T,<br>referred to herein as A11 variant<br>1) | PGPVPPSTAVRELIEELINITQNQKAPLCNGSMVWS<br>IN*L*TAGMYCAALESLINVSGCSAIEKTQRMLSGFCP<br>H<u>K</u>VSAGQFSSLHVRSSKIEVAQFVKDLLFHLRTLFR<br>EGQFN |
| SEQ ID NO: 115<br>(Exemplary sequence<br>comprising L10V, V18I, D87S,<br>T88S, L101F, K104R, K105T,<br>referred to herein as A11 variant<br>2) | PGPVPPSTAVRELIEELINITQNQKAPLCNGSMVWS<br>IN*R*TAGMYCAALESLINVSGCSAIEKTQRMLSGFCP<br>H<u>K</u>VSAGQFSSLHVRSSKIEVAQFVKDLLFHLRTLFR<br>EGQFN |
| SEQ ID NO: 26<br>(Exemplary sequence<br>comprising V18I, R86T, D87G,<br>T88S, L101Y, K104R, K105A,<br>referred to herein as B2) | PGPVPPSTALRELIEELINITQNQKAPLCNGSMVW<br>SINLTAGMYCAALESLINVSGCSAIEKTQRMLSGF<br>CPHKVSAGQFSSLHVTGSKIEVAQFVKDLLYHLRA<br>LFREGQFN |
| SEQ ID NO: 27<br>(Exemplary sequence<br>comprising R11S, V18I, R86K,<br>D87G, T88S, K89M, L101Y, | PGPVPPSTALSELIEELINITQNQKAPLCNGSMVW<br>SINLTAGMYCAALESLINVSGCSAIEKTQRMLSGF<br>CPHKVSAGQFSSLHVKGSMIEVAQFVKDLLYHLRT<br>LFREGQFN |

TABLE 2-continued

List of IL-13 Amino Acid Sequences

| SEQ ID NO:<br>(Information) | Amino acid sequence |
| --- | --- |
| K104R, K105T, referred to<br>herein as B4) | |
| SEQ ID NO: 28<br>(Exemplary sequence<br>comprising L10T, V18I, D87G,<br>T88S, K89K, L10Y1, K104R,<br>K105T, referred to herein as B6) | PGPVPPSTATRELIEELINITQNQKAPLCNGSMVW<br>SINLTAGMYCAALESLINVSGCSAIEKTQRMLSGF<br>CPHKVSAGQFSSLHVRGSKIEVAQFVKDLLYHLRT<br>LFREGQFN |
| SEQ ID NO: 29<br>(Exemplary sequence<br>comprising L10D, R11I, V18I,<br>R86K, D87K, K89R, R108K,<br>referred to herein as C2) | PGPVPPSTADIELIEELINITQNQKAPLCNGSMVW<br>SINLTAGMYCAALESLINVSGCSAIEKTQRMLSGF<br>CPHKVSAGQFSSLHVKKTRIEVAQFVKDLLLHLKK<br>LFKEGQFN |
| SEQ ID NO: 30<br>(Exemplary sequence<br>comprising L10A, R86T, D87G,<br>T88K, K89R, L101N, K104R,<br>K105A, R108K, referred to<br>herein as C3) | PGPVPPSTAARELIEELVNITQNQKAPLCNGSMVW<br>SINLTAGMYCAALESLINVSGCSAIEKTQRMLSGF<br>CPHKVSAGQFSSLHVTGKRIEVAQFVKDLLNHLRA<br>LFKEGQFN |
| SEQ ID NO: 31<br>(Exemplary sequence<br>comprising L10V, K89R, L101N,<br>K105E, R108T, referred to<br>herein as C4) | PGPVPPSTAVRELIEELVNITQNQKAPLCNGSMVW<br>SINLTAGMYCAALESLINVSGCSAIEKTQRMLSGF<br>CPHKVSAGQFSSLHVRDTRIEVAQFVKDLLNHLKE<br>LFTEGQFN |
| SEQ ID NO: 32<br>(Exemplary sequence<br>comprising R11S, I14M, T88S,<br>L101N, K105A, R108K, referred<br>to herein as C7) | PGPVPPSTALSELMEELVNITQNQKAPLCNGSMVW<br>SINLTAGMYCAALESLINVSGCSAIEKTQRMLSGF<br>CPHKVSAGQFSSLHVRDSKIEVAQFVKDLLNHLKA<br>LFKEGQFN |
| SEQ ID NO: 33<br>(Exemplary sequence<br>comprising L10H, R11L, V18I,<br>R86K, D87E, K89R, L101N,<br>K105T, R108K, refered to herein<br>as C9) | PGPVPPSTAHLELIEELINITQNQKAPLCNGSMVW<br>SINLTAGMYCAALESLINVSGCSAIEKTQRMLSGF<br>CPHKVSAGQFSSLHVKETRIEVAQFVKDLLNHLKT<br>LFKEGQFN |
| SEQ ID NO: 34<br>(Exemplary sequence<br>comprising L10H, R11L, V18I,<br>R86M, K89R, R108K, referred to<br>herein as C10) | PGPVPPSTAHLELIEELINITQNQKAPLCNGSMVW<br>SINLTAGMYCAALESLINVSGCSAIEKTQRMLSGF<br>CPHKVSAGQFSSLHVMDTRIEVAQFVKDLLLHLKK<br>LFKEGQFN |
| SEQ ID NO: 35<br>(Exemplary sequence<br>comprising L10H, R86T, D87G,<br>T88R, R108K, referred to herein<br>as C11) | PGPVPPSTAHRELIEELVNITQNQKAPLCNGSMVW<br>SINLTAGMYCAALESLINVSGCSAIEKTQRMLSGF<br>CPHKVSAGQFSSLHVTGRKIEVAQFVKDLLLHLKK<br>LFKEGQFN |
| SEQ ID NO: 36<br>(Exemplary sequence<br>comprising L10H, R86M, T88S,<br>K89R, L101N, K104R, K105A,<br>R108K, referred to herein as<br>C12) | PGPVPPSTAHRELIEELVNITQNQKAPLCNGSMVW<br>SINLTAGMYCAALESLINVSGCSAIEKTQRMLSGF<br>CPHKVSAGQFSSLHVMDSRIEVAQFVKDLLNHLRA<br>LFKEGQFN |
| SEQ ID NO: 37<br>(Exemplary sequence<br>comprising L10A, V18F, R86F,<br>D87F, K89R, L10I1, K104R,<br>R108K, referred to herein as D7) | PGPVPPSTAARELIEELFNITQNQKAPLCNGSMVW<br>SINLTAGMYCAALESLINVSGCSAIEKTQRMLSGF<br>CPHKVSAGQFSSLHVKKTRIEVAQFVKDLLIHLRK<br>LFKEGQFN |
| SEQ ID NO: 38<br>(Exemplary sequence<br>comprising L10V, E12A, V18I,<br>R65D, D87S, T88S, L101F,<br>K104R, K105T, referred to<br>herein as IL-13dn) | PGPVPPSTAVRALIEELINITQNQKAPLCNGSMVW<br>SINLTAGMYCAALESLINVSGCSAIEKTQDMLSGF<br>CPHKVSAGQFSSLHVRSSKIEVAQFVKDLLFHLRT<br>LFREGQFN |

TABLE 2-continued

| SEQ ID NO:(Information) | Amino acid sequence |
|---|---|

| List of IL-13 Amino Acid Sequences | |
|---|---|
| SEQ ID NO: 39<br>signal peptide | MHPLLNPLLLALGLMALLLTTVIALTCLGGFASPG<br>PVPPSTAHRELIEELVNITQNQKAPLCNGSMVWSI<br>NLTAGMYCAALESLINVSGCSAIEKTQRMLSGFCP<br>HKVSAGQFSSLHVTGRKIEVAQFVKDLLLHLKKLF<br>KEGQFN |
| SEQ ID NO: 40<br>(Exemplary sequence<br>comprising L10V, E12A, V18I,<br>R65D, D87S, T88S, L101F,<br>K104R, K105T, referred to<br>herein as IL-13DN variant 1) | PGPVPPSTAVRALIEELINITQNQKAPLCNGSMVW<br>SIN*R*TAGMYCAALESLINVSGCSAIEKTQDMLSGF<br>CPHK̲VSAGQFSSLHVRSSKIEVAQFVKDLLFHLRT<br>LFREGQFN |
| SEQ ID NO: 41<br>(Exemplary sequence<br>comprising L10V, E12A, V18I,<br>R65D, D87S, T88S, L101F,<br>K104R, K105T, referred to<br>herein as IL-13DN variant 2) | PGPVPPSTAVRALIEELINITQNQKAPLCNGSMVW<br>SIN*L̲*TAGMYCAALESLINVSGCSAIEKTQDMLSGF<br>CPHK̲VSAGQFSSLHVRSSKIEVAQFVKDLLFHLRT<br>LFREGQFN |
| SEQ ID NO: 42<br>wild-type IL-13 including an<br>additional methionine at the N-<br>terminus | MPGPVPPSTALRELIEELVNITQNQKAPLCNGSMV<br>WSINLTAGMYCAALESLINVSGCSAIEKTQRMLSG<br>FCPHKVSAGQFSSLHVRDTKIEVAQFVKDLLLHLK<br>KLFREGQFN |
| SEQ ID NO: 43<br>circularly permuted IL-13 | MYCAALESLINVSGCSAIEKTQRMLSGFCPHKVSA<br>GQFSSLHVRDTKIEVAQFVKDLLLHLKKLFREGQF<br>NGGSGPGPVPPSTALRELIEELVNITQNQKAPLCN<br>GSMVWSINLTAG |
| SEQ ID NO: 44<br>Circularly permuted IL-13 | MYCAALESLINVSGCSAIEKTQRMLSGFCPHKVSA<br>GQFSSLHVRDTKIEVAQFVKDLLLHLKKLFREGQF<br>NGGSGMPGPVPPSTALRELIEELVNITQNQKAPLC<br>NGSMVWSINLTAG |
| SEQ ID NO: 45<br>circularly permuted IL-13 "A11"<br>variant | MYCAALESLINVSGCSAIEKTQRMLSGFCPHKVSA<br>GQFSSLHVRSSKIEVAQFVKDLLFHLRTLFREGQF<br>NGGSGPGPVPPSTAVRELIEELINITQNQKAPLCN<br>GSMVWSINRTAG |
| SEQ ID NO: 46<br>circularly permuted IL-13 | MYCAALESLINVSGCSAIEKTQRMLSGFCPHKVSA<br>GQFSSLHVRSSKIEVAQFVKDLLFHLRTLFREGQF<br>NGGSGMPGPVPPSTAVRELIEELINITQNQKAPLC<br>NGSMVWSINRTAG |
| SEQ ID NO: 47<br>circularly permuted IL-13 "DN"<br>variant | MYCAALESLINVSGCSAIEKTQDMLSGFCPHKVSA<br>GQFSSLHVRSSKIEVAQFVKDLLFHLRTLFREGQF<br>NGGSGPGPVPPSTAVRALIEELINITQNQKAPLCN<br>GSMVWSINLTAG |
| SEQ ID NO: 48<br>circular permuted IL-13 | MYCAALESLINVSGCSAIEKTQDMLSGFCPHKVSA<br>GQFSSLHVRSSKIEVAQFVKDLLFHLRTLFREGQF<br>NGGSGMPGPVPPSTAVRALIEELINITQNQKAPLC<br>NGSMVWSINLTAG |

Table of IL-4 sequences is provided below.

TABLE 3

| SEQ ID NO:(Information) | Amino acid sequence |
|---|---|

| List of IL-4 Amino Acid Sequences | |
|---|---|
| SEQ ID NO: 49<br>(IL-4 wildtype with signal<br>peptide) | MGLTSQLLPPLFFLLACAGNFVHGHKCDITLQEII<br>KTLNSLTEQKTLCTELTVTDIFAASKNTTEKETFC<br>RAATVLRQFYSHHEKDTRCLGATAQQFHRHKQLIR<br>FLKRLDRNLWGLAGLNSCPVKEANQSTLENFLERL<br>KTIMREKYSKCSS |
| SEQ ID NO: 50<br>IL-4 including an additional | MHKCDITLQEIIKTLNSLTEQKTLCTELTVTDIFA<br>ASKDTTEKETFCRAATVLRQFYSHHEKDTRCLGAT |

TABLE 3-continued

List of IL-4 Amino Acid Sequences

| SEQ ID NO:<br>(Information) | Amino acid sequence |
|---|---|
| methionine at the N-terminus"<br>starting<br>SEQ ID NO: 51<br>KFR | AQQFHRHKQLIRFLKRLDRNLWGLAGLNSCPVKEA<br>NQSTLENFLERLKTIMREKYSKCSS<br>KCDITLQEIIKTLNSLTEQKTLCTELTVTDIFAAS<br>KNTTEKETFCRAATVLRQFYSHHEKDTRCLGATAQ<br>QFHRHKQLIRFLKRLDRNLWGLAGLNSCPVKEANQ<br>STLENFLERLKTIMKEKFRKCSS |
| SEQ ID NO: 52<br>RGA | MDTTEKETFCRAATVLRQFYSHHEKDTRCLGATAQ<br>QFHRHKQLIRFLKRLDRNLWGLAGLNSCPVKEANQ<br>STLENFLERLRVIMQSKWFKCGAGGNGGHKCDITL<br>QEIIKTLNSLTEQKTLCTELTVTDIFAAS |
| SEQ ID NO: 53<br>cirularly permuted wild-type IL-4 | MDTTEKETFCRAATVLRQFYSHHEKDTRCLGATAQ<br>QFHRHKQLIRFLKRLDRNLWGLAGLNSCPVKEANQ<br>STLENFLERLKTIMREKYSKCSSGGNGGHKCDITL<br>QEIIKTLNSLTEQKTLCTELTVTDIFAAS |
| SEQ ID NO: 54<br>circularly permuted "KFR" IL-4<br>variant | MDTTEKETFCRAATVLRQFYSHHEKDTRCLGATAQ<br>QFHRHKQLIRFLKRLDRNLWGLAGLNSCPVKEANQ<br>STLENFLERLKTIMKEKFRKCSSGGNGGHKCDITL<br>QEIIKTLNSLTEQKTLCTELTVTDIFAASRQFYSH<br>HEKDTRCLGATAQQFHRHKQLIRFLKRLDRNLWGL<br>AGLNSCPVKEANQSTLENFLERLRVIMQSKWEKCG<br>AGGNGGHKCDITLQEIIKTLNSLTEQKTLCTELTV<br>TDIFAAS |
| SEQ ID NO: 55<br>circularly permuted "KF" IL-4<br>variant | MDTTEKETFCRAATVLRQFYSHHEKDTRCLGATAQ<br>QFHRHKQLIRFLKRLDRNLWGLAGLNSCPVKEANQ<br>STLENFLERLKTIMKEKFKCSSGGNGGHKCDITLQ<br>EIIKTLNSLTEQKTLCTELTVTDIFAAS |

Table of cytokine fusions containing either IL-4 or IL-13
sequences is provided below.

TABLE 4

List of Amino Acid Sequences

| SEQ ID NO:<br>(Information) | Amino acid sequence |
|---|---|
| SEQ ID NO: 56<br>IL13-BAD (targeting IL13Ra2;<br>referred to as C11; GGGGS<br>linker) | PGPVPPSTAHRELIEELVNITQNQKAPLCNGSMVWS<br>INLTAGMYCAALESLINVSGCSAIEKTQRMLSGFCP<br>HKVSAGQFSSLHVTGRKIEVAQFVKDLLLHLKKLFK<br>EGQFNGGGGSMFQIPEFEPSEQEDSSSAERGLGPS<br>PAGDGPSGSGKHHRQAPGLLWDASHQQEQPTSSSHH<br>GGAGAVEIRSRHSAYPAGTEDDEGMGEEPSPFRGRS<br>RAAPPNLWAAQRYGRELRRMSDEFVDSFKKGLPRPK<br>SAGTATQMRQSSSWTRVFQSWWDRNLGRGSSAPSQ |
| SEQ ID NO: 57<br>A11-BAD (A11 is an IL13Ra1<br>agonist; GGGGS linker) | PGPVPPSTAVRELIEELINITQNQKAPLCNGSMVWS<br>INRTAGMYCAALESLINVSGCSAIEKTQRMLSGFCP<br>HKVSAGQFSSLHVRSSKIEVAQFVKDLLFHLRTLFR<br>EGQFNGGGGSMFQIPEFEPSEQEDSSSAERGLGPS<br>PAGDGPSGSGKHHRQAPGLLWDASHQQEQPTSSSHH<br>GGAGAVEIRSRHSAYPAGTEDDEGMGEEPSPFRGRS<br>RAAPPNLWAAQRYGRELRRMSDEFVDSFKKGLPRPK<br>SAGTATQMRQSSSWTRVFQSWWDRNLGRGSSAPSQ |
| SEQ ID NO: 58<br>KFR-BAD (KFR targets Type 2<br>IL-4R; GGGGS linker) | KCD ITLQEIIKTL NSLTEQKTLC TELTVTDIFA<br>ASKNTTEKETFCRAATVLRQFYSHHEKDTRCLGATA<br>QQFHRHKQLIRFLKRLDRNLWGLAGLNSCPVKEANQ<br>STLENFLERLKTIMKEKFRKCSSGGGGSMFQIPEFE<br>PSEQEDSSSAERGLGPSPAGDGPSGSGKHHRQAPGL<br>LWDASHQQEQPTSSSHHGGAGAVEIRSRHSAYPAGT<br>EDDEGMGEEPSPFRGRSRAAPPNLWAAQRYGRELRR<br>MSDEFVDSFKKGLPRPKSAGTATQMRQSSSWTRVFQ<br>SWWDRNLGRGSSAPSQ |
| SEQ ID NO: 59<br>pKFR4-Bad-H6 | MDTTEKETFCRAATVLRQFYSHHEKDTRCLGATAQQ<br>FHRHKQLIRFLKRLDRNLWGLAGLNSCPVKEANQST<br>LENFLERLKTIMKEKFRKCSSGGNGGHKCDITLQEI |

TABLE 4-continued

| List of Amino Acid Sequences | |
|---|---|
| SEQ ID NO: (Information) | Amino acid sequence |
| | IKTLNSLTEQKTLCTELTVTDIFAASGSFQIPEFEP SEQEDSSSAERGLGPSPAGDGPSGSGKHHRQAPGLL WDASHQQEQPTSSSHHGGAGAVEIRSRHSAYPAGTE DDEGMGEEPSPFRGRSRAAPPNLWAAQRYGRELRRM SDEFVDSFKKGLPRPKSAGTATQMRQSSSWTRVFQS WWDRNLGRGSSAPSQHHHHHH |
| SEQ ID NO: 60 cpKFR4-Bad fusion; GS linker | MDTTEKETFCRAATVLRQFYSHHEKDTRCLGATAQQ FHRHKQLIRFLKRLDRNLWGLAGLNSCPVKEANQST LENFLERLKTIMKEKFRKCSSGGNGGHKCDITLQEI IKTLNSLTEQKTLCTELTVTDIFAASGSFQIPEFEP SEQEDSSSAERGLGPSPAGDGPSGSGKHHRQAPGLL WDASHQQEQPTSSSHHGGAGAVEIRSRHSAYPAGTE DDEGMGEEPSPFRGRSRAAPPNLWAAQRYGRELRRM SDEFVDSFKKGLPRPKSAGTATQMRQSSSWTRVFQS WWDRNLGRGSSAPSQ |
| SEQ ID NO: 61 cpIL4-BAD; GS linker | MDTTEKETFCRAATVLRQFYSHHEKDTRCLGAT AQQFHRHKQLIRFLKRLDRNLWGLAGLNSCPVKEAN QSTLENFLERLKTIMREKYSKCSSGGNGGHKCDITL QEIIKTLNSLTEQKTLCTELTVTDIFAASGSFQIPE FEPSEQEDSSSAERGLGPSPAGDGPSGSGKHHRQAP GLLWDASHQQEQPTSSSHHGGAGAVEIRSRHSAYPA GTEDDEGMGEEPSPFRGRSRAAPPNLWAAQRYGREL RRMSDEFVDSFKKGLPRPKSAGTATQMRQSSSWTRV FQSWWDRNLGRGSSAPSQ |
| SEQ ID NO: 62 cpIL-4-BAD H6; GS linker | MDTTEKETFCRAATVLRQFYSHHEKDTRCLGATAQQ FHRHKQLIRFLKRLDRNLWGLAGLNSCPVKEANQST LENFLERLKTIMREKYSKCSSGGNGGHKCDITLQEI IKTLNSLTEQKTLCTELTVTDIFAASGSFQIPEFEP SEQEDSSSAERGLGPSPAGDGPSGSGKHHRQAPGLL WDASHQQEQPTSSSHHGGAGAVEIRSRHSAYPAGTE DDEGMGEEPSPFRGRSRAAPPNLWAAQRYGRELRRM SDEFVDSFKKGLPRPKSAGTATQMRQSSSWTRVFQS WWDRNLGRGSSAPSQHHHHHH |
| SEQ ID NO: 63 IL13-BAD (targets IL13Ra1 and is referred to as IL13DN) | PGPVPPSTAVRALIEELINITQNQKAPLCNGSMVWS INRTAGMYCAALESLINVSGCSAIEKTQDMLSGFCP HKVSAGQFSSLHVRSSKIEVAQFVKDLLFHLRTLFR EGQFNGGGGSGGGGSGGGGSFQIPEFEPSEQEDSSS AERGLGPSPAGDGPSGSGKHHRQAPGLLWDASHQQE QPTSSSHHGGAGAVEIRSRHSAYPAGTEDDEGMGEE PSPFRGRSRAAPPNLWAAQRYGRELRRMSDEFVDSF KKGLPRPKSAGTATQMRQSSSWTRVFQSWWDRNLGR GSSAPSQ |
| SEQ ID NO: 64 IL-4-BclxL; GGGGS linker | KCDITLQEIIKTLNSLTEQKTLCTELTVTDIFAASK NTTEKETFCRAATVLRQFYSHHEKDTRCLGATAQQF HRHKQLIRFLKRLDRNLWGLAGLNSCPVKEANQSTL ENFLERLKTIMREKYSKCSSGGGGSMSQSNRELVV DFLSYKLSQKGYSWSQFSDVEENRTEAPEGTESEME TPSAINGNPSWHLADSPAVNGATGHSSSLDAREVIP MAAVKQALREAGDEFELRYRRAFSDLTSQLHITPGT AYQSFEQVVNELFRDGVNWGRIVAFFSEGGALCVES VDKEMQVLVSRIAAWMATYLNDHLEPWIQENGGWDT FVELYGNNAAAESRKGQERFNRWFLTGMTVAGVVLL GSLFSRK |
| SEQ ID NO: 65 PRX321 | MDTTEKETFCRAATVLRQFYSHHEKDTRCLGATAQQ FHRHKQLIRFLKRLDRNLWGLAGLNSCPVKEANQST LENFLERLKTIMREKYSKCSSGGNGGHKCDITLQEI IKTLNSLTEQKTLCTELTVTDIFAASKASGGPEGGS LAALTAHQACHLPLETFTRHRQPRGWEQLEQCGYPV QRLVALYLAARLSWNQVDQVIRNALASPGSGGDLGE AIREQPEQARLALTLAAAESERFVRQGTGNDEAGAA NGPADSGDALLERNYPTGAEFLGDGGDVSFSTRGTQ NWTVERLLQAHRQLEERGYVFVGYHGTFLEAAQSIV FGGVRARSQDLDAIWRGFYIAGDPALAYGYAQDQEP DARGRIRNGALLRVYVPRSSLPGFYRTSLTLAAPEA AGEVERLIGHPLPLRLDAITGPEEEGGRLETILGWP LAERTVVIPSAIPTDPRNVGGDLDPSSIPDKEQAIS ALPDYASQPGKPPKDEL |

TABLE 4-continued

| List of Amino Acid Sequences | |
| --- | --- |
| SEQ ID NO:<br>(Information) | Amino acid sequence |
| SEQ ID NO: 66<br>cpS4-Bad-H6 | MDTTEKETFCRAATVLRQFYSHHEKDTRCLGATAQQ<br>FHRHKQLIRFLKRLDRNLWGLAGLNSCPVKEANQST<br>LENFLERLRVIMQSKWFKCGAGGNGGHKCDITLQEI<br>IKTLNSLTEQKTLCTELTVTDIFAASGSFQIPEFEP<br>SEQEDSSSAERGLGPSPAGDGPSGSGKHHRQAPGLL<br>WDASHQQEQPTSSSHHGGAGAVEIRSRHSAYPAGTE<br>DDEGMGEEPSPFRGRSRAAPPNLWAAQRYGRELRRM<br>SDEFVDSFKKGLPRPKSAGTATQMRQSSSWTRVFQS<br>WWDRNLGRGSSAPSQHHHHHH |
| SEQ ID NO: 67<br>cpS4-Bad | MDTTEKETFCRAATVLRQFYSHHEKDTRCLGATAQQ<br>FHRHKQLIRFLKRLDRNLWGLAGLNSCPVKEANQST<br>LENFLERLRVIMQSKWFKCGAGGNGGHKCDITLQEI<br>IKTLNSLTEQKTLCTELTVTDIFAASGSFQIPEFEP<br>SEQEDSSSAERGLGPSPAGDGPSGSGKHHRQAPGLL<br>WDASHQQEQPTSSSHHGGAGAVEIRSRHSAYPAGTE<br>DDEGMGEEPSPFRGRSRAAPPNLWAAQRYGRELRRM<br>SDEFVDSFKKGLPRPKSAGTATQMRQSSSWTRVFQS<br>WWDRNLGRGSSAPSQ |
| SEQ ID NO: 68<br>IL-4-Bad-H6 | MHKCDITLQEIIKTLNSLTEQKTLCTELTVTDIFAA<br>SKDTTEKETFCRAATVLRQFYSHHEKDTRCLGATAQ<br>QFHRHKQLIRFLKRLDRNLWGLAGLNSCPVKEANQS<br>TLENFLERLKTIMREKYSKCSSGSFQIPEFEPSEQE<br>DSSSAERGLGPSPAGDGPSGSGKHHRQAPGLLWDAS<br>HQQEQPTSSSHHGGAGAVEIRSRHSAYPAGTEDDEG<br>MGEEPSPFRGRSRAAPPNLWAAQRYGRELRRMSDEF<br>VDSFKKGLPRPKSAGTATQMRQSSSWTRVFQSWWDR<br>NLGRGSSAPSQHHHHHH |
| SEQ ID NO: 69<br>IL-4-Bad-H6 | MHKCDITLQEIIKTLNSLTEQKTLCTELTVTDIFAA<br>SKDTTEKETFCRAATVLRQFYSHHEKDTRCLGATAQ<br>QFHRHKQLIRFLKRLDRNLWGLAGLNSCPVKEANQS<br>TLENFLERLKTIMREKYSKCSSGSFQIPEFEPSEQE<br>DSSSAERGLGPSPAGDGPSGSGKHHRQAPGLLWDAS<br>HQQEQPTSSSHHGGAGAVEIRSRHSAYPAGTEDDEG<br>MGEEPSPFRGRSRAAPPNLWAAQRYGRELRRMSDEF<br>VDSFKKGLPRPKSAGTATQMRQSSSWTRVFQSWWDR<br>NLGRGSSAPSQ |

IL-4 and/or IL-13 Mutein Fusion Proteins

The IL-4 and/or IL-13 muteins can be prepared as fusion or chimeric polypeptides, in particular those listed herein, that include a subject IL-4 and/or IL-13 mutein and a heterologous polypeptide (i.e., a polypeptide that is not IL-4 and/or IL-13 or a mutant thereof) (see, e.g., U.S. Pat. No. 6,451,308). Exemplary heterologous polypeptides can increase the circulating half-life of the chimeric polypeptide in vivo, and may, therefore, further enhance the properties of the mutant IL-4 and/or IL-13 polypeptides. In various embodiments, the polypeptide that increases the circulating half-life may be a serum albumin, such as human serum albumin, PEG, PEG-derivatives, or the Fc region of the IgG subclass of antibodies that lacks the IgG heavy chain variable region. Exemplary Fc regions can include a mutation that inhibits complement fixation and Fc receptor binding, or it may be lytic, i.e., able to bind complement or to lyse cells via another mechanism, such as antibody-dependent complement lysis (ADCC; U.S. Ser. No. 08/355,502 filed Dec. 12, 1994).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-4 and/or IL-13 polypeptides can include the entire Fc region, or a smaller portion that retains the ability to extend the circulating half-life of a chimeric polypeptide of which it is a part. In addition, full-length or fragmented Fc regions can be variants of the wild-type molecule. In some embodiments, the IL-4 and/or IL-13 mutein fusion protein (e.g., an IL-4 and/or IL-13 mutein as described herein) includes an IgG1, IgG2, IgG3, or IgG4 Fc region (see, for example, sequences in FIG. 2A-2B). In some embodiments, the Fc region comprises the substitution N297A.

In some embodiments, the IL-4 and/or IL-13 mutein is linked directly or indirectly to the heterologous fusion polypeptide.

In some embodiments, the IL-4 and/or IL-13 mutein is linked directly to the Fc region. In some embodiments, the IL-4 and/or IL-13 mutein is linked to the Fc region via a linker peptide, such as GGGGS. In some embodiments, the linker is (GGGGS)n, wherein n is an integer between 1 and 10. In some embodiments, the linker is GGGGS (SEQ ID NO:117). In some embodiments, the linker is GGGGSGGGGS (SEQ ID NO:118). In some embodiments, the 60 linker is GGGGSGGGGSGGGGS (SEQ ID NO:119). In some embodiments, the linker is GGGGSGGGGSGGGGSGGGGS (SEQ ID NO:120). In some embodiments, the linker is GGGGSGGGGSGGGGSGGGGSGGGGS (SEQ ID NO:121).

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994).

In other embodiments, the chimeric polypeptide can include a subject IL-4 and/or IL-13 mutein and a polypeptide that functions as an antigenic tag, such as a FLAG sequence. FLAG sequences are recognized by biotinylated, highly specific, anti-FLAG antibodies, as described herein (see also Blanar et al., Science 256:1014, 1992; LeClair et al., Proc. Natl. Acad. Sci. USA 89:8145, 1992). In some embodiments, the chimeric polypeptide further comprises a C-terminal c-myc epitope tag.

In other embodiments, the chimeric polypeptide includes the mutant IL-4 and/or IL-13 polypeptide and a heterologous polypeptide that functions to enhance expression or direct cellular localization of the mutant IL-4 and/or IL-13 polypeptide, such as the Aga2p agglutinin subunit (see, e.g., Boder and Wittrup, Nature Biotechnol. 15:553-7, 1997).

In other embodiments, a chimeric polypeptide including a mutant IL-4 and/or IL-13 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the chimeric polypeptide comprises a fusion to an antibody or an antigen-binding portion thereof that disrupts the interaction between the PD-1 receptor and its ligand, PD-L1, and or is an antibody to a component of the PD-1/PD-L1 signaling pathway. Antibodies known in the art which bind to PD-1 and disrupt the interaction between the PD-1 and its ligand, PD-L1, and stimulate an anti-tumor immune response, are suitable for use in the chimeric polypeptides disclosed herein. In some embodiments, the antibody or antigen-binding portion thereof binds specifically to PD-1. For example, antibodies that target PD-1 and which can find used in the present invention include, e.g., but are not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (cemiplimab, Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies include anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in the chimeric polypeptides disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, is suitable for use in the chimeric polypeptides disclosed herein. In some embodiments, the chimeric polypeptide comprises a fusion to an anti-PD-1 antibody. In some embodiments, the chimeric polypeptide comprises a fusion to an anti-PD-L1 antibody.

In some embodiments, the chimeric polypeptide comprises a fusion to an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the chimeric polypeptides disclosed herein. In some embodiments, the chimeric polypeptide comprises a fusion to an anti-CTLA-4 antibody.

In some embodiments, the chimeric polypeptide comprises a fusion to an antibody or an antigen-binding portion thereof that targets LAG-3 and disrupts its interaction with MHC class II molecules. An exemplary antibody that targets LAG-3 is IMP321 (Immutep), currently undergoing human trials. Other suitable antibodies that target LAG-3 are disclosed in U.S. Patent Application 2011/0150892, herein incorporated by reference. It will be understood by one of ordinary skill that any antibody which binds to LAG-3, disrupts its interaction with MHC class II molecules, and stimulates an anti-tumor immune response, is suitable for use in the chimeric polypeptides disclosed herein. In some embodiments, the chimeric polypeptide comprises a fusion to an anti-LAG-3 antibody.

In some embodiments, the chimeric polypeptide comprises a fusion to an antibody or an antigen-binding portion thereof that targets B7-H3 or B7-H4. The B7 family does not have any defined receptors but these ligands are upregulated on tumor cells or tumor-infiltrating cells. An exemplary antibody that targets B7-H3 is MGA271 (Macrogenics) is currently undergoing human trials. Other suitable antibodies that target B7 family members are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the chimeric polypeptides disclosed herein. In some embodiments, the chimeric polypeptide comprises a fusion to an anti-B7-H3 or B7-H4 antibody.

In some embodiments, the chimeric polypeptide comprises a fusion to an antibody or an antigen-binding portion thereof that targets TIM-3 and disrupts its interaction with galectin 9. Suitable antibodies that target TIM-3 are disclosed in U.S. Patent Application 2013/0022623, herein incorporated by reference. It will be understood by one of ordinary skill that any antibody which binds to TIM-3, disrupts its interaction with galectin 9, and stimulates an anti-tumor immune response, is suitable for use in the chimeric polypeptides disclosed herein. In some embodiments, the chimeric polypeptide comprises a fusion to an anti-TIM-3 antibody.

In some embodiments, the chimeric polypeptide comprises a fusion to an antibody or an antigen-binding portion thereof that targets 4-1BB/CD137 and disrupts its interaction with CD137L. It will be understood by one of ordinary skill that any antibody which binds to 4-1BB/CD137, disrupts its interaction with CD137L or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-4-1BB/CD137 antibody.

In some embodiments, the chimeric polypeptide comprises a fusion to an antibody or an antigen-binding portion thereof that targets GITR and disrupts its interaction with its ligand. It will be understood by one of ordinary skill that any antibody which binds to GITR, disrupts its interaction with GITRL or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-GITR antibody.

In some embodiments, the chimeric polypeptide comprises a fusion to an antibody or an antigen-binding portion thereof that targets OX40 and disrupts its interaction with its ligand. It will be understood by one of ordinary skill that any antibody which binds to OX40, disrupts its interaction with OX40L or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-OX40 antibody.

In some embodiments, the chimeric polypeptide comprises a fusion to an antibody or an antigen-binding portion thereof that targets CD40 and disrupts its interaction with its ligand. It will be understood by one of ordinary skill that any antibody which binds to CD40, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-CD40 antibody In some embodiments, the chimeric polypeptide comprises a fusion to an antibody or an antigen-binding portion thereof that targets ICOS and disrupts its interaction with its ligand. It will be understood by one of ordinary skill that any antibody which binds to ICOS, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-ICOS antibody.

In some embodiments, the chimeric polypeptide comprises a fusion to an antibody or an antigen-binding portion thereof that targets CD28 and disrupts its interaction with its ligand. It will be understood by one of ordinary skill that any antibody which binds to CD28, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-CD28 antibody.

In some embodiments, the chimeric polypeptide comprises a fusion to an antibody or an antigen-binding portion thereof that targets IFNα and disrupts its interaction with its ligand. It will be understood by one of ordinary skill that any antibody which binds to IFNα, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-IFNα antibody.

In some embodiments, the chimeric polypeptide comprises a fusion to a tumor antigen or polypeptide targeting a tumor antigen. Generally, tumor antigens allow for distinguishing the tumor cells from their normal cellular counterparts and can include, for example, tumor-specific antigens (TSA) as well as tumor-associated antigens (TAA). In some embodiments, a tumor antigen is a protooncogene and/or a tumor suppressor, as well as overexpressed or aberrantly expressed cellular proteins, tumor antigens produced by oncogenic viruses, oncofetal antigens, altered cell surface glycolipids and glycoproteins, and/or cell type-specific differentiation antigens. Such tumor antigens can include melanoma antigens, cancer-testis antigens, epithelial tumor antigens, cell cycle regulatory proteins, prostate specific antigens (including prostate carcinoma antigens, such as for example those disclosed in U.S. Pat. No. 5,538,866) lymphoma (U.S. Pat. Nos. 4,816,249; 5,068,177; and 5,227, 159). Tumor antigens can include for example, but are not limited to, HMW mucins bound by 2G3 and 369F10, c-erbB-2 related tumor antigen (an approximately 42 kD or 55 kD glycoprotein), the approximately 40, 60, 100 and 200 kD antigens bound by 113F1, 9-O-acetyl GD3, p97, alphafetoprotein (AFP) (for example, for germ cell tumors and/or hepatocellular carcinoma), carcinoembryonic antigen (CEA) (for example, for bowel cancers occasional lung or breast cancer), CA-125 (for example, for ovarian cancer), MUC-1 (for example, for breast cancer), epithelial tumor antigen (ETA) (for example, for breast cancer), tyrosinase (for example, for malignant melanoma), melanoma-associated antigen (MAGE) (for example, for malignant melanoma), cancer/testis antigen 1 (CTAG1B), melanoma-associated antigen 1 (MAGEA1), abnormal Ras products, abnormal p53 products, overexpression of cyclins (including, for example, cyclin B1), mutation in fibronectin, post-translational alteration in the MUC1 glycoprotein, secreted tumor antigens (including, for example, gangliosides).

Included as superkines are amino acid and nucleic acid coding sequences that are 90%, 95%, 98% or 99% identical to these sequences, longer sequences that comprise those sequences but also include additional nucleotides at the 3' or 5' end, for example any number of additional nucleotides or codons, such as 3, 6, 9, 12 or more nucleotides, or up to about 12, 20, 50 or 100 additional nucleotides, and any sequence that encodes the same amino acid sequence as these nucleic acids due to the degeneracy of the genetic code. In particular, sequences that are codon optimized (CO) for expression by the desired host are contemplated as part of the invention. In some embodiments, the amino acid sequence is 90% identical. In some embodiments, the amino acid sequence is 95% identical. In some embodiments, the amino acid sequence is 98% identical. In some embodiments, the amino acid sequence is 99% identical. In some embodiments, the polypeptide is linked to an IL-13 and/or IL-4 superkine immune cell targeting construct. In some embodiments, an IL-13 and/or IL-4 superkine immune cell targeting construct comprises one or more signaling domains derived from CD3-ζ, CD28, DAP10, OX-40, ICOS and CD137. In some embodiments, an IL-13 and/or IL-4 superkine immune cell targeting construct comprises one or more signaling domains derived from CD3-ζ. In some embodiments, an IL-13 and/or IL-4 superkine immune cell targeting construct comprises one or more signaling domains derived from CD28. In some embodiments, an IL-13 and/or IL-4 superkine immune cell targeting construct comprises one or more signaling domains derived from DAP10. In some embodiments, an IL-13 and/or IL-4 superkine immune cell targeting construct comprises one or more signaling domains derived from OX-40. In some embodiments, an IL-13 and/or IL-4 superkine immune cell targeting construct comprises one or more signaling domains derived from CD137. In some embodiments, an IL-13 and/or IL-4 superkine immune cell targeting construct comprises an IL-13 variant/IL-13 superkine including those provided in FIG. 2. In some embodiments, an IL-13 and/or IL-4 superkine immune cell targeting construct comprises an IL-13 variant/IL-13 superkine including those provided in SEQ ID NO:2 through SEQ ID NO:38.

In some embodiments, an IL-13 and/or IL-4 superkine immune cell targeting construct comprises an IL-13 variant/IL-13 superkine including those provided in SEQ ID NO:2 through SEQ ID NO:38 target immunosuppressive cells of the TME (tumor microenvironment) such as tumor associated macrophages and MDSCs (myeloid-derived suppressor cells) in order for T cells, including CAR-T cells, to provide an improved therapeutic benefit. In some embodiments, an IL-13 and/or IL-4 superkine immune cell targeting construct comprises an IL-13 variant/IL-13 superkine including those targeting Type 2 IL4R and/or targeting IL13ra2 which can direct the T cells cells to tumor antigens. In some embodiments, an IL-13 and/or IL-4 superkine immune cell targeting construct comprises an IL-13 variant/IL-13 superkine including those provided in SEQ ID NO:2 through SEQ ID NO:38 can also direct the T cells, including CAR-T cells, cells to tumor antigens.

The present invention also contemplates the use of T-cell targeting, such as for example CAR-T cell targeting, for the delivery of and expression of an IL-4 and/or Il-13 mutein or variant to and/or at the tumor site. In some embodiments, the use of T-cell targeting, such as for example CAR-T cell targeting, is employed for the delivery of an IL-4/and or IL-13 mutein or variant to the tumor site. In some embodiments, the use of T-cell targeting, such as for example CAR-T cell targeting, is employed to obtain the expression of an IL-4/and or IL-13 mutein or variant at the tumor site. As such, the present invention also provides immune cell expressing constructs, wherein the immune cell used for targeting also comprises a transgene encoding and IL-4/and or IL-13 mutein or variant thereof, wherein the IL-4/and or IL-13 mutein or variant thereof is expressed at the tumor site. Immune cell expressing constructs comprising IL-4/and or IL-13 superkine sequences are provided and can include any IL-4/and or IL-13 sequence as described herein. In some embodiments, the IL-4/and or IL-13 mutein is any IL-4/and or IL-13 mutein or variant disclosed herein. In some embodiments, the IL-4/and or IL-13 mutein sequence is 90% identical to any one of SEQ ID NO:2 through SEQ ID NO:38. In some embodiments, the virus is targeted to the tumor by another cytokine, such as an IL-4 or IL-13, and expresses an IL-4 or IL-13 mutein or IL-4 or IL-13 variant, or in some cases and IL-4/Il-13 variant dual cytokine fusion. In some embodiments, the IL-4 and/or IL-13 and/or an IL-4/IL-13 dual cytokine as described herein is used to target immune cell to the tumor cell and the IL-2 or IL-2 variant is expressed by a transgene in the immune cell. In some embodiments, an IL-13 and/or IL-4 superkine immune cell targeting construct comprises an IL-13 variant/IL-13 superkine including those provided in SEQ ID NO:2 through SEQ ID NO:38 that can be expressed by the T cells, including CAR-T cells. In some embodiments, an IL-13Ralpha2 targeting moeity will be used as a targeting moeity and an IL-2 mutein will be a could be the transgene expressed by the targeted immune cell.

TABLE 5

| List of Exemplary IL-2 Muteins | |
|---|---|
| Amino Acid Sequences SEQ ID NO: (Information) | Amino acid sequence |
| SEQ ID NO: 91 (also referred to as H9-F42A) | APTSSSTKKTQLQLEHLLLDLQMILNGINNYKNPKLTRMLTA KFYMPKKATELKHLQCLEEELKPLEEVLNLAQSKNFHFDPRD VVSNINVFVLELKGSETTFMCEYADETATIVEFLNRWITFCQ SIISTLT |
| SEQ ID NO: 92 (also referred to as H9-K43N) | APTSSSTKKTQLQLEHLLLDLQMILNGINNYKNPKLTRMLTF NFYMPKKATELKHLQCLEEELKPLEEVLNLAQSKNFHFDPRD VVSNINVFVLELKGSETTFMCEYADETATIVEFLNRWITFCQ SIISTLT |
| SEQ ID NO: 93 (H9-F42A/Y45A; H9-FYAA) | APTSSSTKKTQLQLEHLLLDLQMILNGINNYKNPKLTRMLTA KFAMPKKATELKHLQCLEEELKPLEEVLNLAQSKNFHFDPRD VVSNINVFVLELKGSETTFMCEYADETATIVEFLNRWITFCQ SIISTLT |

TABLE 5-continued

<u>List of Exemplary IL-2 Muteins</u>

Amino Acid Sequences
SEQ ID NO:
(Information)        Amino acid sequence

SEQ ID NO: 94
(H9-F42A/E62A; H9-FEAA)
APTSSSTKKTQLQLEHLLLDLQMILNGINNYKNPKLTRMLTA
KFYMPKKATELKHLQCLEEALKPLEEVLNLAQSKNFHFDPRD
VVSNINVFVLELKGSETTFMCEYADETATIVEFLNRWITFCQ
SIISTLT

SEQ ID NO: 95
(H9-F42A/Y45A/E62A; H9-
FYEAAA).
APTSSSTKKTQLQLEHLLLDLQMILNGINNYKNPKLTRMLTA
KFAMPKKATELKHLQCLEEALKPLEEVLNLAQSKNFHFDPRD
VVSNINVFVLELKGSETTFMCEYADETATIVEFLNRWITFCQ
SIISTLT

SEQ ID NO: 96
APTSSSTKKTQLQLEHLLLDLQMILNGINNYKNPKLTRMLTF
KFYMPKKATELKHLQCLEEELKPLEEVLNLARSKNFHLRPRD
LISNINVIVLELKGSETTFMCEYADETATIVEFLNRWITFCQ
SIISTLT

SEQ ID NO: 97
APTSSSTKKTQLQLEHLLLDLQMILNGINNYKNPKLTRMLTF
KFYMPKKATELKHLQCLEEELKPLEEVLNLARSKNFHLRPRD
VISNINVIVLELKGSETTFMCEYADETATIVEFLNRWITFCQ
SIISTLT

SEQ ID NO: 98
APTSSSTKKTQLQLEHLLLDLQMILNGINNYKNPKLTRMLTF
KFYMPKKATELKHLQCLEEELKPLEEVLNLARSKNFHLIPRD
VISNINVIVLELKGSETTFMCEYADETATIVEFLNRWITFCQ
SIISTLT

SEQ ID NO: 99
APTSSSTKKTQLQLEHLLLDLQMILNGINNYKNPKLTRMLTF
KFYMPKKATELKHLQCLEEELKPLEEVLNLAHSKNFHLTPRD
VVSNINVFILELKGSETTFMCEYADETATIVEFLNRWITFCQ
SIISTLT

SEQ ID NO: 100
APTSSSTKKTQLQLEHLLLDLQMILNGINNYKNPKLTRMLTF
KFYMPKKATELKHLQCLEEELKPLEEVLNLANSKNFHFDPRD
VVSNVNVFVLELKGSETTFMCEYADETATIVEFLNRWITECQ
SIISTLT

SEQ ID NO: 101
APTSSSTKKTQLQLEHLLLDLQMVLNGINNYKNPKLTRMLTF
KFYMPKKATELKHLQCLEEELKPLEEVLNLASSKNFHFDPRD
VVSNINVFVLELKGSETTFMCEYADETATIVEFLNRWITFCQ
SIISTLT

SEQ ID NO: 102
APTSSSTKKTQLQLEHLLLDLQMILNGINNYKNPKLTRMLTF
KFYMPKKATELKHLQCLEEELKHLEEVLNLANSKNFHVTPRD
VVSNINVFVLELKGSETTFMCEYADETATIVEFLNRWITFCQ
SIISTLT

SEQ ID NO: 103
APTSSSTKKTQLQLEHLLLDLQMILNGINNYKNPKLTRMLTF
KFYMPKKATELKHLQCLEEELKPLEEVLNLAHSKNFHFDPRD
VVSNINVFVLELKGSETTFMCEYADETATIVEFLNRWITFCQ
SIISTLT

SEQ ID NO: 104
APTSSSTKKTQLQLEHLLLDLQMILNGINNYKNPKLTRMLTF
KFYMPKKATELKHLQCLEEELKPLEEVLNLASSKNFHFDPRD
VVSNINVFVLELKGSETTFMCEYADETATIVEFLNRWITFCQ
SIISTLT

SEQ ID NO: 105
APTSSSTKKTQLQLEHLLLDLQMILNGINNYKNPKLTRMLTF
KFYMPKKATELKHLQCLEEELKPLEEVLNLANSKNFHFDPRD
VVSNINVFVLELKGSETTFMCEYADETATIVEFLNRWITFCQ
SIISTLT

SEQ ID NO: 106
APTSSSTKKTQLQLEHLLLDLQMILNGINNYKNPKLTRMLTF
KFYMPKKATELKHLQCLEEELKPLEEVLNLASSKNFHLTPRD
VISNINVFVLELKGSETTFMCEYADETATIVEFLNRWITFCQ
SIISTLT

SEQ ID NO: 107
(H9)
APTSSSTKKTQLQLEHLLLDLQMILNGINNYKNPKLTRMLTF
KFYMPKKATELKHLQCLEEELKPLEEVLNLAQSKNFHFDPRD
VVSNINVFVLELKGSETTFMCEYADETATIVEFLNRWITFCQ
SIISTLT

TABLE 5-continued

List of Exemplary IL-2 Muteins

Amino Acid Sequences
SEQ ID NO:
(Information)                Amino acid sequence SEQ ID NO: 108          H9D10
IL-2 agonist            APTSSSTKKTQLQLEHLLLDLQMILNGINNYKNPKLTRMLTFK
                        FYMPKKATELKHLQCLEEELKPLEEVLNLAHSKNFHFDPRDVVSNI
                        NVFVLELKGSETTFMCEYADETATIVEFLNRWITFCQSIISTLT SEQ ID NO: 109          H9E10
IL-2 agonist            APTSSSTKKTQLQLEHLLLDLQMILNGINNYKNPKLTRMLTFKFYM
                        PKKATELKHLQCLEEELKPLEEVLNLASSKNFHFDPRDVVSNINVF
                        VLELKGSETTFMCEYADETATIVEFLNRWITFCQSIISTLT SEQ ID NO: 110          H9G8
IL-2 agonist            APTSSSTKKTQLQLEHLLLDLQMILNGINNYKNPKLTRMLTFKFYM
                        PKKATELKHLQCLEEELKPLEEVLNLANSKNFHFDPRDVVSNINVF
                        VLELKGSETTFMCEYADETATIVEFLNRWITFCQSIISTLT SEQ ID NO: 111          H9B1
IL-2 agonist            APTSSSTKKTQLQLEHLLLDLQMILNGINNYKNPKLTRMLTFKFYM
                        PKKATELKHLQCLEEELKPLEEVLNLANSKNFHFDPRDVVSNVNVF
                        VLELKGSETTFMCEYADETATIVEFLNRWITFCQSIISTLT SEQ ID NO: 112          APTSSSTKKTQLQLEHLLLDLQMVLNGINNYKNPKLTRMLTFKFYM
B11                     PKKATELKHLQCLEEELKPLEEVLNLASSKNFHFDPRDVVSNINVF
                        VLELKGSETTFMCEYADETATIVEFLNRWITFCQSIISTLT

SEQ ID NO: 113          APTSSSTKKTQLQLEHLLLDLQMILNGINNYKNPKLTRMLTFKFYM
Wild-type IL-2          PKKATELKHLQCLEEELKPLEEVLNLAQSKNFHLRPRDLISNINVI
                        VLELKGSETTFMCEYADETATIVEFLNRWITFCQSIISTLT SEQ ID NO: 114          APTSSSTKKTQLQLEHLLLDLQMILNGINNYKNPKLTRMLTFKFYM
H4 (with linker)        PKKATELKHLQCLEEELKPLEEVLNLASSKNFHLDPRDVISNINVF
                        VLELKGSETTFMCEYADETATIVEFLNRWITFCQSIISTLTGGGGS
                        GGGGSGGGGSDKTHTCPPCPAPELLGGPSVFLFPPKPKDTLMISRT
                        PEVTCVVVDVSHEDPEVKFNWYVDGVEVHNAKTKPRE-
                        EQYASTYRV
                        VSVLTVLHQDWLNGKEYKCKVSNKALPAPIEKTISKAKGQPREPQV
                        YTLPPSREEMTKNQVSLTCLVKGFYPSDIAVEWESNGQPENNYKTT
                        PPVLDSDGSFFLYSKLTVDKSRWQQGNVFSCSVMHEALHNHYTQKS
                        LSLSPGK*

SEQ ID NO: 116          APTSSSTKKTQLQLEHLLLDLQMILNGINNYKNPKLTRMLTFKFYM
H4 (without linker)     PKKATELKHLQCLEEELKPLEEVLNLASSKNFHDDLDPRDVISNINVF
                        VLELKGSETTFMCEYADETATIVEFLNRWITFCQSIISTLT

Table of selected nucleic acid sequences for cytokines and cytokine fusions containing either IL-4 or IL-13 sequences is provided below.

TABLE 6

List of Selected Nucelic Acid Sequences

SEQ ID NO:
(Information)     Nucleic acid sequence

SEQ ID NO: 83    atgcacaaatgcgacattaccctgcaagagatcattaagaccctgaacagcctgac
IL-4             cgagcaaaagaccctgtgtaccgaactgaccgtcacggacatcttcgctgcgtcca
                 aggacactacggaaaaggaaacgttctgtcgtgcggcgacggtgctgcgccagttc
                 tacagccaccatgagaaagatacccgttgcctcggtgcgaccgcgcaacagttcca
                 ccgtcacaaacagctgattcgcttcctgaagcgtctggatcgcaacctgtggggtt
                 tggcgggtctgaactcctgtccagtcaaagaagccaatcagtctacgctggaaaac
                 tttttggagcgtctgaaaactatcatgcgtgagaagtacagcaaatgcagcagc SEQ ID NO: 70    atggataccaccgagaaagaaacgttctgccgtgctgccactgtcctgcgccagtt
cpIL4            ttacagccatcacgaaaaggacacccgttgcctgggtgcgacggcgcagcaattcc
                 accgccacaaacagctgattcgtttcctgaagcgtctggaccgtaacctgtggggt
                 ctggcgggtctgaacagctgtccagtgaaagaagcgaatcagagcaccttggagaa
                 tttcctcgaacgcctgaaaaccatcatgcgtgagaaatacagcaagtgttctagcg
                 gcggtaacggtggccacaaatgcgatatcaccctgcaagagatcattaagacgctg
                 aactccttgacggaacaaaagaccctgtgtactgagctgacggtcaccgacatttt
                 cgcggcgtcc TABLE 6-continued List of Selected Nucelic Acid Sequences

| SEQ ID NO: (Information) | Nucleic acid sequence |
|---|---|
| SEQ ID NO: 71 cpKFR | atggatactaccgagaaagaaacgttttgccgtgctgcgaccgtcctgcgtcagtt ctacagccaccacgaaaaggacacccgctgtctgggtgcgactgcccaacaattcc atcgtcacaaacagctgattcgtttcctgaagcgtctggaccgcaacctgtggggt ctggcgggcttgaactcctgcccagtcaaagaagcgaaccaaagcaccctggaaaa cttcttggagcgtctgaaaacgatcatgaaagagaagttccgcaagtgtagcagcg gtggtaatggtggccacaagtgcgacattacgctgcaggaaatcattaagaccctg aactctctgaccgagcagaaaaccctcgtaccgagctgacggtgacggatatctt tgcggcgagc |
| SEQ ID NO: 72 cpS4 | atggataccaccgaaaaagaaacttttgtcgtgccgcgactgtcctgcgccagtt ctacagccaccacgaaaaggacacccgttgcctgggtgcgaccgctcaacaattcc atcgccacaaacagctgattcgttcctgaaacgtctggatcgcaacctgtggggt ctggcgggtttgaacagctgtccagtcaaagaagcgaaccagagcaccctggaaaa ctttctggagcgtctgcgtgttatcatgcagagcaagtggttcaagtgcggtgcgg gtggcaatggtggccacaagtgtgacattaccttgcaagagattatcaaaacgctg aactctctgaccgagcaaaagacgctgtgcaccgagctgacggtgacggacatctt cgcggcgtcc |
| SEQ ID NO: 73 pro-apoptotic Bcl-2 family member nucleic acid molecule, variant BAD | ggtagctttcagatcccggaatttgagccgagcgagcaagaggattcaagcagcgc ggagcgcggtctgggtccgagcccggcaggcgacggtccgagcggcagcggcaagc atcaccgccaggcgccaggcctgctgtgggatgcatcgcatcaacaggaacaaccg acgagcagcagccatcatggtggcgctggtgcggttgagattagatcgcgccactc cgcatatcctgccggcaccgaagatgacgaaggcatgggcgaggaaccgagcccgt tccgtggccgtagccgtgctgcaccgccgaatctgtgggccgcacagcgttatggt cgcgagttgcgtcgcatgtccgacgagtttgttgactccttcaagaaaaggtttacc gcgtccgaaatctgccggtaccgcgacgcagatgcgtcagagcagcagctggaccc gcgtgtttcaatcttggtgggatcgtaatctgggtcgtggtagcagcgcaccgagc caa |
| SEQ ID NO: 74 IL-4-Bad fusion | atgcacaaatgcgacattaccctgcaagagatcattaagaccctgaacagcctgac cgagcaaaagaccctgtgtaccgaactgaccgtcacggacatcttcgctgcgtcca aggacactacggaaaaggaaacgttctgtcgtgcggcgacggtgctgcgccagttc tacagccaccatgagaaagataccccgttgcctcggtgcgaccgcgcaacagttcca ccgtcacaaacagctgattcgcttcctgaagcgtctggatcgcaacctgtggggtt tggcgggtctgaactcctgtccagtcaaagaagccaatcagtctacgctggaaaac tttttggagcgtctgaaaactatcatgcgtgagaagtacagcaaatgcagcagcgg tagctttcagatcccggaatttgagccgagcgagcaagaggattcaagcagcgcgg agcgcggtctgggtccgagcccggcaggcgacggtccgagcggcagcggcaagcat caccgccaggcgccaggcctgctgtgggatgcatcgcatcaacaggaacaaccgac gagcagcagccatcatggtggcgctggtgcggttgagattagatcgcgccactccg catatcctgccggcaccgaagatgacgaaggcatgggcgaggaaccgagcccgttc cgtggccgtagccgtgctgcaccgccgaatctgtgggccgcacagcgttatggtcg cgagttgcgtcgcatgtccgacgagtttgttgactccttcaagaaaggtttaccgc gtccgaaatctgccggtaccgcgacgcagatgcgtcagagcagcagctggacccgc gtgtttcaatcttggtgggatcgtaatctgggtcgtggtagcagcgcaccgagcaa |
| SEQ ID NO: 75 cpIL4-Bad fusion | atggataccaccgagaaagaaacgttctgccgtgctgccactgtcctgcgccagtt ttacagccatcacgaaaaggacacccgttgcctgggtgcgacggcgcagcaattcc accgccacaaacagctgattcgtttcctgaagcgtctggaccgtaacctgtggggt ctggcgggtctgaacagctgtccagtgaaagaagcgaatcagagcaccttggagaa tttcctcgaacgcctgaaaaccatcatgcgtgagaaatacagcaagtgttctagcg gcggtaacggtggccacaaatgcgatatcaccctgcaagagatcattaagacgctg aactccttgacggaacaaaagaccctgtgtactgagctgacggtcaccgacatttt cgcggcgtccggtagctttcagatcccggaatttgagccgagcgagcaagaggatt caagcagcgcgggagcgcggtctgggtccgagcccggcaggcgacggtccgagcggc agcggcaagcatcaccgccaggcgccaggcctgctgtgggatgcatcgcatcaaca ggaacaaccgacgagcagcagccatcatggtggcgctggtgcggttgagattagat cgcgccactccgcatatcctgccggcaccgaagatgacgaaggcatgggcgaggaa ccgagcccgttccgtggccgtagccgtgctgcaccgccgaatctgtgggccgcaca gcgttatggtcgcgagttgcgtcgcatgtccgacgagtttgttgactccttcaaga aggtttaccgcgtccgaaatctgccggtaccgcgacgcagatgcgtcagagcagc agctggacccgcgtgtttcaatcttggtgggatcgtaatctgggtcgtggtagcag cgcaccgagccaa |
| SEQ ID NO: 76 cpKFR4-Bad fusion | atggatactaccgagaaagaaacgttttgccgtgctgcgaccgtcctgcgtcagtt ctacagccaccacgaaaaggacacccgctgtctgggtgcgactgcccaacaattcc atcgtcacaaacagctgattcgtttcctgaagcgtctggaccgcaacctgtggggt ctggcgggcttgaactcctgcccagtcaaagaagcgaaccaaagcaccctggaaaa cttcttggagcgtctgaaaacgatcatgaaagagaagttccgcaagtgtagcagcg gtggtaatggtggccacaagtgcgacattacgctgcaggaaatcattaagaccctg aactctctgaccgagcagaaaaccctcgtaccgagctgacggtgacggatatctt tgcggcgagcggtagctttcagatcccggaatttgagccgagcgagcaagaggatt caagcagcgcgggagcgcggtctgggtccgagcccggcaggcgacggtccgagcggc agcggcaagcatcaccgccaggcgccaggcctgctgtgggatgcatcgcatcaaca |

TABLE 6-continued

List of Selected Nucelic Acid Sequences

| SEQ ID NO:<br>(Information) | Nucleic acid sequence |
|---|---|
| | ggaacaaccgacgagcagcagccatcatggtggcgctggtgcggttgagattagat<br>cgcgccactccgcatatcctgccggcaccgaagatgacgaaggcatgggcgaggaa<br>ccgagcccgttccgtggccgtagccgtgctgcaccgccgaatctgtgggccgcaca<br>gcgttatggtcgcgagttgcgtcgcatgtccgacgagtttgttgactccttcaaga<br>aaggtttaccgcgtccgaaatctgccggtaccgcgacgcagatgcgtcagagcagc<br>agctggacccgcgtgtttcaatcttggtgggatcgtaatctgggtcgtggtagcag<br>cgcaccgagccaa |
| SEQ ID NO: 77<br>cpS4-Bad<br>fusion | atggataccaccgaaaaagaaacttttttgtcgtgccgcgactgtcctgcgccagtt<br>ctacagccaccacgaaaaggacacccgttgcctgggtgcgaccgctcaacaattcc<br>atcgccacaaacagctgattcgtttcctgaaacgtctggatcgcaacctgtggggt<br>ctggcgggtttgaacagctgtccagtcaaagaagcgaaccagagcaccctggaaaa<br>ctttctggagcgtctgcgtgttatcatgcagagcaagtggttcaagtgcggtgcgg<br>gtggcaatggtggccacaagtgtgacattaccttgcaagagattatcaaaacgctg<br>aactctctgaccgagcaaaagacgctgtgcaccgagctgacggtgacggacatctt<br>cgcggcgtccggtagctttcagatcccggaatttgagccgagcgagcaagaggatt<br>caagcagcgcggagcgcggtctgggtccgagcccggcaggcgacggtccgagcggc<br>agcggcaagcatcaccgccaggcgccaggcctgctgtgggatgcatcgcatcaaca<br>ggaacaaccgacgagcagcagccatcatggtggcgctggtgcggttgagattagat<br>cgcgccactccgcatatcctgccggcaccgaagatgacgaaggcatgggcgaggaa<br>ccgagcccgttccgtggccgtagccgtgctgcaccgccgaatctgtgggccgcaca<br>gcgttatggtcgcgagttgcgtcgcatgtccgacgagtttgttgactccttcaaga<br>aaggtttaccgcgtccgaaatctgccggtaccgcgacgcagatgcgtcagagcagc<br>agctggacccgcgtgtttcaatcttggtgggatcgtaatctgggtcgtggtagcag<br>cgcaccgagccaa |
| SEQ ID NO: 78<br>cpIL-4-Bad | atgcacaaatgcgacattaccctgcaagagatcattaagaccctgaacagcctgac<br>cgagcaaaagaccctgtgtaccgaactgaccgtcacggacatcttcgctgcgtcca<br>aggacactacggaaaaggaaacgttctgtcgtgcggcgacggtgctgcgccagttc<br>tacagccaccatgagaaagataccccgttgcctcggtgcgaccgcgcaacagttcca<br>ccgtcacaaacagctgattcgcttcctgaagcgtctggatcgcaacctgtggggtt<br>tggcgggtctgaactcctgtccagtcaaagaagccaatcagtctacgctggaaaac<br>ttttggagcgtctgaaaactatcatgcgtgagaagtacagcaaatgcagcagcgg<br>tagctttcagatcccggaatttgagccgagcgagcaagaggattcaagcagcgcgg<br>agcgcggtctgggtccgagcccggcaggcgacggtccgagcggcagcggcaagcat<br>caccgccaggcgccaggcctgctgtgggatgcatcgcatcaacaggaacaaccgac<br>gagcagcagccatcatggtggcgctggtgcggttgagattagatcgcgccactccg<br>catatcctgccggcaccgaagatgacgaaggcatgggcgaggaaccgagcccgttc<br>cgtggccgtagccgtgctgcaccgccgaatctgtgggccgcacagcgttatggtcg<br>cgagttgcgtcgcatgtccgacgagtttgttgactccttcaagaaaggtttaccgc<br>gtccgaaatctgccggtaccgcgacgcagatgcgtcagagcagcagctggacccgc<br>gtgtttcaatcttggtgggatcgtaatctgggtcgtggtagcagcgcaccgagcca<br>acaccaccatcaccatcactaa |
| SEQ ID NO: 79<br>bp cpIL-4-<br>Bad | atggataccaccgagaaagaaacgttctgccgtgctgcccactgtcctgcgccagtt<br>ttacagccatcacgaaaaggacacccgttgcctgggtgcgaggcgcagcaattcc<br>accgccacaaacagctgattcgtttcctgaagcgtctggaccgtaacctgtggggt<br>ctggcgggtctgaacagctgtccagtgaaagaagcgaatcagagcaccttggagaa<br>tttcctgaacgcctgaaaaccatcatgcgtgagaaatacagcaagtgttctagcg<br>gcggtaacggtggccacaaatgcgatatcaccctgcaagagatcattaagacgctg<br>aactccttgacggaacaaaagaccctgtgtactgagctgacggtcaccgacatttt<br>cgcggcgtccggtagctttcagatcccggaatttgagccgagcgagcaagaggatt<br>caagcagcgcggagcgcggtctgggtccgagcccggcaggcgacggtccgagcggc<br>agcggcaagcatcaccgccaggcgccaggcctgctgtgggatgcatcgcatcaaca<br>ggaacaaccgacgagcagcagccatcatggtggcgctggtgcggttgagattagat<br>cgcgccactccgcatatcctgccggcaccgaagatgacgaaggcatgggcgaggaa<br>ccgagcccgttccgtggccgtagccgtgctgcaccgccgaatctgtgggccgcaca<br>gcgttatggtcgcgagttgcgtcgcatgtccgacgagtttgttgactccttcaaga<br>aaggtttaccgcgtccgaaatctgccggtaccgcgacgcagatgcgtcagagcagc<br>agctggacccgcgtgtttcaatcttggtgggatcgtaatctgggtcgtggtagcag<br>cgcaccgagccaacaccaccatcaccatcac |
| SEQ ID NO: 80<br>bp cpS4-Bad | atggataccaccgaaaaagaaacttttttgtcgtgccgcgactgtcctgcgccagtt<br>ctacagccaccacgaaaaggacacccgttgcctgggtgcgaccgctcaacaattcc<br>atcgccacaaacagctgattcgtttcctgaaacgtctggatcgcaacctgtggggt<br>ctggcgggtttgaacagctgtccagtcaaagaagcgaaccagagcaccctggaaaa<br>ctttctggagcgtctgcgtgttatcatgcagagcaagtggttcaagtgcggtgcgg<br>gtggcaatggtggccacaagtgtgacattaccttgcaagagattatcaaaacgctg<br>aactctctgaccgagcaaaagacgctgtgcaccgagctgacggtgacggacatctt<br>cgcggcgtccggtagctttcagatcccggaatttgagccgagcgagcaagaggatt<br>caagcagcgcggagcgcggtctgggtccgagccccggcaggcgacggtccgagcggc<br>agcggcaagcatcaccgccaggcgccaggcctgctgtgggatgcatcgcatcaaca<br>ggaacaaccgacgagcagcagccatcatggtggcgctggtgcggttgagattagat<br>cgcgccactccgcatatcctgccggcaccgaagatgacgaaggcatgggcgaggaa<br>ccgagcccgttccgtggccgtagccgtgctgcaccgccgaatctgtgggccgcaca |

TABLE 6-continued

| List of Selected Nucelic Acid Sequences |
| --- |

| SEQ ID NO: (Information) | Nucleic acid sequence |
| --- | --- |
| | gcgttatggtcgcgagttgcgtcgcatgtccgacgagtttgttgactccttcaaga aaggtttaccgcgtccgaaatctgccggtaccgcgacgcagatgcgtcagagcagc agctggacccgcgtgtttcaatcttggtgggatcgtaatctgggtcgtggtagcag cgcaccgagccaacaccaccatcaccatcactaa |
| SEQ ID NO: 81 bp pKFR4-Bad-H6 | atggatactaccgagaaagaaacgttttgccgtgctgcgaccgtcctgcgtcagtt ctacagccaccacgaaaaggacacccgctgtctgggtgcgactgcccaacaattcc atcgtcacaaacagctgattcgtttcctgaagcgtctggaccgcaacctgtggggt ctggcgggcttgaactcctgcccagtcaaagaagcgaaccaaagcaccctggaaaa cttcttggagcgtctgaaaacgatcatgaaagagaagttccgcaagtgtagcagcg gtggtaatggtggccacaagtgcgacattacgctgcaggaaatcattaagaccctg aactctctgaccgagcagaaaaccctctgtaccgagctgacggtgacggatatctt tgcggcgagcggtagctttcagatcccggaatttgagccgagcgagcaagaggatt caagcagcgcgggagcgcggtctgggtccgagcccggcaggcgacggtccgagcggc agcggcaagcatcaccgccaggcgccaggcctgctgtgggatgcatcgcatcaaca ggaacaaccgacgagcagcagccatcatggtggcgctggtgcggttgagattagat cgcgccactccgcatatcctgccggcaccgaagatgacgaaggcatgggcgaggaa ccgagcccgttccgtggccgtagccgtgctgcaccgccgaatctgtgggccgcaca gcgttatggtcgcgagttgcgtcgcatgtccgacgagtttgttgactccttcaaga aaggtttaccgcgtccgaaatctgccggtaccgcgacgcagatgcgtcagagcagc agctggacccgcgtgtttcaatcttggtgggatcgtaatctgggtcgtggtagcag cgcaccgagccaacaccaccatcaccatca |
| SEQ ID NO: 82 IL-13DN | TTTGTAATAAAAAAAACCTATAAATATTCCGGATTATTCATACCGTCCCACCATCGG GCGCGGATCTATGCTACTAGTAAATCAGTCACACCAAGGCTTCAATAAGGAACACA CAAGCAAGATGGTAAGCGCTATTGTTTTATATGTGCTTTTGGCGGCGGCGGCGCAT TCTGCCTTTGCGGGATCCGCGCCCCCATGCCCATCATGCCCAGCACCTGAGTTCCT GGGGGGACCATCAGTCTTCCTGTTCCCCCCAAAACCCAAGGACACTCTCATGATCT CCCGGACCCCTGAGGTCACGTGCGTGGTGGTGGACGTGAGCCAGGAAGACCCCGAG GTCCAGTTCAACTGGTACGTGGATGGCGTGGAGGTGCATAATGCCAAGACAAAGCC GCGGGAGGAGCAGTTCAACAGCACGTACCGTGTGGTCAGCGTCCTCACCGTCCTGC ACCAGGACTGGCTGAACGGCAAGGAGTACAAGTGCAAGGTCTCCAACAAAGGCCTC CCGTCCTCCATCGAGAAAACCATCTCCAAAGCCAAAGGGCAGCCCCGAGAGCCACA GGTGTACACCCTGCCCCCATCCCAGGAGGAGATGACCAAGAACCAGGTCAGCCTGA CCTGCCTGGTCAAAGGCTTCTACCCCAGCGACATCGCCGTGGAGTGGGAGAGCAAT GGGCAGCCGGAGAACAACTACAAGACCACGCCTCCCGTGCTGGACTCCGACGGCTC CTTCTTCCTCTACAGCAGGCTAACCGTGGACAAGAGCAGGTGGCAGGAGGGGAATG TCTTCTCATGCTCCGTGATGCATGAGGCTCTGCACAACCACTACACACAGAAGAGC CTCTCCCTGTCTCCGGGTAAAGGAGGCGGAAGCGGATCCCCAGGCCCTGTGCCTCC CTCTACAGCCGTTCGTGCGCTCATTGAGGAGCTGATTAACATCACCCAGAACCAGA AGGCTCCGCTCTGCAATGGCAGCATGGTATGGAGCATCAACCGGACAGCTGGCATG TACTGTGCAGCCCTGGAATCCCTGATCAACGTGTCAGGCTGCAGTGCCATCGAGAA GACCCAGGACATGCTGAGCGGATTCTGCCCGCACAAGGTCTCAGCTGGGCAGTTTT CCAGCTTGCATGTCAGGAGTAGTAAGATCGAGGTGGCCCAGTTTGTAAAGGACCTG CTCTTCCATTTAAGGACTCTTTTTAGGGAGGGACAGTTCAACGCGGCCGCCCATCA TCACCACCATCACCACCATTAATGAAGATCTGATCCTTTCCTGGGACCCGGCAAGA ACCAAAAACTCACTCTCTTCAAGGAAATCCGTAATGTTAAACCCGACACGATGAAG CTTGTCGTTGGATGGAAAGGAAAAGAGTTCTACAGGGAAACTTGGACCCGCTTCAT GGAAGACAGCTTCCCCATTGTTAACGACCAAGAAGTGATGGATGTTTTCCTTGTTG TCAACATGCGTCCCACTAGACCCAACC |

TABLE 7

| List of Selected Fusuion Partners |
| --- |

| SEQ ID NO: (Information) | Amino acid sequence | | |
| --- | --- | --- | --- |
| SEQ ID NO: 84 BAD amino acid sequence | MFQIP KHHRQAPGLL TSSSHHGGAG MGEEPSPFRG RMSDEFVDSF SWTRVFQSWW | EFEPSEQEDS WDASHQQEQP AVEIRSRHSA RSRAAPPNLW KKGLPRPKSA DRNLGRGSSA | SSAERGLGPS PAGDGPSGSG YPAGTEDDEG AAQRYGRELR GTATQMRQSS PSQ |
| SEQ ID NO: 85 Bcl-2 amino acid sequence | MAHAGRTGYD DAGDVGAAPP ASRDPVARTS PVVHLTLRQA LTPFTARGRF FEFGGVMCVE LNRHLHTWIQ | NREIVMKYIH GAAPAPGIFS PLQTPAAPGA GDDFSRRYRR ATVVEELFRD SVNREMSPLV DNGGWDAFVE | YKLSQRGYEW SQPGHTPHPA AAGPALSPVP DFAEMSSQLH GVNWGRIVAF DNIALWMTEY |

TABLE 7-continued

List of Selected Fusuion Partners

| SEQ ID NO:<br>(Information) | Amino acid sequence | | |
| --- | --- | --- | --- |
| | LYGPSMRPLF<br>TLGAYLGHK | DFSWLSLKTL | LSLALVGACI |
| SEQ ID NO: 86<br>HsBAD_Q92934-1(UniProtKB) | MFQIPEFEPS<br>PSGSGKHHRQ<br>QQEQPTSSSH<br>EDDEGMGEEP<br>PPNLWAAQRY<br>RPKSAGTATQ<br>FQSWWDRNLG | EQEDSSSAER<br>APGLLWDASH<br>HGGAGAVEIR<br>SPFRGRSRSA<br>GRELRRMSDE<br>MRQSSSWTRV<br>RGSSAPSQ | GLGPSPAGDG<br><br>SRHSSYPAGT<br><br>FVDSFKKGLP |
| SEQ ID NO: 87<br>HsBAX_Q07812-1(UniProtKB) | MDGSGEQPRG<br>IQDRAGRMGG<br>PQDASTKKLS<br>AAVDTDSPRE<br>SDGNFNWGRV<br>ELIRTIMGWT<br>WIQDQGGWDG<br>LTASLTIWKK | GGPTSSEQIM<br>EAPELALDPV<br>ECLKRIGDEL<br>VFFRVAADMF<br>VALFYFASKL<br>LDFLRERLLG<br>LLSYFGTPTW<br>MG | KTGALLLQGF<br><br>DSNMELQRMI<br><br>VLKALCTKVP<br><br>QTVTIFVAGV |
| SEQ ID NO: 88<br>HsBAK1_Q16611-1(UniProtKB) | MASGQGPGPP<br>TEEVFRSYVF<br>GVAAPADPEM<br>IGDDINRRYD<br>QPTAENAYEY<br>LLGFGYRLAL<br>LGQVTRFVVD<br>LNLGNGPILN<br>GQFVVRRFFK | RQECGEPALP<br>YRHQQEQEAE<br>VTLPLQPSST<br>SEFQTMLQHL<br>FTKIATSLFE<br>HVYQHGLTGF<br>FMLHHCIARW<br>VLVVLGVVLL<br>S | SASEEQVAQD<br><br>MGQVGRQLAI<br><br>SGINWGRVVA<br><br>IAQRGGWVAA |
| SEQ ID NO: 89<br>HsBIK_Q13323-1(UniProtKB) | MSEVRPLSRD<br>GMTDSEEDLD<br>MEGSDALALR<br>SEVAMHSLGL<br>RDVLRSFMDG<br>VSCEQVLLAL<br>LSGGLHLLLK | ILMETLLYEQ<br>PMEDFDSLEC<br>LACIGDEMDV<br>AFIYDQTEDI<br>FTTLKENIMR<br>LLLLALLLPL | LLEPPTMEVL<br><br>SLRAPRLAQL<br><br>FWRSPNPGSW |
| SEQ ID NO: 90<br>HsBID_P55957-1(UniProtKB) | MDCEVNNGSS<br>NSFRRELDAL<br>WEGYDELQTD<br>DIIRNIARHL<br>IPPGLVNGLA<br>LEQLLQAYPR<br>LALLLAKKVA<br>NLRTYVRSLA | LRDECITNLL<br>GHELPVLAPQ<br>GNRSSHSRLG<br>AQVGDSMDRS<br>LQLRNTSRSE<br>DMEKEKTMLV<br>SHTPSLLRDV<br>RNGMD | VFGFLQSCSD<br><br>RIEADSESQE<br><br>EDRNRDLATA<br><br>FHTTVNFINQ |

NK Cells

In some embodiments the immune cells are natural killer (NK) cells. NK cells recognize infected or transformed cells through multiple cell surface receptors including NKG2D, CD16, and natural cytotoxicity receptors (NCRs) such as NKp44, NKp46, and NKp30. These receptors activate signaling adapter proteins such as DAP10, DAP12, and CD3ζ, which contain immuno-tyrosine activation motifs (ITAMs) that initiate the release of cytolytic granules containing perforin and granzymes, as well as mediate production and release of cytokines and chemokines such as IFN-γ and TNF-α. Importantly, NK cell-mediated cytotoxicity does not rely on the presentation of self HLA. Therefore, NK cells hold significant clinical interest as a cell-based therapy for cancer because of their ability to be used in an allogeneic setting and potentially provide an off-the-shelf cellular product.

Natural killer cells provide an alternative to the use of T cells for adoptive immunotherapy since they do not require HLA matching, so can be used as allogeneic effector cells. Clinical trials of adoptively transferred allogeneic NK cells demonstrate these cells can survive in patients for several weeks to months. Additionally, expression of CARs in NK cells allow these cells to more effectively kill solid tumors that are often resistant to NK cell-mediated activity compared to hematologic malignancies (especially acute myelogenous leukemia) that are typically more NK cell-sensitive. CARs useful in NK cell targeting include, for example, first generation CAR constructs that contain CD3ζ as the sole signaling domain. Second and third generation CARs are also useful in NK cells. In some embodiments the ectodomain of NKG2D, an NK cell activation receptor, is linked directly to CD3ζ.

NK cells for modification include cell lines, or peripheral blood NK cells, which can be isolated from donors through simple blood draws or by apheresis if larger numbers of cells are needed. Activated PB-NK cells express a wider range of activating receptors, such as CD16, NKp44, and NKp46 as well as KIRs, which play an important role in NK cell licensing. In addition, PB-NK cells can be given without irradiating the cells so have the ability to expand in vivo. Another source of NK cells suitable for CAR expression are NK cells derived from human pluripotent stem cells—both induced pluripotent stem cells (iPSCs) or human embryonic stem cells (hESCs). These NK cells display a similar phenotype to PB-NK cells, and hESC/iPSC-NK cells can be grown on a clinical scale.

Chimerica Antigen Receptors (CARs)

In addition to the superkine sequence, CARs contain the signaling domain for CD3ζ and the signaling domains of one or more costimulatory receptors that further promote the recycling, survival and/or expansion of immune cells expressing the CARs. The signaling domains of the costimulatory receptors are the intracellular portions of each receptor protein that generate the activating signal in the cell. Examples are amino acids 180-220 of the native CD28 molecule and amino acids 214-255 of the native 4-1BB molecule.

Examples of suitable hinge and transmembrane regions to link the superkine to the signaling region may include without limitation the constant (Fc) regions of immunoglobins, human CD8a, and artificial linkers that serve to move the targeting moiety away from the cell surface for improved access to and binding on target cells. Examples of suitable transmembrane domains include the transmembrane domains of the leukocyte CD markers, preferably that of CD4 or CD28. Examples of intracellular receptor signaling domains include the T cell antigen receptor complex, preferably the zeta chain of CD3, however any transmembrane region sufficient to anchor the CAR in the membrane can be used. Persons of skill are aware of numerous transmembrane regions and the structural elements (such as lipophilic amino acid regions) that produce transmembrane domains in numerous membrane proteins and therefore can substitute any convenient sequence. T cell costimulatory signaling receptors suitable for improving the function and activity of CAR-expressing cells include, but are not limited to, CD28, CD137, and OX-40.

Signaling via CD28 is required for IL2 production and proliferation, but does not play a primary role in sustaining T cell function and activity. CD137 (a tumor necrosis factor-receptor family member expressed following CD28 activation) and OX-40 are involved in driving long-term survival of T cells, and accumulation of T cells. The ligands for these receptors typically are expressed on professional antigen presenting cells such as dendritic cells and activated macrophages, but not on tumor cells. Expressing a CAR that incorporates CD28 and/or 4-1BB signaling domains in CD4$^+$ T cells enhances the activity and anti-tumor potency of those cells compared to those expressing a CAR that contains only the CD3ζ signaling domain, which constructs may be referred to as second or third generation CARs.

Included as CAR constructs of interest are tandem CARs, e.g. see Hegde et al. (2016) J. Clin. Invest 126(8):3036-3052, herein specifically incorporated by reference. In such constructs a binding moiety for a tumor specific antigen is combined in tandem with an IL-13 superkine. The binding moiety may be, for example, an scFv specific for a tumor cell antigen, including without limitation HER-2, EGFR, CD20, etc. as known in the art.

In various embodiments, the antigen binding domain binds to an antigen on a target cell, e.g., a cancer cell. The antigen binding domain can bind an antigen, such as but not limited to a tumor target antigen. In some case, the antigen binding domain binds one or more antigens. Exemplary antigen binding domains can bind to an antigen including, but not limited to, D19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAcα Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp 100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51 E2 (OR51 E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART 1); Rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the antigen binding domain comprises a monoclonal antibody, a polyclonal antibody, a synthetic antibody, a human antibody, a humanized antibody, a non-human antibody, a nanobody, a single-chain variable fragment (scFv), F(ab')2, Fab', Fab, Fv, and the like. The antigen binding domain can be linked to the transmembrane domain of the CAR. In some embodiments, a nucleic acid encoding the antigen binding domain is operably linked to a nucleic acid encoding a transmembrane domain of the CAR.

In some embodiments, the transmembrane domain can be derived from a membrane-bound or transmembrane protein. In certain embodiments, the transmembrane domain comprises one or more, e.g., 1, 2, 3, 4, 5, 6, 7, 8 or more amino acid modifications (e.g., substitutions, insertions, and deletions) compared to the wild-type amino acid sequence of the transmembrane domain of the membrane-bound or transmembrane protein. Non-limiting examples of a transmembrane domain of a CAR include at least the transmembrane region(s) of the alpha, beta or zeta chain of the T-cell receptor, CD28, CD3 epsilon (CD3), CD45, CD4, CD5, CD8, CD9, CD16, CD22, CD33, CD37, CD64, CD80, CD86, CD134, CD137, CD154, or an erythropoietin receptor. In some embodiments, the transmembrane domain includes a human immunoglobulin (Ig) hinge region, e.g., an IgG4Fc hinge. In other embodiments, the transmembrane domain is a recombinant or synthetic domain comprising hydrophobic amino acid residues (e.g., leucine and valine). In some cases, the transmembrane domain includes a phenylalanine, tryptophan and valine at one or both ends of the domain.

The transmembrane domain links the antigen binding domain to the intracellular signaling domain of the CAR. In some embodiments, the nucleic acid encoding the antigen binding domain is operably linked to the nucleic acid encoding the transmembrane domain that is operably linked to the nucleic acid encoding the intracellular signaling domain.

In some embodiments, the intracellular signaling domain of a CAR comprises a signal activation or signal transduction domain. As such, an intracellular signaling domain includes any portion of an intracellular signaling domain of a protein sufficient to transduce or transmit a signal, e.g., an activation signal or to mediate a cellular response within a cell. Non-limiting examples include TCR, CD2, CD3 zeta, CD3 gamma, CD3 delta, CD3 epsilon, CD7, CD27, CD86, common FcR gamma, FcR beta, CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, any derivative, variant, or fragment thereof. In certain embodiments, the intracellular signaling domain comprises an intracellular domain of a co-stimulatory molecule such as from CD3, CD27, CD28, CD127, ICOS, 4-1BB (CD137), PD-1, T cell receptor (TCR), any derivative thereof, or any variant thereof. In some embodiments, the intracellular signaling domain of the CAR is selected from the group consisting of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

BiTES

Bi-specific T-cell engagers (BiTEs) are fusion proteins comprising an IL-13 superkine fused to an antibody variable region that specifically binds to CD3. In some embodiments the antibody variable region in a single-chain variable fragments (scFvs). THe superkine may be fused to the variable region through a linker. An Fc region is optionally provided.

TACs

A TAC construct comprises an IL-13 superkine fused to a ligand that binds a protein associated with the TCR complex; fused to a T cell receptor signaling domain polypeptide. The domains may be separated by linkers. The protein associated with the TCR complex may be CD3. The ligand that binds a protein associated with the TCR complex may be a single chain antibody. The ligand that binds a protein associated with the TCR complex may be UCHT1, or a variant thereof. The T cell receptor signaling domain polypeptide may comprise a cytosolic domain and a transmembrane domain.

The cytosolic domain may be a CD4 cytosolic domain and the transmembrane domain is a CD4 transmembrane domain.

ACTRs

ACTRs are a hybrid approach to CARs and the established monoclonal antibody oncology therapeutics. ACTRs are composed of a typical CAR construct that can bind the heavy chain of an antibody through a high-affinity variant of the Fc receptor CD16. A superkine is fused to a moiety recognized by the CAR, which may include, without limitation, an Fc region of an antibody with high affinity for CD16.

An immune cell targeting construct coding sequence can be produced by any means known in the art, including recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region may be inserted into an expression vector and used to transform a suitable expression host cell line, e.g. a population of allogeneic or autologous T lymphocytes, allogeneic or autologous NK cells, including primary cultures, cell lines, iPSC derived cells, etc. The methods can be used on cells in vitro (e.g., in a cell-free system), in culture, e.g. in vitro or ex vivo. For example, IL-13 superkine CAR-expressing cells can be cultured and expanded in vitro in culture medium.

An IL13 superkine immune cell targeting construct can specifically direct immune cells to target IL13Rα2-expressing glioma cells, renal carcinoma cells and cells of any cancer expressing IL13Rα2, in an MHC-independent manner. IL13Rα2 has been identified as an over-expressed cell-surface target on various human tumors, including breast cancer, head and neck cancer, kidney cancer, ovarian cancer and Kaposi's sarcoma as well as gliomas. Anti-tumor effector cells, e.g. CD4$^+$ or CD8$^+$ effector T cells, are generated to be re-directed to recognize such tumor cells by introducing into the T cells an IL-13 and/or IL-4 superkine immune cell targeting construct comprising one or more signaling domains derived from CD3-ζ, CD28, DAP10, OX-40, ICOS and CD137.

The IL-13 and/or IL-4 superkine immune cell targeting construct is infected or transfected into human immune cells, e.g. using a non-viral plasmid vector and electroporation methods; a viral vector and infection methods, etc. as known in the art. A CAR comprising co-stimulatory signaling domains may enhance the duration and/or retention of anti-tumor activity in a manner that can significantly improve the clinical efficacy of adoptive therapy protocols. CD4$^+$ and CD8$^+$ T cell effector functions, and NK cell functions can be triggered via these receptors, therefore these cell types are contemplated for use with the invention. CD8$^+$ T cells expressing the IL13 superkine CARs of this invention may be used to lyse target cells and to produce IL-2 in the presence of target cells, among the other functions of these cells. Expression of the appropriate costimulatory CAR in either or both CD4$^+$ and CD8$^+$ T cells is used to provide the most effective population of cells for adoptive immunotherapy, consisting therefore of either or both professional helper and killer T cells that exhibit enhanced and/or long term viability and anti-tumor activity. In some embodiments, an IL-13 and/or IL-4 superkine immune cell targeting construct comprises an IL-13 variant/IL-13 superkine including those provided in FIG. 2. In some embodiments, an IL-13 and/or IL-4 superkine immune cell targeting construct comprises an IL-13 variant/IL-13 superkine including those provided in SEQ ID NO:2 through SEQ ID NO:38.

Polypeptides of the present invention can be further modified, e.g., joined to a wide variety of other oligopeptides or proteins for a variety of purposes. For example, post-translationally modified, for example by prenylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes.

Methods which are well known to those skilled in the art can be used to construct T cell targeting construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

According to the present invention, immune cell targeting construct vectors and immune cell targeting construct modified cells can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent, e.g., another anti-tumor agent.

Therapeutic entities of the present invention are often administered as pharmaceutical compositions comprising an active therapeutic agent and a other pharmaceutically acceptable excipient. Such formulations can include one or more non-toxic pharmaceutically acceptable carriers, diluents, excipients and/or adjuvants. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The maximum tolerated dose (MTD) of CAR immune cells may be determined during clinical trial development, for example at up to about $10^4$ T cells/kg of body weight, up to about $10^5$ cells/kg of body weight, up to about $10^6$ cells/kg of body weight, up to about $5\times10^6$ cells/kg of body weight, up to about $10^7$ cells/kg of body weight, up to about $5\times10^7$ cells/kg of body weight, or more, as empirically determined. In some embodiments, the maximum tolerated dose (MTD) of CAR immune cells is up to about 104 T cells/kg of body weight. In some embodiments, the maximum tolerated dose (MTD) of CAR immune cells is up to about $10^5$ T cells/kg of body weight. In some embodiments, the maximum tolerated dose (MTD) of CAR immune cells is up to about $10^6$ T cells/kg of body weight. In some embodiments, the maximum tolerated dose (MTD) of CAR immune cells is up to about $10^7$ T cells/kg of body weight. In some embodiments, the maximum tolerated dose (MTD) of CAR immune cells is up to about $5\times10^6$ T cells/kg of body weight. In some embodiments, the maximum tolerated dose (MTD) of CAR immune cells is up to about $5\times10^7$ T cells/kg of body weight.

Toxicity of the cells described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

After a dose escalation phase, patients in the expansion cohort are treated with immune cells at the MTD. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient.

In prophylactic applications, e.g. to maintain remission in a patient, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Examples of additional therapeutic agents that can be coadministered and/or coformulated with an immune cell targeting construct include: anti-proliferative, or cytoreductive therapy, which is used therapeutically to eliminate tumor cells and other undesirable cells in a host, and includes the use of therapies such as delivery of ionizing radiation, and administration of chemotherapeutic agents. Chemotherapeutic agents are well-known in the art and are used at conventional doses and regimens, or at reduced dosages or regimens, including for example, topoisomerase inhibitors such as anthracyclines, including the compounds daunorubicin, adriamycin (doxorubicin), epirubicin, idarubicin, anamycin, MEN 10755, and the like. Other topoisomerase inhibitors include the podophyllotoxin analogues etoposide and teniposide, and the anthracenediones, mitoxantrone and amsacrine. Other anti-proliferative agent interferes with microtubule assembly, e.g. the family of vinca alkaloids. Examples of vinca alkaloids include vinblastine, vincristine; vinorelbine (NAVELBINE); vindesine; vindoline; vincamine; etc. DNA-damaging agent include nucleotide analogs, alkylating agents, etc. Alkylating agents include nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Nucleotide analogs include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other chemotherapeutic agents of interest include metal complexes, e.g. cisplatin (cis-DDP), carboplatin, oxaliplatin, etc.; ureas, e.g. hydroxyurea; and hydrazines, e.g. N-methylhydrazine.

For example, ionizing radiation (IR) is used to treat about 60% of cancer patients, by depositing energy that injures or destroys cells in the area being treated, and for the purposes of the present invention may be delivered at conventional doses and regimens, or at reduced doses. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area. A suitable dose of ionizing radiation may range from at least about 2 Gy to not more than about 10 Gy, usually about 5 Gy. A suitable dose of ultraviolet radiation may range from at least about 5 J/m² to not more than about 50 J/m², usually about 10 J/m². The sample may be collected from at least about 4 and not more than about 72 hours following ultraviolet radiation, usually around about 4 hours.

Treatment may also be combined with immunoregulatory modulating agents, including an agent that agonizes an immune costimulatory molecule, e.g. CD40, OX40, etc.; and/or (iii) an agent that antagonizes an immune inhibitory molecule, e.g. CTLA-4, PD-1, PD-L1, etc. The active agents are administered within a period of time to produce an additive or synergistic effect on depletion of cancer cells in the host. Methods of administration include, without limitation, systemic administration, intra-tumoral administration, etc.

In some embodiments, an individual cancer is selected for treatment with a combination therapy because the cancer is a cancer type that is responsive to a checkpoint inhibitor, e.g. a PD-1 antagonist, a PD-L1 antagonist, a CTLA4 antagonist, a TIM-3 antagonist, a BTLA antagonist, a VISTA antagonist, a LAG3 antagonist; etc. In some embodiments, such an immunoregulatory agent is a CTLA-4, PD1 or PDL1 antagonist, e.g. avelumab, nivolumab, pembrolizumab, ipilimumab, and the like. In some such embodiments the cancer is, without limitation, melanoma or small cell lung cancer. In some such embodiments, the cancer is a type that has a high neoantigen, or mutagenesis, burden (see Vogelstein et al. (2013) Science 339(6127):1546-1558, herein specifically incorporated by reference).

In some embodiments, an individual cancer is selected for treatment with a combination therapy of the present invention because the cancer is a cancer type that is responsive to an immune response agonist, e.g. a CD28 agonist, an OX40 agonist; a GITR agonist, a CD137 agonist, a CD27 agonist, an HVEM agonist, etc. In some embodiments, such an immunoregulatory agent is an OX40, CD137, or GITR agonist e.g. tremelimumab, and the like. In some such embodiments the cancer is, without limitation, melanoma or small cell lung cancer. In some such embodiments, the cancer is a type that has a high neoantigen, or mutagenesis, burden.

In some embodiments, the combination therapy includes an antibody known in the art which binds to PD-1 and disrupt the interaction between the PD-1 and its ligand, PD-1, and stimulate an anti-tumor immune response. In some embodiments, the antibody or antigen-binding portion thereof binds specifically to PD-1. For example, antibodies that target PD-1 and which can find used in the present invention include, e.g., but are not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies include anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in the combination treatment methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, is suitable for use in the combination treatment methods.

In some embodiments, the combination therapy includes an antibody known in the art which binds CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the combination treatment methods. In some embodiments, the combination therapy includes an antibody known in the art which binds LAG-3 and disrupts its interaction with MHC class II molecules. An exemplary antibody that targets LAG-3 is IMP321 (Immutep), currently undergoing human trials. Other suitable antibodies that target LAG-3 are disclosed in U.S. Patent Application 2011/0150892, herein incorporated by reference. It will be understood by one of ordinary skill that any antibody which binds to LAG-3, disrupts its interaction with MHC class II molecules, and stimulates an anti-tumor immune response, is suitable for use in the combination treatment methods.

In some embodiments, the combination therapy includes an antibody known in the art which binds TIM-3 and disrupts its interaction with galectin 9. Suitable antibodies that target TIM-3 are disclosed in U.S. Patent Application 2013/0022623, herein incorporated by reference. It will be understood by one of ordinary skill that any antibody which binds to TIM-3, disrupts its interaction with galectin 9, and stimulates an anti-tumor immune response, is suitable for use in the combination treatment methods.

In some embodiments, the combination therapy includes an antibody known in the art which binds 4-1BB/CD137 and disrupts its interaction with CD137L. It will be understood by one of ordinary skill that any antibody which binds to 4-1BB/CD137, disrupts its interaction with CD137L or another ligand, and stimulates an anti-tumor immune response or an immune stimulatory response that results in anti-tumor activity overall, is suitable for use in the combination treatment methods.

In some embodiments, the combination therapy includes an antibody known in the art which binds GITR and disrupts its interaction with its ligand. It will be understood by one of ordinary skill that any antibody which binds to GITR, disrupts its interaction with GITRL or another ligand, and stimulates an anti-tumor immune response or an immune stimulatory response that results in anti-tumor activity overall, is suitable for use in the combination treatment methods.

In some embodiments, the combination therapy includes an antibody known in the art which binds OX40 and disrupts its interaction with its ligand. It will be understood by one of ordinary skill that any antibody which binds to OX40, disrupts its interaction with OX40L or another ligand, and stimulates an anti-tumor immune response or an immune stimulatory response that results in anti-tumor activity overall, is suitable for use in the combination treatment methods.

In some embodiments, the combination therapy includes an antibody known in the art which binds CD40 and disrupts its interaction with its ligand. It will be understood by one of ordinary skill that any antibody which binds to CD40, disrupts its interaction with its ligand, and stimulates an anti-tumor immune response or an immune stimulatory response that results in anti-tumor activity overall, is suitable for use in the combination treatment methods.

In some embodiments, the combination therapy includes an antibody known in the art which binds ICOS and disrupts its interaction with its ligand. It will be understood by one of ordinary skill that any antibody which binds to ICOS, disrupts its interaction with its ligand, and stimulates an anti-tumor immune response or an immune stimulatory response that results in anti-tumor activity overall, is suitable for use in the combination treatment methods.

In some embodiments, the combination therapy includes an antibody known in the art which binds CD28 and disrupts its interaction with its ligand. It will be understood by one of ordinary skill that any antibody which binds to CD28, disrupts its interaction with its ligand, and stimulates an anti-tumor immune response or an immune stimulatory response that results in anti-tumor activity overall, is suitable for use in the combination treatment methods.

In some embodiments, the combination therapy includes an antibody known in the art which binds IFNα and disrupts its interaction with its ligand. It will be understood by one of ordinary skill that any antibody which binds to IFNα, disrupts its interaction with its ligand, and stimulates an anti-tumor immune response or an immune stimulatory response that results in anti-tumor activity overall, is suitable for use in the combination treatment methods.

An "anti-cancer therapeutic" is a compound, composition, or treatment (e.g., surgery) that prevents or delays the growth and/or metastasis of cancer cells. Such anti-cancer therapeutics include, but are not limited to, surgery (e.g., removal of all or part of a tumor), chemotherapeutic drug treatment, radiation, gene therapy, hormonal manipulation, immunotherapy (e.g., therapeutic antibodies and cancer vaccines) and antisense or RNAi oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C, Avastin, Herceptin®, flurouracil, and temozolamide and the like. The compounds are also suitable for use with standard combination therapies employing two or more chemotherapeutic agents. It is to be understood that anti-cancer therapeutics includes novel compounds or treatments developed in the future.

The pharmaceutical compositions and/or formulations described above include one or more therapeutic entities in an amount effective to achieve the intended purpose. Thus the term "therapeutically effective dose" refers to the amount of the therapeutic entities that ameliorates the symptoms of cancer. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Also within the scope of the invention are kits comprising the compositions of the invention and instructions for use. The kit may further contain a least one additional reagent, e.g. a chemotherapeutic drug, anti-tumor antibody, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention. In some embodiments, the kit comprises an IL-13 and/or IL-4 superkine immune cell targeting construct comprising an IL-13 variant/IL-13 superkine as described herein. In some embodiments, the kit comprises an IL-13 and/or IL-4 superkine immune cell targeting construct comprising an IL-13 variant/IL-13 superkine including those provided in FIG. 2. In some embodiments, an IL-13 and/or IL-4 superkine immune cell targeting construct comprises an IL-13 variant/IL-13 superkine including those provided in SEQ ID NO:2 through SEQ ID NO:38.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Methods:

Protein expression and purification. Human IL-13 and human IL-13Rα1 and IL-13Rα2-selective variants were cloned into the insect expression vector pAcGP67 (BD Biosciences) with C-terminal 6×Histidine tag and produced in insect Hi5 cells using recombinant baculovirus. Proteins were recovered from Hi5 supernatant after 60 hr of infection by nickel agarose and concentrated and purified by size exclusion chromatography on a Superdex-200 column into HBS (10 mM Hepes pH 7.4, 150 mM NaCl). biotinylated IL-13Rα1 (amino acids 1-310) and IL-4Rα1 (amino acids 1-202) ectodomains were obtained by cloning into the pAcGP67-A vector with a C-terminal biotin acceptor peptide (BAP)-LNDIFEAQKIEWHE and hexahistidine tag. Receptor proteins were coexpressed with BirA ligase with excess biotin (100 µM).

Surface Plasmon Resonance. SPR experiments were conducted on a Biacore T100 instrument. Experiments used a Biacore SA sensor chip (GE Healthcare). Biotinylated IL-13Rα1 and IL-13Rα2 receptors were captured at a low density (100-200 RU) and kinetic runs were conducted at 40 µL/min. An unrelated biotinylated protein was immobilized as a reference surface for the SA sensor chip with matching RU to the experimental surface. All data was analyzed using the Biacore T100 evaluation software version 2.0 with a 1:1 Langmuir binding model. Serial dilutions of unbiotinylated IL-13 variants in the running buffer [1×HBS-P (GE Healthcare)+0.5% BSA] were flowed over the chip and IL-13Rα1/ IL-13Rα2 were regenerated by using one 60 second injections of 7 mM glycine (pH 3.0).

Phospho-flow cytometry assay. The IL-13 responsive cell line A549 was stimulated with the indicated doses of IL-13 and IL-13 specific variants for 15 min. Samples were then fixed in PFA for 15 min at room temperature, washed with PBS 0.5% BSA and permeabilized with cold (4° C.) methanol for 10 min. The levels of phosphorylated Stat6 were detected using a maybe anti-pY641 Stat6 coupled to the fluorophore Alexi 488 (BD Bioscience). Analysis was performed on a Becton Dickinson LSRII equipped with 405, 488, and 640 nm lasers. Data analysis was performed in Citibank software. Log median fluorescence intensity values were plotted against cytokine concentration to yield dose-response curves.

TF-1 cells proliferation assay. TF-1 cells were seed to $2\times10^5$ cells/ml in the presence of the indicated doses of IL-13 or the different IL-13 variants for 96 hr. Cells were washed 3× with cold (4 C) PBS and fixed with 4% PFA for 15 min at room temperature. Number of cells in each well was determined by flow cytometry. Number of cells were represented as percentage and plotted against cytokine concentration to obtain dose-response curves.

Dendritic cells differentiation assay. CD14$^+$ monocytes were isolated (>97% purity) from peripheral blood mononuclear cells by magnetic separation with anti-CD14 conjugated microbeads (Miltenyi Biotec). $5\times10^5$ CD14$^+$ monocytes were subsequently cultured with 50 ng/mL GM-CSF alone or with the indicated concentrations of IL-13 in the presence of 2 g/ml of isotype control antibody, anti-IL-4Rα1 antibody or IL-13dn in 2 ml well plates containing IMDM medium (Gibco) supplemented with 10% human AB serum, 100 U/mL penicillin, 100 µg/mL streptomycin, 2 mM L-glutamine, sodium pyruvate, non-essential amino acids and 50 µM 2-ME. Cells were processed on day 6 with 5 mM EDTA and subsequently stained with DAPI (Invitrogen), fluorescently labeled isotype control mAbs, or mAbs against CD14, CD86, CD209 and HLA-DR (BD Biosciences). Dendritic cell differentiation was assessed by flow cytometry with a BD LSRII flow cytometer and median fluorescent intensities were generated by FlowJo (Treestar).

In vivo test of IL-13dn efficacy. 360 ng of mouse IL-13 were injected intra-tracheally with or without 150 g of IL-13dn on days 0, 3 and 5. Lungs were harvest on day six. RNA was extracted and the expression levels of Muc5ac, Periostin, Arg1, CHIA, YM1, Fizz1 were assessed by quantitative PCR.

Example 2

This example provides exemplary mutein sequences for the CAR constructs provided by the present invention.

The constructs prepared were synthesized based IL-13 sequence of SEQ ID NO:18 alone and in combination with an IL-2 Mutein of SEQ ID NO:107 (H9). Signal peptide sequence in the N-terminus is underlined below in the listed sequences. CAR sequence followed the IL-13 sequence of SEQ ID NO:18.

The PMC 393 of FIG. 8 contained the IL-13 sequence of SEQ ID NO:18. For that vector, the sequence tethered to the CAR was:

MALPVTALLLPLALLLHAARPASPGPVPPSTAHRELIE ELVNITQNQKAPLCNGSMVWSI NLTAGMYCAALES-LINVSGCSAIEKTQRMLSGFCPHKVSAGQFSSLHVT-GRKIEVAQFV KDLLLHLKKLFKEGQFN-[CAR . . . ]

The PMC 394 of FIG. 9 contained the IL-13 sequence of SEQ ID NO:18 and the IL-2 Mutein of SEQ ID NO: 107 (H9). For that vector, the sequence tethered to the CAR was: MALPVTALLLPLALLLHAARPASPGPVPPSTAH-RELIEELVNITQNQKAPLCNGSMVWSI NLTAGMY-CAALESLINVSGC-SAIEKTQRMLSGFCPHKVSAGQFSSLHVTGRKIEVAQ FV KDLLLHLKKLFKEGQFN-[CAR . . . ]

The IL-2 Mutein was SEQ ID NO: 107 (H9) which was secreted was: APTSSSTKKTQLQLEHLLLD-LQMILNGINNYKNPKLTRMLTFKFYMPK-KATELKHLQCLE EELKPLEEVLN-LAQSKNFHFDPRDVVSNINVFVLELKGSETTFMCEY ADETATIVEFLNR WITFCQSIISTLT.

Design:

Pre-transduction analysis: Lentiviral plasmids were used to transiently transfect HEK293 cells as validation. Result showed that there was expression.

The second batch of lentivirus was generated.

Lentivirus containing IL13RA-CAR was used to transduce human PBMCs (donor 871) and expanded for 14 days.

FACS analysis showed 99% and 96% expression (flag tag) from PMC 393 and 394, respectively (see, FIG. 10). See also the data provided in FIGS. 12-20.

FACS Analysis

In total, 6 cell lines were harvested fresh from culture. Cells were washed 3 times with FACS buffer (PBS+2% FBS) and FcR blocked with 1:100 normal mouse serum.

Cells were stained with:

a) anti-IL13RA2 clone 47 b) anti-IL13RA2 clone SHM38 c) 7-AAD (dead cell)-gated out

Staining included 20 ul each for 30 minutes at 4° C. in FACS staining buffer.

Cells were acquired on FACSCalibur and assayed as provided in FIGS. 17-20.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered byway of example only, and the application is to be limited only by the terms of the appended claims, along with the full scope of equivalents to which the claims are entitled.

What is claimed is:

1. A composition comprising an immune cell targeting construct and an IL-2 or an IL-2 mutein, wherein the immune cell targeting construct comprises:

an IL-13 superkine engineered to have increased affinity for interleukin 13 receptor α2 (IL-13Rα2), relative to native human IL-13 protein and decreased affinity for interleukin 13 receptor α1 (IL-13Rα1) relative to native human IL-13 protein and comprising at least one amino acid change relative to the wild-type IL-13 at one or more of positions selected from L10, R11, E12, I14, V18, R65, R86, D87, T88, K89, L101, K104, K105, F107, and R108, wherein the immune cell targeting construct targets a tumor and/or tumor microenvironment and/or targeting tumor antigens.

2. The composition of claim 1 wherein the immune cell targeting construct is a chimeric antigen receptor (CAR) and wherein the IL-13 superkine is fused to a transmembrane domain; linked to an intracellular signaling region.

3. The composition of claim 2, wherein the intracellular signaling region comprises one or more of a CD3ζ signaling domain, a CD28 signaling domain, a CD137 signaling domain, an OX-40 signaling domain, an ICOS signaling domain, and a DAP10 signaling domain.

4. The composition of claim 1 wherein the IL-13 super-kine comprises a set of amino acid substitutions selected from: [L10D, R11I, V18I, R86K, D87K, K89R, R108K]; [L10A, R86T, D87G, T88K, K89R, L101N, K104R, K105A, R108K]; [L10V, K89R, L101N, K105E, R108T]; [R11S, I14M, T88S, L101N, K105A, R108K]; [L10H, R11L, V18I, R86K, D87E, K89R, L101N, K105T, R108K]; [L10H, R11L, V18I, R86M, K89R, R108K]; [L10H, R86T, D87G, T88R, R108K]; [L10H, R86M, T88S, K89R, L101N, K104R, K105A, R108K]; and [L10A, V18F, R86K, K89R, L101I, K104R, R108K].

* * * * *

SEQUENCE LISTING

```
<160> NUMBER OF SEQ ID NOS: 121

<210> SEQ ID NO 1
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 1

Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Gln Phe
                100                 105                 110

Asn

<210> SEQ ID NO 2
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 2

Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80
```

-continued

```
Ser Ser Leu His Val Arg Ser Ser Lys Ile Glu Val Ala Gln Phe Val
                85              90              95

Lys Asp Leu Leu Phe His Leu Arg Thr Leu Phe Arg Glu Gly Gln Phe
        100             105             110

Asn

<210> SEQ ID NO 3
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 3

Pro Gly Pro Val Pro Pro Ser Thr Ala Ile Arg Glu Leu Ile Glu Glu
1               5               10              15

Leu Ile Asn Ile Thr Gln Asn Gln Lys Ala Pro Leu Cys Asn Gly Ser
            20              25              30

Met Val Trp Ser Ile Asn Leu Thr Ala Gly Met Tyr Cys Ala Ala Leu
        35              40              45

Glu Ser Leu Ile Asn Val Ser Gly Cys Ser Ala Ile Glu Lys Thr Gln
    50              55              60

Arg Met Leu Ser Gly Phe Cys Pro His Lys Val Ser Ala Gly Gln Phe
65              70              75              80

Ser Ser Leu His Val Arg Gly Ser Lys Ile Glu Val Ala Gln Phe Val
                85              90              95

Lys Asp Leu Leu His His Leu Arg Ala Leu Phe Arg Glu Gly Gln Phe
        100             105             110

Asn

<210> SEQ ID NO 4
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 4

Pro Gly Pro Val Pro Pro Ser Thr Ala Val Arg Glu Leu Ile Glu Glu
1               5               10              15

Leu Ile Asn Ile Thr Gln Asn Gln Lys Ala Pro Leu Cys Asn Gly Ser
            20              25              30

Met Val Trp Ser Ile Asn Arg Thr Ala Gly Met Tyr Cys Ala Ala Leu
        35              40              45

Glu Ser Leu Ile Asn Val Ser Gly Cys Ser Ala Ile Glu Lys Thr Gln
    50              55              60

Arg Met Leu Ser Gly Phe Cys Pro His Lys Val Ser Ala Gly Gln Phe
65              70              75              80

Ser Ser Leu His Val Arg Ser Ser Lys Ile Glu Val Ala Gln Phe Val
                85              90              95

Lys Asp Leu Leu Phe His Leu Arg Thr Leu Phe Arg Glu Gly Gln Phe
        100             105             110

Asn

<210> SEQ ID NO 5
<211> LENGTH: 113
<212> TYPE: PRT
<213> ORGANISM: Artificial Sequence
```

<220> FEATURE:
<223> OTHER INFORMATION: IL-13 wildtype

<400> SEQUENCE: 5

Pro Gly Pro Val Pro Pro Ser Thr Ala Leu Ile Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Ile Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Gly Ser Lys Ile Glu Val Ala Gln Phe Val
                85                  90                  95

Lys Asp Leu Leu His His Leu Arg Ala Leu Met Arg Glu Gly Gln Phe
            100                 105                 110

Asn

<210> SEQ ID NO 6
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 6

Pro Gly Pro Val Pro Pro Ser Thr Ala Ile Arg Glu Leu Ile Glu Glu
1               5                   10                  15

Leu Leu Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Lys Ser Lys Ile Glu Val Ala Gln Phe Val
                85                  90                  95

Lys Asp Leu Leu His His Leu Arg Ala Leu Phe Arg Glu Gly Gln Phe
            100                 105                 110

Asn

<210> SEQ ID NO 7
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 7

Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

-continued

```
Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Ser Arg Ile Glu Val Ala Gln Phe Val
                85                  90                  95

Lys Asp Leu Leu His His Leu Arg Thr Leu Phe Arg Glu Gly Gln Phe
            100                 105                 110

Asn
```

<210> SEQ ID NO 8
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 8

```
Pro Gly Pro Val Pro Pro Ser Thr Ala Leu Arg Glu Leu Ile Glu Glu
1               5                   10                  15

Leu Ile Asn Ile Thr Gln Asn Glu Lys Ala Pro Leu Cys Asn Gly Ser
                20                  25                  30

Met Val Trp Ser Ile Asn Leu Thr Ala Gly Ile Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Ser Lys Ile Glu Val Ala Gln Phe Val
                85                  90                  95

Lys Asp Leu Leu Tyr His Leu Arg Ala Leu Phe Arg Glu Gly Gln Phe
            100                 105                 110

Asn
```

<210> SEQ ID NO 9
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 9

```
Pro Gly Pro Val Pro Pro Ser Thr Ala Leu Ser Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Pro Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ala Ala Gly Gln Phe
65                  70                  75                  80

Ser Ser Leu His Asp Lys Gly Ser Met Ile Glu Val Ala Gln Phe Val
                85                  90                  95

Lys Asp Leu Leu Tyr His Leu Arg Thr Leu Phe Arg Glu Gly Gln Phe
            100                 105                 110
```

Asn

```
<210> SEQ ID NO 10
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 10

Pro Gly Pro Val Pro Pro Ser Thr Ala Thr Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Asp Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Val Gly Gln Phe
65                  70                  75                  80

Ser Ser Leu His Val Arg Gly Ser Lys Ile Glu Val Ala Gln Phe Val
                85                  90                  95

Lys Asp Leu Leu Tyr His Leu Arg Thr Leu Phe Arg Glu Gly Gln Phe
            100                 105                 110
```

Asn

```
<210> SEQ ID NO 11
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 11

Pro Gly Pro Val Pro Pro Ser Thr Ala Asp Ile Glu Leu Ile Ala Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Asp Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110
```

Asn

```
<210> SEQ ID NO 12
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 12

Pro Gly Pro Val Pro Pro Ser Thr Ala Ala Arg Glu Leu Ile Glu Glu
```

-continued

```
1               5                    10                    15

Leu Val Asn Ile Thr Gln Asn Gln Lys Ala Pro Leu Cys Asn Gly Ser
            20                   25                   30

Met Val Trp Ser Ile Asn Leu Thr Ala Gly Met Tyr Cys Ala Ala Leu
        35                   40                   45

Glu Ser Leu Ile Asn Val Ser Gly Cys Ser Ala Ile Glu Lys Thr Gln
    50                   55                   60

Arg Met Leu Ser Gly Phe Cys Pro His Lys Val Ser Ala Gly Gln Leu
65                   70                   75                   80

Ser Ser Leu His Val Thr Gly Lys Arg Ile Glu Val Ala Gln Phe Val
                85                   90                   95

Lys Asp Leu Leu Asn His Leu Arg Ala Leu Phe Lys Glu Gly Gln Phe
            100                  105                  110

Asn
```

<210> SEQ ID NO 13
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 13

```
Pro Gly Pro Val Pro Pro Ser Thr Ala Val Arg Glu Leu Ile Glu Glu
1               5                    10                    15

Leu Val Asn Ile Thr Gln Asn Gln Lys Ala Pro Leu Cys Asn Gly Ser
            20                   25                   30

Met Val Trp Ser Ile Asn Leu Thr Ala Gly Met Tyr Cys Ala Ala Leu
        35                   40                   45

Glu Ser Leu Ile Asn Val Ser Gly Cys Ser Ala Ile Glu Lys Thr Gln
    50                   55                   60

Arg Met Leu Ser Gly Phe Cys Pro His Lys Val Ser Ala Gly Gln Phe
65                   70                   75                   80

Ser Ser Leu His Val Arg Asp Thr Arg Ile Glu Val Ala Gln Phe Val
                85                   90                   95

Lys Asp Leu Leu Asn His Leu Lys Glu Leu Phe Thr Glu Gly Gln Phe
            100                  105                  110

Asn
```

<210> SEQ ID NO 14
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 14

```
Pro Gly Pro Val Pro Pro Ser Thr Ala Leu Ser Glu Leu Met Glu Glu
1               5                    10                    15

Leu Val Asn Ile Thr Gln Asn Gln Lys Ala Pro Leu Cys Asn Gly Ser
            20                   25                   30

Met Val Trp Ser Ile Asn Leu Thr Ala Gly Met Tyr Cys Ala Ala Leu
        35                   40                   45

Glu Ser Leu Ile Asn Val Ser Gly Cys Ser Ala Ile Glu Lys Thr Gln
    50                   55                   60

Arg Met Leu Ser Gly Phe Cys Pro His Lys Val Ser Ala Gly Gln Phe
65                   70                   75                   80
```

-continued

```
Ser Ser Leu His Val Arg Asp Ser Lys Ile Glu Val Ala Gln Phe Val
                85                  90                  95

Lys Asp Leu Leu Asn His Leu Lys Ala Leu Phe Lys Glu Gly Gln Phe
            100                 105                 110

Asn

<210> SEQ ID NO 15
<211> LENGTH: 112
<212> TYPE: PRT
<213> ORGANISM: Artificial Sequence
<220> FEATURE:
<223> OTHER INFORMATION: IL-13 wildtype

<400> SEQUENCE: 15

Gly Pro Val Pro Pro Ser Thr Ala Phe Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Pro Gly Gln Phe Ser
65                  70                  75                  80

Ser Leu His Val Thr Asn Ser Arg Ile Glu Val Ala Gln Phe Val Lys
                85                  90                  95

Asp Leu Leu Asn His Leu Lys Ala Leu Phe Lys Glu Gly Gln Tyr Asn
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: IL-13 wildtype

<400> SEQUENCE: 16

Gly Pro Val Pro Pro Ser Thr Ala His Leu Glu Leu Ile Glu Glu Leu
1               5                   10                  15

Ile Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Lys Glu Thr Arg Ile Glu Val Ala Gln Phe Val Lys
                85                  90                  95

Asp Leu Leu Asn His Leu Lys Thr Leu Phe Lys Glu Gly Gln Phe Asn
            100                 105                 110

<210> SEQ ID NO 17
<211> LENGTH: 113
<212> TYPE: PRT
<213> ORGANISM: Artificial Sequence
<220> FEATURE:
<223> OTHER INFORMATION: IL-13 wildtype
```

-continued

<400> SEQUENCE: 17

```
Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Pro Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Met Asp Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110

Asn
```

<210> SEQ ID NO 18
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 18

```
Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn
```

<210> SEQ ID NO 19
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 19

```
Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Arg Ile Asn Arg Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60
```

-continued

```
Arg Met Leu Ser Gly Phe Cys Pro His Lys Val Ser Ala Gly Gln Phe
65                  70              75                  80

Ser Ser Leu His Val Met Asp Ser Arg Ile Glu Val Ala Gln Phe Val
                85              90                  95

Lys Asp Leu Leu Asn His Leu Arg Ala Leu Phe Lys Glu Gly Gln Phe
            100             105                 110

Asn

<210> SEQ ID NO 20
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 20

Pro Gly Pro Val Pro Pro Ser Thr Ala Ala Arg Glu Leu Ile Glu Glu
1               5               10                  15

Leu Phe Asn Ile Thr Gln Asn Gln Lys Ala Pro Leu Cys Asn Gly Ser
            20              25                  30

Met Val Trp Ser Ile Asn Leu Thr Ala Gly Met Tyr Cys Ala Ala Leu
        35              40                  45

Glu Ser Leu Ile Asn Val Ser Gly Cys Ser Ala Ile Glu Lys Thr Lys
    50              55                  60

Arg Met Leu Ser Gly Phe Cys Pro His Lys Val Ser Ala Gly Gln Phe
65                  70              75                  80

Pro Ser Leu His Val Lys Lys Thr Arg Ile Glu Val Ala Gln Phe Val
                85              90                  95

Lys Asp Leu Leu Ile His Leu Arg Lys Leu Phe Lys Glu Gly Gln Phe
            100             105                 110

Asn

<210> SEQ ID NO 21
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 21

Pro Gly Pro Val Pro Pro Ser Thr Ala Leu Ile Glu Leu Ile Glu Glu
1               5               10                  15

Leu Ile Asn Ile Thr Gln Asn Gln Lys Ala Pro Leu Cys Asn Gly Ser
            20              25                  30

Met Val Trp Ser Ile Asn Leu Thr Ala Gly Met Tyr Cys Ala Ala Leu
        35              40                  45

Glu Ser Leu Ile Asn Val Ser Gly Cys Ser Ala Ile Glu Lys Thr Gln
    50              55                  60

Arg Met Leu Ser Gly Phe Cys Pro His Lys Val Ser Ala Gly Gln Phe
65                  70              75                  80

Ser Ser Leu His Val Lys Gly Ser Lys Ile Glu Val Ala Gln Phe Val
                85              90                  95

Lys Asp Leu Leu His His Leu Arg Ala Leu Met Arg Glu Gly Gln Phe
            100             105                 110

Asn
```

<210> SEQ ID NO 22
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 22

Pro Gly Pro Val Pro Pro Ser Thr Ala Ile Arg Glu Leu Ile Glu Glu
1               5                   10                  15

Leu Leu Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Lys Ser Lys Ile Glu Val Ala Gln Phe Val
                85                  90                  95

Lys Asp Leu Leu His His Leu Arg Ala Leu Phe Arg Glu Gly Gln Phe
            100                 105                 110

Asn

<210> SEQ ID NO 23
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 23

Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Gly Ser Lys Ile Glu Val Ala Gln Phe Val
                85                  90                  95

Lys Asp Leu Leu His His Leu Arg Ala Leu Phe Arg Glu Gly Gln Phe
            100                 105                 110

Asn

<210> SEQ ID NO 24
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 24

Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser

```
                20                    25                    30

Met Val Trp Ser Ile Asn Leu Thr Ala Gly Met Tyr Cys Ala Ala Leu
            35                    40                    45

Glu Ser Leu Ile Asn Val Ser Gly Cys Ser Ala Ile Glu Lys Thr Gln
        50                    55                    60

Arg Met Leu Ser Gly Phe Cys Pro His Lys Val Ser Ala Gly Gln Phe
65                    70                    75                    80

Ser Ser Leu His Val Arg Ser Ser Arg Ile Glu Val Ala Gln Phe Val
                85                    90                    95

Lys Asp Leu Leu His His Leu Arg Thr Leu Phe Arg Glu Gly Gln Phe
            100                   105                   110

Asn
```

<210> SEQ ID NO 25
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 25

```
Pro Gly Pro Val Pro Pro Ser Thr Ala Val Arg Glu Leu Ile Glu Glu
1                   5                    10                   15

Leu Ile Asn Ile Thr Gln Asn Gln Lys Ala Pro Leu Cys Asn Gly Ser
                20                    25                    30

Met Val Trp Ser Ile Asn Leu Thr Ala Gly Met Tyr Cys Ala Ala Leu
            35                    40                    45

Glu Ser Leu Ile Asn Val Ser Gly Cys Ser Ala Ile Glu Lys Thr Gln
        50                    55                    60

Arg Met Leu Ser Gly Phe Cys Pro His Lys Val Ser Ala Gly Gln Phe
65                    70                    75                    80

Ser Ser Leu His Val Arg Ser Ser Lys Ile Glu Val Ala Gln Phe Val
                85                    90                    95

Lys Asp Leu Leu Phe His Leu Arg Thr Leu Phe Arg Glu Gly Gln Phe
            100                   105                   110

Asn
```

<210> SEQ ID NO 26
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 26

```
Pro Gly Pro Val Pro Pro Ser Thr Ala Leu Arg Glu Leu Ile Glu Glu
1                   5                    10                   15

Leu Ile Asn Ile Thr Gln Asn Gln Lys Ala Pro Leu Cys Asn Gly Ser
                20                    25                    30

Met Val Trp Ser Ile Asn Leu Thr Ala Gly Met Tyr Cys Ala Ala Leu
            35                    40                    45

Glu Ser Leu Ile Asn Val Ser Gly Cys Ser Ala Ile Glu Lys Thr Gln
        50                    55                    60

Arg Met Leu Ser Gly Phe Cys Pro His Lys Val Ser Ala Gly Gln Phe
65                    70                    75                    80

Ser Ser Leu His Val Thr Gly Ser Lys Ile Glu Val Ala Gln Phe Val
                85                    90                    95
```

-continued

```
Lys Asp Leu Leu Tyr His Leu Arg Ala Leu Phe Arg Glu Gly Gln Phe
            100                 105                 110

Asn

<210> SEQ ID NO 27
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 27

Pro Gly Pro Val Pro Pro Ser Thr Ala Leu Ser Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Gly Ser Met Ile Glu Val Ala Gln Phe Val
                85                  90                  95

Lys Asp Leu Leu Tyr His Leu Arg Thr Leu Phe Arg Glu Gly Gln Phe
            100                 105                 110

Asn

<210> SEQ ID NO 28
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 28

Pro Gly Pro Val Pro Pro Ser Thr Ala Thr Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Gly Ser Lys Ile Glu Val Ala Gln Phe Val
                85                  90                  95

Lys Asp Leu Leu Tyr His Leu Arg Thr Leu Phe Arg Glu Gly Gln Phe
            100                 105                 110

Asn

<210> SEQ ID NO 29
<211> LENGTH: 113
<212> TYPE: PRT
<213> ORGANISM: Artificial Sequence
<220> FEATURE:
<223> OTHER INFORMATION: IL-13 wildtype
```

<400> SEQUENCE: 29

Pro Gly Pro Val Pro Pro Ser Thr Ala Asp Ile Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 30
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 30

Pro Gly Pro Val Pro Pro Ser Thr Ala Ala Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Thr Gly Lys Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn

<210> SEQ ID NO 31
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 31

Pro Gly Pro Val Pro Pro Ser Thr Ala Val Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln

```
                50                    55                    60

Arg Met Leu Ser Gly Phe Cys Pro His Lys Val Ser Ala Gly Gln Phe
65                  70                  75                  80

Ser Ser Leu His Val Arg Asp Thr Arg Ile Glu Val Ala Gln Phe Val
                85                  90                  95

Lys Asp Leu Leu Asn His Leu Lys Glu Leu Phe Thr Glu Gly Gln Phe
                100                 105                 110

Asn

<210> SEQ ID NO 32
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 32

Pro Gly Pro Val Pro Pro Ser Thr Ala Leu Ser Glu Leu Met Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
                35                  40                  45

Glu Ser Leu Ile Asn Val Ser Gly Cys Ser Ala Ile Glu Lys Thr Gln
                50                  55                  60

Arg Met Leu Ser Gly Phe Cys Pro His Lys Val Ser Ala Gly Gln Phe
65                  70                  75                  80

Ser Ser Leu His Val Arg Asp Ser Lys Ile Glu Val Ala Gln Phe Val
                85                  90                  95

Lys Asp Leu Leu Asn His Leu Lys Ala Leu Phe Lys Glu Gly Gln Phe
                100                 105                 110

Asn

<210> SEQ ID NO 33
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 33

Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
                35                  40                  45

Glu Ser Leu Ile Asn Val Ser Gly Cys Ser Ala Ile Glu Lys Thr Gln
                50                  55                  60

Arg Met Leu Ser Gly Phe Cys Pro His Lys Val Ser Ala Gly Gln Phe
65                  70                  75                  80

Ser Ser Leu His Val Lys Glu Thr Arg Ile Glu Val Ala Gln Phe Val
                85                  90                  95

Lys Asp Leu Leu Asn His Leu Lys Thr Leu Phe Lys Glu Gly Gln Phe
                100                 105                 110

Asn
```

<210> SEQ ID NO 34
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 34

Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 35
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 35

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 36
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 36

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Ser Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn

<210> SEQ ID NO 37
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 37

Pro Gly Pro Val Pro Pro Ser Thr Ala Ala Arg Glu Leu Ile Glu Glu
1               5                   10                  15

Leu Phe Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
                85                  90                  95

Lys Asp Leu Leu Ile His Leu Arg Lys Leu Phe Lys Glu Gly Gln Phe
            100                 105                 110

Asn

<210> SEQ ID NO 38
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 38

Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val

```
                    85                  90                  95

Lys Asp Leu Leu Phe His Leu Arg Thr Leu Phe Arg Glu Gly Gln Phe
                   100                 105                 110

Asn

<210> SEQ ID NO 39
<211> LENGTH: 146
<212> TYPE: PRT
<213> ORGANISM: Artificial Sequence
<220> FEATURE:
<223> OTHER INFORMATION: signal peptide

<400> SEQUENCE: 39

Met His Pro Leu Leu Asn Pro Leu Leu Leu Ala Leu Gly Leu Met Ala
1                   5                  10                  15

Leu Leu Leu Thr Thr Val Ile Ala Leu Thr Cys Leu Gly Gly Phe Ala
                   20                  25                  30

Ser Pro Gly Pro Val Pro Pro Ser Thr Ala His Arg Glu Leu Ile Glu
              35                  40                  45

Glu Leu Val Asn Ile Thr Gln Asn Gln Lys Ala Pro Leu Cys Asn Gly
        50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                   85                  90                  95

Gln Arg Met Leu Ser Gly Phe Cys Pro His Lys Val Ser Ala Gly Gln
                   100                 105                 110

Phe Ser Ser Leu His Val Thr Gly Arg Lys Ile Glu Val Ala Gln Phe
              115                 120                 125

Val Lys Asp Leu Leu Leu His Leu Lys Lys Leu Phe Lys Glu Gly Gln
              130                 135                 140

Phe Asn
145

<210> SEQ ID NO 40
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 40

Pro Gly Pro Val Pro Pro Ser Thr Ala Val Arg Ala Leu Ile Glu Glu
1                   5                  10                  15

Leu Ile Asn Ile Thr Gln Asn Gln Lys Ala Pro Leu Cys Asn Gly Ser
                   20                  25                  30

Met Val Trp Ser Ile Asn Arg Thr Ala Gly Met Tyr Cys Ala Ala Leu
              35                  40                  45

Glu Ser Leu Ile Asn Val Ser Gly Cys Ser Ala Ile Glu Lys Thr Gln
        50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                   85                  90                  95

Lys Asp Leu Leu Phe His Leu Arg Thr Leu Phe Arg Glu Gly Gln Phe
                   100                 105                 110

Asn
```

<210> SEQ ID NO 41
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 41

Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn

<210> SEQ ID NO 42
<211> LENGTH: 114
<212> TYPE: PRT
<213> ORGANISM: Artificial Sequence
<220> FEATURE:
<223> OTHER INFORMATION: IL-13 wildtype

<400> SEQUENCE: 42

Met Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
        50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Gln
            100                 105                 110

Phe Asn

<210> SEQ ID NO 43
<211> LENGTH: 117
<212> TYPE: PRT
<213> ORGANISM: Artificial Sequence
<220> FEATURE:
<223> OTHER INFORMATION: IL-13 wildtype

<400> SEQUENCE: 43

Met Tyr Cys Ala Ala Leu Glu Ser Leu Ile Asn Val Ser Gly Cys Ser
1               5                   10                  15

-continued

```
Ala Ile Glu Lys Thr Gln Arg Met Leu Ser Gly Phe Cys Pro His Lys
            20                  25                  30

Val Ser Ala Gly Gln Phe Ser Ser Leu His Val Arg Asp Thr Lys Ile
            35                  40                  45

Glu Val Ala Gln Phe Val Lys Asp Leu Leu Leu His Leu Lys Lys Leu
        50                  55                  60

Phe Arg Glu Gly Gln Phe Asn Gly Gly Ser Gly Pro Gly Pro Val Pro
65                  70                  75                  80

Pro Ser Thr Ala Leu Arg Glu Leu Ile Glu Glu Leu Val Asn Ile Thr
                85                  90                  95

Gln Asn Gln Lys Ala Pro Leu Cys Asn Gly Ser Met Val Trp Ser Ile
            100                 105                 110

Asn Leu Thr Ala Gly
        115

<210> SEQ ID NO 44
<211> LENGTH: 118
<212> TYPE: PRT
<213> ORGANISM: Artificial Sequence
<220> FEATURE:
<223> OTHER INFORMATION: IL-13 wildtype

<400> SEQUENCE: 44

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Asp Thr Lys Ile
            35                  40                  45

Glu Val Ala Gln Phe Val Lys Asp Leu Leu Leu His Leu Lys Lys Leu
        50                  55                  60

Phe Arg Glu Gly Gln Phe Asn Gly Gly Ser Gly Met Pro Gly Pro Val
65                  70                  75                  80

Pro Pro Ser Thr Ala Leu Arg Glu Leu Ile Glu Glu Leu Val Asn Ile
                85                  90                  95

Thr Gln Asn Gln Lys Ala Pro Leu Cys Asn Gly Ser Met Val Trp Ser
            100                 105                 110

Ile Asn Leu Thr Ala Gly
        115

<210> SEQ ID NO 45
<211> LENGTH: 117
<212> TYPE: PRT
<213> ORGANISM: Artificial Sequence
<220> FEATURE:
<223> OTHER INFORMATION: IL-13 wildtype

<400> SEQUENCE: 45

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Ser Ser Lys Ile
            35                  40                  45

Glu Val Ala Gln Phe Val Lys Asp Leu Leu Phe His Leu Arg Thr Leu
        50                  55                  60

Phe Arg Glu Gly Gln Phe Asn Gly Gly Ser Gly Pro Gly Pro Val Pro
```

```
65              70              75              80

Pro Ser Thr Ala Val Arg Glu Leu Ile Glu Glu Leu Ile Asn Ile Thr
                85              90              95

Gln Asn Gln Lys Ala Pro Leu Cys Asn Gly Ser Met Val Trp Ser Ile
                100             105             110

Asn Arg Thr Ala Gly
        115

<210> SEQ ID NO 46
<211> LENGTH: 118
<212> TYPE: PRT
<213> ORGANISM: Artificial Sequence
<220> FEATURE:
<223> OTHER INFORMATION: IL-13 wildtype

<400> SEQUENCE: 46

Met Tyr Cys Ala Ala Leu Glu Ser Leu Ile Asn Val Ser Gly Cys Ser
1               5               10              15

Ala Ile Glu Lys Thr Gln Arg Met Leu Ser Gly Phe Cys Pro His Lys
                20              25              30

Val Ser Ala Gly Gln Phe Ser Ser Leu His Val Arg Ser Ser Lys Ile
        35              40              45

Glu Val Ala Gln Phe Val Lys Asp Leu Leu Phe His Leu Arg Thr Leu
        50              55              60

Phe Arg Glu Gly Gln Phe Asn Gly Gly Ser Gly Met Pro Gly Pro Val
65              70              75              80

Pro Pro Ser Thr Ala Val Arg Glu Leu Ile Glu Glu Leu Ile Asn Ile
                85              90              95

Thr Gln Asn Gln Lys Ala Pro Leu Cys Asn Gly Ser Met Val Trp Ser
                100             105             110

Ile Asn Arg Thr Ala Gly
        115

<210> SEQ ID NO 47
<211> LENGTH: 117
<212> TYPE: PRT
<213> ORGANISM: Artificial Sequence
<220> FEATURE:
<223> OTHER INFORMATION: IL-13 wildtype

<400> SEQUENCE: 47

Met Tyr Cys Ala Ala Leu Glu Ser Leu Ile Asn Val Ser Gly Cys Ser
1               5               10              15

Ala Ile Glu Lys Thr Gln Asp Met Leu Ser Gly Phe Cys Pro His Lys
                20              25              30

Val Ser Ala Gly Gln Phe Ser Ser Leu His Val Arg Ser Ser Lys Ile
        35              40              45

Glu Val Ala Gln Phe Val Lys Asp Leu Leu Phe His Leu Arg Thr Leu
        50              55              60

Phe Arg Glu Gly Gln Phe Asn Gly Gly Ser Gly Pro Gly Pro Val Pro
65              70              75              80

Pro Ser Thr Ala Val Arg Ala Leu Ile Glu Glu Leu Ile Asn Ile Thr
                85              90              95

Gln Asn Gln Lys Ala Pro Leu Cys Asn Gly Ser Met Val Trp Ser Ile
                100             105             110

Asn Leu Thr Ala Gly
        115
```

-continued

<210> SEQ ID NO 48
<211> LENGTH: 118
<212> TYPE: PRT
<213> ORGANISM: Artificial Sequence
<220> FEATURE:
<223> OTHER INFORMATION: IL-13 wildtype

<400> SEQUENCE: 48

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
                20                  25                  30

Val Ser Ala Gly Gln Phe Ser Ser Leu His Val Arg Ser Ser Lys Ile
            35                  40                  45

Glu Val Ala Gln Phe Val Lys Asp Leu Leu Phe His Leu Arg Thr Leu
        50                  55                  60

Phe Arg Glu Gly Gln Phe Asn Gly Gly Ser Gly Met Pro Gly Pro Val
65                  70                  75                  80

Pro Pro Ser Thr Ala Val Arg Ala Leu Ile Glu Glu Leu Ile Asn Ile
                85                  90                  95

Thr Gln Asn Gln Lys Ala Pro Leu Cys Asn Gly Ser Met Val Trp Ser
            100                 105                 110

Ile Asn Leu Thr Ala Gly
        115

<210> SEQ ID NO 49
<211> LENGTH: 153
<212> TYPE: PRT
<213> ORGANISM: Artificial Sequence
<220> FEATURE:
<223> OTHER INFORMATION: IL-4 wildtype

<400> SEQUENCE: 49

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
        50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 50
<211> LENGTH: 130
<212> TYPE: PRT
<213> ORGANISM: Artificial Sequence
<220> FEATURE:
<223> OTHER INFORMATION: IL-4 wildtype

<400> SEQUENCE: 50

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
                20                  25                  30

Ile Phe Ala Ala Ser Lys Asp Thr Thr Glu Lys Glu Thr Phe Cys Arg
            35                  40                  45

Ala Ala Thr Val Leu Arg Gln Phe Tyr Ser His His Glu Lys Asp Thr
        50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130
```

<210> SEQ ID NO 51
<211> LENGTH: 128
<212> TYPE: PRT
<213> ORGANISM: Artificial Sequence
<220> FEATURE:
<223> OTHER INFORMATION: IL-4 wildtype

<400> SEQUENCE: 51

```
Lys Cys Asp Ile Thr Leu Gln Glu Ile Ile Lys Thr Leu Asn Ser Leu
1               5                   10                  15

Thr Glu Gln Lys Thr Leu Cys Thr Glu Leu Thr Val Thr Asp Ile Phe
                20                  25                  30

Ala Ala Ser Lys Asn Thr Thr Glu Lys Glu Thr Phe Cys Arg Ala Ala
            35                  40                  45

Thr Val Leu Arg Gln Phe Tyr Ser His His Glu Lys Asp Thr Arg Cys
        50                  55                  60

Leu Gly Ala Thr Ala Gln Gln Phe His Arg His Lys Gln Leu Ile Arg
65                  70                  75                  80

Phe Leu Lys Arg Leu Asp Arg Asn Leu Trp Gly Leu Ala Gly Leu Asn
                85                  90                  95

Ser Cys Pro Val Lys Glu Ala Asn Gln Ser Thr Leu Glu Asn Phe Leu
            100                 105                 110

Glu Arg Leu Lys Thr Ile Met Lys Glu Lys Phe Arg Lys Cys Ser Ser
        115                 120                 125
```

<210> SEQ ID NO 52
<211> LENGTH: 134
<212> TYPE: PRT
<213> ORGANISM: Artificial Sequence
<220> FEATURE:
<223> OTHER INFORMATION: IL-4 wildtype

<400> SEQUENCE: 52

```
Met Asp Thr Thr Glu Lys Glu Thr Phe Cys Arg Ala Ala Thr Val Leu
1               5                   10                  15
```

-continued

```
Arg Gln Phe Tyr Ser His His Glu Lys Asp Thr Arg Cys Leu Gly Ala
        20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser
        130
```

```
<210> SEQ ID NO 53
<211> LENGTH: 134
<212> TYPE: PRT
<213> ORGANISM: Artificial Sequence
<220> FEATURE:
<223> OTHER INFORMATION: IL-4 wildtype

<400> SEQUENCE: 53
```

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
        20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser
        130
```

```
<210> SEQ ID NO 54
<211> LENGTH: 252
<212> TYPE: PRT
<213> ORGANISM: Artificial Sequence
<220> FEATURE:
<223> OTHER INFORMATION: IL-4 wildtype

<400> SEQUENCE: 54
```

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
        20                  25                  30

Thr Ala Gln Gln Phe His Arg His Lys Gln Leu Ile Arg Phe Leu Lys
        35                  40                  45
```

-continued

```
Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Arg Gln Phe Tyr Ser His His Glu Lys Asp
    130                 135                 140

Thr Arg Cys Leu Gly Ala Thr Ala Gln Gln Phe His Arg His Lys Gln
145                 150                 155                 160

Leu Ile Arg Phe Leu Lys Arg Leu Asp Arg Asn Leu Trp Gly Leu Ala
            165                 170                 175

Gly Leu Asn Ser Cys Pro Val Lys Glu Ala Asn Gln Ser Thr Leu Glu
            180                 185                 190

Asn Phe Leu Glu Arg Leu Arg Val Ile Met Gln Ser Lys Trp Phe Lys
        195                 200                 205

Cys Gly Ala Gly Gly Asn Gly Gly His Lys Cys Asp Ile Thr Leu Gln
    210                 215                 220

Glu Ile Ile Lys Thr Leu Asn Ser Leu Thr Glu Gln Lys Thr Leu Cys
225                 230                 235                 240

Thr Glu Leu Thr Val Thr Asp Ile Phe Ala Ala Ser
            245                 250
```

```
<210> SEQ ID NO 55
<211> LENGTH: 133
<212> TYPE: PRT
<213> ORGANISM: Artificial Sequence
<220> FEATURE:
<223> OTHER INFORMATION: IL-4 wildtype

<400> SEQUENCE: 55
```

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Lys Cys Ser Ser Gly Gly Asn Gly
                85                  90                  95

Gly His Lys Cys Asp Ile Thr Leu Gln Glu Ile Ile Lys Thr Leu Asn
            100                 105                 110

Ser Leu Thr Glu Gln Lys Thr Leu Cys Thr Glu Leu Thr Val Thr Asp
        115                 120                 125

Ile Phe Ala Ala Ser
    130
```

```
<210> SEQ ID NO 56
```

```
<211> LENGTH: 286
<212> TYPE: PRT
<213> ORGANISM: Artificial Sequence
<220> FEATURE:
<223> OTHER INFORMATION: Cytokine Fusion

<400> SEQUENCE: 56

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn Gly Gly Gly Gly Ser Met Phe Gln Ile Pro Glu Phe Glu Pro Ser
            115                 120                 125

Glu Gln Glu Asp Ser Ser Ser Ala Glu Arg Gly Leu Gly Pro Ser Pro
    130                 135                 140

Ala Gly Asp Gly Pro Ser Gly Ser Gly Lys His His Arg Gln Ala Pro
145                 150                 155                 160

Gly Leu Leu Trp Asp Ala Ser His Gln Gln Glu Gln Pro Thr Ser Ser
                165                 170                 175

Ser His His Gly Gly Ala Gly Ala Val Glu Ile Arg Ser Arg His Ser
            180                 185                 190

Ala Tyr Pro Ala Gly Thr Glu Asp Asp Glu Gly Met Gly Glu Glu Pro
            195                 200                 205

Ser Pro Phe Arg Gly Arg Ser Arg Ala Ala Pro Pro Asn Leu Trp Ala
    210                 215                 220

Ala Gln Arg Tyr Gly Arg Glu Leu Arg Arg Met Ser Asp Glu Phe Val
225                 230                 235                 240

Asp Ser Phe Lys Lys Gly Leu Pro Arg Pro Lys Ser Ala Gly Thr Ala
                245                 250                 255

Thr Gln Met Arg Gln Ser Ser Ser Trp Thr Arg Val Phe Gln Ser Trp
            260                 265                 270

Trp Asp Arg Asn Leu Gly Arg Gly Ser Ser Ala Pro Ser Gln
            275                 280                 285

<210> SEQ ID NO 57
<211> LENGTH: 286
<212> TYPE: PRT
<213> ORGANISM: Artificial Sequence
<220> FEATURE:
<223> OTHER INFORMATION: Cytokine Fusion

<400> SEQUENCE: 57

Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
```

-continued

```
              35                    40                    45
Glu Ser Leu Ile Asn Val Ser Gly Cys Ser Ala Ile Glu Lys Thr Gln
              50                    55                    60

Arg Met Leu Ser Gly Phe Cys Pro His Lys Val Ser Ala Gly Gln Phe
65                    70                    75                    80

Ser Ser Leu His Val Arg Ser Ser Lys Ile Glu Val Ala Gln Phe Val
                        85                    90                    95

Lys Asp Leu Leu Phe His Leu Arg Thr Leu Phe Arg Glu Gly Gln Phe
                    100                   105                   110

Asn Gly Gly Gly Ser Met Phe Gln Ile Pro Glu Phe Glu Pro Ser
                    115                   120                   125

Glu Gln Glu Asp Ser Ser Ser Ala Glu Arg Gly Leu Gly Pro Ser Pro
        130                   135                   140

Ala Gly Asp Gly Pro Ser Gly Ser Gly Lys His His Arg Gln Ala Pro
145                   150                   155                   160

Gly Leu Leu Trp Asp Ala Ser His Gln Gln Glu Gln Pro Thr Ser Ser
                    165                   170                   175

Ser His His Gly Gly Ala Gly Ala Val Glu Ile Arg Ser Arg His Ser
                    180                   185                   190

Ala Tyr Pro Ala Gly Thr Glu Asp Asp Glu Gly Met Gly Glu Glu Pro
                    195                   200                   205

Ser Pro Phe Arg Gly Arg Ser Arg Ala Ala Pro Pro Asn Leu Trp Ala
        210                   215                   220

Ala Gln Arg Tyr Gly Arg Glu Leu Arg Arg Met Ser Asp Glu Phe Val
225                   230                   235                   240

Asp Ser Phe Lys Lys Gly Leu Pro Arg Pro Lys Ser Ala Gly Thr Ala
                    245                   250                   255

Thr Gln Met Arg Gln Ser Ser Ser Trp Thr Arg Val Phe Gln Ser Trp
                    260                   265                   270

Trp Asp Arg Asn Leu Gly Arg Gly Ser Ser Ala Pro Ser Gln
                    275                   280                   285
```

```
<210> SEQ ID NO 58
<211> LENGTH: 301
<212> TYPE: PRT
<213> ORGANISM: Artificial Sequence
<220> FEATURE:
<223> OTHER INFORMATION: Cytokine Fusion

<400> SEQUENCE: 58
```

```
Lys Cys Asp Ile Thr Leu Gln Glu Ile Ile Lys Thr Leu Asn Ser Leu
1                   5                     10                    15

Thr Glu Gln Lys Thr Leu Cys Thr Glu Leu Thr Val Thr Asp Ile Phe
                    20                    25                    30

Ala Ala Ser Lys Asn Thr Thr Glu Lys Glu Thr Phe Cys Arg Ala Ala
              35                    40                    45

Thr Val Leu Arg Gln Phe Tyr Ser His His Glu Lys Asp Thr Arg Cys
        50                    55                    60

Leu Gly Ala Thr Ala Gln Gln Phe His Arg His Lys Gln Leu Ile Arg
65                    70                    75                    80

Phe Leu Lys Arg Leu Asp Arg Asn Leu Trp Gly Leu Ala Gly Leu Asn
                        85                    90                    95

Ser Cys Pro Val Lys Glu Ala Asn Gln Ser Thr Leu Glu Asn Phe Leu
                    100                   105                   110

Glu Arg Leu Lys Thr Ile Met Lys Glu Lys Phe Arg Lys Cys Ser Ser
```

-continued

```
              115                 120                 125
Gly Gly Gly Gly Ser Met Phe Gln Ile Pro Glu Phe Glu Pro Ser Glu
    130                 135                 140

Gln Glu Asp Ser Ser Ser Ala Glu Arg Gly Leu Gly Pro Ser Pro Ala
145                 150                 155                 160

Gly Asp Gly Pro Ser Gly Ser Gly Lys His His Arg Gln Ala Pro Gly
                165                 170                 175

Leu Leu Trp Asp Ala Ser His Gln Gln Glu Gln Pro Thr Ser Ser Ser
            180                 185                 190

His His Gly Gly Ala Gly Ala Val Glu Ile Arg Ser Arg His Ser Ala
            195                 200                 205

Tyr Pro Ala Gly Thr Glu Asp Asp Glu Gly Met Gly Glu Glu Pro Ser
    210                 215                 220

Pro Phe Arg Gly Arg Ser Arg Ala Ala Pro Pro Asn Leu Trp Ala Ala
225                 230                 235                 240

Gln Arg Tyr Gly Arg Glu Leu Arg Arg Met Ser Asp Glu Phe Val Asp
                245                 250                 255

Ser Phe Lys Lys Gly Leu Pro Arg Pro Lys Ser Ala Gly Thr Ala Thr
            260                 265                 270

Gln Met Arg Gln Ser Ser Ser Trp Thr Arg Val Phe Gln Ser Trp Trp
            275                 280                 285

Asp Arg Asn Leu Gly Arg Gly Ser Ser Ala Pro Ser Gln
    290                 295                 300
```

```
<210> SEQ ID NO 59
<211> LENGTH: 309
<212> TYPE: PRT
<213> ORGANISM: Artificial Sequence
<220> FEATURE:
<223> OTHER INFORMATION: Cytokine Fusion

<400> SEQUENCE: 59
```

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser Gly Ser Phe Gln Ile Pro Glu Phe Glu Pro
    130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
```

-continued

```
                180                 185                 190
Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
        210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
                260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln His
        290                 295                 300

His His His His His
305

<210> SEQ ID NO 60
<211> LENGTH: 303
<212> TYPE: PRT
<213> ORGANISM: Artificial Sequence
<220> FEATURE:
<223> OTHER INFORMATION: Cytokine Fusion

<400> SEQUENCE: 60

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
                100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
        130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
                180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
        210                 215                 220

Pro Ser Pro Phe Arg Gly Arg Ser Arg Ala Ala Pro Pro Asn Leu Trp
```

```
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
                260                 265                 270

Ala Thr Gln Met Arg Gln Ser Ser Ser Trp Thr Arg Val Phe Gln Ser
                275                 280                 285

Trp Trp Asp Arg Asn Leu Gly Arg Gly Ser Ser Ala Pro Ser Gln
    290                 295                 300

<210> SEQ ID NO 61
<211> LENGTH: 303
<212> TYPE: PRT
<213> ORGANISM: Artificial Sequence
<220> FEATURE:
<223> OTHER INFORMATION: Cytokine Fusion

<400> SEQUENCE: 61

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
                35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
                100                 105                 110

Asn Ser Leu Thr Glu Gln Lys Thr Leu Cys Thr Glu Leu Thr Val Thr
                115                 120                 125

Asp Ile Phe Ala Ala Ser Gly Ser Phe Gln Ile Pro Glu Phe Glu Pro
    130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
                180                 185                 190

Ser Ser His His Gly Gly Ala Gly Ala Val Glu Ile Arg Ser Arg His
                195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
                260                 265                 270

Ala Thr Gln Met Arg Gln Ser Ser Ser Trp Thr Arg Val Phe Gln Ser
                275                 280                 285

Trp Trp Asp Arg Asn Leu Gly Arg Gly Ser Ser Ala Pro Ser Gln
```

-continued

```
      290                295                300
```

<210> SEQ ID NO 62
<211> LENGTH: 309
<212> TYPE: PRT
<213> ORGANISM: Artificial Sequence
<220> FEATURE:
<223> OTHER INFORMATION: Cytokine Fusion

<400> SEQUENCE: 62

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser Gly Ser Phe Gln Ile Pro Glu Phe Glu Pro
        130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
            165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
            195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
            245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln His
    290                 295                 300

His His His His His
305

<210> SEQ ID NO 63
<211> LENGTH: 295
<212> TYPE: PRT
<213> ORGANISM: Artificial Sequence
<220> FEATURE:
<223> OTHER INFORMATION: Cytokine Fusion

<400> SEQUENCE: 63

```
Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn Gly Gly Gly Gly Ser Gly Gly Gly Gly Ser Gly Gly Gly Gly Ser
            115                 120                 125

Phe Gln Ile Pro Glu Phe Glu Pro Ser Glu Gln Glu Asp Ser Ser Ser
    130                 135                 140

Ala Glu Arg Gly Leu Gly Pro Ser Pro Ala Gly Asp Gly Pro Ser Gly
145                 150                 155                 160

Ser Gly Lys His His Arg Gln Ala Pro Gly Leu Leu Trp Asp Ala Ser
                165                 170                 175

His Gln Gln Glu Gln Pro Thr Ser Ser Ser His His Gly Gly Ala Gly
            180                 185                 190

Ala Val Glu Ile Arg Ser Arg His Ser Ala Tyr Pro Ala Gly Thr Glu
            195                 200                 205

Asp Asp Glu Gly Met Gly Glu Glu Pro Ser Pro Phe Arg Gly Arg Ser
    210                 215                 220

Arg Ala Ala Pro Pro Asn Leu Trp Ala Ala Gln Arg Tyr Gly Arg Glu
225                 230                 235                 240

Leu Arg Arg Met Ser Asp Glu Phe Val Asp Ser Phe Lys Lys Gly Leu
            245                 250                 255

Pro Arg Pro Lys Ser Ala Gly Thr Ala Thr Gln Met Arg Gln Ser Ser
            260                 265                 270

Ser Trp Thr Arg Val Phe Gln Ser Trp Trp Asp Arg Asn Leu Gly Arg
            275                 280                 285

Gly Ser Ser Ala Pro Ser Gln
    290                 295
```

<210> SEQ ID NO 64
<211> LENGTH: 366
<212> TYPE: PRT
<213> ORGANISM: Artificial Sequence
<220> FEATURE:
<223> OTHER INFORMATION: Cytokine Fusion

<400> SEQUENCE: 64

```
Lys Cys Asp Ile Thr Leu Gln Glu Ile Ile Lys Thr Leu Asn Ser Leu
1               5                   10                  15

Thr Glu Gln Lys Thr Leu Cys Thr Glu Leu Thr Val Thr Asp Ile Phe
            20                  25                  30

Ala Ala Ser Lys Asn Thr Thr Glu Lys Glu Thr Phe Cys Arg Ala Ala
            35                  40                  45
```

-continued

```
Thr Val Leu Arg Gln Phe Tyr Ser His His Glu Lys Asp Thr Arg Cys
    50                  55                  60

Leu Gly Ala Thr Ala Gln Gln Phe His Arg His Lys Gln Leu Ile Arg
65                  70                  75                  80

Phe Leu Lys Arg Leu Asp Arg Asn Leu Trp Gly Leu Ala Gly Leu Asn
                85                  90                  95

Ser Cys Pro Val Lys Glu Ala Asn Gln Ser Thr Leu Glu Asn Phe Leu
            100                 105                 110

Glu Arg Leu Lys Thr Ile Met Arg Glu Lys Tyr Ser Lys Cys Ser Ser
        115                 120                 125

Gly Gly Gly Gly Ser Met Ser Gln Ser Asn Arg Glu Leu Val Val Asp
    130                 135                 140

Phe Leu Ser Tyr Lys Leu Ser Gln Lys Gly Tyr Ser Trp Ser Gln Phe
145                 150                 155                 160

Ser Asp Val Glu Glu Asn Arg Thr Glu Ala Pro Glu Gly Thr Glu Ser
                165                 170                 175

Glu Met Glu Thr Pro Ser Ala Ile Asn Gly Asn Pro Ser Trp His Leu
            180                 185                 190

Ala Asp Ser Pro Ala Val Asn Gly Ala Thr Gly His Ser Ser Ser Leu
        195                 200                 205

Asp Ala Arg Glu Val Ile Pro Met Ala Ala Val Lys Gln Ala Leu Arg
    210                 215                 220

Glu Ala Gly Asp Glu Phe Glu Leu Arg Tyr Arg Arg Ala Phe Ser Asp
225                 230                 235                 240

Leu Thr Ser Gln Leu His Ile Thr Pro Gly Thr Ala Tyr Gln Ser Phe
                245                 250                 255

Glu Gln Val Val Asn Glu Leu Phe Arg Asp Gly Val Asn Trp Gly Arg
            260                 265                 270

Ile Val Ala Phe Phe Ser Phe Gly Gly Ala Leu Cys Val Glu Ser Val
        275                 280                 285

Asp Lys Glu Met Gln Val Leu Val Ser Arg Ile Ala Ala Trp Met Ala
    290                 295                 300

Thr Tyr Leu Asn Asp His Leu Glu Pro Trp Ile Gln Glu Asn Gly Gly
305                 310                 315                 320

Trp Asp Thr Phe Val Glu Leu Tyr Gly Asn Asn Ala Ala Ala Glu Ser
                325                 330                 335

Arg Lys Gly Gln Glu Arg Phe Asn Arg Trp Phe Leu Thr Gly Met Thr
            340                 345                 350

Val Ala Gly Val Val Leu Leu Gly Ser Leu Phe Ser Arg Lys
        355                 360                 365
```

```
<210> SEQ ID NO 65
<211> LENGTH: 485
<212> TYPE: PRT
<213> ORGANISM: Artificial Sequence
<220> FEATURE:
<223> OTHER INFORMATION: Cytokine Fusion

<400> SEQUENCE: 65
```

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
        35                  40                  45
```

```
Leu Arg Asp Arg Asn Leu Trp Gly Leu Ala Gly Leu Asn Ser Cys Pro
    50              55                  60

Val Lys Glu Ala Asn Gln Ser Thr Leu Glu Asn Phe Leu Glu Arg Leu
65              70                  75                  80

Lys Thr Ile Met Arg Glu Lys Tyr Ser Lys Cys Ser Ser Gly Gly Asn
            85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Lys Ala Ser Gly Gly Pro Glu Gly Gly Ser
    130                 135                 140

Leu Ala Ala Leu Thr Ala His Gln Ala Cys His Leu Pro Leu Glu Thr
145             150                 155                 160

Phe Thr Arg His Arg Gln Pro Arg Gly Trp Glu Gln Leu Glu Gln Cys
            165                 170                 175

Gly Tyr Pro Val Gln Arg Leu Val Ala Leu Tyr Leu Ala Ala Arg Leu
            180                 185                 190

Ser Trp Asn Gln Val Asp Gln Val Ile Arg Asn Ala Leu Ala Ser Pro
        195                 200                 205

Gly Ser Gly Gly Asp Leu Gly Glu Ala Ile Arg Glu Gln Pro Glu Gln
    210                 215                 220

Ala Arg Leu Ala Leu Thr Leu Ala Ala Ala Glu Ser Glu Arg Phe Val
225             230                 235                 240

Arg Gln Gly Thr Gly Asn Asp Glu Ala Gly Ala Ala Asn Gly Pro Ala
            245                 250                 255

Asp Ser Gly Asp Ala Leu Leu Glu Arg Asn Tyr Pro Thr Gly Ala Glu
            260                 265                 270

Phe Leu Gly Asp Gly Gly Asp Val Ser Phe Ser Thr Arg Gly Thr Gln
        275                 280                 285

Asn Trp Thr Val Glu Arg Leu Leu Gln Ala His Arg Gln Leu Glu Glu
    290                 295                 300

Arg Gly Tyr Val Phe Val Gly Tyr His Gly Thr Phe Leu Glu Ala Ala
305             310                 315                 320

Gln Ser Ile Val Phe Gly Gly Val Arg Ala Arg Ser Gln Asp Leu Asp
            325                 330                 335

Ala Ile Trp Arg Gly Phe Tyr Ile Ala Gly Asp Pro Ala Leu Ala Tyr
            340                 345                 350

Gly Tyr Ala Gln Asp Gln Glu Pro Asp Ala Arg Gly Arg Ile Arg Asn
        355                 360                 365

Gly Ala Leu Leu Arg Val Tyr Val Pro Arg Ser Ser Leu Pro Gly Phe
    370                 375                 380

Tyr Arg Thr Ser Leu Thr Leu Ala Ala Pro Glu Ala Ala Gly Glu Val
385             390                 395                 400

Glu Arg Leu Ile Gly His Pro Leu Pro Leu Arg Leu Asp Ala Ile Thr
            405                 410                 415

Gly Pro Glu Glu Glu Gly Gly Arg Leu Glu Thr Ile Leu Gly Trp Pro
            420                 425                 430

Leu Ala Glu Arg Thr Val Val Ile Pro Ser Ala Ile Pro Thr Asp Pro
        435                 440                 445

Arg Asn Val Gly Gly Asp Leu Asp Pro Ser Ser Ile Pro Asp Lys Glu
    450                 455                 460

Gln Ala Ile Ser Ala Leu Pro Asp Tyr Ala Ser Gln Pro Gly Lys Pro
```

-continued

```
465            470            475            480
```

Pro Lys Asp Glu Leu
                485

<210> SEQ ID NO 66
<211> LENGTH: 309
<212> TYPE: PRT
<213> ORGANISM: Artificial Sequence
<220> FEATURE:
<223> OTHER INFORMATION: Cytokine Fusion

<400> SEQUENCE: 66

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser Gly Ser Phe Gln Ile Pro Glu Phe Glu Pro
    130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
            195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
            275                 280                 285

Trp Trp Asp Arg Asn Leu Gly Arg Gly Ser Ser Ala Pro Ser Gln His
    290                 295                 300

His His His His His
305

<210> SEQ ID NO 67
<211> LENGTH: 303
<212> TYPE: PRT

<213> ORGANISM: Artificial Sequence
<220> FEATURE:
<223> OTHER INFORMATION: Cytokine Fusion

<400> SEQUENCE: 67

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
    130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln
    290                 295                 300
```

<210> SEQ ID NO 68
<211> LENGTH: 305
<212> TYPE: PRT
<213> ORGANISM: Artificial Sequence
<220> FEATURE:
<223> OTHER INFORMATION: Cytokine Fusion

<400> SEQUENCE: 68

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
                20                  25                  30
```

-continued

```
Ile Phe Ala Ala Ser Lys Asp Thr Thr Glu Lys Glu Thr Phe Cys Arg
        35              40              45

Ala Ala Thr Val Leu Arg Gln Phe Tyr Ser His His Glu Lys Asp Thr
    50              55              60

Arg Cys Leu Gly Ala Thr Ala Gln Gln Phe His Arg His Lys Gln Leu
65              70              75              80

Ile Arg Phe Leu Lys Arg Leu Asp Arg Asn Leu Trp Gly Leu Ala Gly
                85              90              95

Leu Asn Ser Cys Pro Val Lys Glu Ala Asn Gln Ser Thr Leu Glu Asn
                100             105             110

Phe Leu Glu Arg Leu Lys Thr Ile Met Arg Glu Lys Tyr Ser Lys Cys
        115             120             125

Ser Ser Gly Ser Phe Gln Ile Pro Glu Phe Glu Pro Ser Glu Gln Glu
    130             135             140

Asp Ser Ser Ser Ala Glu Arg Gly Leu Gly Pro Ser Pro Ala Gly Asp
145             150             155             160

Gly Pro Ser Gly Ser Gly Lys His His Arg Gln Ala Pro Gly Leu Leu
                165             170             175

Trp Asp Ala Ser His Gln Gln Glu Gln Pro Thr Ser Ser Ser His His
            180             185             190

Gly Gly Ala Gly Ala Val Glu Ile Arg Ser Arg His Ser Ala Tyr Pro
        195             200             205

Ala Gly Thr Glu Asp Asp Glu Gly Met Gly Glu Glu Pro Ser Pro Phe
        210             215             220

Arg Gly Arg Ser Arg Ala Ala Pro Pro Asn Leu Trp Ala Ala Gln Arg
225             230             235             240

Tyr Gly Arg Glu Leu Arg Arg Met Ser Asp Glu Phe Val Asp Ser Phe
            245             250             255

Lys Lys Gly Leu Pro Arg Pro Lys Ser Ala Gly Thr Ala Thr Gln Met
            260             265             270

Arg Gln Ser Ser Ser Trp Thr Arg Val Phe Gln Ser Trp Trp Asp Arg
        275             280             285

Asn Leu Gly Arg Gly Ser Ser Ala Pro Ser Gln His His His His His
    290             295             300

His
305
```

```
<210> SEQ ID NO 69
<211> LENGTH: 299
<212> TYPE: PRT
<213> ORGANISM: Artificial Sequence
<220> FEATURE:
<223> OTHER INFORMATION: Cytokine Fusion

<400> SEQUENCE: 69
```

```
Met His Lys Cys Asp Ile Thr Leu Gln Glu Ile Ile Lys Thr Leu Asn
1               5               10              15

Ser Leu Thr Glu Gln Lys Thr Leu Cys Thr Glu Leu Thr Val Thr Asp
                20              25              30

Ile Phe Ala Ala Ser Lys Asp Thr Thr Glu Lys Glu Thr Phe Cys Arg
        35              40              45

Ala Ala Thr Val Leu Arg Gln Phe Tyr Ser His His Glu Lys Asp Thr
    50              55              60

Arg Cys Leu Gly Ala Thr Ala Gln Gln Phe His Arg His Lys Gln Leu
65              70              75              80
```

```
Ile Arg Phe Leu Lys Arg Leu Asp Arg Asn Leu Trp Gly Leu Ala Gly
              85              90              95

Leu Asn Ser Cys Pro Val Lys Glu Ala Asn Gln Ser Thr Leu Glu Asn
              100             105             110

Phe Leu Glu Arg Leu Lys Thr Ile Met Arg Glu Lys Tyr Ser Lys Cys
              115             120             125

Ser Ser Gly Ser Phe Gln Ile Pro Glu Phe Glu Pro Ser Glu Gln Glu
              130             135             140

Asp Ser Ser Ser Ala Glu Arg Gly Leu Gly Pro Ser Pro Ala Gly Asp
145             150             155             160

Gly Pro Ser Gly Ser Gly Lys His His Arg Gln Ala Pro Gly Leu Leu
              165             170             175

Trp Asp Ala Ser His Gln Gln Glu Gln Pro Thr Ser Ser Ser His His
              180             185             190

Gly Gly Ala Gly Ala Val Glu Ile Arg Ser Arg His Ser Ala Tyr Pro
              195             200             205

Ala Gly Thr Glu Asp Asp Glu Gly Met Gly Glu Glu Pro Ser Pro Phe
              210             215             220

Arg Gly Arg Ser Arg Ala Ala Pro Pro Asn Leu Trp Ala Ala Gln Arg
225             230             235             240

Tyr Gly Arg Glu Leu Arg Arg Met Ser Asp Glu Phe Val Asp Ser Phe
              245             250             255

Lys Lys Gly Leu Pro Arg Pro Lys Ser Ala Gly Thr Ala Thr Gln Met
              260             265             270

Arg Gln Ser Ser Ser Trp Thr Arg Val Phe Gln Ser Trp Trp Asp Arg
              275             280             285

Asn Leu Gly Arg Gly Ser Ser Ala Pro Ser Gln
    290             295
```

<210> SEQ ID NO 70
<211> LENGTH: 402
<212> TYPE: DNA
<213> ORGANISM: Artificial Sequence
<220> FEATURE:
<223> OTHER INFORMATION: cpIL4

<400> SEQUENCE: 70

```
atggatacca ccgagaaaga aacgttctgc cgtgctgcca ctgtcctgcg ccagtttttac      60 agccatcacg aaaaggacac ccgttgcctg ggtgcgacgg cgcagcaatt ccaccgccac     120
aaacagctga ttcgtttcct gaagcgtctg accgtaacc tgtggggtct ggcgggtctg      180
aacagctgtc cagtgaaaga agcgaatcag agcaccttgg agaatttcct cgaacgcctg     240
aaaaccatca tgcgtgagaa atacagcaag tgttctagcg gcggtaacgg tggccacaaa     300
tgcgatatca ccctgcaaga gatcattaag acgctgaact ccttgacgga acaaaagacc     360
ctgtgtactg agctgacggt caccgacatt ttcgcggcgt cc                        402
```

<210> SEQ ID NO 71
<211> LENGTH: 402
<212> TYPE: DNA
<213> ORGANISM: Artificial Sequence
<220> FEATURE:
<223> OTHER INFORMATION: cpKFR

<400> SEQUENCE: 71

```
atggatacta ccgagaaaga aacgttttgc cgtgctgcga ccgtcctgcg tcagttctac      60
agccaccacg aaaaggacac ccgctgtctg ggtgcgactg cccaacaatt ccatcgtcac     120
```

-continued

```
aaacagctga ttcgtttcct gaagcgtctg gaccgcaacc tgtggggtct ggcgggcttg      180
aactcctgcc cagtcaaaga agcgaaccaa agcaccctgg aaaacttctt ggagcgtctg      240
aaaacgatca tgaaagagaa gttccgcaag tgtagcagcg gtggtaatgg tggccacaag      300
tgcgacatta cgctgcagga aatcattaag accctgaact ctctgaccga gcagaaaacc      360
ctctgtaccg agctgacggt gacggatatc tttgcggcga gc      402
```

```
<210> SEQ ID NO 72
<211> LENGTH: 402
<212> TYPE: DNA
<213> ORGANISM: Artificial Sequence
<220> FEATURE:
<223> OTHER INFORMATION: cpS4

<400> SEQUENCE: 72
```

```
atggatacca ccgaaaaaga aactttttgt cgtgccgcga ctgtcctgcg ccagttctac      60
agccaccacg aaaaggacac ccgttgcctg ggtgcgaccg ctcaacaatt ccatcgccac      120
aaacagctga ttcgtttcct gaaacgtctg gatcgcaacc tgtggggtct ggcgggtttg      180
aacagctgtc cagtcaaaga agcgaaccag agcaccctgg aaaactttct ggagcgtctg      240
cgtgttatca tgcagagcaa gtggttcaag tgcggtgcgg gtggcaatgg tggccacaag      300
tgtgacatta ccttgcaaga gattatcaaa acgctgaact ctctgaccga gcaaaagacg      360
ctgtgcaccg agctgacggt gacggacatc ttcgcggcgt cc      402
```

```
<210> SEQ ID NO 73
<211> LENGTH: 507
<212> TYPE: DNA
<213> ORGANISM: Artificial Sequence
<220> FEATURE:
<223> OTHER INFORMATION: variant BAD

<400> SEQUENCE: 73
```

```
ggtagctttc agatcccgga atttgagccg agcgagcaag aggattcaag cagcgcggag      60
cgcggtctgg gtccgagccc ggcaggcgac ggtccgagcg gcagcggcaa gcatcaccgc      120
caggcgccag gcctgctgtg ggatgcatcg catcaacagg aacaaccgac gagcagcagc      180
catcatggtg cgctgggtgc ggttgagatt agatcgcgcc actccgcata tcctgccggc      240
accgaagatg acgaaggcat gggcgaggaa ccgagcccgt tccgtggccg tagccgtgct      300
gcaccgccga atctgtgggc cgcacagcgt tatggtcgcg agttgcgtcg catgtccgac      360
gagtttgttg actccttcaa gaaaggttta ccgcgtccga aatctgccgg taccgcgacg      420
cagatgcgtc agagcagcag ctggacccgc gtgtttcaat cttggtggga tcgtaatctg      480
ggtcgtggta gcagcgcacc gagccaa      507
```

```
<210> SEQ ID NO 74
<211> LENGTH: 897
<212> TYPE: DNA
<213> ORGANISM: Artificial Sequence
<220> FEATURE:
<223> OTHER INFORMATION: IL-4-Bad fusion

<400> SEQUENCE: 74
```

```
atgcacaaat gcgacattac cctgcaagag atcattaaga ccctgaacag cctgaccgag      60
caaaagaccc tgtgtaccga actgaccgtc acggacatct tcgctgcgtc caaggacact      120
acggaaaagg aaacgttctg tcgtgcggcg acggtgctgc gccagttcta cagccaccat      180
```

-continued

```
gagaaagata cccgttgcct cggtgcgacc gcgcaacagt tccaccgtca caaacagctg      240
attcgcttcc tgaagcgtct ggatcgcaac ctgtggggtt tggcgggtct gaactcctgt      300
ccagtcaaag aagccaatca gtctacgctg gaaaactttt tggagcgtct gaaaactatc      360
atgcgtgaga agtacagcaa atgcagcagc ggtagctttc agatcccgga atttgagccg      420
agcgagcaag aggattcaag cagcgcggag cgcggtctgg gtccgagccc ggcaggcgac      480
ggtccgagcg gcagcggcaa gcatcaccgc caggcgccag gcctgctgtg ggatgcatcg      540
catcaacagg aacaaccgac gagcagcagc catcatggtg gcgctggtgc ggttgagatt      600
agatcgcgcc actccgcata tcctgccggc accgaagatg acgaaggcat gggcgaggaa      660
ccgagcccgt ccgtggccg tagccgtgct gcaccgccga atctgtgggc cgcacagcgt       720
tatggtcgcg agttgcgtcg catgtccgac gagtttgttg actccttcaa gaaaggttta      780
ccgcgtccga aatctgccgg taccgcgacg cagatgcgtc agagcagcag ctggacccgc      840
gtgtttcaat cttggtggga tcgtaatctg ggtcgtggta gcagcgcacc gagccaa       897
```

```
<210> SEQ ID NO 75
<211> LENGTH: 909
<212> TYPE: DNA
<213> ORGANISM: Artificial Sequence
<220> FEATURE:
<223> OTHER INFORMATION: cpIL4-Bad fusion

<400> SEQUENCE: 75
```

```
atggatacca ccgagaaaga aacgttctgc cgtgctgcca ctgtcctgcg ccagttttac       60
agccatcacg aaaaggacac ccgttgcctg ggtgcgacgg cgcagcaatt ccaccgccac      120
aaacagctga ttcgtttcct gaagcgtctg accgtaacc tgtggggtct ggcgggtctg       180
aacagctgtc cagtgaaaga agcgaatcag agcaccttgg agaatttcct cgaacgcctg      240
aaaaccatca tgcgtgagaa atacagcaag tgttctagcg gcggtaacgg tggccacaaa      300
tgcgatatca ccctgcaaga gatcattaag acgctgaact ccttgacgga acaaaagacc      360
ctgtgtactg agctgacggt caccgacatt ttcgcggcgt ccggtagctt tcagatcccg      420
gaatttgagc cgagcgagca agaggattca agcagcgcgg agcgcggtct gggtccgagc      480
ccggcaggcg acggtccgag cggcagcggc aagcatcacc gccaggcgcc aggcctgctg      540
tgggatgcat cgcatcaaca ggaacaaccg acgagcagca gccatcatgg tggcgctggt      600
gcggttgaga ttagatcgcg ccactccgca tatcctgccg gcaccgaaga tgacgaaggc      660
atgggcgagg aaccgagccc gttccgtggc cgtagccgtg ctgcaccgcc gaatctgtgg      720
gccgcacagc gttatggtcg cgagttgcgt cgcatgtccg acgagtttgt tgactccttc      780
aagaaaggtt taccgcgtcc gaaatctgcc ggtaccgcga cgcagatgcg tcagagcagc      840
agctggaccc gcgtgtttca atcttggtgg gatcgtaatc tgggtcgtgg tagcagcgca      900
ccgagccaa                                                             909
```

```
<210> SEQ ID NO 76
<211> LENGTH: 909
<212> TYPE: DNA
<213> ORGANISM: Artificial Sequence
<220> FEATURE:
<223> OTHER INFORMATION: cpKFR4-Bad fusion

<400> SEQUENCE: 76
```

```
atggatacta ccgagaaaga aacgttttgc cgtgctgcga ccgtcctgcg tcagttctac       60
agccaccacg aaaaggacac ccgctgtctg ggtgcgactg cccaacaatt ccatcgtcac      120
```
aaacagctga ttcgtttcct gaagcgtctg gaccgcaacc tgtggggtct ggcgggcttg      180
aactcctgcc cagtcaaaga agcgaaccaa agcaccctgg aaaacttctt ggagcgtctg      240
aaaacgatca tgaaagagaa gttccgcaag tgtagcagcg gtggtaatgg tggccacaag      300
tgcgacatta cgctgcagga aatcattaag accctgaact ctctgaccga gcagaaaacc      360
ctctgtaccg agctgacggt gacggatatc tttgcggcga gcggtagctt tcagatcccg      420
gaatttgagc cgagcgagca agaggattca agcagcgcgg agcgcggtct gggtccgagc      480
ccggcaggcg acggtccgag cggcagcggc aagcatcacc gccaggcgcc aggcctgctg      540
tgggatgcat cgcatcaaca ggaacaaccg acgagcagca gccatcatgg tggcgctggt      600
gcggttgaga ttagatcgcg ccactccgca tatcctgccg gcaccgaaga tgacgaaggc      660
atgggcgagg aaccgagccc gttccgtggc cgtagccgtg ctgcaccgcc gaatctgtgg      720
gccgcacagc gttatggtcg cgagttgcgt cgcatgtccg acgagtttgt tgactccttc      780
aagaaaggtt taccgcgtcc gaaatctgcc ggtaccgcga cgcagatgcg tcagagcagc      840
agctggaccc gcgtgtttca atcttggtgg gatcgtaatc tgggtcgtgg tagcagcgca      900
ccgagccaa      909

<210> SEQ ID NO 77
<211> LENGTH: 909
<212> TYPE: DNA
<213> ORGANISM: Artificial Sequence
<220> FEATURE:
<223> OTHER INFORMATION: cpS4-Bad fusion

<400> SEQUENCE: 77
atggatacca ccgaaaaaga aactttttgt cgtgccgcga ctgtcctgcg ccagttctac       60
agccaccacg aaaaggacac ccgttgcctg ggtgcgaccg ctcaacaatt ccatcgccac      120
aaacagctga ttcgtttcct gaaacgtctg gatcgcaacc tgtggggtct ggcgggtttg      180
aacagctgtc cagtcaaaga agcgaaccag agcaccctgg aaaactttct ggagcgtctg      240
cgtgttatca tgcagagcaa gtggttcaag tgcggtgcgg gtggcaatgg tggccacaag      300
tgtgacatta ccttgcaaga gattatcaaa acgctgaact ctctgaccga gcaaaagacg      360
ctgtgcaccg agctgacggt gacggacatc ttcgcggcgt ccggtagctt tcagatcccg      420
gaatttgagc cgagcgagca agaggattca agcagcgcgg agcgcggtct gggtccgagc      480
ccggcaggcg acggtccgag cggcagcggc aagcatcacc gccaggcgcc aggcctgctg      540
tgggatgcat cgcatcaaca ggaacaaccg acgagcagca gccatcatgg tggcgctggt      600
gcggttgaga ttagatcgcg ccactccgca tatcctgccg gcaccgaaga tgacgaaggc      660
atgggcgagg aaccgagccc gttccgtggc cgtagccgtg ctgcaccgcc gaatctgtgg      720
gccgcacagc gttatggtcg cgagttgcgt cgcatgtccg acgagtttgt tgactccttc      780
aagaaaggtt taccgcgtcc gaaatctgcc ggtaccgcga cgcagatgcg tcagagcagc      840
agctggaccc gcgtgtttca atcttggtgg gatcgtaatc tgggtcgtgg tagcagcgca      900
ccgagccaa      909

<210> SEQ ID NO 78
<211> LENGTH: 918
<212> TYPE: DNA
<213> ORGANISM: Artificial Sequence
<220> FEATURE:
<223> OTHER INFORMATION: cpIL-4-Bad

<400> SEQUENCE: 78
atgcacaaat gcgacattac cctgcaagag atcattaaga ccctgaacag cctgaccgag        60
caaaagaccc tgtgtaccga actgaccgtc acggacatct tcgctgcgtc caaggacact       120
acggaaaagg aaacgttctg tcgtgcggcg acggtgctgc gccagttcta cagccaccat       180
gagaaagata cccgttgcct cggtgcgacc gcgcaacagt tccaccgtca caaacagctg       240
attcgcttcc tgaagcgtct ggatcgcaac ctgtgggggt tggcgggtct gaactcctgt       300
ccagtcaaag aagccaatca gtctacgctg gaaaacttt tggagcgtct gaaaactatc       360
atgcgtgaga gtacagcaa atgcagcagc ggtagctttc agatcccgga atttgagccg       420
agcgagcaag aggattcaag cagcgcggag cgcggtctgg gtccgagccc ggcaggcgac       480
ggtccgagcg gcagcggcaa gcatcaccgc caggcgccag gcctgctgtg ggatgcatcg       540
catcaacagg aacaaccgac gagcagcagc catcatggtg gcgctggtgc ggttgagatt       600
agatcgcgcc actccgcata tcctgccggc accgaagatg acgaaggcat gggcgaggaa       660
ccgagcccgt tccgtggccg tagccgtgct gcaccgccga atctgtgggc cgcacagcgt       720
tatggtcgcg agttgcgtcg catgtccgac gagtttgttg actccttcaa gaaaggttta       780
ccgcgtccga atctgccgg taccgcgacg cagatgcgtc agagcagcag ctggacccgc       840
gtgtttcaat cttggtggga tcgtaatctg ggtcgtggta gcagcgcacc gagccaacac       900
caccatcacc atcactaa                                                    918

<210> SEQ ID NO 79
<211> LENGTH: 927
<212> TYPE: DNA
<213> ORGANISM: Artificial Sequence
<220> FEATURE:
<223> OTHER INFORMATION: bp cpIL-4-Bad

<400> SEQUENCE: 79
atggatacca ccgagaaaga aacgttctgc cgtgctgcca ctgtcctgcg ccagttttac        60
agccatcacg aaaaggacac ccgttgcctg ggtgcgacgg cgcagcaatt ccaccgccac       120
aaacagctga ttcgtttcct gaagcgtctg accgtaacc tgtggggtct ggcgggtctg       180
aacagctgtc cagtgaaaga agcgaatcag agcaccttgg agaatttcct cgaacgcctg       240
aaaaccatca tgcgtgagaa atacagcaag tgttctagcg gcggtaacgg tggccacaaa       300
tgcgatatca ccctgcaaga gatcattaag acgctgaact ccttgacgga acaaaagacc       360
ctgtgtactg agctgacggt caccgacatt ttcgcggcgt ccggtagctt tcagatcccg       420
gaatttgagc cgagcgagca agaggattca agcagcgcgg agcgcggtct gggtccgagc       480
ccggcaggcg acggtccgag cggcagcggc aagcatcacc gccaggcgcc aggcctgctg       540
tgggatgcat cgcatcaaca ggaacaaccg acgagcagca gccatcatgg tggcgctggt       600
gcggttgaga ttagatcgcg ccactccgca tatcctgccg gcaccgaaga tgacgaaggc       660
atgggcgagg aaccgagccc gttccgtggc cgtagccgtg ctgcaccgcc gaatctgtgg       720
gccgcacagc gttatggtcg cgagttgcgt cgcatgtccg acgagtttgt tgactccttc       780
aagaaaggtt taccgcgtcc gaaatctgcc ggtaccgcga cgcagatgcg tcagagcagc       840
agctggaccc gcgtgtttca atcttggtgg gatcgtaatc tgggtcgtgg tagcagcgca       900
ccgagccaac accaccatca ccatcac                                          927

<210> SEQ ID NO 80
<211> LENGTH: 930

-continued

```
<212> TYPE: DNA
<213> ORGANISM: Artificial Sequence
<220> FEATURE:
<223> OTHER INFORMATION: bp cpS4-Bad

<400> SEQUENCE: 80
atggatacca ccgaaaaaga aactttttgt cgtgccgcga ctgtcctgcg ccagttctac        60
agccaccacg aaaaggacac ccgttgcctg ggtgcgaccg ctcaacaatt ccatcgccac       120
aaacagctga ttcgtttcct gaaacgtctg gatcgcaacc tgtggggtct ggcgggtttg       180
aacagctgtc cagtcaaaga agcgaaccag agcaccctgg aaaactttct ggagcgtctg       240
cgtgttatca tgcagagcaa gtggttcaag tgcggtgcgg gtggcaatgg tggccacaag       300
tgtgacatta ccttgcaaga gattatcaaa cgctgaact  ctctgaccga gcaaaagacg       360
ctgtgcaccg agctgacggt gacggacatc ttcgcggcgt ccggtagctt tcagatcccg       420
gaatttgagc cgagcgagca agaggattca agcagcgcgg agcgcggtct gggtccgagc       480
ccggcaggcg acggtccgag cggcagcggc aagcatcacc gccaggcgcc aggcctgctg       540
tgggatgcat cgcatcaaca ggaacaaccg acgagcagca gccatcatgg tggcgctggt       600
gcggttgaga ttagatcgcg ccactccgca tatcctgccg gcaccgaaga tgacgaaggc       660
atgggcgagg aaccgagccc gttccgtggc cgtagccgtg ctgcaccgcc gaatctgtgg       720
gccgcacagc gttatggtcg cgagttgcgt cgcatgtccg acgagtttgt tgactccttc       780
aagaaaggtt taccgcgtcc gaaatctgcc ggtaccgcga cgcagatgcg tcagagcagc       840
agctggaccc gcgtgtttca atcttggtgg gatcgtaatc tgggtcgtgg tagcagcgca       900
ccgagccaac accaccatca ccatcactaa                                        930

<210> SEQ ID NO 81
<211> LENGTH: 926
<212> TYPE: DNA
<213> ORGANISM: Artificial Sequence
<220> FEATURE:
<223> OTHER INFORMATION: bp pKFR4-Bad-H6

<400> SEQUENCE: 81
atggatacta ccgagaaaga aacgtttttgc cgtgctgcga ccgtcctgcg tcagttctac        60
agccaccacg aaaaggacac ccgctgtctg ggtgcgactg cccaacaatt ccatcgtcac       120
aaacagctga ttcgtttcct gaagcgtctg accgcaacc  tgtggggtct ggcgggcttg       180
aactcctgcc cagtcaaaga agcgaaccaa agcaccctgg aaaacttctt ggagcgtctg       240
aaaacgatca tgaaagagaa gttccgcaag tgtagcagcg gtggtaatgg tggccacaag       300
tgcgacatta cgctgcagga aatcattaag accctgaact ctctgaccga gcagaaaacc       360
ctctgtaccg agctgacggt gacggatatc tttgcggcga gcggtagctt tcagatcccg       420
gaatttgagc cgagcgagca agaggattca agcagcgcgg agcgcggtct gggtccgagc       480
ccggcaggcg acggtccgag cggcagcggc aagcatcacc gccaggcgcc aggcctgctg       540
tgggatgcat cgcatcaaca ggaacaaccg acgagcagca gccatcatgg tggcgctggt       600
gcggttgaga ttagatcgcg ccactccgca tatcctgccg gcaccgaaga tgacgaaggc       660
atgggcgagg aaccgagccc gttccgtggc cgtagccgtg ctgcaccgcc gaatctgtgg       720
gccgcacagc gttatggtcg cgagttgcgt cgcatgtccg acgagtttgt tgactccttc       780
aagaaaggtt taccgcgtcc gaaatctgcc ggtaccgcga cgcagatgcg tcagagcagc       840
agctggaccc gcgtgtttca atcttggtgg gatcgtaatc tgggtcgtgg tagcagcgca       900
```

-continued

```
ccgagccaac accaccatca ccatca                                        926

<210> SEQ ID NO 82
<211> LENGTH: 1483
<212> TYPE: DNA
<213> ORGANISM: Artificial Sequence
<220> FEATURE:
<223> OTHER INFORMATION: IL-13DN

<400> SEQUENCE: 82
tttgtaataa aaaaacctat aaatattccg gattattcat accgtcccac catcgggcgc    60
ggatctatgc tactagtaaa tcagtcacac caaggcttca ataaggaaca cacaagcaag   120
atggtaagcg ctattgtttt atatgtgctt ttggcggcgg cggcgcattc tgcctttgcg   180
ggatccgcgc ccccatgccc atcatgccca gcacctgagt tcctgggggg accatcagtc   240
ttcctgttcc ccccaaaacc caaggacact ctcatgatct cccggacccc tgaggtcacg   300
tgcgtggtgg tggacgtgag ccaggaagac cccgaggtcc agttcaactg gtacgtggat   360
ggcgtggagg tgcataatgc caagacaaag ccgcgggagg agcagttcaa cagcacgtac   420
cgtgtggtca gcgtcctcac cgtcctgcac caggactggc tgaacggcaa ggagtacaag   480
tgcaaggtct ccaacaaagg cctcccgtcc tccatcgaga aaaccatctc caaagccaaa   540
gggcagcccc gagagccaca ggtgtacacc ctgcccccat cccaggagga tgaccaag    600 aaccaggtca gcctgacctg cctggtcaaa ggcttctacc ccagcgacat cgccgtggag   660
tgggagagca atgggcagcc ggagaacaac tacaagacca cgcctcccgt gctggactcc   720
gacggctcct tcttcctcta cagcaggcta accgtggaca gagcaggtg gcaggagggg   780 aatgtcttct catgctccgt gatgcatgag gctctgcaca accactacac acagaagagc   840
ctctccctgt ctccgggtaa aggaggcgga agcggatccc caggccctgt gcctccctct   900
acagccgttc gtgcgctcat tgaggagctg attaacatca cccagaacca gaaggctccg   960
ctctgcaatg gcagcatggt atggagcatc aaccggacag ctggcatgta ctgtgcagcc  1020
ctggaatccc tgatcaacgt gtcaggctgc agtgccatcg agaagaccca ggacatgctg  1080
agcggattct gcccgcacaa ggtctcagct gggcagtttt ccagcttgca tgtcaggagt  1140
agtaagatcg aggtggccca gtttgtaaag gacctgctct tccatttaag gactctttt  1200 agggagggac agttcaacgc ggccgcccat catcaccacc atcaccacca ttaatgaaga  1260
tctgatcctt tcctgggacc cggcaagaac caaaaactca ctctcttcaa ggaaatccgt  1320
aatgttaaac ccgacacgat gaagcttgtc gttggatgga aggaaaaga gttctacagg  1380 gaaacttgga cccgcttcat ggaagacagc ttccccattg ttaacgacca agaagtgatg  1440 gatgtttcc ttgttgtcaa catgcgtccc actagacccca acc                    1483

<210> SEQ ID NO 83
<211> LENGTH: 390
<212> TYPE: DNA
<213> ORGANISM: Artificial Sequence
<220> FEATURE:
<223> OTHER INFORMATION: IL-4

<400> SEQUENCE: 83
atgcacaaat gcgacattac cctgcaagag atcattaaga ccctgaacag cctgaccgag    60
caaaagaccc tgtgtaccga actgaccgtc acggacatct tcgctgcgtc caaggacact   120
acggaaaagg aaacgttctg tcgtgcggcg acggtgctgc gccagttcta cagccaccat   180
gagaaagata cccgttgcct cggtgcgacc gcgcaacagt tccaccgtca caaacagctg   240
```

-continued

```
attcgcttcc tgaagcgtct ggatcgcaac ctgtggggtt tggcgggtct gaactcctgt      300
ccagtcaaag aagccaatca gtctacgctg gaaaactttt tggagcgtct gaaaactatc      360
atgcgtgaga agtacagcaa atgcagcagc                                       390
```

<210> SEQ ID NO 84
<211> LENGTH: 168
<212> TYPE: PRT
<213> ORGANISM: Artificial Sequence
<220> FEATURE:
<223> OTHER INFORMATION: BAD amino acid

<400> SEQUENCE: 84

```
Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser Ser His His Gly Gly Ala
    50                  55                  60

Gly Ala Val Glu Ile Arg Ser Arg His Ser Ala Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ala Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165
```

<210> SEQ ID NO 85
<211> LENGTH: 239
<212> TYPE: PRT
<213> ORGANISM: Artificial Sequence
<220> FEATURE:
<223> OTHER INFORMATION: Bcl-2 amino acid

<400> SEQUENCE: 85

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
```

-continued

```
              100                 105                 110

Ala Glu Met Ser Ser Gln Leu His Leu Thr Pro Phe Thr Ala Arg Gly
          115                 120                 125

Arg Phe Ala Thr Val Val Glu Glu Leu Phe Arg Asp Gly Val Asn Trp
     130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
               165                 170                 175

Met Thr Glu Tyr Leu Asn Arg His Leu His Thr Trp Ile Gln Asp Asn
               180                 185                 190

Gly Gly Trp Asp Ala Phe Val Glu Leu Tyr Gly Pro Ser Met Arg Pro
               195                 200                 205

Leu Phe Asp Phe Ser Trp Leu Ser Leu Lys Thr Leu Leu Ser Leu Ala
     210                 215                 220

Leu Val Gly Ala Cys Ile Thr Leu Gly Ala Tyr Leu Gly His Lys
225                 230                 235
```

```
<210> SEQ ID NO 86
<211> LENGTH: 168
<212> TYPE: PRT
<213> ORGANISM: Artificial Sequence
<220> FEATURE:
<223> OTHER INFORMATION: HsBAD_Q92934-1

<400> SEQUENCE: 86

Met Phe Gln Ile Pro Glu Phe Glu Pro Ser Glu Gln Glu Asp Ser Ser
1               5                  10                  15

Ser Ala Glu Arg Gly Leu Gly Pro Ser Pro Ala Gly Asp Gly Pro Ser
          20                  25                  30

Gly Ser Gly Lys His His Arg Gln Ala Pro Gly Leu Leu Trp Asp Ala
          35                  40                  45

Ser His Gln Gln Glu Gln Pro Thr Ser Ser Ser His His Gly Gly Ala
     50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
               85                  90                  95

Ser Arg Ser Ala Pro Pro Asn Leu Trp Ala Ala Gln Arg Tyr Gly Arg
          100                 105                 110

Glu Leu Arg Arg Met Ser Asp Glu Phe Val Asp Ser Phe Lys Lys Gly
          115                 120                 125

Leu Pro Arg Pro Lys Ser Ala Gly Thr Ala Thr Gln Met Arg Gln Ser
     130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
               165
```

```
<210> SEQ ID NO 87
<211> LENGTH: 192
<212> TYPE: PRT
<213> ORGANISM: Artificial Sequence
<220> FEATURE:
<223> OTHER INFORMATION: HsBAX_Q07812-1

<400> SEQUENCE: 87
```

-continued

```
Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190
```

```
<210> SEQ ID NO 88
<211> LENGTH: 211
<212> TYPE: PRT
<213> ORGANISM: Artificial Sequence
<220> FEATURE:
<223> OTHER INFORMATION: HsBAK1_Q16611-1

<400> SEQUENCE: 88
```

```
Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
            35                  40                  45

Ala Glu Gly Val Ala Ala Pro Ala Asp Pro Glu Met Val Thr Leu Pro
    50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
            115                 120                 125

Val Ala Leu Leu Gly Phe Gly Tyr Arg Leu Ala Leu His Val Tyr Gln
    130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175
```

-continued

```
Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205

Phe Lys Ser
    210

<210> SEQ ID NO 89
<211> LENGTH: 160
<212> TYPE: PRT
<213> ORGANISM: Artificial Sequence
<220> FEATURE:
<223> OTHER INFORMATION: HsBIK_Q13323-1

<400> SEQUENCE: 89

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
    50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
    130                 135                 140

Ala Leu Leu Leu Pro Leu Leu Ser Gly Gly Leu His Leu Leu Leu Lys
145                 150                 155                 160

<210> SEQ ID NO 90
<211> LENGTH: 195
<212> TYPE: PRT
<213> ORGANISM: Artificial Sequence
<220> FEATURE:
<223> OTHER INFORMATION: HsBID_P55957-1

<400> SEQUENCE: 90

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110
```

-continued

```
Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
                180                 185                 190

Gly Met Asp
        195

<210> SEQ ID NO 91
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 91

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
        20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 92
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 92

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
        20                  25                  30

Asn Pro Lys Leu Thr Arg Met Leu Thr Phe Asn Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
```

-continued

```
65                    70                    75                    80

Asp Pro Arg Asp Val Val Ser Asn Ile Asn Val Phe Val Leu Glu Leu
                85                    90                    95

Lys Gly Ser Glu Thr Thr Phe Met Cys Glu Tyr Ala Asp Glu Thr Ala
                100                   105                   110

Thr Ile Val Glu Phe Leu Asn Arg Trp Ile Thr Phe Cys Gln Ser Ile
            115                   120                   125

Ile Ser Thr Leu Thr
        130

<210> SEQ ID NO 93
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 93

Ala Pro Thr Ser Ser Ser Thr Lys Lys Thr Gln Leu Gln Leu Glu His
1               5                     10                    15

Leu Leu Leu Asp Leu Gln Met Ile Leu Asn Gly Ile Asn Asn Tyr Lys
                20                    25                    30

Asn Pro Lys Leu Thr Arg Met Leu Thr Ala Lys Phe Ala Met Pro Lys
            35                    40                    45

Lys Ala Thr Glu Leu Lys His Leu Gln Cys Leu Glu Glu Glu Leu Lys
        50                    55                    60

Pro Leu Glu Glu Val Leu Asn Leu Ala Gln Ser Lys Asn Phe His Phe
65                    70                    75                    80

Asp Pro Arg Asp Val Val Ser Asn Ile Asn Val Phe Val Leu Glu Leu
                85                    90                    95

Lys Gly Ser Glu Thr Thr Phe Met Cys Glu Tyr Ala Asp Glu Thr Ala
                100                   105                   110

Thr Ile Val Glu Phe Leu Asn Arg Trp Ile Thr Phe Cys Gln Ser Ile
            115                   120                   125

Ile Ser Thr Leu Thr
        130

<210> SEQ ID NO 94
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 94

Ala Pro Thr Ser Ser Ser Thr Lys Lys Thr Gln Leu Gln Leu Glu His
1               5                     10                    15

Leu Leu Leu Asp Leu Gln Met Ile Leu Asn Gly Ile Asn Asn Tyr Lys
                20                    25                    30

Asn Pro Lys Leu Thr Arg Met Leu Thr Ala Lys Phe Tyr Met Pro Lys
            35                    40                    45

Lys Ala Thr Glu Leu Lys His Leu Gln Cys Leu Glu Glu Ala Leu Lys
        50                    55                    60

Pro Leu Glu Glu Val Leu Asn Leu Ala Gln Ser Lys Asn Phe His Phe
65                    70                    75                    80

Asp Pro Arg Asp Val Val Ser Asn Ile Asn Val Phe Val Leu Glu Leu
                85                    90                    95
```

-continued

Lys Gly Ser Glu Thr Thr Phe Met Cys Glu Tyr Ala Asp Glu Thr Ala
            100                     105                     110

Thr Ile Val Glu Phe Leu Asn Arg Trp Ile Thr Phe Cys Gln Ser Ile
            115                     120                     125

Ile Ser Thr Leu Thr
        130

<210> SEQ ID NO 95
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 95

Ala Pro Thr Ser Ser Ser Thr Lys Lys Thr Gln Leu Gln Leu Glu His
1               5                       10                      15

Leu Leu Leu Asp Leu Gln Met Ile Leu Asn Gly Ile Asn Asn Tyr Lys
            20                      25                      30

Asn Pro Lys Leu Thr Arg Met Leu Thr Ala Lys Phe Ala Met Pro Lys
        35                      40                      45

Lys Ala Thr Glu Leu Lys His Leu Gln Cys Leu Glu Glu Ala Leu Lys
        50                      55                      60

Pro Leu Glu Glu Val Leu Asn Leu Ala Gln Ser Lys Asn Phe His Phe
65                      70                      75                      80

Asp Pro Arg Asp Val Val Ser Asn Ile Asn Val Phe Val Leu Glu Leu
                85                      90                      95

Lys Gly Ser Glu Thr Thr Phe Met Cys Glu Tyr Ala Asp Glu Thr Ala
            100                     105                     110

Thr Ile Val Glu Phe Leu Asn Arg Trp Ile Thr Phe Cys Gln Ser Ile
            115                     120                     125

Ile Ser Thr Leu Thr
        130

<210> SEQ ID NO 96
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 96

Ala Pro Thr Ser Ser Ser Thr Lys Lys Thr Gln Leu Gln Leu Glu His
1               5                       10                      15

Leu Leu Leu Asp Leu Gln Met Ile Leu Asn Gly Ile Asn Asn Tyr Lys
            20                      25                      30

Asn Pro Lys Leu Thr Arg Met Leu Thr Phe Lys Phe Tyr Met Pro Lys
        35                      40                      45

Lys Ala Thr Glu Leu Lys His Leu Gln Cys Leu Glu Glu Glu Leu Lys
        50                      55                      60

Pro Leu Glu Glu Val Leu Asn Leu Ala Arg Ser Lys Asn Phe His Leu
65                      70                      75                      80

Arg Pro Arg Asp Leu Ile Ser Asn Ile Asn Val Ile Val Leu Glu Leu
                85                      90                      95

Lys Gly Ser Glu Thr Thr Phe Met Cys Glu Tyr Ala Asp Glu Thr Ala
            100                     105                     110

Thr Ile Val Glu Phe Leu Asn Arg Trp Ile Thr Phe Cys Gln Ser Ile
            115                     120                     125

```
Ile Ser Thr Leu Thr
    130

<210> SEQ ID NO 97
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 97

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Arg Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 98
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 98

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Ile Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

-continued

```
<210> SEQ ID NO 99
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 99

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Leu
65                  70                  75                  80

Thr Pro Arg Asp Val Val Ser Asn Ile Asn Val Phe Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 100
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 100

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 101
<211> LENGTH: 133
<212> TYPE: PRT
<213> ORGANISM: Artificial Sequence
<220> FEATURE:
```

<223> OTHER INFORMATION: IL-2 Mutein

<400> SEQUENCE: 101

Ala Pro Thr Ser Ser Ser Thr Lys Lys Thr Gln Leu Gln Leu Glu His
1               5                   10                  15

Leu Leu Leu Asp Leu Gln Met Val Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 102
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 102

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

His Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 103
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 103

Ala Pro Thr Ser Ser Ser Thr Lys Lys Thr Gln Leu Gln Leu Glu His

-continued

```
1                    5                        10                        15

Leu Leu Leu Asp Leu Gln Met Ile Leu Asn Gly Ile Asn Asn Tyr Lys
                20                    25                    30

Asn Pro Lys Leu Thr Arg Met Leu Thr Phe Lys Phe Tyr Met Pro Lys
                35                    40                    45

Lys Ala Thr Glu Leu Lys His Leu Gln Cys Leu Glu Glu Glu Leu Lys
                50                    55                    60

Pro Leu Glu Glu Val Leu Asn Leu Ala His Ser Lys Asn Phe His Phe
65                        70                    75                    80

Asp Pro Arg Asp Val Val Ser Asn Ile Asn Val Phe Val Leu Glu Leu
                        85                    90                    95

Lys Gly Ser Glu Thr Thr Phe Met Cys Glu Tyr Ala Asp Glu Thr Ala
                100                    105                    110

Thr Ile Val Glu Phe Leu Asn Arg Trp Ile Thr Phe Cys Gln Ser Ile
                115                    120                    125

Ile Ser Thr Leu Thr
    130
```

<210> SEQ ID NO 104
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 104

```
Ala Pro Thr Ser Ser Ser Thr Lys Lys Thr Gln Leu Gln Leu Glu His
1                    5                        10                        15

Leu Leu Leu Asp Leu Gln Met Ile Leu Asn Gly Ile Asn Asn Tyr Lys
                20                    25                    30

Asn Pro Lys Leu Thr Arg Met Leu Thr Phe Lys Phe Tyr Met Pro Lys
                35                    40                    45

Lys Ala Thr Glu Leu Lys His Leu Gln Cys Leu Glu Glu Glu Leu Lys
                50                    55                    60

Pro Leu Glu Glu Val Leu Asn Leu Ala Ser Ser Lys Asn Phe His Phe
65                        70                    75                    80

Asp Pro Arg Asp Val Val Ser Asn Ile Asn Val Phe Val Leu Glu Leu
                        85                    90                    95

Lys Gly Ser Glu Thr Thr Phe Met Cys Glu Tyr Ala Asp Glu Thr Ala
                100                    105                    110

Thr Ile Val Glu Phe Leu Asn Arg Trp Ile Thr Phe Cys Gln Ser Ile
                115                    120                    125

Ile Ser Thr Leu Thr
    130
```

<210> SEQ ID NO 105
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 105

```
Ala Pro Thr Ser Ser Ser Thr Lys Lys Thr Gln Leu Gln Leu Glu His
1                    5                        10                        15

Leu Leu Leu Asp Leu Gln Met Ile Leu Asn Gly Ile Asn Asn Tyr Lys
                20                    25                    30
```

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
        130
```

<210> SEQ ID NO 106
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 106

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Leu
65                  70                  75                  80

Thr Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
        130
```

<210> SEQ ID NO 107
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 107

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
        50                  55                  60
```

-continued

```
Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 108
<211> LENGTH: 133
<212> TYPE: PRT
<213> ORGANISM: Artificial Sequence
<220> FEATURE:
<223> OTHER INFORMATION: IL-2 agonist H9D10

<400> SEQUENCE: 108

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 109
<211> LENGTH: 133
<212> TYPE: PRT
<213> ORGANISM: Artificial Sequence
<220> FEATURE:
<223> OTHER INFORMATION: IL-2 agonist H9E10

<400> SEQUENCE: 109

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
```

```
                    85              90              95

Lys Gly Ser Glu Thr Thr Phe Met Cys Glu Tyr Ala Asp Glu Thr Ala
            100             105             110

Thr Ile Val Glu Phe Leu Asn Arg Trp Ile Thr Phe Cys Gln Ser Ile
        115             120             125

Ile Ser Thr Leu Thr
    130

<210> SEQ ID NO 110
<211> LENGTH: 133
<212> TYPE: PRT
<213> ORGANISM: Artificial Sequence
<220> FEATURE:
<223> OTHER INFORMATION: IL-2 agonist H9G8

<400> SEQUENCE: 110

Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
        35              40              45

Lys Ala Thr Glu Leu Lys His Leu Gln Cys Leu Glu Glu Glu Leu Lys
    50              55              60

Pro Leu Glu Glu Val Leu Asn Leu Ala Asn Ser Lys Asn Phe His Phe
65              70              75              80

Asp Pro Arg Asp Val Val Ser Asn Ile Asn Val Phe Val Leu Glu Leu
            85              90              95

Lys Gly Ser Glu Thr Thr Phe Met Cys Glu Tyr Ala Asp Glu Thr Ala
            100             105             110

Thr Ile Val Glu Phe Leu Asn Arg Trp Ile Thr Phe Cys Gln Ser Ile
        115             120             125

Ile Ser Thr Leu Thr
    130

<210> SEQ ID NO 111
<211> LENGTH: 133
<212> TYPE: PRT
<213> ORGANISM: Artificial Sequence
<220> FEATURE:
<223> OTHER INFORMATION: IL-2 agonist H9B1

<400> SEQUENCE: 111

Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
        35              40              45

Lys Ala Thr Glu Leu Lys His Leu Gln Cys Leu Glu Glu Glu Leu Lys
    50              55              60

Pro Leu Glu Glu Val Leu Asn Leu Ala Asn Ser Lys Asn Phe His Phe
65              70              75              80

Asp Pro Arg Asp Val Val Ser Asn Val Asn Val Phe Val Leu Glu Leu
            85              90              95

Lys Gly Ser Glu Thr Thr Phe Met Cys Glu Tyr Ala Asp Glu Thr Ala
            100             105             110
```

-continued

```
Thr Ile Val Glu Phe Leu Asn Arg Trp Ile Thr Phe Cys Gln Ser Ile
        115                 120                 125

Ile Ser Thr Leu Thr
    130

<210> SEQ ID NO 112
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 112

Ala Pro Thr Ser Ser Ser Thr Lys Lys Thr Gln Leu Gln Leu Glu His
1               5                   10                  15

Leu Leu Leu Asp Leu Gln Met Val Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 113
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 113

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 114
<211> LENGTH: 375
<212> TYPE: PRT
<213> ORGANISM: Artificial Sequence
<220> FEATURE:
<223> OTHER INFORMATION: IL-2 Mutein

<400> SEQUENCE: 114

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Leu
65                  70                  75                  80

Asp Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Gly Gly Gly Gly Ser Gly
    130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
            165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
            195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
            245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
            275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

```
Leu Ser Leu Ser Pro Gly Lys
    370             375

<210> SEQ ID NO 115
<211> LENGTH: 113
<212> TYPE: PRT
<213> ORGANISM: Artificial Sequence
<220> FEATURE:
<223> OTHER INFORMATION: IL-13 wildtype

<400> SEQUENCE: 115

Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn

<210> SEQ ID NO 116
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 116

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Leu
65                  70                  75                  80

Asp Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 117
<211> LENGTH: 5
<212> TYPE: PRT
<213> ORGANISM: Artificial Sequence
```

```
<220> FEATURE:
<223> OTHER INFORMATION: linker

<400> SEQUENCE: 117

Gly Gly Gly Gly Ser
1               5

<210> SEQ ID NO 118
<211> LENGTH: 10
<212> TYPE: PRT
<213> ORGANISM: Artificial Sequence
<220> FEATURE:
<223> OTHER INFORMATION: linker

<400> SEQUENCE: 118

Gly Gly Gly Gly Ser Gly Gly Gly Gly Ser
1               5                   10

<210> SEQ ID NO 119
<211> LENGTH: 15
<212> TYPE: PRT
<213> ORGANISM: Artificial Sequence
<220> FEATURE:
<223> OTHER INFORMATION: linker

<400> SEQUENCE: 119

Gly Gly Gly Gly Ser Gly Gly Gly Gly Ser Gly Gly Gly Gly Ser
1               5                   10                  15

<210> SEQ ID NO 120
<211> LENGTH: 20
<212> TYPE: PRT
<213> ORGANISM: Artificial Sequence
<220> FEATURE:
<223> OTHER INFORMATION: linker

<400> SEQUENCE: 120

Gly Gly Gly Gly Ser Gly Gly Gly Gly Ser Gly Gly Gly Gly Ser Gly
1               5                   10                  15

Gly Gly Gly Ser
            20

<210> SEQ ID NO 121
<211> LENGTH: 20
<212> TYPE: PRT
<213> ORGANISM: Artificial Sequence
<220> FEATURE:
<223> OTHER INFORMATION: linker

<400> SEQUENCE: 121

Gly Gly Gly Gly Ser Gly Gly Gly Gly Ser Gly Gly Gly Gly Ser Gly
1               5                   10                  15

Gly Gly Gly Ser
            20
```